US008722350B2

(12) United States Patent
Markowitz

(10) Patent No.: US 8,722,350 B2
(45) Date of Patent: May 13, 2014

(54) METHODS AND COMPOSITIONS FOR CATEGORIZING PATIENTS

(75) Inventor: Sanford D. Markowitz, Pepper Pike, OH (US)

(73) Assignee: Case Western Reserve University, Cleveland, OH (US)

(*) Notice: Subject to any disclaimer, the term of this patent is extended or adjusted under 35 U.S.C. 154(b) by 40 days.

(21) Appl. No.: 13/485,519

(22) Filed: May 31, 2012

(65) Prior Publication Data

US 2012/0329077 A1  Dec. 27, 2012

Related U.S. Application Data

(63) Continuation of application No. 12/386,176, filed on Apr. 13, 2009, now Pat. No. 8,268,568, which is a continuation of application No. 10/649,591, filed on Aug. 26, 2003, now abandoned, which is a continuation-in-part of application No. 10/274,177, filed on Oct. 18, 2002, now Pat. No. 7,118,912, which is a continuation-in-part of application No. 10/229,345, filed on Aug. 26, 2002, now Pat. No. 7,081,516.

(51) Int. Cl.
*G01N 33/574* (2006.01)

(52) U.S. Cl.
USPC ............. 435/7.23; 435/7.1; 436/64; 436/501; 530/350; 530/387.1; 530/387.7; 530/387.9; 530/391.3

(58) Field of Classification Search
USPC ............. 530/350, 387.1, 387.7, 387.9, 391.3; 435/7.1, 7.23; 436/64, 501
See application file for complete search history.

(56) References Cited

U.S. PATENT DOCUMENTS

| | | |
|---|---|---|
| 2003/0077568 A1 | 4/2003 | Gish et al. |
| 2003/0232350 A1 | 12/2003 | Afar et al. |
| 2003/0235820 A1 | 12/2003 | Mack et al. |
| 2004/0002120 A1 | 1/2004 | Kekuda et al. |
| 2004/0005563 A1 | 1/2004 | Mack et al. |
| 2004/0038220 A1 | 2/2004 | Markowitz et al. |
| 2004/0038225 A1 | 2/2004 | Markowitz et al. |

FOREIGN PATENT DOCUMENTS

| | | |
|---|---|---|
| WO | WO 99/38881 A1 | 8/1999 |
| WO | WO 01/22920 A2 | 4/2001 |
| WO | WO 01/75067 A2 | 10/2001 |
| WO | WO 01/90357 A1 | 11/2001 |
| WO | WO 01/96523 A2 | 12/2001 |
| WO | WO 02/00939 A2 | 1/2002 |
| WO | WO 02/21996 A1 | 3/2002 |
| WO | WO 02/30268 A1 | 4/2002 |
| WO | WO 02/50301 A1 | 6/2002 |
| WO | WO 02/068677 A1 | 9/2002 |
| WO | WO 02/086443 A1 | 10/2002 |
| WO | WO 02079398 A2 * | 10/2002 |
| WO | WO 02/102235 A1 | 12/2002 |
| WO | WO 03/012070 A2 | 2/2003 |
| WO | WO 03/025138 A2 | 3/2003 |
| WO | WO 03/042661 A2 | 5/2003 |
| WO | WO 2004/018647 A2 | 3/2004 |
| WO | WO 2004/018648 A2 | 3/2004 |

OTHER PUBLICATIONS

Tiwari et al. (PLoS One. Jul. 23, 2013; 8 (7): e69473; pp. 1-14).*
Sabates-Bellver et al. (Mol. Cancer Res. Dec. 2007; 5 (12): 1263-75).*
Alon, U. et al. Broad patterns of gene expression revealed by clustering analysis of tumor and normal colon tissues probed by oligonucleotide arrays. PNAS 96, 745-6750 (Jun. 1999).
Bieller, A. et al. Isolation and Characterization of the Human Forkhead Gene FOXQ1. DNA Cell Biol. 20, 555-561 (2001).
Bowie et al., "Deciphering the Message in Protein Sequences: Tolerance to Amino Acid Substitutions," Science, 247:1306-1310 (1990).
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," The Journal of Cell Biology, 111:2129-2138 (1990).
Chen et al., "Discordant Protein and mRNA Expression in Lung Adenocarcinomas", Molecular & Cellular Protemics, DOI 10.1074/mcp.M200008-MCP200:304-313(2002).
Critchfield, G.C., "The Future of DNA Diagnostics," Disease Markers, 15:108-111 (1999).
Database Embl, "*Homo sapiens* mRNA for KIAA1199 protein, partial cds," Database accession No. AB033025, Nov. 11, 1999.
De Plaen et al., "Structure, chromosomal localization, and expression of 12 genes of the MAGE family," Immunogenetics, 40:360-369 (1994).
Deng, G. et al. Methylation of CpG in a Small Region of the hMLH1 Promoter Invariably Correlates with the Absence of Gene Expression. Cancer Res. 59, 2029-2033 (May 1, 1999).
Esteller, M. et al. Detection of Aberrant Promoter Hypermethylation of Tumor Suppressor Genes in Serum DNA from Non-Small Cell Lung Cancer Patients. Cancer Res. 59, 67-70 (Jan. 1, 1999).
Gebauer et al., "O-glucosylation and O-fucosylation occur together in close proximity on the first epidermal growth factor repeat of AMACO (VWA2 protein)," The Journal of Biological Chemistry, 283(26):17846-17854 (2008).
GenBank Accession No. AAG41062 (Aug. 29, 2000).
GenBank Accession No. A1357412 (Jan. 6, 1999).
GenBank Accession No. A1590539 (Apr. 9, 1999).
GenBank Accession No. A1870708 (Jul. 21, 1999).

(Continued)

*Primary Examiner* — Stephen Rawlings
(74) *Attorney, Agent, or Firm* — Ropes & Gray LLP

(57) ABSTRACT

The disclosure provides, among other things, molecular markers for categorizing the neoplastic state of a patient, methods for using the molecular markers in diagnostic tests, nucleic acid and amino acid sequences related to the molecular markers, reagents for detection of molecular markers, and methods for identifying candidate molecular markers in highly parallel gene expression data.

13 Claims, 62 Drawing Sheets

(56) References Cited

OTHER PUBLICATIONS

GenBank Accession No. AY007815 (Aug. 29, 2000).
GenBank Accession No. BAA92054 (Feb. 16, 2000).
GenBank Accession No. W07459 (Apr. 25, 1996).
GenBank Accession No. XM_061091 (Jul. 31, 2002).
Gray, Marion., "Clinical Use of Serum Prostate-Specific Antigen: a Review", Clin. Lab, 51:127-133(2005).
Guo et al., "Protein tolerance to random amino acid change," Proc. Natl. Acad. Sci. USA., vol. 101(25), 9205-9210 (2004).
Hardy, R.G. et al. Aberrant P-cadherin expression is an early event in hyperplastic and dysplastic transformation in the colon. Gut 50, 513-519 (2002).
Herman, J.G. et al. Incidence and functional consequences of hMLH1 promoter hypermethylation in colorectal carcinoma. PNAS 95, 6870-6875 (Jun. 1998).
Hibi, K. et al. Molecular Detection of Genetic Alterations in the Serum of Colorectal Cancer Patients. Cancer Res. 58, 1405-1407 (Apr. 1, 1998).
Hong et al., "The Winged Helix/Forkhead Transcription Factor Foxq1 Regulates Differentiation of Hair in Satin Mice", Genesis 29:163-171(2001).
Kane, M.F. et al. Methylation of the hMLH1 Promoter Correlates with Lack of Expression of hMLH1 in Sporadic Colon Tumors and Mismatch Repair-defective Human Tumor Cell Lines. Cancer Res. 57, 808-811 (Mar. 1, 1997).
Kennel, David E., "Principles and Practices of Nucleic Acid Hybridization", Nucl. Acid Res. Mol. Biol. 11:259(1971).
Kobayashi, A. et al. Molecular Cloning and Functional Characterization of a New Cap'n'Collar Family Transcription Factor Nrf3. J. Biol. Chem. 274, 6443-6452 (Mar. 5, 1999).
Lazar et al., "Transforming Growth Factor α: Mutation of Aspartic Acid 47 and Leucine 48 Results in Different Biological Activities," Molecular and Cellular Biology, 8(3):1247-1252 (1988).
Liu et al., "Detection of Low Level HER-2/neu Gene Amplification in Prostate Cancer by Flourescence In Situ Hybridization", The Cancer Journal, 7(5):395-403(2001).
Markowitz, S. et al. Inactivation of the Type II TGF-$\beta$ Receptor in Colon Cancer Cells with Microsatellite Instability. Science 268, 1336-1338 (1995).
Michishita et al., "Upregulation of the KIAA1199 gene is associated with cellular mortality," Cancer Letters, 239:71-77 (2006).
Radice, G.L. et al. Precocious Mammary Gland Development in P-Cadherin-deficient Mice. J. Cell Biol. 139, 1025-1032 (Nov. 17, 1997).
Rae et al., "Novel Association of a Diverse Range of Genes with Renal Cell Carcinoma as Identified by Differential Display," International Journal of Cancer, 88:726-732 (2000).
Roessler et al., "Identification of Nicotinamide N-Methyltransferase as a Novel Serum Tumor Marker for Colorectal Cancer," Clinical Cancer Research, 11(18):6550-6557 (2005).
Roessler et al., "Identification of PSME3 as a Novel Serum Tumor Marker for Colorectal Cancer by Combining Two-dimensional Polyacrylamide Gel Electrophoresis with a Strictly Mass Spectrometry-based Approach for Data Analysis," Molecular & Cellular Proteomics, 5(11): 2092-2101 (2006).
Scott, D.A. et al. Refining the DFNB7-DFNB11 deafness locus using intragenic polymorphisms in a novel gene, TMEM2. Gene 246, 265-274 (2000).
Sengle Gerhard et al, "Identification and characterization of AMACO, a new member of the von Willebrand factor A-like domain protein superfamily with a regulated expression in the kidney," The Journal of Biological Chemistry, 278(50):50240-50249 (2003).
Shimoyama, Y. et al. Molecular Cloning of a Human Ca2+-dependent Cell-Cell Adhesion Molecule Homologous to Mouse Placental Cadherin: Its Low Expression in Human Placental Tissues. J. Cell Biol. 109, 1787-1794 (1989).
Sidransky et al., "Nucleic Acid-Based Methods for the Detection of Cancer," Science, 278:1054-1058 (1997).
Skolnick et al., "From genes to protein structure and function: novel applications of computational approaches in the genomic era," Trends Biotechnol, 18(1):34-39 (2000).
Srivastava et al., "Biomarkers for Early Detection of Colon Cancer," Clinical Cancer Research 7:1118-1126 (2001).
Takada et al., "Alteration of a Single Amino Acid in Peroxisome Proliferator-Activated Receptor-α(PPARα) Generates a PPARo Phenotype," Molecular Endocrinology, 14(5):733-740 (2000).
Tockman et al., "Considerations in Bringing a Cancer Biomarker to Clinical Application," Cancer Research (Suppl.), 52:2711s-2718s (1992).
Veigl, M.L. et al. Biallelic inactivation of hMLH1 by epigenetic gene silencing, a novel mechanism causing human MSI cancers. PNAS 95, 8698-8702 (Jul. 1998).
Ward A. Milford, "Tumour Markers," Developmental Oncology, 21:91-106 (1985).
Weber, G.F. The metastasis gene osteopontin: a candidate target for cancer therapy. Biochim. Biophys. Acta. 1552, 61-85 (2001).
Willis et al., "Colon cancer secreting protein-2 is expressed in a spectrum of common adenocarcinomas", Laboratory Investigation, 88(1):140A (2008).
Wines, M.E. et al. Identification of Mesoderm Development (mesd) Candidate Genes by Comparative Mapping and Genome Sequence Analysis. Genomics 88-98 (2001).
Wong, I.H.N. et al. Detection of Aberrant p16 Methylation in the Plasma and Serum of Liver Cancer Patients. Cancer Res. 59, 71-73 (Jan. 1, 1999).
Xin et al., "Colon Cancer Secreted Protein-2 (CCSP-2), A Novel Candidate Serological Marker of Colon Neoplasia," Oncogene24:724-731 (2005).
Zhang, J.-S. et al. Keratin 23 (K23), a Novel Acidic Keratin, Is Highly Induced by Histone Deacetylase Inhibitors During Differentiation of Pancreatic Cancer Cells. Genes Chromosomes Cancer 30, 123-135 (2001).
Zolg et al., "How Industry Is Approaching the Search of New Diagnostic Markers and Biomarkers," Molecular & Cellular Proteomics, vol. 3(4), pp. 345-354 (2004).

* cited by examiner

Figure 1A. Amino acid sequence of secreted ColoUp1 protein (I) (SEQ ID NO: 1)

```
TVAAGCPDQSPELQPWNPGHDQDHHVHIGQGKTLLLTSSATVYSIHISEGGKLVIKDHD
EPIVLRTRHILIDNGGELHAGSALCPFQGNFTIILYGRADEGIQPDPYYGLKYIGVKG
GALELHGQKKLSWTFLNKTLHPGGMAEGGYFFERSWGHRGVIVHVIDPKSGTVIHSDRF
DTYRSKKESERLVQYLNAVPDGRILSVAVNDEGSRNLDDMARKAMTKLGSKHFLHLGFR
HPWSFLTVKGNPSSSVEDHIEYHGHRGSAAARVFKLFQTEHGEYFNVSLSSEWVQDVEW
TEWFDHDKVSQTKGGEKISDLWKAHPGKICNRPIDIQATTMDGVNLSTEVVYKKGQDYR
FACYDRGRACRSYRVRFLCGKPVRPKLTVTIDTNVNSTILNLEDNVQSWKPGDTLVIAS
TDYSMYQAEEFQVLPCRSCAPNQVKVAGKPMYLHIGEEIDGVDMRAEVGLLSRNIIVMG
EMEDKCYPYRNHICNFFDFDTFGGHIKFALGFKAAHLEGTELKHMGQQLVGQYPIHFHL
AGDVDERGGYDPPTYIRDLSIHHTFSRCVTVHGSNGLLIKDVVGYNSLGHCFFTEDGPE
ERNTFDHCLGLLVKSGTLLPSDRDSKMCKMITEDSYPGYIPKPRQDCNAVSTFWMANPN
NNLINCAAAGSEETGFWFIFHHVPTGPSVGMYSPGYSEHIPLGKFYNNRAHSNYRAGMI
IDNGVKTTEASAKDKRPFLSIISARYSPHQDADPLKPREPAIIRHFIAYKNQDHGAWLR
GGDVWLDSCRFADNGIGLTLASGGTFPYDDGSKQEIKNSLFVGESGNVGTEMMDNRIWG
PGGLDHSGRTLPIGQNFPIRGIQLYDGPINIQNCTFRKFVALEGRHTSALAFRLNNAWQ
SCPHNNVTGIAFEDVPITSRVFFGEPGPWFNQLDMDGDKTSVFHDVDGSVSEYPGSYLT
KNDNWLVRHPDCINVPDWRGAICSGCYAQMYIQAYKTSNLRMKIIKNDFPSHPLYLEGA
LTRSTHYQQYQPVVTLQKGYTIHWDQTAPAELAIWLINFNKGDWIRVGLCYPRGTTFSI
LSDVHNRLLKQTSKTGVFVRTLQMDKVEQSYPGRSHYYWDEDSGLLFLKLKAQNEREKF
AFCSMKGCERIKIKALIPKNAGVSDCTATAYPKFTERAVVDVPMPKKLFGSQLKTKDHF
LEVKMESSKQHFFHLWNDFAYIEVDGKKYPSSEDGIQVVVIDGNQGRVVSHTSFRNSIL
QGIPWQLFNYVATIPDNSIVLMASKGRYVSRGPWTRVLEKLGADRGLKLKEQMAFVGFK
GSFRPIWVTLDTEDHKAKIFQVVPIPVVKKKKL
```

Figure 1B. Amino acid sequence of secreted ColoUp1 protein (II) (SEQ ID NO: 2)

```
AGCPDQSPELQPWNPGHDQDHHVHIGQGKTLLLTSSATVYSIHISEGGKLVIKDHDEPI
VLRTRHILIDNGGELHAGSALCPFQGNFTIILYGRADEGIQPDPYYGLKYIGVGKGGAL
ELHGQKKLSWTFLNKTLHPGGMAEGGYFFERSWGHRGVIVHVIDPKSGTVIHSDRFDTY
RSKKESERLVQYLNAVPDGRILSVAVNDEGSRNLDDMARKAMTKLGSKHFLHLGFRHPW
SFLTVKGNPSSSVEDHIEYHGHRGSAAARVFKLFQTEHGEYFNVSLSSEWVQDVEWTEW
FDHDKVSQTKGGEKISDLWKAHPGKICNRPIDIQATTMDGVNLSTEVVYKKGQDYRFAC
YDRGRACRSYRVRFLCGKPVRPKLTVTIDTNVNSTILNLEDNVQSWKPGDTLVIASTDY
SMYQAEEFQVLPCRSCAPNQVKVAGKPMYLHIGEEIDGVDMRAEVGLLSRNIIVMGEME
DKCYPYRNHICNFFDFDTFGGHIKFALGFKAAHLEGTELKHMGQQLVGQYPIHFHLAGD
VDERGGYDPPTYIRDLSIHHTFSRCVTVHGSNGLLIKDVVGYNSLGHCFFTEDGPEERN
TFDHCLGLLVKSGTLLPSDRDSKMCKMITEDSYPGYIPKPRQDCNAVSTFWMANPNNNL
INCAAAGSEETGFWFIFHHVPTGPSVGMYSPGYSEHIPLGKFYNNRAHSNYRAGMIIDN
GVKTTEASAKDKRPFLSIISARYSPHQDADPLKPREPAIIRHFIAYKNQDHGAWLRGGD
VWLDSCRFADNGIGLTLASGGTFPYDDGSKQEIKNSLFVGESGNVGTEMMDNRIWGPGG
LDHSGRTLPIGQNFPIRGIQLYDGPINIQNCTFRKFVALEGRHTSALAFRLNNAWQSCP
HNNVTGIAFEDVPITSRVFFGEPGPWFNQLDMDGDKTSVFHDVDGSVSEYPGSYLTKND
NWLVRHPDCINVPDWRGAICSGCYAQMYIQAYKTSNLRMKIIKNDFPSHPLYLEGALTR
STHYQQYQPVVTLQKGYTIHWDQTAPAELAIWLINFNKGDWIRVGLCYPRGTTFSILSD
VHNRLLKQTSKTGVFVRTLQMDKVEQSYPGRSHYYWDEDSGLLFLKLKAQNEREKFAFC
SMKGCERIKIKALIPKNAGVSDCTATAYPKFTERAVVDVPMPKKLFGSQLKTKDHFLEV
KMESSKQHFFHLWNDFAYIEVDGKKYPSSEDGIQVVVIDGNQGRVVSHTSFRNSILQGI
PWQLFNYVATIPDNSIVLMASKGRYVSRGPWTRVLEKLGADRGLKLKEQMAFVGFKGSF
RPIWVTLDTEDHKAKIFQVVPIPVVKKKKL
```

Figure 2. Amino acid sequence of secreted ColoUp2 protein (SEQ ID NO: 3)

```
LQEVHVSKETIGKISAASKMMWCSAAVDIMFLLDGSNSVGKGSFERSKHFAITVCDGLD
ISPERVRVGAFQFSSTPHLEFPLDSFSTQQEVKARIKRMVFKGGRTETELALKYLLHRG
LPGGRNASVPQILIIVTDGKSQGDVALPSKQLKERGVTVFAVGVRFPRWEELHALASEP
RGQHVLLAEQVEDATNGLFSTLSSSAICSSATPDCRVEAHPCEHRTLEMVREFAGNAPC
WRGSRRTLAVLAAHCPFYSWKRVFLTHPATCYRTTCPGPCDSQPCQNGGTCVPEGLDGY
QCLCPLAFGGEANCALKLSLECRVDLLFLLDSSAGTTLDGFLRAKVFVKRFVRAVLSED
SRARVGVATYSRELLVAVPVGEYQDVPDLVWSLDGIPFRGGPTLTGSALRQAAERGFGS
ATRTGQDRPRRVVVLLTESHSEDEVAGPARHARARELLLLGVGSEAVRAELEEITGSPK
HVMVYSDPQDLFNQIPELQGKLCSRQRPGCRTQALDLVFMLDTSASVGPENFAQMQSFV
RSCALQFEVNPDVTQVGLVVYGSQVQTAFGLDTKPTRAAMLRAISQAPYLGGVGSAGTA
LLHIYDKVMTVQRGARPGVPKAVVVLTGGRGAEDAAVPAQKLRNNGISVLVVGVGPVLS
EGLRRLAGPRDSLIHVAAYADLRYHQDVLIEWLCGEAKQPVNLCKPSPCMNEGSCVLQN
GSYRCKCRDGWEGPHCENRFLRRP
```

Figure 3A: Nucleic acid sequence of Coloup1 (SEQ ID NO: 4)

```
CGTGACACTGTCTCGGCTACAGACCCAGAGGGAGCACACTGCCAGGATGGGAGCTGCTG
GGAGGCAGGACTTCCTCTTCAAGGCCATGCTGACCATCAGCTGGCTCACTCTGACCTGC
TTCCCTGGGGCCACATCCACAGTGGCTGCTGGGTGCCCTGACCAGAGCCCTGAGTTGCA
ACCCTGGAACCCTGGCCATGACCAAGACCACCATGTGCATATCGGCCAGGGCAAGACAC
TGCTGCTCACCTCTTCTGCCACGGTCTATTCCATCCACATCTCAGAGGGAGGCAAGCTG
GTCATTAAAGACCACGACGAGCCGATTGTTTTGCGAACCCGGCACATCCTGATTGACAA
CGGAGGAGAGCTGCATGCTGGGAGTGCCCTCTGCCCTTTCCAGGGCAATTTCACCATCA
TTTTGTATGGAAGGGCTGATGAAGGTATTCAGCCGGATCCTTACTATGGTCTGAAGTAC
ATTGGGGTTGGTAAAGGAGGCGCTCTTGAGTTGCATGGACAGAAAAAGCTCTCCTGGAC
ATTTCTGAACAAGACCCTTCACCCAGGTGGCATGGCAGAAGGAGGCTATTTTTTTGAAA
GGAGCTGGGGCCACCGTGGAGTTATTGTTCATGTCATCGACCCCAAATCAGGCACAGTC
ATCCATTCTGACCGGTTTGACACCTATAGATCCAAGAAAGAGAGTGAACGTCTGGTCCA
GTATTTGAACGCGGTGCCCGATGGCAGGATCCTTTCTGTTGCAGTGAATGATGAAGGTT
CTCGAAATCTGGATGACATGGCCAGGAAGGCGATGACCAAATTGGGAAGCAAACACTTC
CTGCACCTTGGATTTAGACACCCTTGGAGTTTTCTAACTGTGAAAGGAAATCCATCATC
TTCAGTGGAAGACCATATTGAATATCATGGACATCGAGGCTCTGCTGCTGCCCGGGTAT
TCAAATTGTTCCAGACAGAGCATGGCGAATATTTCAATGTTTCTTTGTCCAGTGAGTGG
GTTCAAGACGTGGAGTGGACGGAGTGGTTCGATCATGATAAAGTATCTCAGACTAAAGG
TGGGGAGAAAATTTCAGACCTCTGGAAAGCTCACCCAGGAAAAATATGCAATCGTCCCA
TTGATATACAGGCCACTACAATGGATGGAGTTAACCTCAGCACCGAGGTTGTCTACAAA
AAAGGCCAGGATTATAGGTTTGCTTGCTACGACCGGGGCAGAGCCTGCCGGAGCTACCG
TGTACGGTTCCTCTGTGGGAAGCCTGTGAGGCCCAAACTCACAGTCACCATTGACACCA
ATGTGAACAGCACCATTCTGAACTTGGAGGATAATGTACAGTCATGGAAACCTGGAGAT
ACCCTGGTCATTGCCAGTACTGATTACTCCATGTACCAGGCAGAAGAGTTCCAGGTGCT
TCCCTGCAGATCCTGCGCCCCCAACCAGGTCAAAGTGGCAGGGAAACCAATGTACCTGC
ACATCGGGGAGGAGATAGACGGCGTGGACATGCGGGCGGAGGTTGGGCTTCTGAGCCGG
AACATCATAGTGATGGGGGAGATGGAGGACAAATGCTACCCCTACAGAAACCACATCTG
CAATTTCTTTGACTTCGATACCTTTGGGGGCCACATCAAGTTTGCTCTGGGATTTAAGG
CAGCACACTTGGAGGGCACGGAGCTGAAGCATATGGGACAGCAGCTGGTGGGTCAGTAC
CCGATTCACTTCCACCTGGCCGGTGATGTAGACGAAAGGGGAGGTTATGACCCACCCAC
ATACATCAGGGACCTCTCCATCCATCATACATTCTCTCGCTGCGTCACAGTCCATGGCT
CCAATGGCTTGTTGATCAAGGACGTTGTGGGCTATAACTCTTTGGGCCACTGCTTCTTC
ACGGAAGATGGGCCGGAGGAACGCAACACTTTTGACCACTGTCTTGGCCTCCTTGTCAA
GTCTGGAACCCTCCTCCCCTCGGACCGTGACAGCAAGATGTGCAAGATGATCACAGAGG
ACTCCTACCCAGGGTACATCCCCAAGCCCAGGCAAGACTGCAATGCTGTGTCCACCTTC
TGGATGGCCAATCCCAACAACAACCTCATCAACTGTGCCGCTGCAGGATCTGAGGAAAC
TGGATTTTGGTTTATTTTTCACCACGTACCAACGGGCCCCTCCGTGGGAATGTACTCCC
CAGGTTATTCAGAGCACATTCCACTGGGAAAATTCTATAACAACCGAGCACATTCCAAC
TACCGGGCTGGCATGATCATAGACAACGGAGTCAAAACCACCGAGGCCTCTGCCAAGGA
CAAGCGGCCGTTCCTCTCAATCATCTCTGCCAGATACAGCCCTCACCAGGACGCCGACC
CGCTGAAGCCCCGGGAGCCGGCCATCATCAGACACTTCATTGCCTACAAGAACCAGGAC
CACGGGGCCTGGCTGCGCGGCGGGGATGTGTGGCTGGACAGCTGCCGGTTTGCTGACAA
TGGCATTGGCCTGACCCTGGCCAGTGGTGGAACCTTCCCGTATGACGACGGCTCCAAGC
AAGAGATAAAGAACAGCTTGTTTGTTGGCGAGAGTGGCAACGTGGGACGGAAATGATG
GACAATAGGATCTGGGGCCCTGGCGGCTTGGACCATAGCGGAAGGACCCTCCCTATAGG
```

Figure 3B

CCAGAATTTTCCAATTAGAGGAATTCAGTTATATGATGGCCCCATCAACATCCAAAACT
GCACTTTCCGAAAGTTTGTGGCCCTGGAGGGCCGGCACACCAGCGCCCTGGCCTTCCGC
CTGAATAATGCCTGGCAGAGCTGCCCCCATAACAACGTGACCGGCATTGCCTTTGAGGA
CGTTCCGATTACTTCCAGAGTGTTCTTCGGAGAGCCTGGGCCCTGGTTCAACCAGCTGG
ACATGGATGGGGATAAGACATCTGTGTTCCATGACGTCGACGGCTCCGTGTCCGAGTAC
CCTGGCTCCTACCTCACGAAGAATGACAACTGGCTGGTCCGGCACCCAGACTGCATCAA
TGTTCCCGACTGGAGAGGGGCCATTTGCAGTGGGTGCTATGCACAGATGTACATTCAAG
CCTACAAGACCAGTAACCTGCGAATGAAGATCATCAAGAATGACTTCCCCAGCCACCCT
CTTTACCTGGAGGGGCGCTCACCAGGAGCACCCATTACCAGCAATACCAACCGGTTGT
CACCCTGCAGAAGGGCTACACCATCCACTGGGACCAGACGGCCCCCGCCGAACTCGCCA
TCTGGCTCATCAACTTCAACAAGGGCGACTGGATCCGAGTGGGGCTCTGCTACCCGCGA
GGCACCACATTCTCCATCCTCTCGGATGTTCACAATCGCCTGCTGAAGCAAACGTCCAA
GACGGGCGTCTTCGTGAGGACCTTGCAGATGGACAAAGTGGAGCAGAGCTACCCTGGCA
GGAGCCACTACTACTGGGACGAGGACTCAGGGCTGTTGTTCCTGAAGCTGAAAGCTCAG
AACGAGAGAGAGAAGTTTGCTTTCTGCTCCATGAAAGGCTGTGAGAGGATAAAGATTAA
AGCTCTGATTCCAAAGAACGCAGGCGTCAGTGACTGCACAGCCACAGCTTACCCCAAGT
TCACCGAGAGGGCTGTCGTAGACGTGCCGATGCCCAAGAAGCTCTTTGGTTCTCAGCTG
AAAACAAAGGACCATTTCTTGGAGGTGAAGATGGAGAGTTCCAAGCAGCACTTCTTCCA
CCTCTGGAACGACTTCGCTTACATTGAAGTGGATGGGAAGAAGTACCCCAGTTCGGAGG
ATGGCATCCAGGTGGTGGTGATTGACGGGAACCAAGGGCGCGTGGTGAGCCACACGAGC
TTCAGGAACTCCATTCTGCAAGGCATACCATGGCAGCTTTTCAACTATGTGGCGACCAT
CCCTGACAATTCCATAGTGCTTATGGCATCAAAGGGAAGATACGTCTCCAGAGGCCCAT
GGACCAGAGTGCTGGAAAAGCTTGGGGCAGACAGGGGTCTCAAGTTGAAAGAGCAAATG
GCATTCGTTGGCTTCAAAGGCAGCTTCCGGCCCATCTGGGTGACACTGGACACTGAGGA
TCACAAAGCCAAAATCTTCCAAGTTGTGCCCATCCCTGTGGTGAAGAAGAAGAAGTTG<u>T</u>
<u>GA</u>GGACAGCTGCCGCCCGGTGCCACCTCGTGGTAGACTATG

Figure 4A: Nucleic acid sequence of Coloup2 (SEQ ID NO: 5)

```
GCCCCCTGGCCCGAGCCGCGCCCGGGTCTGTGAGTAGAGCCGCCCGGGCACCGAGCGCT
GGTCGCCGCTCTCCTTCCGTTATATCAACATGCCCCCTTTCCTGTTGCTGGAAGCCGTC
TGTGTTTTCCTGTTTTCCAGAGTGCCCCCATCTCTCCCTCTCCAGGAAGTCCATGTAAG
CAAAGAAACCATCGGGAAGATTTCAGCTGCCAGCAAAATGATGTGGTGCTCGGCTGCAG
TGGACATCATGTTTCTGTTAGATGGGTCTAACAGCGTCGGGAAAGGGAGCTTTGAAAGG
TCCAAGCACTTTGCCATCACAGTCTGTGACGGTCTGGACATCAGCCCCGAGAGGGTCAG
AGTGGGAGCATTCCAGTTCAGTTCCACTCCTCATCTGGAATTCCCCTTGGATTCATTTT
CAACCCAACAGGAAGTGAAGGCAAGAATCAAGAGGATGGTTTTCAAAGGAGGGCGCACG
GAGACGGAACTTGCTCTGAAATACCTTCTGCACAGAGGGTTGCCTGGAGGCAGAAATGC
TTCTGTGCCCCAGATCCTCATCATCGTCACTGATGGGAAGTCCCAGGGGGATGTGGCAC
TGCCATCCAAGCAGCTGAAGGAAAGGGGTGTCACTGTGTTTGCTGTGGGGTCAGGTTT
CCCAGGTGGGAGGAGCTGCATGCACTGGCCAGCGAGCCTAGAGGGCAGCACGTGCTGTT
GGCTGAGCAGGTGGAGGATGCCACCAACGGCCTCTTCAGCACCCTCAGCAGCTCGGCCA
TCTGCTCCAGCGCCACGCCAGACTGCAGGGTCGAGGCTCACCCCTGTGAGCACAGGACG
CTGGAGATGGTCCGGGAGTTCGCTGGCAATGCCCCATGCTGGAGAGGATCGCGGCGGAC
CCTTGCGGTGCTGGCTGCACACTGTCCCTTCTACAGCTGGAAGAGAGTGTTCCTAACCC
ACCCTGCCACCTGCTACAGGACCACCTGCCCAGGCCCTGTGACTCGCAGCCCTGCCAG
AATGGAGGCACATGTGTTCCAGAAGGACTGGACGGCTACCAGTGCCTCTGCCCGCTGGC
CTTTGGAGGGGAGGCTAACTGTGCCCTGAAGCTGAGCCTGGAATGCAGGGTCGACCTCC
TCTTCCTGCTGGACAGCTCTGCGGGCACCACTCTGGACGGCTTCCTGCGGCCAAAGTC
TTCGTGAAGCGGTTTGTGCGGGCCGTGCTGAGCGAGGACTCTCGGGCCCGAGTGGGTGT
GGCCACATACAGCAGGGAGCTGCTGGTGGCGGTGCCTGTGGGGAGTACCAGGATGTGC
CTGACCTGGTCTGGAGCCTCGATGGCATTCCCTTCCGTGGTGGCCCCACCCTGACGGGC
AGTGCCTTGCGGCAGGCGGCAGAGCGTGGCTTCGGGAGCGCCACCAGGACAGGCCAGGA
CCGGCCACGTAGAGTGGTGGTTTTGCTCACTGAGTCACACTCCGAGGATGAGGTTGCGG
GCCCAGCGCGTCACGCAAGGGCGCGAGAGCTGCTCCTGCTGGGTGTAGGCAGTGAGGCC
GTGCGGGCAGAGCTGGAGGAGATCACAGGCAGCCCAAAGCATGTGATGGTCTACTCGGA
TCCTCAGGATCTGTTCAACCAAATCCCTGAGCTGCAGGGGAAGCTGTGCAGCCGGCAGC
GGCCAGGGTGCCGGACACAAGCCCTGGACCTCGTCTTCATGTTGGACACCTCTGCCTCA
GTAGGGCCCGAGAATTTTGCTCAGATGCAGAGCTTTGTGAGAAGCTGTGCCCTCCAGTT
TGAGGTGAACCCTGACGTGACACAGGTCGGCCTGGTGGTGTATGGCAGCCAGGTGCAGA
CTGCCTTCGGGCTGGACACCAAACCCACCCGGGCTGCGATGCTGCGGGCCATTAGCCAG
GCCCCCTACCTAGGTGGGGTGGGCTCAGCCGGCACCGCCCTGCTGCACATCTATGACAA
AGTGATGACCGTCCAGAGGGGTGCCCGGCCTGGTGTCCCCAAAGCTGTGGTGGTGCTCA
CAGGCGGGAGAGGCGCAGAGGATGCAGCCGTTCCTGCCCAGAAGCTGAGGAACAATGGC
ATCTCTGTCTTGGTCGTGGGCGTGGGGCCTGTCCTAAGTGAGGGTCTGCGGAGGCTTGC
AGGTCCCCGGGATTCCCTGATCCACGTGGCAGCTTACGCCGACCTGCGGTACCACCAGG
ACGTGCTCATTGAGTGGCTGTGTGGAGAAGCCAAGCAGCCAGTCAACCTCTGCAAACCC
AGCCCGTGCATGAATGAGGGCAGCTGCGTCCTGCAGAATGGGAGCTACCGCTGCAAGTG
TCGGGATGGCTGGGAGGGCCCCACTGCGAGAACCGATTCTTGAGACGCCCCTGAGGCA
CATGGCTCCCGTGCAGGAGGGCAGCAGCCGTACCCCTCCCAGCAACTACAGAGAAGGCC
TGGGCACTGAAATGGTGCCTACCTTCTGGAATGTCTGTGCCCCAGGTCCTTAGAATGTC
TGCTTCCCGCCGTGGCCAGGACCACTATTCTCACTGAGGGAGGAGGATGTCCCAACTGC
AGCCATGCTGCTTAGAGACAAGAAAGCAGCTGATGTCACCCACAAACGATGTTGTTGAA
AAGTTTTGATGTGTAAGTAAATACCCACTTTCTGTACCTGCTGTGCCTTGTTGAGGCTA
```

Figure 4B

TGTCATCTGCCACCTTTCCCTTGAGGATAAACAAGGGGTCCTGAAGACTTAAATTTAGC
GGCCTGACGTTCCTTTGCACACAATCAATGCTCGCCAGAATGTTGTTGACACAGTAATG
CCCAGCAGAGGCCTTTACTAGAGCATCCTTTGGACGG

Figure 5. Nucleic acid sequence of Osteopontin (SEQ ID NO: 6)

GCAGAGCACAGCATCGTCGGGACCAGACTCGTCTCAGGCCAGTTGCAGCCTTCTCAGCC
AAACGCCGACCAAGGAAAACTCACTACCATGAGAATTGCAGTGATTTGCTTTTGCCTCC
TAGGCATCACCTGTGCCATACCAGTTAAACAGGCTGATTCTGGAAGTTCTGAGGAAAAG
CAGCTTTACAACAAATACCCAGATGCTGTGGCCACATGGCTAAACCCTGACCCATCTCA
GAAGCAGAATCTCCTAGCCCCACAGACCCTTCCAAGTAAGTCCAACGAAAGCCATGACC
ACATGGATGATATGGATGATGAAGATGATGATGACCATGTGGACAGCCAGGACTCCATT
GACTCGAACGACTCTGATGATGTAGATGACACTGATGATTCTCACCAGTCTGATGAGTC
TCACCATTCTGATGAATCTGATGAACTGGTCACTGATTTTCCCACGGACCTGCCAGCAA
CCGAAGTTTTCACTCCAGTTGTCCCCACAGTAGACACATATGATGGCCGAGGTGATAGT
GTGGTTTATGGACTGAGGTCAAAATCTAAGAAGTTTCGCAGACCTGACATCCAGTACCC
TGATGCTACAGACGAGGACATCACCTCACACATGGAAAGCGAGGAGTTGAATGGTGCAT
ACAAGGCCATCCCCGTTGCCCAGGACCTGAACGCGCCTTCTGATTGGGACAGCCGTGGG
AAGGACAGTTATGAAACGAGTCAGCTGGATGACCAGAGTGCTGAAACCCACAGCCACAA
GCAGTCCAGATTATATAAGCGGAAAGCCAATGATGAGAGCAATGAGCATTCCGATGTGA
TTGATAGTCAGGAACTTTCCAAAGTCAGCCGTGAATTCCACAGCCATGAATTTCACAGC
CATGAAGATATGCTGGTTGTAGACCCCAAAAGTAAGGAAGAAGATAAACACCTGAAATT
TCGTATTTCTCATGAATTAGATAGTGCATCTTCTGAGGTCAATTAAAAGGAGAAAAAAT
ACAATTTCTCACTTTGCATTTAGTCAAAAGAAAAAATGCTTTATAGCAAAATGAAAGAG
AACATGAAATGCTTCTTTCTCAGTTTATTGGTTGAATGTGTATCTATTTGAGTCTGGAA
ATAACTAATGTGTTTGATAATTAGTTTAGTTTGTGGCTTCATGGAAACTCCCTGTAAAC
TAAAAGCTTCAGGGTTATGTCTATGTTCATTCTATAGAAGAAATGCAAACTATCACTGT
ATTTTAATATTTGTTATTCTCTCATGAATAGAAATTTATGTAGAAGCAAACAAAATACT
TTTACCCACTTAAAAAGAGAATATAACATTTTATGTCACTATAATCTTTTGTTTTTTAA
GTTAGTGTATATTTTGTTGTGATTATCTTTTTGTGGTGTGAATAAATCTTTTATCTTGA
ATGTAATAAGAATTTGGTGGTGTCAATTGCTTATTTGTTTTCCCACGGTTGTCCAGCAA
TTAATAAAACATAACCTTTTTACTGCCTAAAAAAAAAAAAAAAAAAAA

Figure 6A: Nucleic acid sequence of Coloup3 (SEQ ID NO: 7)

```
AAAGGGGCAAGAGCTGAGCGGAACACCGGCCCGCCGTCGCGGCAGCTGCTTCACCCCTC
TCTCTGCAGCCATGGGGCTCCCTCGTGGACCTCTCGCGTCTCTCCTCCTTCTCCAGGTT
TGCTGGCTGCAGTGCGCGGCCTCCGAGCCGTGCCGGGCGGTCTTCAGGGAGGCTGAAGT
GACCTTGGAGGCGGGAGGCGCGGAGCAGGAGCCCGGCCAGGCGCTGGGGAAAGTATTCA
TGGGCTGCCCTGGGCAAGAGCCAGCTCTGTTTAGCACTGATAATGATGACTTCACTGTG
CGGAATGGCGAGACAGTCCAGGAAAGAAGGTCACTGAAGGAAAGGAATCCATTGAAGAT
CTTCCCATCCAAACGTATCTTACGAAGACACAAGAGAGATTGGGTGGTTGCTCCAATAT
CTGTCCCTGAAAATGGCAAGGGTCCCTTCCCCAGAGACTGAATCAGCTCAAGTCTAAT
AAAGATAGAGACACCAAGATTTTCTACAGCATCACGGGGCCGGGGGCAGACAGCCCCCC
TGAGGGTGTCTTCGCTGTAGAGAAGGAGACAGGCTGGTTGTTGTTGAATAAGCCACTGG
ACCGGGAGGAGATTGCCAAGTATGAGCTCTTTGGCCACGCTGTGTCAGAGAATGGTGCC
TCAGTGGAGGACCCCATGAACATCTCCATCATCGTGACCGACCAGAATGACCACAAGCC
CAAGTTTACCCAGGACACCTTCCGAGGGAGTGTCTTAGAGGGAGTCCTACCAGGTACTT
CTGTGATGCAGGTGACAGCCACGGATGAGGATGATGCCATCTACACCTACAATGGGGTG
GTTGCTTACTCCATCCATAGCCAAGAACCAAAGGACCCACACGACCTCATGTTCACCAT
TCACCGGAGCACAGGCACCATCAGCGTCATCTCCAGTGGCCTGGACCGGGAAAAAGTCC
CTGAGTACACACTGACCATCCAGGCCACAGACATGGATGGGACGGCTCCACCACCACG
GCAGTGGCAGTAGTGGAGATCCTTGATGCCAATGACAATGCTCCCATGTTTGACCCCCA
GAAGTACGAGGCCCATGTGCCTGAGAATGCAGTGGGCCATGAGGTGCAGAGGCTGACGG
TCACTGATCTGGACGCCCCCAACTCACCAGCGTGGCGTGCCACCTACCTTATCATGGGC
GGTGACGACGGGGACCATTTTACCATCACCACCCACCCTGAGAGCAACCAGGGCATCCT
GACAACCAGGAAGGGTTTGGATTTTGAGGCCAAAAACCAGCACACCCTGTACGTTGAAG
TGACCAACGAGGCCCCTTTTGTGCTGAAGCTCCCAACCTCCACAGCCACCATAGTGGTC
CACGTGGAGGATGTGAATGAGGCACCTGTGTTTGTCCCACCCTCCAAAGTCGTTGAGGT
CCAGGAGGGCATCCCCACTGGGGAGCCTGTGTGTGTCTACACTGCAGAAGACCCTGACA
AGGAGAATCAAAAGATCAGCTACCGCATCCTGAGAGACCCAGCAGGGTGGCTAGCCATG
GACCCAGACAGTGGGCAGGTCACAGCTGTGGGCACCCTCGACCGTGAGGATGAGCAGTT
TGTGAGGAACAACATCTATGAAGTCATGGTCTTGGCCATGGACAATGGAAGCCCTCCCA
CCACTGGCACGGGAACCCTTCTGCTAACACTGATTGATGTCAATGACCATGGCCCAGTC
CCTGAGCCCCGTCAGATCACCATCTGCAACCAAAGCCCTGTGCGCCAGGTGCTGAACAT
CACGGACAAGGACCTGTCTCCCCACACCTCCCCTTTCCAGGCCCAGCTCACAGATGACT
CAGACATCTACTGGACGGCAGAGGTCAACGAGGAAGGTGACACAGTGGTCTTGTCCCTG
AAGAAGTTCCTGAAGCAGGATACATATGACGTGCACCTTTCTCTGTCTGACCATGGCAA
CAAAGAGCAGCTGACGGTGATCAGGGCCACTGTGTGCGACTGCCATGGCCATGTCGAAA
CCTGCCCTGGACCCTGGAAGGGAGGTTTCATCCTCCCTGTGCTGGGGGCTGTCCTGGCT
CTGCTGTTCCTCCTGCTGGTGCTGCTTTTGTTGGTGAGAAAGAAGCGGAAGATCAAGGA
GCCCCTCCTACTCCCAGAAGATGACACCCGTGACAACGTCTTCTACTATGGCGAAGAGG
GGGGTGGCGAAGAGGACCAGGACTATGACATCACCCAGCTCCACCGAGGTCTGGAGGCC
AGGCCGGAGGTGGTTCTCCGCAATGACGTGGCACCAACCATCATCCCGACACCCATGTA
CCGTCCTCGGCCAGCCAACCCAGATGAAATCGGCAACTTTATAATTGAGAACCTGAAGG
CGGCTAACACAGACCCCACAGCCCCGCCCTACGACACCCTCTTGGTGTTCGACTATGAG
GGCAGCGGCTCCGACGCCGCGTCCCTGAGCTCCCTCACCTCCTCCGCCTCCGACCAAGA
CCAAGATTACGATTATCTGAACGAGTGGGGCAGCCGCTTCAAGAAGCTGGCAGACATGT
ACGGTGGCGGGAGGACGACTAGGCGGCCTGCCTGCAGGGCTGGGGACCAAACGTCAGG
CCACAGAGCATCTCCAAGGGGTCTCAGTTCCCCCTTCAGCTGAGGACTTCGGAGCTTGT
```

Figure 6B

```
CAGGAAGTGGCCGTAGCAACTTGGCGGAGACAGGCTATGAGTCTGACGTTAGAGTGGTT
GCTTCCTTAGCCTTTCAGGATGGAGGAATGTGGGCAGTTTGACTTCAGCACTGAAAACC
TCTCCACCTGGGCCAGGGTTGCCTCAGAGGCCAAGTTTCCAGAAGCCTCTTACCTGCCG
TAAAATGCTCAACCCTGTGTCCTGGGCCTGGGCCTGCTGTGACTGACCTACAGTGGACT
TTCTCTCTGGAATGGAACCTTCTTAGGCCTCCTGGTGCAACTTAATTTTTTTTTTAAT
GCTATCTTCAAAACGTTAGAGAAAGTTCTTCAAAAGTGCAGCCCAGAGCTGCTGGGCCC
ACTGGCCGTCCTGCATTTCTGGTTTCCAGACCCCAATGCCTCCCATTCGGATGGATCTC
TGCGTTTTTATACTGAGTGTGCCTAGGTTGCCCCTTATTTTTATTTTCCCTGTTGCGT
TGCTATAGATGAAGGGTGAGGACAATCGTGTATATGTACTAGAACTTTTTATTAAAGA
AACTTTTCCCAGAAAAAAA
```

Figure 7. Nucleic acid sequence of ColoUp4 (SEQ ID NO: 8)

ATGAAGCACCTGAAGCGGTGGTGGTCGGCCGGCGGCGGCCTCCTGCACCTCACCCTCCT
GCTGAGCTTGGCGGGGCTCCGCGTAGACCTAGATCTTTACCTGCTGCTGCCGCCGCCCA
CCCTGCTGCAGGACGAGCTGCTGTTCCTGGGCGGCCCGGCCAGCTCCGCCTACGCGCTC
AGCCCCTTCTCGGCCTCGGGAGGGTGGGGCGCGCGGGCCACTTGCACCCCAAGGGCCG
GGAGCTGGACCCTGCCGCGCCGCCCGAGGGCCAGCTGCTCCGGGAGGTGCGCGCGCTCG
GGGTCCCCTTCGTCCCTCGCACCAGCGTGGATGCATGGCTGGTGCACAGCGTGGCTGCC
GGGAGCGCGGACGAGGCCCACGGGCTGCTCGGCGCCGCCGCCGCCTCGTCCACCGGAGG
AGCCGGCGCCAGCGTGGACGGCGGCAGCCAGGCTGTGCAGGGGGGCGGCGGGGACCCCC
GAGCGGCTCGGAGTGGCCCCTTGGACGCCGGGGAAGAGGAGAAGGCACCCGCGGAACCG
ACGGCTCAGGTGCCGGACGCTGGCGGATGTGCGAGCGAGGAGAATGGGGTACTAAGAGA
AAAGCACGAAGCTGTGGATCATAGTTCCCAGCATGAGGAAAATGAAGAAAGGGTGTCAG
CCCAGAAGGAGAACTCACTTCAGCAGAATGATGATGATGAAAACAAAATAGCAGAGAAA
CCTGACTGGGAGGCAGAAAAGACCACTGAATCTAGAAATGAGAGACATCTGAATGGGAC
AGATACTTCTTTCTCTGGAAGACTTATTCCAGTTGCTTTCATCACAGCCTGAAAATT
CACTGGAGGGCATCTCATTGGGAGATATTCCTCTTCCAGGCAGTATCAGTGATGGCATG
AATTCTTCAGCACATTATCATGTAAACTTCAGCCAGGCTATAAGTCAGGATGTGAATCT
TCATGAGGCCATCTTGCTTTGTCCCAACAATACATTTAGAAGAGATCCAACAGCAAGGA
CTTCACAGTCACAAGAACCATTTCTGCAGTTAAATTCTATACCACCAATCCTGAGCAA
ACCCTTCCTGGAACTAATTTGACAGGATTTCTTTCACCGGTTGACAATCATATGAGGAA
TCTAACAAGCCAAGACCTACTGTATGACCTTGACATAAATATATTTGATGAGATAAACT
TAATGTCATTGGCCACAGAAGACAACTTTGATCCAATCGATGTTTCTCAGCTTTTTGAT
GAACCAGATTCTGATTCTGGCCTTTCTTTAGATTCAAGTCACAATAATACCTCTGTCAT
CAAGTCTAATTCCTCTCACTCTGTGTGTGATGAAGGTGCTATAGGTTATTGCACTGACC
ATGAATCTAGTTCCCATCATGACTTAGAAGGTGCTGTAGGTGGCTACTACCCAGAACCC
AGTAAGCTTTGTCACTTGGATCAAAGTGATTCTGATTTCCATGGAGATCTTACATTTCA
ACACGTATTTCATAACCACACTTACCACTTACAGCCAACTGCACCAGAATCTACTTCTG
AACCTTTTCCGTGGCCTGGGAAGTCACAGAAGATAAGGAGTAGATACCTTGAAGACACA
GATAGAAACTTGAGCCGTGATGAACAGCGTGCTAAAGCTTTGCATATCCCTTTTTCTGT
AGATGAAATTGTCGGCATGCCTGTTGATTCTTTCAATAGCATGTTAAGTAGATATTATC
TGACAGACCTACAAGTCTCACTTATCCGTGACATCAGACGAAGAGGGAAAAATAAAGTT
GCTGCGCAGAACTGTCGTAAACGCAAATTGGACATAATTTTGAATTTAGAAGATGATGT
ATGTAACTTGCAAGCAAAGAAGGAAACTCTTAAGAGAGAGCAAGCACAATGTAACAAAG
CTATTAACATAATGAAACAGAAACTGCATGACCTTTATCATGATATTTTTAGTAGATTA
AGAGATGACCAAGGTAGGCCAGTCAATCCCAACCACTATGCTCTCCAGTGTACCCATGA
TGGAAGTATCTTGATAGTACCCAAAGAACTGGTGGCCTCAGGCCACAAAAAGGAAACCC
AAAAGGGAAAGAGAAAGTGAGAAGAAACTGAAGATGGACTCTATTATGTGAAGTAGTAA
TGTTCAGAAACTGATTATTTGGATCAGAAACCATTGAAACTGCTTCAAGAATTGTATCT
TTAAGTACTGCTACTTGAATAACTCAGTTAACGCTGTTTTGAAGCTTACATGGACAAAT
GTTTAGGACTTCAAGATCACACTTGTGGGCAATCTGGGGAGCCACAACTTTTCATGAA
GTGCATTGTATACAAAATTCATAGTTATGTCCAAAGAATAGGTTAACATGAAAACCCAG
TAAGACTTTCCATCTTGGCAGCCATCCTTTTAAGAGTAAGTTGGTTACTTCAAAAAGA
GCAAACACTGGGGATCAAATTATTTAAGAGGTATTTCAGTTTTAAATGCAAAATAGCC
TTATTTTCATTTAGTTTGTTAGCACTATAGTGAGCTTTTCAAACACTATTTTAATCTTT
ATATTTAACTTATAAATTTTGCTTTCTATGGAAATAAATTTTGTATTTGTATTAAAAAA
AAAAAAA

Figure 8. Nucleic acid sequence of ColoUp5 (SEQ ID NO: 9)

ATGAAGTTGGAGGTGTTCGTCCCTCGCGCGGCCCACGGGGACAAGCAGGGCAGTGACCT
GGAGGGCGCGGGCGGCAGCGACGCGCCGTCCCCGCTGTCGGCGGCGGGAGACGACTCCC
TGGGCTCAGATGGGGACTGCGCGGCCAAGCCGTCCGCGGGCGGCGGCGCCAGAGATACG
CAGGGCGACGGCGAACAGAGTGCGGGAGGCGGGCCGGGCGCGGAGGAGGCGATCCCGGC
AGCAGCTGCTGCAGCGGTGGTGGCGGAGGGCGCGGAGGCCGGGCGGCGGGGCCAGGCG
CGGGCGGCGCGGGGAGCGGCGAGGGTGCACGCAGCAAGCCATATACGCGGCGGCCCAAG
CCCCCCTACTCGTACATCGCGCTCATCGCCATGGCCATCCGCGACTCGGCGGGCGGGCG
CTTGACGCTGGCGGAGATCAACGAGTACCTCATGGGCAAGTTCCCCTTTTTCCGCGGCA
GCTACACGGGCTGGCGCAACTCCGTGCGCCACAACCTTTCGCTCAACGACTGCTTCGTC
AAGGTGCTGCGCGACCCCTCGCGGCCCTGGGGCAAGGACAACTACTGGATGCTCAACCC
CAACAGCGAGTACACCTTCGCCGACGGGGTCTTCCGCCGCCGCCGCAAGCGCCTCAGCC
ACCGCGCGCCGGTCCCCGCGCCCGGGCTGCGGCCCGAGGAGGCCCCGGGCCTCCCCGCC
GCCCCGCCGCCCGCGCCCGCCGCCCCGGCCTCGCCCCGCATGCGCTCGCCCGCCCGCCA
GGAGGAGCGCGCCAGCCCCGCGGGCAAGTTCTCCAGCTCCTTCGCCATCGACAGCATCC
TGCGCAAGCCCTTCCGCAGCCGTCGCCTCAGGGACACGGCCCCCGGGACGACGCTTCAG
TGGGGCGCCGCGCCCTGCCCGCCGCTGCCCGCGTTCCCCGCGCTCCTCCCCGCGGCGCC
CTGCAGGGCCCTGCTGCCGCTCTGCGCGTACGGCGCGGGCGAGCCGGCGCGGCTGGGCG
CGCGCGAGGCCGAGGTGCCACCGACCGCGCCGCCCCTCCTGCTTGCACCTCTCCCGGCG
GCGGCCCCCGCCAAGCCACTCCGAGGCCCGGCGGCCGGCGGCGCGCACCTGTACTGCCC
CCTGCGGCTGCCCGCAGCCCTGCAGGCGGCCTTAGTCCGNCGTCCTGGCCCGCACCTGT
CGTACCCGGTGGAGACGCTCCTAGCTTGA

Figure 9. Nucleic acid sequence of ColoUp6 (SEQ ID NO: 10)

GGCAGATGAAATATAAGATTCATCAACCACATTTGACAGCCCATGGCAGGTTTCCTGTT
TTCCATCGTCCCTCTGCAGGTCACAGACACACAGAGCCCAGCCGTGGCAGGCTCAGCCG
GGGTCCGGGGCTGCTAACAACGGCTACATTCCTCCCCCAGGGCCAAGGGAAATCCTGAG
CGCAGGCCAGGGTTGTTTGGTTTTGAGGTGTGCTGGGATGAAAGGCACCCTGGAAGTGG
AAGGTTCGGTCATTCATTAATTAATTACATCTATAATTGAGGGTTTGTTCTTAAGAGCG
AGTCCTTTGAAAGTACTTTCCTTCAAACAGTGACTGCCACAAAGGCATCAGATATTCAC
CACCTTCTCGGCTGCCTCAGCACAGCAAGCTTTATTCTGGGACCTGAGATCCTGTTCTG
AGCTGGCTTTCCCTTCTCCAGGCTCGCTCACCCTCCCTTTAGAGATAGTGGATGGTAAG
ATGACCAATGCTCAGATTATTCTTCTCATTGACAATGCCAGGATGGCAGTGGATGACTT
CAACCTCAAGAAATGGAGAAGCATCATGTGCCAAGTGACTTCAATGTCAATGTGAAGGT
GGATACAGGTCCCAGGGAAGATCTGATTAAGGTCCTGGAGGATATGAGACAAGAATATG
AGCTTATAATAAAGAAGAAGCATCGAGACTTGGACACTTGGTATAAAGAACAGTCTGCA
GCCATGTCCCAGGAGGCAGCCAGTCCAGCCACTGTGCAGAGCAGACAAGGTGACATCCA
CGAACTGAAGCGCACATTCCAGGCCCTGGAGATTGACCTGCAGGCACAGTACAGCACGA
AATCTGCTTTGGAAAACATGTTATCCGAGACCCAGTCTCGGTACTCCTGCAAGCTCCAG
GACATGCAAGAGATCATCTCCCACTATGAGGAGGAACTGACGCAGCTACGCCACGAACT
GGAGCGGCAGAACAATGAATACCAAGTGCTGCTGGGCATCAAAACCCACCTGGAGAAGG
AAATCACCACGTACCGACGGCTCCTGGAGGGAGAGAGTGAAGGGACACGGGAAGAATCA
AGTCGAGCATGAAAGTGTCTGCAACTCCAAAGATCAAGGCCATAACCCAGGAGACCAT
CAACGGAAGATTAGTTCTTTGTCAAGTGAATGAAATCCAAAAGCACGCATGAGACCAAT
GAAAGTTTCCGCCTGTTGTAAAATCTATTTTCCCCCAAGGAAAGTCCTTGCACAGACAC
CAGTGAGTGAGTTCTAAAAGATACCCTTGGAATTATCAGACTCAGAAACTTTTATTTTT
TTTTTCTGTAACAGTCTCACCAGACTTCTCATAATGCTCTTAATATATTGCACTTTTCT
AATCAAAGTGCGAGTTTATGAGGGTAAAGCTCTACTTTCCTACTGCAGCCTTCAGATTC
TCATCATTTTGCATCTATTTTGTAGCCAATAAAACTCCGCACTAGCAAAAAAAAAAAA

Figure 10. Nucleic acid sequence of ColoUp7 (SEQ ID NO: 11)

```
TTTTTTTTTTAAAAAAAGAGGCTTGGTAAGTTTTTGATGCTTAGTTGACTTTTAGCATT
ATCCAGCATTTGTATTATGAACCAGTGAGTACTGTAATTTTTCTTTCCCTTTCAGAAAG
ACTCAAAGGGAACATATAAATGTTTCCTATTTTAATGTGGCAATAGTGTAGCTAACAC
TGGTACAGACGGAATAAACACACCTCTAATATTCTCCTGAAGATTTGGTGATCCAGTTT
CAAATAAGGTATGGGAAAAACAGATGTTTTCATTATCGCCACTTAATCCTTACTTCCGA
TTATAATTATACATGTTTGGCTGTAATAACTATACTAAAGCATGCTTGTGAAAGTAGAC
TTCTACAAGGACAGAAAACCCACAACAACAAAGATCGATCACGAAAGACAAGGCATA
```

Figure 11. Nucleic acid sequence of ColoUp8 (SEQ ID NO: 12)

CTTTTCTTCCGCACGGTTGGAGGAGGTCGGCTGGTTATCGGGAGTTGGAGGGCTGAGGT
CGGGAGGGTGGTGTGTACAGAGCTCTAGGACTCACGCACCAGGCCAGTCGCGGATTTTG
GGCCGAGGCCTGGGTTACAAGCAGCAAGTGCGCGGTTGGGGCCACTGCGAGGCCGTTTT
AGAAAACTGTTTAAAACAAAGAGCAATG<u>ATG</u>GATAAATCAGGAATAGATTCTCTTGAC
CATGTGACATCTGATGCTGTGGAACTTGCAAATCGAAGTGATAACTCTTCTGATAGCAG
CTTATTTAAAACTCAGTGTATCCCTTACTCACCTAAAGGGGAGAAAAGAAACCCCATTC
GAAAATTTGTTCGTACACCTGAAAGTGTTCACGCAAGTGATTCATCAAGTGACTCATCT
TTTGAACCAATACCATTGACTATAAAAGCTATTTTTGAAAGATTCAAGAACAGGAAAAA
GAGATATAAAAAAAGAAAAGAGGAGGTACCAGCCAACAGGAAGACCACGGGGAAGAC
CAGAAGGAAGGAGAAATCCTATATACTCACTAATAGATAAGAAGAAACAATTTAGAAGC
AGAGGATCTGGCTTCCCATTTTTAGAATCAGAGAATGAAAAAAACGCACCTTGGAGAAA
AATTTTAACGTTTGAGCAAGCTGTTGCAAGAGGATTTTTTAACTATATTGAAAGCTGA
AGTATGAACACCACCTGAAAGAATCATTGAAGCAAATGAATGTTGGTGAAGATTTAGAA
AATGAAGATTTTGACAGTCGTAGATACAAATTTTTGGATGATGATGGATCCATTTCTCC
TATTGAGGAGTCAACAGCAGAGGATGAGGATGCAACACATCTTGAAGATAACGAATGTG
ATATCAAATTGGCAGGGGATAGTTTCATAGTAAGTTCTGAATTCCCTGTAAGACTGAGT
GTATACTTAGAAGAAGAGGATATTACTGAAGAAGCTGCTTTGTCTAAAAAGAGAGCTAC
AAAAGCCAAAAATACTGGACAGAGAGGCCTGAAAATG<u>TGA</u>CAGGATCATGAATGTCAAA
GGCTTTTATCTTGAGAACATGGTGTCTGGAGTTAAAGGTATTGGCATACTCCACACATC
TGTACCATTCTTGAGTGATCGCTTAGGAATGAATGTGATTTGAACTCATTCATGTTGAG
AGGGTGTCAAATTGAGAACCAGGTAGATCCCCACCACCTACAGTAAAAAGGACCCTAAA
GTAAATTGGTTGAAGAAATTAGATCCCAAAGATTCTTGGTGAATTTTGAAGTCTTCATC
AGTATATCCATATTAAAACGAGATGACAGAAGCCAAAGTAATTATGGCAAGTAATGGTT
TTTATCTTAACTATAAGTTATTTGCTCAAGGGTGTAATGGTCATTACCAAGGCTTTTAG
AATGCAGTTTCTCATTTGCTGTGGACATGACCATAAAAAAAAATTTCCCAGTAGGTTTT
CTATCTGCTACGTTGCTAGCAATCAGCTTATTGGGAACAGTTGATTAACTGTAATAGAA
ATGCAATACAAATAAAATGTGAACCACATGTGATTTTTCTTTAAAATCAGTGAGATTTG
AAAATTCTCCTAGATCTCTTGAATCATGCAAATTTGCTTTGCCTTTATATTGTAACCCT
TGTGGGTTGCTAATAACCAAGCAGTTTGTAGTAGAGTTAACTCAGGCTCGTTCTAGGGA
CTCATTCATGTTCACTCACTGTACACTCATCTCTGGAAATGTAAAATTTACTTTTATAC
TATTGTTATGTAGGGCTGACAGGACAACTGGATCAGTTTCATTAAAAAGGTATGTATGC
ATTAGAAAAGACATTTGTATGGGTCATTTCAAAGAGGGCTTATGAGGCTGTGAAACCCA
GAGCTCTTAACGCTGTGACCAAAGATGGAAGTTCTCTATAGGAAGCCATAGCACTCCTA
ATGTTTGGTGCTATGTTTTCCTGAGGAGATATAAAACGTAATAATCCATGATTGTTGCC
ATGTGAGAGTTTTAAAGGTTAATCAAAATTTCTCTTCTTCAGGGCAAACTTGAAGATAA
ATCTTTTGACTCCAGCTCTTTAGAGGATCTAAAGTGACCTTGATGGACAGTGGAAGAAA
TCACAACATGGAATTCCTCGAATAACAATTTATTGACTTTAAATAATTTTGTCTAATGC
TACATATACACAATTAAAAAACCTTTACACTATTTCTAGAAAGTCAGCATGTATTTTTG
GCTCGAAGTTTCTCTAGTGTTTTCTGTGGAAGGAATAAAAATTTGAGTTTCAAAAAAAA
AAAAAAAAAAAAAAAAAAAAAAAAAAAAAAAA

Figure 12. Amino acid sequence of full-length ColoUp1 protein (SEQ ID NO: 13)

```
MGAAGRQDFLFKAMLTISWLTLTCFPGATSTVAAGCPDQSPELQPWNPGHDQDHHVHIG
QGKTLLLTSSATVYSIHISEGGKLVIKDHDEPIVLRTRHILIDNGGELHAGSALCPFQG
NFTIILYGRADEGIQPDPYYGLKYIGVGKGGALELHGQKKLSWTFLNKTLHPGGMAEGG
YFFERSWGHRGVIVHVIDPKSGTVIHSDRFDTYRSKKESERLVQYLNAVPDGRILSVAV
NDEGSRNLDDMARKAMTKLGSKHFLHLGFRHPWSFLTVKGNPSSSVEDHIEYHGHRGSA
AARVFKLFQTEHGEYFNVSLSSEWVQDVEWTEWFDHDKVSQTKGGEKISDLWKAHPGKI
CNRPIDIQATTMDGVNLSTEVVYKKGQDYRFACYDRGRACRSYRVRFLCGKPVRPKLTV
TIDTNVNSTILNLEDNVQSWKPGDTLVIASTDYSMYQAEEFQVLPCRSCAPNQVKVAGK
PMYLHIGEEIDGVDMRAEVGLLSRNIIVMGEMEDKCYPYRNHICNFFDFDTFGGHIKFA
LGFKAAHLEGTELKHMGQQLVGQYPIHFHLAGDVDERGGYDPPTYIRDLSIHHTFSRCV
TVHGSNGLLIKDVVGYNSLGHCFFTEDGPEERNTFDHCLGLLVKSGTLLPSDRDSKMCK
MITEDSYPGYIPKPRQDCNAVSTFWMANPNNNLINCAAAGSEETGFWFIFHHVPTGPSV
GMYSPGYSEHIPLGKFYNNRAHSNYRAGMIIDNGVKTTEASAKDKRPFLSIISARYSPH
QDADPLKPREPAIIRHFIAYKNQDHGAWLRGGDVWLDSCRFADNGIGLTLASGGTFPYD
DGSKQEIKNSLFVGESGNVGTEMMDNRIWGPGGLDHSGRTLPIGQNFPIRGIQLYDGPI
NIQNCTFRKFVALEGRHTSALAFRLNNAWQSCPHNNVTGIAFEDVPITSRVFFGEPGPW
FNQLDMDGDKTSVFHDVDGSVSEYPGSYLTKNDNWLVRHPDCINVPDWRGAICSGCYAQ
MYIQAYKTSNLRMKIIKNDFPSHPLYLEGALTRSTHYQQYQPVVTLQKGYTIHWDQTAP
AELAIWLINFNKGDWIRVGLCYPRGTTFSILSDVHNRLLKQTSKTGVFVRTLQMDKVEQ
SYPGRSHYYWDEDSGLLFLKLKAQNEREKFAFCSMKGCERIKIKALIPKNAGVSDCTAT
AYPKFTERAVVDVPMPKKLFGSQLKTKDHFLEVKMESSKQHFFHLWNDFAYIEVDGKKY
PSSEDGIQVVVIDGNQGRVVSHTSFRNSILQGIPWQLFNYVATIPDNSIVLMASKGRYV
SRGPWTRVLEKLGADRGLKLKEQMAFVGFKGSFRPIWVTLDTEDHKAKIFQVVPIPVVK
KKKL
```

Figure 13. Amino acid sequence of full-length ColoUp2 protein (SEQ ID NO: 14)

```
MPPFLLLEAVCVFLFSRVPPSLPLQEVHVSKETIGKISAASKMMWCSAAVDIMFLLDGS
NSVGKGSFERSKHFAITVCDGLDISPERVRVGAFQFSSTPHLEFPLDSFSTQQEVKARI
KRMVFKGGRTETELALKYLLHRGLPGGRNASVPQILIIVTDGKSQGDVALPSKQLKERG
VTVFAVGVRFPRWEELHALASEPRGQHVLLAEQVEDATNGLFSTLSSSAICSSATPDCR
VEAHPCEHRTLEMVREFAGNAPCWRGSRRTLAVLAAHCPFYSWKRVFLTHPATCYRTTC
PGPCDSQPCQNGGTCVPEGLDGYQCLCPLAFGGEANCALKLSLECRVDLLFLLDSSAGT
TLDGFLRAKVFVKRFVRAVLSEDSRARVGVATYSRELLVAVPVGEYQDVPDLVWSLDGI
PFRGGPTLTGSALRQAAERGFGSATRTGQDRPRRVVVLLTESHSEDEVAGPARHARARE
LLLLGVGSEAVRAELEEITGSPKHVMVYSDPQDLFNQIPELQGKLCSRQRPGCRTQALD
LVFMLDTSASVGPENFAQMQSFVRSCALQFEVNPDVTQVGLVVYGSQVQTAFGLDTKPT
RAAMLRAISQAPYLGGVGSAGTALLHIYDKVMTVQRGARPGVPKAVVVLTGGRGAEDAA
VPAQKLRNNGISVLVVGVPVLSEGLRRLAGPRDSLIHVAAYADLRYHQDVLIEWLCGE
AKQPVNLCKPSPCMNEGSCVLQNGSYRCKCRDGWEGPHCENRFLRRP
```

Figure 14. Amino acid sequence of full-length Osteopontin protein (SEQ ID NO: 15)

```
MRIAVICFCLLGITCAIPVKQADSGSSEEKQLYNKYPDAVATWLNPDPSQKQNLLAPQT
LPSKSNESHDHMDDMDDEDDDDHVDSQDSIDSNDSDDVDDTDDSHQSDESHHSDESDEL
VTDFPTDLPATEVFTPVVPTVDTYDGRGDSVVYGLRSKSKKFRRPDIQYPDATDEDITS
HMESEELNGAYKAIPVAQDLNAPSDWDSRGKDSYETSQLDDQSAETHSHKQSRLYKRKA
NDESNEHSDVIDSQELSKVSREFHSHEFHSHEDMLVVDPKSKEEDKHLKFRISHELDSA
SSEVN
```

Figure 15. Amino acid sequence of full-length ColoUp3 protein (SEQ ID NO: 16)

MGLPRGPLASLLLLQVCWLQCAASEPCRAVFREAEVTLEAGGAEQEPGQALGKVFMGCP
GQEPALFSTDNDDFTVRNGETVQERRSLKERNPLKIFPSKRILRRHKRDWVVAPISVPE
NGKGPFPQRLNQLKSNKDRDTKIFYSITGPGADSPPEGVFAVEKETGWLLLNKPLDREE
IAKYELFGHAVSENGASVEDPMNISIIVTDQNDHKPKFTQDTFRGSVLEGVLPGTSVMQ
VTATDEDDAIYTYNGVVAYSIHSQEPKDPHDLMFTIHRSTGTISVISSGLDREKVPEYT
LTIQATDMDGDGSTTTAVAVVEILDANDNAPMFDPQKYEAHVPENAVGHEVQRLTVTDL
DAPNSPAWRATYLIMGGDDGDHFTITTHPESNQGILTTRKGLDFEAKNQHTLYVEVTNE
APFVLKLPTSTATIVVHVEDVNEAPVFVPPSKVVEVQEGIPTGEPVCVYTAEDPDKENQ
KISYRILRDPAGWLAMDPDSGQVTAVGTLDREDEQFVRNNIYEVMVLAMDNGSPPTTGT
GTLLLTLIDVNDHGPVPEPRQITICNQSPVRQVLNITDKDLSPHTSPFQAQLTDDSDIY
WTAEVNEEGDTVVLSLKKFLKQDTYDVHLSLSDHGNKEQLTVIRATVCDCHGHVETCPG
PWKGGFILPVLGAVLALLFLLLVLLLLVRKKRKIKEPLLLPEDDTRDNVFYYGEEGGGE
EDQDYDITQLHRGLEARPEVVLRNDVAPTIIPTPMYRPRPANPDEIGNFIIENLKAANT
DPTAPPYDTLLVFDYEGSGSDAASLSSLTSSASDQDQDYDYLNEWGSRFKKLADMYGGG
EDD

Figure 16. Amino acid sequence of full-length ColoUp4 protein (SEQ ID NO: 17)

```
MKHLKRWWSAGGGLLHLTLLLSLAGLRVDLDLYLLLPPPTLLQDELLFLGGPASSAYAL
SPFSASGGWGRAGHLHPKGRELDPAAPPEGQLLREVRALGVPFVPRTSVDAWLVHSVAA
GSADEAHGLLGAAAASSTGGAGASVDGGSQAVQGGGGDPRAARSGPLDAGEEEKAPAEP
TAQVPDAGGCASEENGVLREKHEAVDHSSQHEENEERVSAQKENSLQQNDDDENKIAEK
PDWEAEKTTESRNERHLNGTDTSFSLEDLFQLLSSQPENSLEGISLGDIPLPGSISDGM
NSSAHYHVNFSQAISQDVNLHEAILLCPNNTFRRDPTARTSQSQEPFLQLNSHTTNPEQ
TLPGTNLTGFLSPVDNHMRNLTSQDLLYDLDINIFDEINLMSLATEDNFDPIDVSQLFD
EPDSDSGLSLDSSHNNTSVIKSNSSHSVCDEGAIGYCTDHESSSHHDLEGAVGGYYPEP
SKLCHLDQSDSDFHGDLTFQHVFHNHTYHLQPTAPESTSEPFPWPGKSQKIRSRYLEDT
DRNLSRDEQRAKALHIPFSVDEIVGMPVDSFNSMLSRYYLTDLQVSLIRDIRRRGKNKV
AAQNCRKRKLDIILNLEDDVCNLQAKKETLKREQAQCNKAINIMKQKLHDLYHDIFSRL
RDDQGRPVNPNHYALQCTHDGSILIVPKELVASGHKKETQKGKRK
```

Figure 17. Amino acid sequence of full-length ColoUp5 protein (SEQ ID NO: 18)

MKLEVFVPRAAHGDKQGSDLEGAGGSDAPSPLSAAGDDSLGSDGDCAAKPSAGGGARDT
QGDGEQSAGGGPGAEEAIPAAAAAAVVAEGAEAGAAGPGAGGAGSGEGARSKPYTRRPK
PPYSYIALIAMAIRDSAGGRLTLAEINEYLMGKFPFFRGSYTGWRNSVRHNLSLNDCFV
KVLRDPSRPWGKDNYWMLNPNSEYTFADGVFRRRRKRLSHRAPVPAPGLRPEEAPGLPA
APPPAPAAPASPRMRSPARQEERASPAGKFSSSFAIDSILRKPFRSRRLRDTAPGTTLQ
WGAAPCPPLPAFPALLPAAPCRALLPLCAYGAGEPARLGAREAEVPPTAPPLLLAPLPA
AAPAKPLRGPAAGGAHLYCPLRLPAALQAALVRRPGPHLSYPVETLLA

Figure 18. Amino acid sequence of full-length ColoUp6 protein (SEQ ID NO: 19)

MEKHHVPSDFNVNVKVDTGPREDLIKVLEDMRQEYELIIKKKHRDLDTWYKEQSAAMSQ
EAASPATVQSRQGDIHELKRTFQALEIDLQAQYSTKSALENMLSETQSRYSCKLQDMQE
IISHYEEELTQLRHELERQNNEYQVLLGIKTHLEKEITTYRRLLEGESEGTREESKSSM
KVSATPKIKAITQETINGRLVLCQVNEIQKHA

Figure 19. Amino acid sequence of full-length ColoUp8 protein (SEQ ID NO: 20)

```
MDKSGIDSLDHVTSDAVELANRSDNSSDSSLFKTQCIPYSPKGEKRNPIRKFVRTPESV
HASDSSSDSSFEPIPLTIKAIFERFKNRKKRYKKKKKRRYQPTGRPRGRPEGRRNPIYS
LIDKKKQFRSRGSGFPFLESENEKNAPWRKILTFEQAVARGFFNYIEKLKYEHHLKESL
KQMNVGEDLENEDFDSRRYKFLDDDGSISPIEESTAEDEDATHLEDNECDIKLAGDSFI
VSSEFPVRLSVYLEEEDITEEAALSKKRATKAKNTGQRGLKM
```

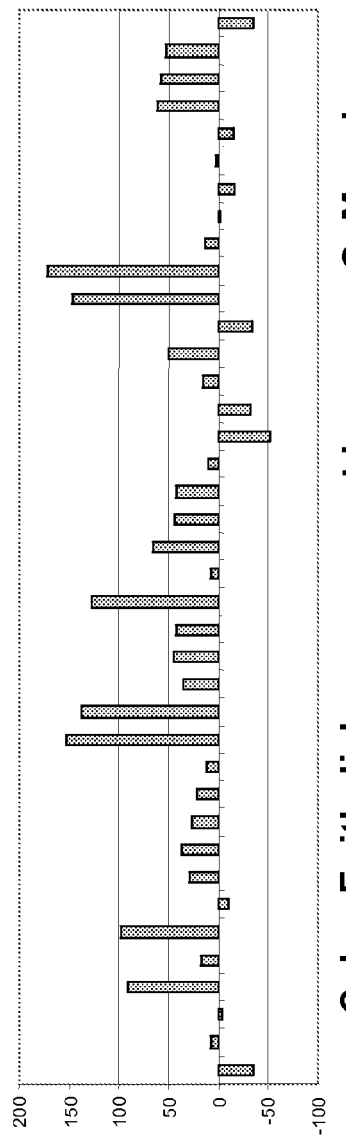
Figure 27A
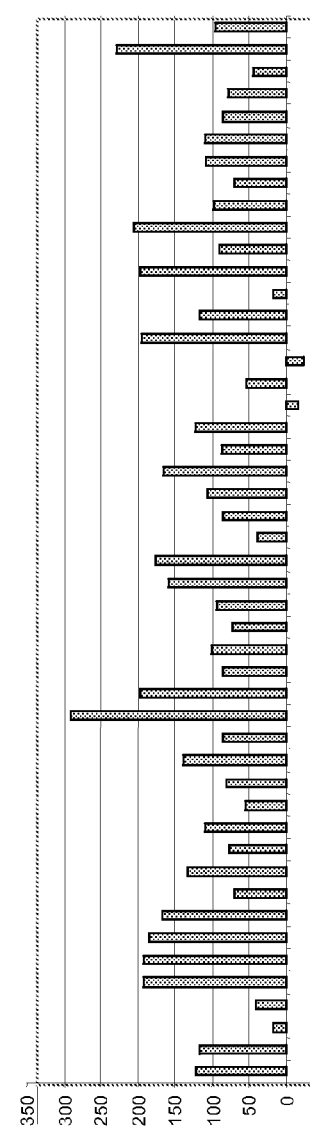
Figure 27B
Figure 27C

Figure 35A

| | | | | | | | | | | | | |
|---|---|---|---|---|---|---|---|---|---|---|---|---|
| human foxq1 | 1 | A | T | G | A | A | G | T | T | G | G | A | G | G | T |
| mouse foxq1 | 1 | A | T | G | A | A | A | T | T | G | G | A | G | G | T |
| rat foxq1 | 1 | A | T | G | A | A | A | T | T | G | G | A | G | G | T |

| human foxq1 | 81 | C | G | C | G | C | C | G | T | C | C | C | G | C |
| mouse foxq1 | 81 | C | G | T | G | C | C | A | T | C | T | C | A | C |
| rat foxq1 | 81 | C | G | T | G | C | C | A | T | C | T | C | C | G | C |

| human foxq1 | 161 | G | C | G | C | G | G | C | G | C | C | A | G | A |
| mouse foxq1 | 161 | G | C | A | G | C | G | G | C | G | C | C | G | G |
| rat foxq1 | 161 | G | C | A | G | A | G | G | C | G | C | C | G | T | G |

| human foxq1 | 238 | G | C | A | G | C | A | G | C | T | G | C | T | G | C |
| mouse foxq1 | 238 | G | A | G | G | C | A | A | C | T | G | - | - | - | - |
| rat foxq1 | 238 | G | A | G | G | T | G | A | C | C | G | - | - | - | - |

| human foxq1 | 318 | C | G | A | G | G | T | G | C | A | C | G | C | A |
| mouse foxq1 | 306 | C | G | A | G | G | G | C | G | C | G | C | G | C | A |
| rat foxq1 | 306 | T | G | A | G | G | G | C | G | C | G | C | G | C | A |

| human foxq1 | 398 | G | C | G | A | C | T | C | G | G | C | G | G | G | C |
| mouse foxq1 | 386 | G | C | G | A | C | T | C | C | G | C | G | G | G | C |
| rat foxq1 | 386 | G | C | G | A | C | T | C | C | G | C | G | G | G | C |

| human foxq1 | 478 | T | A | C | A | C | G | G | G | C | T | G | G | C | G |
| mouse foxq1 | 466 | T | A | C | A | C | G | G | G | C | T | G | G | C | G |
| rat foxq1 | 466 | T | A | C | A | C | G | G | G | C | T | G | G | C | G |

| human foxq1 | 558 | G | C | C | C | T | G | G | G | G | C | A | A | G | G |
| mouse foxq1 | 546 | G | C | C | C | T | G | G | G | G | C | A | A | G | G |
| rat foxq1 | 546 | G | C | C | C | T | G | G | G | G | C | A | A | G | G |

Figure 35B

| | | | | | | | | | | | | | | |
|---|---|---|---|---|---|---|---|---|---|---|---|---|---|---|
| human foxq1 | 638 | G | C | A | A | G | C | G | C | C | T | C | A | G | C |
| mouse foxq1 | 626 | G | C | A | A | G | C | G | C | C | T | C | A | G | C |
| rat foxq1 | 626 | G | C | A | A | G | C | G | C | C | T | C | A | G | C |

| | | | | | | | | | | | | | | |
|---|---|---|---|---|---|---|---|---|---|---|---|---|---|---|
| human foxq1 | 715 | C | C | G | C | C | G | C | C | C | G | C | G | C | C |
| mouse foxq1 | 706 | C | C | G | C | A | G | C | C | C | G | C | G | C | C |
| rat foxq1 | 706 | C | C | G | C | A | G | C | C | C | G | C | G | C | C |

| | | | | | | | | | | | | | | |
|---|---|---|---|---|---|---|---|---|---|---|---|---|---|---|
| human foxq1 | 795 | C | A | A | G | T | T | C | T | C | C | A | G | C | T |
| mouse foxq1 | 786 | C | A | A | G | T | T | C | T | C | C | A | G | C | T |
| rat foxq1 | 786 | C | A | A | G | T | T | C | T | C | C | A | G | C | T |

| | | | | | | | | | | | | | | |
|---|---|---|---|---|---|---|---|---|---|---|---|---|---|---|
| human foxq1 | 875 | G | G | A | C | G | A | C | G | C | T | T | C | A | G |
| mouse foxq1 | 866 | G | G | G | T | G | C | A | G | C | T | A | C | C | C |
| rat foxq1 | 866 | G | G | G | T | G | C | A | G | C | T | A | C | C | C |

| | | | | | | | | | | | | | | |
|---|---|---|---|---|---|---|---|---|---|---|---|---|---|---|
| human foxq1 | 955 | G | C | C | C | T | G | C | T | G | C | C | G | C | T |
| mouse foxq1 | 946 | G | C | T | C | T | G | C | T | A | C | C | G | C | T |
| rat foxq1 | 946 | G | C | C | C | T | G | C | T | G | C | C | G | C | T |

| | | | | | | | | | | | | | | |
|---|---|---|---|---|---|---|---|---|---|---|---|---|---|---|
| human foxq1 | 1035 | G | C | C | G | C | C | C | T | C | C | T | G | C | |
| mouse foxq1 | 1023 | G | G | C | G | C | C | C | T | T | C | T | G | C | |
| rat foxq1 | 1023 | G | G | C | G | C | C | C | T | G | T | T | G | C | |

| | | | | | | | | | | | | | | |
|---|---|---|---|---|---|---|---|---|---|---|---|---|---|---|
| human foxq1 | 1112 | A | C | C | T | G | T | A | C | T | G | C | C | C | C |
| mouse foxq1 | 1103 | A | C | C | T | G | T | A | C | T | G | C | C | C | C |
| rat foxq1 | 1103 | A | C | C | T | G | T | A | C | T | G | C | C | C | C |

| | | | | | | | | | | | | | | |
|---|---|---|---|---|---|---|---|---|---|---|---|---|---|---|
| human foxq1 | 1192 | G | T | G | G | A | G | A | C | G | C | T | C | C | T |
| mouse foxq1 | 1183 | G | T | G | G | A | G | A | C | T | C | T | G | C | T |
| rat foxq1 | 1183 | G | T | G | G | A | G | A | C | G | C | T | G | C | T |

Figure 35C

| | | | | | | | | | | | | | | | | |
|---|---|---|---|---|---|---|---|---|---|---|---|---|---|---|---|---|
| G | T | T | C | G | T | C | C | C | T | C | G | C | G | C | G | G | C | C | C | A | C | G |
| G | T | T | C | G | T | C | C | C | A | C | G | C | G | C | A | G | C | C | C | A | C | G |
| A | T | T | T | G | C | C | C | C | A | C | G | C | G | C | A | G | C | C | C | A | C | G |

| T | G | T | C | G | C | G | G | C | G | G | A | G | A | C | G | A | C | T | C | C |
|---|---|---|---|---|---|---|---|---|---|---|---|---|---|---|---|---|---|---|---|---|
| T | G | T | C | C | G | C | G | G | C | T | G | G | T | G | A | C | G | A | C | T | C | C |
| T | G | T | C | C | G | C | G | G | C | T | G | G | C | G | A | C | G | A | C | T | C | C |

| G | A | T | A | C | G | C | A | G | G | G | - | - | - | C | G | A | C | G | G | C | G | A |
|---|---|---|---|---|---|---|---|---|---|---|---|---|---|---|---|---|---|---|---|---|---|---|
| G | A | T | C | T | G | G | A | A | G | G | T | G | G | C | G | G | C | G | G | C | G | A |
| G | A | T | C | T | G | G | A | A | G | G | C | G | G | C | G | G | C | G | G | C | G | A |

| A | G | C | G | G | T | G | G | T | G | G | C | G | G | A | G | G | C | G | C | G | G |
|---|---|---|---|---|---|---|---|---|---|---|---|---|---|---|---|---|---|---|---|---|---|
| - | - | - | - | A | T | G | A | C | A | G | C | A | G | A | A | C | G | C | - | - | - | - |
| - | - | - | - | A | T | G | G | C | A | G | C | A | G | A | A | C | G | C | - | - | - | - |

| G | C | A | A | G | C | C | A | T | A | T | A | C | G | C | G | G | C | G | G | C | C | C |
|---|---|---|---|---|---|---|---|---|---|---|---|---|---|---|---|---|---|---|---|---|---|---|
| G | C | A | A | G | C | C | G | T | A | C | A | C | G | C | G | G | C | G | G | C | C | C |
| G | C | A | A | G | C | C | G | T | A | C | A | C | G | C | G | G | C | G | G | C | C | C |

| G | G | G | C | G | C | T | T | G | A | C | G | C | T | G | G | C | G | A | G | A | T |
|---|---|---|---|---|---|---|---|---|---|---|---|---|---|---|---|---|---|---|---|---|---|
| G | G | A | C | G | C | C | T | G | A | C | A | C | T | G | G | C | C | G | A | G | A | T |
| G | G | A | C | G | C | C | T | G | A | C | G | C | T | G | G | C | C | G | A | G | A | T |

| C | A | A | C | T | C | C | G | T | G | C | G | C | C | A | C | A | A | C | C | T | T | T |
|---|---|---|---|---|---|---|---|---|---|---|---|---|---|---|---|---|---|---|---|---|---|---|
| C | A | A | C | T | C | C | G | T | G | C | G | C | C | A | C | A | A | C | C | T | C | T |
| C | A | A | C | T | C | C | G | T | G | C | G | C | C | A | C | A | A | C | C | T | C | T |

| A | C | A | A | C | T | A | C | T | G | G | A | T | G | C | T | C | A | A | C | C | C | C |
|---|---|---|---|---|---|---|---|---|---|---|---|---|---|---|---|---|---|---|---|---|---|---|
| A | C | A | A | C | T | A | C | T | G | G | A | T | G | C | T | C | A | A | C | C | C | C |
| A | C | A | A | T | T | A | C | T | G | G | A | T | G | C | T | C | A | A | C | C | C | C |

| G G G A C A A G | C A | G G G C A G T G A C C T G |
| G G G A C A A | A | T G G G C A G | C | G A | T | C T G |
| G G G A C A A G A T G G G C A G T G A C C T G |

| C | T | G | G C T C A G A | T | G G G A C T G | C | G C |
| T T A G G C T C A G A C G G G A C T G T G C |
| T T A G G C T C | T | G A C G G G A C T G T G C |

| A C A | G A | T | G C | G | G A | G G C G G G C C G | G |
| G A G G A A T T C G A G T G G C G G G C C G A |
| G A G G A A T T C G A G T G G C G G G | G | C G A |

| A G G C C | G G | G C G G C G G G G C C | A G | G C |
| A G G C C T C C | G C G G C | A | G G G C C G T G C |
| A G G C C T C C | C | C G G | T | G G G C C G T G C |

| A A G C C C C C C T A C T C | G | T A C A T C G C |
| A A G C C C C C | A | T A C T C C T A C A T C G C |
| A A G C C C C C C T A C T C C T A C A T C G C |

| C A A C G A G T A C C T C A T G G G C A A G T |
| C A A C G A G T A C C T C A T G G G C A A G T |
| C A A C G A G T A C C T C A T G G G C A A G T |

| C G C T C A A C G A C T G | C | T T C G T C A A G |
| C G C T C A A C G A C T G T T T C G T C A A G |
| C G C T C A A C G A C T G T T T C G T C A A G |

| A A C A G C G A | G | T A C A C C T T C G C C G A |
| A A C A G C G A A T A C A C C T T C G C C G A |
| A A C A G C G A A T A C A C C T T C G C C G A |

Figure 35G

| | | | | | | | | | | | | | | | | | | | | |
|---|---|---|---|---|---|---|---|---|---|---|---|---|---|---|---|---|---|---|---|---|
| G | A | G | G | G | C | G | C | G | G | G | C | G | C | A | G | C | G | A | 80 |
| G | A | G | G | G | G | G | C | C | G | G | C | A | G | C | A | G | C | G | A | 80 |
| G | A | G | G | G | G | G | C | C | G | G | C | A | G | C | A | G | C | G | A | 80 |

| G | C | C | A | A | C | A | G | C | C | C | G | G | C | G | C | G | G | 160 |
| A | G | C | C | A | A | C | A | G | C | C | C | G | G | C | G | G | C | G | G | 160 |
| A | G | C | C | A | A | C | A | G | C | C | C | G | G | C | G | G | C | G | G | 160 |

| G | C | G | C | G | G | A | G | G | A | G | G | C | G | A | T | C | C | C | G | 237 |
| G | C | G | C | C | C | A | A | G | A | - | - | C | G | G | T | C | C | - | G | 237 |
| G | C | A | C | C | C | A | A | G | A | - | - | C | G | A | T | C | C | - | C | 237 |

| G | C | G | G | G | C | G | G | C | G | C | G | G | G | G | A | G | C | G | G | 317 |
| G | C | G | G | G | C | G | G | C | G | T | G | G | G | C | G | G | C | G | G | 305 |
| G | C | G | G | G | C | A | G | C | G | T | G | G | G | C | G | G | C | G | G | 305 |

| G | C | T | C | A | T | C | G | C | C | A | T | G | G | C | C | A | T | C | C | 397 |
| T | C | T | C | A | T | C | G | C | C | A | T | G | G | C | C | A | T | C | C | 385 |
| A | C | T | C | A | T | C | G | C | C | A | T | G | G | C | C | A | T | C | C | 385 |

| T | C | C | C | C | T | T | T | T | T | C | C | G | C | G | G | C | A | G | C | 477 |
| T | C | C | C | C | T | T | T | T | T | C | C | G | G | G | G | C | A | G | C | 465 |
| T | C | C | C | C | T | T | T | T | T | C | C | G | G | G | G | C | A | G | C | 465 |

| G | T | G | C | T | G | C | G | C | G | A | C | C | C | C | T | C | G | C | G | 557 |
| G | T | G | C | T | G | C | G | C | G | A | C | C | C | C | T | C | G | C | G | 545 |
| G | T | G | C | T | G | C | G | C | G | A | C | C | C | C | T | C | G | C | G | 545 |

| C | G | G | G | G | T | C | T | T | C | C | G | C | C | G | C | C | G | C | C | 637 |
| C | G | G | G | G | T | C | T | T | C | C | G | C | C | G | C | C | G | C | C | 625 |
| C | G | G | G | G | T | C | T | T | C | C | G | C | C | G | C | C | G | C | C | 625 |

Figure 35H

| | | | | | | | | | | | | | | | | | | |
|---|---|---|---|---|---|---|---|---|---|---|---|---|---|---|---|---|---|---|
| C | G | G | G | C | T | C | C | C | G | C | C | G | - | - | - | C | C | 714 |
| C | A | C | C | C | G | G | A | C | C | T | G | C | C | G | G | A | C | C | 705 |
| C | A | C | C | C | G | G | A | C | C | T | G | C | G | G | G | A | C | C | 705 |

| G | A | G | C | G | C | G | C | C | A | G | C | C | C | C | G | C | G | G | 794 |
| G | A | G | C | G | C | T | C | C | A | G | C | C | C | T | G | C | G | A | G | 785 |
| G | A | G | G | C | T | C | C | A | G | C | C | C | G | G | C | G | A | G | 785 |

| C | C | T | C | A | G | G | A | C | A | C | G | G | C | C | C | C | G | 874 |
| C | G | A | C | G | G | C | G | A | C | T | C | G | G | C | T | C | T | G | G | 865 |
| C | G | A | C | G | G | C | G | A | C | C | C | G | G | C | T | C | T | G | G | 865 |

| T | C | C | C | C | G | C | G | G | C | G | C | C | C | T | G | C | A | G | G | 954 |
| T | T | C | C | C | G | C | G | G | C | G | C | C | C | G | G | T | G | G | C | 945 |
| T | T | C | C | C | G | C | G | T | C | G | T | C | C | G | G | C | G | G | T | 945 |

| G | C | C | G | A | G | G | T | G | C | A | C | C | G | A | C | C | G | C | 1034 |
| A | C | C | G | A | G | G | T | G | C | A | G | C | C | - | - | - | C | G | C | 1022 |
| G | C | C | G | A | G | G | T | G | C | A | G | C | C | - | - | - | C | G | C | 1022 |

| G | G | C | G | G | C | C | G | C | G | G | C | G | C | G | - | - | - | C | 1111 |
| G | G | A | G | A | C | C | G | C | C | G | G | C | G | C | G | G | C | G | C | 1102 |
| G | G | A | G | A | C | C | G | C | C | G | G | C | G | C | G | G | C | G | C | 1102 |

| G | C | C | C | G | C | A | C | C | T | G | C | C | G | T | A | C | C | C | G | 1191 |
| G | T | C | C | G | C | A | C | C | T | G | T | C | C | T | A | C | C | C | G | 1182 |
| G | T | C | C | G | C | A | C | C | T | G | T | C | C | T | A | C | C | G | G | 1182 |

| Day | Resistance | % GFP Exp. |
|---|---|---|
| 0 | 300 | 0 |
| 1 | 415 | 10 |
| 2 | 260 | 20 |
| 3 | 206 | 25 |
| 4 | 218 | 25 |

Amino Acid Sequence of a Secreted C-terminal Portion of ColoUp2

AVLAAHCPFYSWKRVFLTHPATCYRTTCPGPCDSQPCQNGGTCVPEGLDGYQCL
CPLAFGGEANCALKLSLECRVDLLFLLDSSAGTTLDGFLRAKVFVKRFVRAVLSE
DSRARVGVATYSRELLVAVPVGEYQDVPDLVWSLDGIPFRGGPTLTGSALRQAA
ERGFGSATRTGQDRPRRVVVLLTESHSEDEVAGPARHARARELLLLGVGSEAVR
AELEEITGSPKHVMVYSDPQDLFNQIPELQGKLCSRQRPGCRTQALDLVFMLDTS
ASVGPENFAQMQSFVRSCALQFEVNPDVTQVGLVVYGSQVQTAFGLDTKPTRA
AMLRAISQAPYLGGVGSAGTALLHIYDKVMTVQRGARPGVPKAVVVLTGGRGA
EDAAVPAQKLRNNGISVLVVGVGPVLSEGLRRLAGPRDSLIHVAAYADLRYHQD
VLIEWLCGEAKQPVNLCKPSPCMNEGSCVLQNGSYRCKCRDGWEGPHCENRFL
RRP (SEQ ID NO:21)

Figure 41

SEQUENCE LISTING

```
<160> NUMBER OF SEQ ID NOS: 28

<210> SEQ ID NO 1
<211> LENGTH: 1331
<212> TYPE: PRT
<213> ORGANISM: Homo sapiens

<400> SEQUENCE: 1

Thr Val Ala Ala Gly Cys Pro Asp Gln Ser Pro Glu Leu Gln Pro Trp
 1               5                  10                  15

Asn Pro Gly His Asp Gln Asp His His Val His Ile Gly Gln Gly Lys
            20                  25                  30

Thr Leu Leu Leu Thr Ser Ser Ala Thr Val Tyr Ser Ile His Ile Ser
        35                  40                  45

Glu Gly Gly Lys Leu Val Ile Lys Asp His Asp Glu Pro Ile Val Leu
    50                  55                  60

Arg Thr Arg His Ile Leu Ile Asp Asn Gly Gly Glu Leu His Ala Gly
65                  70                  75                  80

Ser Ala Leu Cys Pro Phe Gln Gly Asn Phe Thr Ile Ile Leu Tyr Gly
                85                  90                  95

Arg Ala Asp Glu Gly Ile Gln Pro Asp Pro Tyr Tyr Gly Leu Lys Tyr
            100                 105                 110

Ile Gly Val Gly Lys Gly Gly Ala Leu Glu Leu His Gly Gln Lys Lys
        115                 120                 125

Leu Ser Trp Thr Phe Leu Asn Lys Thr Leu His Pro Gly Gly Met Ala
    130                 135                 140

Glu Gly Gly Tyr Phe Phe Glu Arg Ser Trp Gly His Arg Gly Val Ile
145                 150                 155                 160

Val His Val Ile Asp Pro Lys Ser Gly Thr Val Ile His Ser Asp Arg
```

-continued

```
                165                 170                 175
Phe Asp Thr Tyr Arg Ser Lys Lys Glu Ser Glu Arg Leu Val Gln Tyr
            180                 185                 190
Leu Asn Ala Val Pro Asp Gly Arg Ile Leu Ser Val Ala Val Asn Asp
        195                 200                 205
Glu Gly Ser Arg Asn Leu Asp Asp Met Ala Arg Lys Ala Met Thr Lys
    210                 215                 220
Leu Gly Ser Lys His Phe Leu His Leu Gly Phe Arg His Pro Trp Ser
225                 230                 235                 240
Phe Leu Thr Val Lys Gly Asn Pro Ser Ser Val Glu Asp His Ile
                245                 250                 255
Glu Tyr His Gly His Arg Gly Ser Ala Ala Arg Val Phe Lys Leu
            260                 265                 270
Phe Gln Thr Glu His Gly Glu Tyr Phe Asn Val Ser Leu Ser Ser Glu
        275                 280                 285
Trp Val Gln Asp Val Glu Trp Thr Glu Trp Phe Asp His Asp Lys Val
    290                 295                 300
Ser Gln Thr Lys Gly Gly Glu Lys Ile Ser Asp Leu Trp Lys Ala His
305                 310                 315                 320
Pro Gly Lys Ile Cys Asn Arg Pro Ile Asp Ile Gln Ala Thr Thr Met
                325                 330                 335
Asp Gly Val Asn Leu Ser Thr Glu Val Val Tyr Lys Lys Gly Gln Asp
            340                 345                 350
Tyr Arg Phe Ala Cys Tyr Asp Arg Gly Arg Ala Cys Arg Ser Tyr Arg
        355                 360                 365
Val Arg Phe Leu Cys Gly Lys Pro Val Arg Pro Lys Leu Thr Val Thr
    370                 375                 380
Ile Asp Thr Asn Val Asn Ser Thr Ile Leu Asn Leu Glu Asp Asn Val
385                 390                 395                 400
Gln Ser Trp Lys Pro Gly Asp Thr Leu Val Ile Ala Ser Thr Asp Tyr
                405                 410                 415
Ser Met Tyr Gln Ala Glu Glu Phe Gln Val Leu Pro Cys Arg Ser Cys
            420                 425                 430
Ala Pro Asn Gln Val Lys Val Ala Gly Lys Pro Met Tyr Leu His Ile
        435                 440                 445
Gly Glu Glu Ile Asp Gly Val Asp Met Arg Ala Glu Val Gly Leu Leu
    450                 455                 460
Ser Arg Asn Ile Ile Val Met Gly Glu Met Glu Asp Lys Cys Tyr Pro
465                 470                 475                 480
Tyr Arg Asn His Ile Cys Asn Phe Phe Asp Phe Asp Thr Phe Gly Gly
                485                 490                 495
His Ile Lys Phe Ala Leu Gly Phe Lys Ala Ala His Leu Glu Gly Thr
            500                 505                 510
Glu Leu Lys His Met Gly Gln Gln Leu Val Gly Gln Tyr Pro Ile His
        515                 520                 525
Phe His Leu Ala Gly Asp Val Asp Glu Arg Gly Gly Tyr Asp Pro Pro
    530                 535                 540
Thr Tyr Ile Arg Asp Leu Ser Ile His His Thr Phe Ser Arg Cys Val
545                 550                 555                 560
Thr Val His Gly Ser Asn Gly Leu Leu Ile Lys Asp Val Val Gly Tyr
                565                 570                 575
Asn Ser Leu Gly His Cys Phe Phe Thr Glu Asp Gly Pro Glu Glu Arg
            580                 585                 590
```

```
Asn Thr Phe Asp His Cys Leu Gly Leu Leu Val Lys Ser Gly Thr Leu
            595                 600                 605

Leu Pro Ser Asp Arg Asp Ser Lys Met Cys Lys Met Ile Thr Glu Asp
610                 615                 620

Ser Tyr Pro Gly Tyr Ile Pro Lys Pro Arg Gln Asp Cys Asn Ala Val
625                 630                 635                 640

Ser Thr Phe Trp Met Ala Asn Pro Asn Asn Leu Ile Asn Cys Ala
                645                 650                 655

Ala Ala Gly Ser Glu Glu Thr Gly Phe Trp Phe Ile Phe His His Val
            660                 665                 670

Pro Thr Gly Pro Ser Val Gly Met Tyr Ser Pro Gly Tyr Ser Glu His
            675                 680                 685

Ile Pro Leu Gly Lys Phe Tyr Asn Asn Arg Ala His Ser Asn Tyr Arg
690                 695                 700

Ala Gly Met Ile Ile Asp Asn Gly Val Lys Thr Thr Glu Ala Ser Ala
705                 710                 715                 720

Lys Asp Lys Arg Pro Phe Leu Ser Ile Ile Ser Ala Arg Tyr Ser Pro
                725                 730                 735

His Gln Asp Ala Asp Pro Leu Lys Pro Arg Glu Pro Ala Ile Ile Arg
            740                 745                 750

His Phe Ile Ala Tyr Lys Asn Gln Asp His Gly Ala Trp Leu Arg Gly
            755                 760                 765

Gly Asp Val Trp Leu Asp Ser Cys Arg Phe Ala Asp Asn Gly Ile Gly
770                 775                 780

Leu Thr Leu Ala Ser Gly Gly Thr Phe Pro Tyr Asp Gly Ser Lys
785                 790                 795                 800

Gln Glu Ile Lys Asn Ser Leu Phe Val Gly Glu Ser Gly Asn Val Gly
                805                 810                 815

Thr Glu Met Met Asp Asn Arg Ile Trp Gly Pro Gly Leu Asp His
            820                 825                 830

Ser Gly Arg Thr Leu Pro Ile Gly Gln Asn Phe Pro Ile Arg Gly Ile
            835                 840                 845

Gln Leu Tyr Asp Gly Pro Ile Asn Ile Gln Asn Cys Thr Phe Arg Lys
850                 855                 860

Phe Val Ala Leu Glu Gly Arg His Thr Ser Ala Leu Ala Phe Arg Leu
865                 870                 875                 880

Asn Asn Ala Trp Gln Ser Cys Pro His Asn Asn Val Thr Gly Ile Ala
                885                 890                 895

Phe Glu Asp Val Pro Ile Thr Ser Arg Val Phe Phe Gly Glu Pro Gly
            900                 905                 910

Pro Trp Phe Asn Gln Leu Asp Met Asp Gly Asp Lys Thr Ser Val Phe
            915                 920                 925

His Asp Val Asp Gly Ser Val Ser Glu Tyr Pro Gly Ser Tyr Leu Thr
930                 935                 940

Lys Asn Asp Asn Trp Leu Val Arg His Pro Asp Cys Ile Asn Val Pro
945                 950                 955                 960

Asp Trp Arg Gly Ala Ile Cys Ser Gly Cys Tyr Ala Gln Met Tyr Ile
                965                 970                 975

Gln Ala Tyr Lys Thr Ser Asn Leu Arg Met Lys Ile Ile Lys Asn Asp
            980                 985                 990

Phe Pro Ser His Pro Leu Tyr Leu Glu Gly Ala Leu Thr Arg Ser Thr
            995                 1000                1005

His Tyr Gln Gln Tyr Gln Pro Val Val Thr Leu Gln Lys Gly Tyr Thr
1010                1015                1020
```

```
Ile His Trp Asp Gln Thr Ala Pro Ala Glu Leu Ala Ile Trp Leu Ile
1025                1030                1035                1040

Asn Phe Asn Lys Gly Asp Trp Ile Arg Val Gly Leu Cys Tyr Pro Arg
            1045                1050                1055

Gly Thr Thr Phe Ser Ile Leu Ser Asp Val His Asn Arg Leu Leu Lys
        1060                1065                1070

Gln Thr Ser Lys Thr Gly Val Phe Val Arg Thr Leu Gln Met Asp Lys
    1075                1080                1085

Val Glu Gln Ser Tyr Pro Gly Arg Ser His Tyr Tyr Trp Asp Glu Asp
1090                1095                1100

Ser Gly Leu Leu Phe Leu Lys Leu Lys Ala Gln Asn Glu Arg Glu Lys
1105                1110                1115                1120

Phe Ala Phe Cys Ser Met Lys Gly Cys Glu Arg Ile Lys Ile Lys Ala
            1125                1130                1135

Leu Ile Pro Lys Asn Ala Gly Val Ser Asp Cys Thr Ala Thr Ala Tyr
        1140                1145                1150

Pro Lys Phe Thr Glu Arg Ala Val Val Asp Val Pro Met Pro Lys Lys
    1155                1160                1165

Leu Phe Gly Ser Gln Leu Lys Thr Lys Asp His Phe Leu Glu Val Lys
1170                1175                1180

Met Glu Ser Ser Lys Gln His Phe Phe His Leu Trp Asn Asp Phe Ala
1185                1190                1195                1200

Tyr Ile Glu Val Asp Gly Lys Lys Tyr Pro Ser Ser Glu Asp Gly Ile
            1205                1210                1215

Gln Val Val Ile Asp Gly Asn Gln Gly Arg Val Val Ser His Thr
        1220                1225                1230

Ser Phe Arg Asn Ser Ile Leu Gln Gly Ile Pro Trp Gln Leu Phe Asn
    1235                1240                1245

Tyr Val Ala Thr Ile Pro Asp Asn Ser Ile Val Leu Met Ala Ser Lys
1250                1255                1260

Gly Arg Tyr Val Ser Arg Gly Pro Trp Thr Arg Val Leu Glu Lys Leu
1265                1270                1275                1280

Gly Ala Asp Arg Gly Leu Lys Leu Lys Glu Gln Met Ala Phe Val Gly
            1285                1290                1295

Phe Lys Gly Ser Phe Arg Pro Ile Trp Val Thr Leu Thr Glu Asp
        1300                1305                1310

His Lys Ala Lys Ile Phe Gln Val Val Pro Ile Pro Val Val Lys Lys
    1315                1320                1325

Lys Lys Leu
    1330

<210> SEQ ID NO 2
<211> LENGTH: 1328
<212> TYPE: PRT
<213> ORGANISM: Homo sapiens

<400> SEQUENCE: 2

Ala Gly Cys Pro Asp Gln Ser Pro Glu Leu Gln Pro Trp Asn Pro Gly
 1               5                  10                  15

His Asp Gln Asp His His Val His Ile Gly Gln Gly Lys Thr Leu Leu
            20                  25                  30

Leu Thr Ser Ser Ala Thr Val Tyr Ser Ile His Ile Ser Glu Gly Gly
        35                  40                  45

Lys Leu Val Ile Lys Asp His Asp Glu Pro Ile Val Leu Arg Thr Arg
    50                  55                  60
```

His Ile Leu Ile Asp Asn Gly Gly Glu Leu His Ala Gly Ser Ala Leu
65                  70                  75                  80

Cys Pro Phe Gln Gly Asn Phe Thr Ile Ile Leu Tyr Gly Arg Ala Asp
                85                  90                  95

Glu Gly Ile Gln Pro Asp Pro Tyr Tyr Gly Leu Lys Tyr Ile Gly Val
            100                 105                 110

Gly Lys Gly Gly Ala Leu Glu Leu His Gly Gln Lys Lys Leu Ser Trp
        115                 120                 125

Thr Phe Leu Asn Lys Thr Leu His Pro Gly Gly Met Ala Glu Gly Gly
    130                 135                 140

Tyr Phe Phe Glu Arg Ser Trp Gly His Arg Gly Val Ile Val His Val
145                 150                 155                 160

Ile Asp Pro Lys Ser Gly Thr Val Ile His Ser Asp Arg Phe Asp Thr
                165                 170                 175

Tyr Arg Ser Lys Lys Glu Ser Glu Arg Leu Val Gln Tyr Leu Asn Ala
            180                 185                 190

Val Pro Asp Gly Arg Ile Leu Ser Val Ala Val Asn Asp Glu Gly Ser
        195                 200                 205

Arg Asn Leu Asp Asp Met Ala Arg Lys Ala Met Thr Lys Leu Gly Ser
    210                 215                 220

Lys His Phe Leu His Leu Gly Phe Arg His Pro Trp Ser Phe Leu Thr
225                 230                 235                 240

Val Lys Gly Asn Pro Ser Ser Val Glu Asp His Ile Glu Tyr His
                245                 250                 255

Gly His Arg Gly Ser Ala Ala Ala Arg Val Phe Lys Leu Phe Gln Thr
            260                 265                 270

Glu His Gly Glu Tyr Phe Asn Val Ser Leu Ser Ser Glu Trp Val Gln
        275                 280                 285

Asp Val Glu Trp Thr Glu Trp Phe Asp His Asp Lys Val Ser Gln Thr
    290                 295                 300

Lys Gly Gly Glu Lys Ile Ser Asp Leu Trp Lys Ala His Pro Gly Lys
305                 310                 315                 320

Ile Cys Asn Arg Pro Ile Asp Ile Gln Ala Thr Thr Met Asp Gly Val
                325                 330                 335

Asn Leu Ser Thr Glu Val Val Tyr Lys Lys Gly Gln Asp Tyr Arg Phe
            340                 345                 350

Ala Cys Tyr Asp Arg Gly Arg Ala Cys Arg Ser Tyr Arg Val Arg Phe
        355                 360                 365

Leu Cys Gly Lys Pro Val Arg Pro Lys Leu Thr Val Thr Ile Asp Thr
    370                 375                 380

Asn Val Asn Ser Thr Ile Leu Asn Leu Glu Asp Asn Val Gln Ser Trp
385                 390                 395                 400

Lys Pro Gly Asp Thr Leu Val Ile Ala Ser Thr Asp Tyr Ser Met Tyr
                405                 410                 415

Gln Ala Glu Glu Phe Gln Val Leu Pro Cys Arg Ser Cys Ala Pro Asn
            420                 425                 430

Gln Val Lys Val Ala Gly Lys Pro Met Tyr Leu His Ile Gly Glu Glu
        435                 440                 445

Ile Asp Gly Val Asp Met Arg Ala Glu Val Gly Leu Leu Ser Arg Asn
    450                 455                 460

Ile Ile Val Met Gly Glu Met Glu Asp Lys Cys Tyr Pro Tyr Arg Asn
465                 470                 475                 480

His Ile Cys Asn Phe Phe Asp Phe Asp Thr Phe Gly Gly His Ile Lys

```
                    485                 490                 495
Phe Ala Leu Gly Phe Lys Ala Ala His Leu Glu Gly Thr Glu Leu Lys
                500                 505                 510
His Met Gly Gln Gln Leu Val Gly Gln Tyr Pro Ile His Phe His Leu
                515                 520                 525
Ala Gly Asp Val Asp Glu Arg Gly Gly Tyr Asp Pro Pro Thr Tyr Ile
                530                 535                 540
Arg Asp Leu Ser Ile His His Thr Phe Ser Arg Cys Val Thr Val His
545                 550                 555                 560
Gly Ser Asn Gly Leu Leu Ile Lys Asp Val Val Gly Tyr Asn Ser Leu
                565                 570                 575
Gly His Cys Phe Phe Thr Glu Asp Gly Pro Glu Glu Arg Asn Thr Phe
                580                 585                 590
Asp His Cys Leu Gly Leu Leu Val Lys Ser Gly Thr Leu Leu Pro Ser
                595                 600                 605
Asp Arg Asp Ser Lys Met Cys Lys Met Ile Thr Glu Asp Ser Tyr Pro
                610                 615                 620
Gly Tyr Ile Pro Lys Pro Arg Gln Asp Cys Asn Ala Val Ser Thr Phe
625                 630                 635                 640
Trp Met Ala Asn Pro Asn Asn Asn Leu Ile Asn Cys Ala Ala Ala Gly
                645                 650                 655
Ser Glu Glu Thr Gly Phe Trp Phe Ile Phe His His Val Pro Thr Gly
                660                 665                 670
Pro Ser Val Gly Met Tyr Ser Pro Gly Tyr Ser Glu His Ile Pro Leu
                675                 680                 685
Gly Lys Phe Tyr Asn Asn Arg Ala His Ser Asn Tyr Arg Ala Gly Met
                690                 695                 700
Ile Ile Asp Asn Gly Val Lys Thr Thr Glu Ala Ser Ala Lys Asp Lys
705                 710                 715                 720
Arg Pro Phe Leu Ser Ile Ser Ala Arg Tyr Ser Pro His Gln Asp
                725                 730                 735
Ala Asp Pro Leu Lys Pro Arg Glu Pro Ala Ile Ile Arg His Phe Ile
                740                 745                 750
Ala Tyr Lys Asn Gln Asp His Gly Ala Trp Leu Arg Gly Gly Asp Val
                755                 760                 765
Trp Leu Asp Ser Cys Arg Phe Ala Asp Asn Gly Ile Gly Leu Thr Leu
                770                 775                 780
Ala Ser Gly Gly Thr Phe Pro Tyr Asp Asp Gly Ser Lys Gln Glu Ile
785                 790                 795                 800
Lys Asn Ser Leu Phe Val Gly Glu Ser Gly Asn Val Gly Thr Glu Met
                805                 810                 815
Met Asp Asn Arg Ile Trp Gly Pro Gly Leu Asp His Ser Gly Arg
                820                 825                 830
Thr Leu Pro Ile Gly Gln Asn Phe Pro Ile Arg Gly Ile Gln Leu Tyr
                835                 840                 845
Asp Gly Pro Ile Asn Ile Gln Asn Cys Thr Phe Arg Lys Phe Val Ala
                850                 855                 860
Leu Glu Gly Arg His Thr Ser Ala Leu Ala Phe Arg Leu Asn Asn Ala
865                 870                 875                 880
Trp Gln Ser Cys Pro His Asn Asn Val Thr Gly Ile Ala Phe Glu Asp
                885                 890                 895
Val Pro Ile Thr Ser Arg Val Phe Phe Gly Glu Pro Gly Pro Trp Phe
                900                 905                 910
```

```
Asn Gln Leu Asp Met Asp Gly Asp Lys Thr Ser Val Phe His Asp Val
    915                 920                 925

Asp Gly Ser Val Ser Glu Tyr Pro Gly Ser Tyr Leu Thr Lys Asn Asp
    930                 935                 940

Asn Trp Leu Val Arg His Pro Asp Cys Ile Asn Val Pro Asp Trp Arg
945                 950                 955                 960

Gly Ala Ile Cys Ser Gly Cys Tyr Ala Gln Met Tyr Ile Gln Ala Tyr
                965                 970                 975

Lys Thr Ser Asn Leu Arg Met Lys Ile Ile Lys Asn Asp Phe Pro Ser
            980                 985                 990

His Pro Leu Tyr Leu Glu Gly Ala Leu Thr Arg Ser Thr His Tyr Gln
        995                 1000                1005

Gln Tyr Gln Pro Val Val Thr Leu Gln Lys Gly Tyr Thr Ile His Trp
    1010                1015                1020

Asp Gln Thr Ala Pro Ala Glu Leu Ala Ile Trp Leu Ile Asn Phe Asn
1025                1030                1035                1040

Lys Gly Asp Trp Ile Arg Val Gly Leu Cys Tyr Pro Arg Gly Thr Thr
                1045                1050                1055

Phe Ser Ile Leu Ser Asp Val His Asn Arg Leu Leu Lys Gln Thr Ser
            1060                1065                1070

Lys Thr Gly Val Phe Val Arg Thr Leu Gln Met Asp Lys Val Glu Gln
        1075                1080                1085

Ser Tyr Pro Gly Arg Ser His Tyr Tyr Trp Asp Glu Asp Ser Gly Leu
    1090                1095                1100

Leu Phe Leu Lys Leu Lys Ala Gln Asn Glu Arg Glu Lys Phe Ala Phe
1105                1110                1115                1120

Cys Ser Met Lys Gly Cys Glu Arg Ile Lys Ile Lys Ala Leu Ile Pro
                1125                1130                1135

Lys Asn Ala Gly Val Ser Asp Cys Thr Ala Thr Ala Tyr Pro Lys Phe
            1140                1145                1150

Thr Glu Arg Ala Val Val Asp Val Pro Met Pro Lys Lys Leu Phe Gly
        1155                1160                1165

Ser Gln Leu Lys Thr Lys Asp His Phe Leu Glu Val Lys Met Glu Ser
    1170                1175                1180

Ser Lys Gln His Phe Phe His Leu Trp Asn Asp Phe Ala Tyr Ile Glu
1185                1190                1195                1200

Val Asp Gly Lys Lys Tyr Pro Ser Ser Glu Asp Gly Ile Gln Val Val
                1205                1210                1215

Val Ile Asp Gly Asn Gln Gly Arg Val Val Ser His Thr Ser Phe Arg
            1220                1225                1230

Asn Ser Ile Leu Gln Gly Ile Pro Trp Gln Leu Phe Asn Tyr Val Ala
        1235                1240                1245

Thr Ile Pro Asp Asn Ser Ile Val Leu Met Ala Ser Lys Gly Arg Tyr
    1250                1255                1260

Val Ser Arg Gly Pro Trp Thr Arg Val Leu Glu Lys Leu Gly Ala Asp
1265                1270                1275                1280

Arg Gly Leu Lys Leu Lys Glu Gln Met Ala Phe Val Gly Phe Lys Gly
                1285                1290                1295

Ser Phe Arg Pro Ile Trp Val Thr Leu Asp Thr Glu Asp His Lys Ala
            1300                1305                1310

Lys Ile Phe Gln Val Val Pro Ile Pro Val Val Lys Lys Lys Lys Leu
        1315                1320                1325

<210> SEQ ID NO 3
```

<211> LENGTH: 732
<212> TYPE: PRT
<213> ORGANISM: Homo sapiens

<400> SEQUENCE: 3

```
Leu Gln Glu Val His Val Ser Lys Glu Thr Ile Gly Lys Ile Ser Ala
 1               5                  10                  15

Ala Ser Lys Met Met Trp Cys Ser Ala Ala Val Asp Ile Met Phe Leu
             20                  25                  30

Leu Asp Gly Ser Asn Ser Val Gly Lys Gly Ser Phe Glu Arg Ser Lys
         35                  40                  45

His Phe Ala Ile Thr Val Cys Asp Gly Leu Asp Ile Ser Pro Glu Arg
     50                  55                  60

Val Arg Val Gly Ala Phe Gln Phe Ser Ser Thr Pro His Leu Glu Phe
 65                  70                  75                  80

Pro Leu Asp Ser Phe Ser Thr Gln Gln Glu Val Lys Ala Arg Ile Lys
                 85                  90                  95

Arg Met Val Phe Lys Gly Gly Arg Thr Glu Thr Glu Leu Ala Leu Lys
            100                 105                 110

Tyr Leu Leu His Arg Gly Leu Pro Gly Gly Arg Asn Ala Ser Val Pro
        115                 120                 125

Gln Ile Leu Ile Ile Val Thr Asp Gly Lys Ser Gln Gly Asp Val Ala
    130                 135                 140

Leu Pro Ser Lys Gln Leu Lys Glu Arg Gly Val Thr Val Phe Ala Val
145                 150                 155                 160

Gly Val Arg Phe Pro Arg Trp Glu Glu Leu His Ala Leu Ala Ser Glu
                165                 170                 175

Pro Arg Gly Gln His Val Leu Leu Ala Glu Gln Val Glu Asp Ala Thr
            180                 185                 190

Asn Gly Leu Phe Ser Thr Leu Ser Ser Ser Ala Ile Cys Ser Ser Ala
        195                 200                 205

Thr Pro Asp Cys Arg Val Glu Ala His Pro Cys Glu His Arg Thr Leu
    210                 215                 220

Glu Met Val Arg Glu Phe Ala Gly Asn Ala Pro Cys Trp Arg Gly Ser
225                 230                 235                 240

Arg Arg Thr Leu Ala Val Leu Ala Ala His Cys Pro Phe Tyr Ser Trp
                245                 250                 255

Lys Arg Val Phe Leu Thr His Pro Ala Thr Cys Tyr Arg Thr Thr Cys
            260                 265                 270

Pro Gly Pro Cys Asp Ser Gln Pro Cys Gln Asn Gly Gly Thr Cys Val
        275                 280                 285

Pro Glu Gly Leu Asp Gly Tyr Gln Cys Leu Cys Pro Leu Ala Phe Gly
    290                 295                 300

Gly Glu Ala Asn Cys Ala Leu Lys Leu Ser Leu Glu Cys Arg Val Asp
305                 310                 315                 320

Leu Leu Phe Leu Leu Asp Ser Ser Ala Gly Thr Thr Leu Asp Gly Phe
                325                 330                 335

Leu Arg Ala Lys Val Phe Val Lys Arg Phe Val Arg Ala Val Leu Ser
            340                 345                 350

Glu Asp Ser Arg Ala Arg Val Gly Val Ala Thr Tyr Ser Arg Glu Leu
        355                 360                 365

Leu Val Ala Val Pro Val Gly Glu Tyr Gln Asp Val Pro Asp Leu Val
    370                 375                 380

Trp Ser Leu Asp Gly Ile Pro Phe Arg Gly Gly Pro Thr Leu Thr Gly
385                 390                 395                 400
```

```
Ser Ala Leu Arg Gln Ala Ala Glu Arg Gly Phe Gly Ser Ala Thr Arg
                405                 410                 415

Thr Gly Gln Asp Arg Pro Arg Val Val Leu Thr Glu Ser
        420                 425                 430

His Ser Glu Asp Glu Val Ala Gly Pro Ala Arg His Ala Arg Ala Arg
                435                 440                 445

Glu Leu Leu Leu Leu Gly Val Gly Ser Glu Ala Val Arg Ala Glu Leu
            450                 455                 460

Glu Glu Ile Thr Gly Ser Pro Lys His Val Met Val Tyr Ser Asp Pro
465                 470                 475                 480

Gln Asp Leu Phe Asn Gln Ile Pro Glu Leu Gln Gly Lys Leu Cys Ser
                485                 490                 495

Arg Gln Arg Pro Gly Cys Arg Thr Gln Ala Leu Asp Leu Val Phe Met
                500                 505                 510

Leu Asp Thr Ser Ala Ser Val Gly Pro Glu Asn Phe Ala Gln Met Gln
                515                 520                 525

Ser Phe Val Arg Ser Cys Ala Leu Gln Phe Glu Val Asn Pro Asp Val
            530                 535                 540

Thr Gln Val Gly Leu Val Val Tyr Gly Ser Gln Val Gln Thr Ala Phe
545                 550                 555                 560

Gly Leu Asp Thr Lys Pro Thr Arg Ala Ala Met Leu Arg Ala Ile Ser
                565                 570                 575

Gln Ala Pro Tyr Leu Gly Gly Val Gly Ser Ala Gly Thr Ala Leu Leu
            580                 585                 590

His Ile Tyr Asp Lys Val Met Thr Val Gln Arg Gly Ala Arg Pro Gly
            595                 600                 605

Val Pro Lys Ala Val Val Leu Thr Gly Gly Arg Gly Ala Glu Asp
            610                 615                 620

Ala Ala Val Pro Ala Gln Lys Leu Arg Asn Asn Gly Ile Ser Val Leu
625                 630                 635                 640

Val Val Gly Val Gly Pro Val Leu Ser Glu Gly Leu Arg Arg Leu Ala
                645                 650                 655

Gly Pro Arg Asp Ser Leu Ile His Val Ala Ala Tyr Ala Asp Leu Arg
                660                 665                 670

Tyr His Gln Asp Val Leu Ile Glu Trp Leu Cys Gly Glu Ala Lys Gln
            675                 680                 685

Pro Val Asn Leu Cys Lys Pro Ser Pro Cys Met Asn Glu Gly Ser Cys
        690                 695                 700

Val Leu Gln Asn Gly Ser Tyr Arg Cys Lys Cys Arg Asp Gly Trp Glu
705                 710                 715                 720

Gly Pro His Cys Glu Asn Arg Phe Leu Arg Arg Pro
                725                 730

<210> SEQ ID NO 4
<211> LENGTH: 4171
<212> TYPE: DNA
<213> ORGANISM: Homo sapiens

<400> SEQUENCE: 4
cgtgacactg tctcggctac agacccagag ggagcacact gccaggatgg gagctgctgg     60
gaggcaggac ttcctcttca aggccatgct gaccatcagc tggctcactc tgacctgctt    120
ccctggggcc acatccacag tggctgctgg gtgccctgac cagagccctg agttgcaacc    180
ctggaaccct ggccatgacc aagaccacca tgtgcatatc ggccagggca agacactgct    240
```

-continued

```
gctcacctct tctgccacgg tctattccat ccacatctca gagggaggca agctggtcat     300
taaagaccac gacgagccga ttgttttgcg aacccggcac atcctgattg acaacggagg     360
agagctgcat gctgggagtg ccctctgccc tttccagggc aatttcacca tcattttgta     420
tggaagggct gatgaaggta ttcagccgga tccttactat ggtctgaagt acattggggt     480
tggtaaagga ggcgctcttg agttgcatgg acagaaaaag ctctcctgga catttctgaa     540
caagaccctt cacccaggtg gcatggcaga aggaggctat ttttttgaaa ggagctgggg     600
ccaccgtgga gttattgttc atgtcatcga ccccaaatca ggcacagtca tccattctga     660
ccggtttgac acctatagat ccaagaaaga gagtgaacgt ctggtccagt atttgaacgc     720
ggtgcccgat ggcaggatcc tttctgttgc agtgaatgat gaaggttctc gaaatctgga     780
tgacatggcc aggaaggcga tgaccaaatt gggaagcaaa cacttcctgc accttggatt     840
tagacaccct tggagttttc taactgtgaa aggaaatcca tcatcttcag tggaagacca     900
tattgaatat catggacatc gaggctctgc tgctgcccgg gtattcaaat tgttccagac     960
agagcatggc gaatatttca tgtttctttt gtccagtgag tgggttcaag acgtggagtg    1020
gacggagtgg ttcgatcatg ataaagtatc tcagactaaa ggtggggaga aaatttcaga    1080
cctctggaaa gctcacccag gaaaaatatg caatcgtccc attgatatac aggccactac    1140
aatggatgga gttaacctca gcaccgaggt tgtctacaaa aaaggccagg attataggtt    1200
tgcttgctac gaccggggca gagcctgccg gagctaccgt gtacggttcc tctgtgggaa    1260
gcctgtgagg cccaaactca cagtcaccat tgacaccaat gtgaacagca ccattctgaa    1320
cttggaggat aatgtacagt catggaaacc tggagatacc ctggtcattg ccagtactga    1380
ttactccatg taccaggcag aagagttcca ggtgcttccc tgcagatcct gcgcccccaa    1440
ccaggtcaaa gtggcaggga accaatgtac cctgcacatc ggggaggaga tagacggcgt    1500
ggacatgcgg gcgagggttg ggcttctgag ccggaacatc atagtgatgg gggagatgga    1560
ggacaaatgc taccccctaca gaaaccacat ctgcaatttc tttgacttcg ataccttttgg    1620 gggccacatc aagtttgctc tgggatttaa ggcagcacac ttggagggca cggagctgaa    1680
gcatatggga cagcagctgg tgggtcagta cccgattcac ttccacctgg ccggtgatgt    1740
agacgaaagg ggaggttatg acccacccac atacatcagg gacctctcca tccatcatac    1800
attctctcgc tgcgtcacag tccatggctc caatggcttg ttgatcaagg acgttgtggg    1860
ctataactct ttgggccact gcttcttcac ggaagatggg ccggaggaac gcaacacttt    1920
tgaccactgt cttggcctcc ttgtcaagtc tggaaccctc ctcccctcgg accgtgacag    1980
caagatgtgc aagatgatca cagaggactc ctacccaggg tacatccccca agcccaggca    2040 agactgcaat gctgtgtcca ccttctggat ggccaatccc aacaacaacc tcatcaactg    2100
tgccgctgca ggatctgagg aaactggatt ttggtttatt tttcaccacg taccaacggg    2160
cccctccgtg ggaatgtact ccccaggtta ttcagagcac attccactgg gaaaattcta    2220
taacaaccga gcacattcca actaccgggc tggcatgatc atagacaacg gagtcaaaac    2280
caccgaggcc tctgccaagg acaagcggcc gttcctctca atcatctctg ccagatacag    2340
ccctcaccag gacgccgacc cgctgaagcc ccgggagccg gccatcatca gacacttcat    2400
tgcctacaag aaccaggacc acggggcctg gctgcgcggc gggatgtgt ggctggacag    2460 ctgccggttt gctgacaatg gcattggcct gaccctggcc agtggtggaa ccttcccgta    2520
tgacgacggc tccaagcaag agataaagaa cagcttgttt gttggcgaga gtggcaacgt    2580
ggggacggaa atgatggaca ataggatctg ggccctggc ggcttggacc atagcggaag    2640
```

| | |
|---|---|
| gaccctccct ataggccaga attttccaat tagaggaatt cagttatatg atggccccat | 2700 |
| caacatccaa aactgcactt tccgaaagtt tgtggccctg gagggccggc acaccagcgc | 2760 |
| cctggccttc cgcctgaata atgcctggca gagctgcccc cataacaacg tgaccggcat | 2820 |
| tgcctttgag gacgttccga ttacttccag agtgttcttc ggagagcctg ggccctggtt | 2880 |
| caaccagctg gacatggatg gggataagac atctgtgttc catgacgtcg acggctccgt | 2940 |
| gtccgagtac cctggctcct acctcacgaa gaatgacaac tggctggtcc ggcacccaga | 3000 |
| ctgcatcaat gttcccgact ggagagggc catttgcagt gggtgctatg cacagatgta | 3060 |
| cattcaagcc tacaagacca gtaacctgcg aatgaagatc atcaagaatg acttccccag | 3120 |
| ccaccctctt tacctggagg gggcgctcac caggagcacc cattaccagc aataccaacc | 3180 |
| ggttgtcacc ctgcagaagg gctacaccat ccactgggac cagacggccc ccgccgaact | 3240 |
| cgccatctgg ctcatcaact tcaacaaggg cgactggatc cgagtggggc tctgctaccc | 3300 |
| gcgaggcacc acattctcca tcctctcgga tgttcacaat cgcctgctga agcaaacgtc | 3360 |
| caagacgggc gtcttcgtga ggaccttgca gatggacaaa gtggagcaga gctaccctgg | 3420 |
| caggagccac tactactggg acgaggactc agggctgttg ttcctgaagc tgaaagctca | 3480 |
| gaacgagaga gagaagtttg ctttctgctc catgaaaggc tgtgagagga taaagattaa | 3540 |
| agctctgatt ccaaagaacg caggcgtcag tgactgcaca gccacagctt accccaagtt | 3600 |
| caccgagagg gctgtcgtag acgtgccgat gcccaagaag ctctttggtt ctcagctgaa | 3660 |
| aacaaaggac catttcttgg aggtgaagat ggagagttcc aagcagcact tcttccacct | 3720 |
| ctggaacgac ttcgcttaca ttgaagtgga tgggaagaag taccccagtt cggaggatgg | 3780 |
| catccaggtg gtggtgattg acgggaacca agggcgcgtg gtgagccaca cgagcttcag | 3840 |
| gaactccatt ctgcaaggca taccatggca gcttttcaac tatgtggcga ccatccctga | 3900 |
| caattccata gtgcttatgg catcaaaggg aagatacgtc tccagaggcc catggaccag | 3960 |
| agtgctggaa aagcttgggg cagacagggg tctcaagttg aaagagcaaa tggcattcgt | 4020 |
| tggcttcaaa ggcagcttcc ggcccatctg ggtgacactg gacactgagg atcacaaagc | 4080 |
| caaaatcttc caagttgtgc ccatccctgt ggtgaagaag aagaagttgt gaggacagct | 4140 |
| gccgcccggt gccacctcgt ggtagactat g | 4171 |

<210> SEQ ID NO 5
<211> LENGTH: 2810
<212> TYPE: DNA
<213> ORGANISM: Homo sapiens

<400> SEQUENCE: 5

| | |
|---|---|
| gcccctggc ccgagccgcg cccgggtctg tgagtagagc cgcccgggca ccgagcgctg | 60 |
| gtcgccgctc tccttccgtt atatcaacat gccccctttc ctgttgctgg aagccgtctg | 120 |
| tgttttcctg ttttccagag tgccccatc tctccctctc caggaagtcc atgtaagcaa | 180 |
| agaaaccatc gggaagattt cagctgccag caaaatgatg tggtgctcgg ctgcagtgga | 240 |
| catcatgttt ctgttagatg ggtctaacag cgtcggaaa gggagctttg aaaggtccaa | 300 |
| gcactttgcc atcacagtct gtgacggtct ggacatcagc cccgagaggg tcagagtggg | 360 |
| agcattccag ttcagttcca ctcctcatct ggaattcccc ttggattcat tttcaaccca | 420 |
| acaggaagtg aaggcaagaa tcaagaggat ggttttcaaa ggagggcgca cggagacgga | 480 |
| acttgctctg aaataccttc tgcacagagg gttgctggga ggcagaaatg cttctgtgcc | 540 |
| ccagatcctc atcatcgtca ctgatgggaa gtcccagggg gatgtggcac tgccatccaa | 600 |

```
gcagctgaag gaaaggggtg tcactgtgtt tgctgtgggg gtcaggtttc ccaggtggga    660
ggagctgcat gcactggcca gcgagcctag agggcagcac gtgctgttgg ctgagcaggt    720
ggaggatgcc accaacggcc tcttcagcac cctcagcagc tcggccatct gctccagcgc    780
cacgccagac tgcagggtcg aggctcaccc ctgtgagcac aggacgctgg agatggtccg    840
ggagttcgct ggcaatgccc catgctggag aggatcgcgg cggacccttg cggtgctggc    900
tgcacactgt cccttctaca gctggaagag agtgttccta acccaccctg ccacctgcta    960
caggaccacc tgcccaggcc cctgtgactc gcagccctgc cagaatggag gcacatgtgt   1020
tccagaagga ctggacggct accagtgcct ctgcccgctg gcctttggag gggaggctaa   1080
ctgtgccctg aagctgagcc tggaatgcag ggtcgacctc ctcttcctgc tggacagctc   1140
tgcgggcacc actctggacg gcttcctgcg gccaaagtc ttcgtgaagc ggtttgtgcg   1200
ggccgtgctg agcgaggact ctcgggcccg agtgggtgtg ccacataca gcagggagct   1260 gctggtggcg gtgcctgtgg gggagtacca ggatgtgcct gacctggtct ggagcctcga   1320
tggcattccc ttccgtggtg gccccaccct gacgggcagt gccttgcggc aggcggcaga   1380
gcgtggcttc gggagcgcca ccaggacagg ccaggaccgg ccacgtagag tggtggtttt   1440
gctcactgag tcacactccg aggatgaggt tgcgggccca gcgcgtcacg caagggcgcg   1500
agagctgctc ctgctgggtg taggcagtga ggccgtgcgg gcagagctgg aggagatcac   1560
aggcagccca aagcatgtga tggtctactc ggatcctcag gatctgttca accaaatccc   1620
tgagctgcag gggaagctgt gcagccggca gcggccaggg tgccggacac aagccctgga   1680
cctcgtcttc atgttggaca cctctgcctc agtagggccc gagaattttg ctcagatgca   1740
gagctttgtg agaagctgtg ccctccagtt tgaggtgaac cctgacgtga cacaggtcgg   1800
cctggtggtg tatggcagcc aggtgcagac tgccttcggg ctggacacca aacccacccg   1860
ggctgcgatg ctgcgggcca ttagccaggc cccctaccta ggtggggtgg gctcagccgg   1920
caccgccctg ctgcacatct atgacaaagt gatgaccgtc cagaggggtg cccggcctgg   1980
tgtccccaaa gctgtggtgg tgctcacagg cgggagaggc gcagaggatg cagccgttcc   2040
tgcccagaag ctgaggaaca atggcatctc tgtcttggtc gtgggcgtgg ggcctgtcct   2100
aagtgagggt ctgcggaggc ttgcaggtcc ccgggattcc ctgatccacg tggcagctta   2160
cgccgacctg cggtaccacc aggacgtgct cattgagtgg ctgtgtggag aagccaagca   2220
gccagtcaac ctctgcaaac ccagccgtg catgaatgag ggcagctgcg tcctgcagaa   2280
tgggagctac cgctgcaagt gtcgggatgg ctgggagggc ccccactgcg agaaccgatt   2340
cttgagacgc ccctgaggca catggctccc gtgcaggagg gcagcagccg taccccctccc   2400 agcaactaca gagaaggcct gggcactgaa atggtgccta ccttctggaa tgtctgtgcc   2460
ccaggtcctt agaatgtctg cttcccgccg tggccaggac cactattctc actgagggag   2520
gaggatgtcc caactgcagc catgctgctt agagacaaga aagcagctga tgtcacccac   2580
aaacgatgtt gttgaaaagt tttgatgtgt aagtaaatac ccactttctg tacctgctgt   2640
gccttgttga ggctatgtca tctgccacct ttcccttgag gataaacaag gggtcctgaa   2700
gacttaaatt tagcggcctg acgttccttt gcacacaatc aatgctcgcc agaatgttgt   2760
tgacacagta atgcccagca gaggccttta ctagagcatc ctttggacgg              2810
```

<210> SEQ ID NO 6
<211> LENGTH: 1524
<212> TYPE: DNA
<213> ORGANISM: Homo sapiens

<400> SEQUENCE: 6

```
gcagagcaca gcatcgtcgg gaccagactc gtctcaggcc agttgcagcc ttctcagcca      60
aacgccgacc aaggaaaact cactaccatg agaattgcag tgatttgctt ttgcctccta     120
ggcatcacct gtgccatacc agttaaacag gctgattctg gaagttctga ggaaaagcag     180
ctttacaaca ataccagga tgctgtggcc acatggctaa accctgaccc atctcagaag     240
cagaatctcc tagccccaca gacccttcca gtaagtcca acgaaagcca tgaccacatg     300
gatgatatgg atgatgaaga tgatgatgac catgtggaca gccaggactc cattgactcg     360
aacgactctg atgatgtaga tgacactgat gattctcacc agtctgatga gtctcaccat     420
tctgatgaat ctgatgaact ggtcactgat tttcccacgg acctgccagc aaccgaagtt     480
ttcactccag ttgtccccac agtagacaca tatgatggcc gaggtgatag tgtggtttat     540
ggactgaggt caaaatctaa gaagtttcgc agacctgaca tccagtaccc tgatgctaca     600
gacgaggaca tcacctcaca catggaaagc gaggagttga atggtgcata caaggccatc     660
cccgttgccc aggacctgaa cgcgccttct gattgggaca gccgtgggaa ggacagttat     720
gaaacgagtc agctggatga ccagagtgct gaaacccaca gccacaagca gtccagatta     780
tataagcgga aagccaatga tgagagcaat gagcattccg atgtgattga tagtcaggaa     840
cttttccaaag tcagccgtga attccacagc catgaatttc acagccatga agatatgctg     900
gttgtagacc ccaaaagtaa ggaagaagat aaacacctga atttcgtat ttctcatgaa     960
ttagatagtg catcttctga ggtcaattaa aaggagaaaa aatacaattt ctcactttgc    1020
atttagtcaa aagaaaaaat gctttatagc aaaatgaaag agaacatgaa atgcttcttt    1080
ctcagtttat tggttgaatg tgtatctatt tgagtctgga aataactaat gtgtttgata    1140
attagtttag tttgtggctt catggaaact ccctgtaaac taaaagcttc agggttatgt    1200
ctatgttcat tctatagaag aaatgcaaac tatcactgta ttttaatatt tgttattctc    1260
tcatgaatag aaatttatgt agaagcaaac aaaatacttt tacccactta aaagagaat     1320
ataacatttt atgtcactat aatcttttgt tttttaagtt agtgtatatt ttgttgtgat    1380
tatcttttg tggtgtgaat aaatcttta tcttgaatgt aataagaatt tggtggtgtc      1440
aattgcttat ttgttttccc acggttgtcc agcaattaat aaaacataac ctttttact     1500
gcctaaaaaa aaaaaaaaa aaaa                                             1524
```

<210> SEQ ID NO 7
<211> LENGTH: 3205
<212> TYPE: DNA
<213> ORGANISM: Homo sapiens

<400> SEQUENCE: 7

```
aaagggggcaa gagctgagcg gaacaccggc ccgccgtcgc ggcagctgct tcaccctct      60
ctctgcagcc atgggctcc ctcgtggacc tctcgcgtct ctcctcttc tccaggtttg     120
ctggctgcag tgcgcggcct ccgagccgtg ccggcggtc ttcagggagg ctgaagtgac     180
cttggaggcg ggaggcgcgg agcaggagcc cggccaggcg ctggggaaag tattcatggg     240
ctgccctggg caagagccag ctctgtttag cactgataat gatgacttca ctgtgcggaa     300
tggcgagaca gtccaggaaa gaaggtcact gaaggaaagg aatccattga agatcttccc     360
atccaaacgt atcttacgaa gacacaagag agattgggtg gttgctccaa tatctgtccc     420
tgaaaatggc aagggtccct tcccccagag actgaatcag ctcaagtcta ataaagatag     480
agacaccaag atttttctaca gcatcacggg gccgggggca gacagccccc ctgagggtgt     540
```

```
cttcgctgta gagaaggaga caggctggtt gttgttgaat aagccactgg accgggagga    600
gattgccaag tatgagctct ttggccacgc tgtgtcagag aatggtgcct cagtggagga    660
ccccatgaac atctccatca tcgtgaccga ccagaatgac cacaagccca agtttaccca    720
ggacaccttc cgagggagtg tcttagaggg agtcctacca ggtacttctg tgatgcaggt    780
gacagccacg gatgaggatg atgccatcta cacctacaat ggggtggttg cttactccat    840
ccatagccaa gaaccaaagg acccacacga cctcatgttc accattcacc ggagcacagg    900
caccatcagc gtcatctcca gtggcctgga ccgggaaaaa gtccctgagt acacactgac    960
catccaggcc acagacatgg atggggacgg ctccaccacc acggcagtgg cagtagtgga   1020
gatccttgat gccaatgaca atgctcccat gtttgacccc cagaagtacg aggcccatgt   1080
gcctgagaat gcagtgggcc atgaggtgca gaggctgacg gtcactgatc tggacgcccc   1140
caactcacca gcgtggcgtg ccacctacct tatcatgggc ggtgacgacg ggaccatttt   1200
taccatcacc acccacccctg agagcaacca gggcatcctg acaaccagga agggtttgga   1260
ttttgaggcc aaaaaccagc acaccctgta cgttgaagtg accaacgagg ccccttttgt   1320
gctgaagctc ccaacctcca cagccaccat agtggtccac gtggaggatg tgaatgaggc   1380
acctgtgttt gtcccaccct ccaaagtcgt tgaggtccag gagggcatcc ccactgggga   1440
gcctgtgtgt gtctacactg cagaagaccc tgacaaggag aatcaaaaga tcagctaccg   1500
catcctgaga gacccagcag ggtggctagc catggaccca gacagtgggc aggtcacagc   1560
tgtgggcacc ctcgaccgtg aggatgagca gtttgtgagg aacaacatct atgaagtcat   1620
ggtcttggcc atggacaatg gaagccctcc caccactggc acgggaaccc ttctgctaac   1680
actgattgat gtcaatgacc atggcccagt ccctgagccc cgtcagatca ccatctgcaa   1740
ccaaagccct gtgcgccagg tgctgaacat cacggacaag gacctgtctc cccacacctc   1800 cccttttccag gcccagctca cagatgactc agacatctac tggacggcag aggtcaacga   1860
ggaaggtgac acagtggtct tgtccctgaa gaagttcctg aagcaggata catatgacgt   1920 gcaccttttct ctgtctgacc atggcaacaa agagcagctg acggtgatca gggccactgt   1980
gtgcgactgc catggccatg tcgaaacctg ccctggaccc tggaagggag gtttcatcct   2040
ccctgtgctg ggggctgtcc tggctctgct gttcctcctg ctggtgctgc ttttgttggt   2100
gagaaagaag cggaagatca aggagcccct cctactccca gaagatgaca cccgtgacaa   2160
cgtcttctac tatggcgaag agggggtgg cgaagaggac caggactatg acatcacccca   2220 gctccaccga ggtctggagg ccaggccgga ggtggttctc cgcaatgacg tggccaccaa   2280
catcatcccg acacccatgt accgtcctcg gccagccaac ccagatgaaa tcggcaactt   2340
tataattgag aacctgaagg cggctaacac agaccccaca gccccgccct acgacaccct   2400
cttggtgttc gactatgagg gcagcggctc cgacgccgcg tccctgagct ccctcacctc   2460
ctccgcctcc gaccaagacc aagattacga ttatctgaac gagtggggca ccgcttcaa    2520 gaagctggca gacatgtacg gtggcgggga ggacgactag gcggcctgcc tgcagggctg   2580
gggaccaaac gtcaggccac agagcatctc caagggtctc cagttccccc ttcagctgag   2640
gacttcggag cttgtcagga agtggccgta gcaacttggc ggagacaggc tatgagtctg   2700
acgttagagt ggttgcttcc ttagccttc aggatggagg aatgtgggca gtttgacttc    2760
agcactgaaa acctctccac ctgggccagg gttgcctcag aggccaagtt ccagaagcc    2820 tcttacctgc cgtaaaatgc tcaaccctgt gtcctgggcc tgggcctgct gtgactgacc   2880
tacagtggac tttctctctg gaatggaacc ttcttaggcc tcctggtgca acttaatttt   2940
```

| | | | | |
|---|---|---|---|---|
| tttttttaat | gctatcttca | aaacgttaga | gaaagttctt | caaaagtgca | gcccagagct | 3000 |
| gctgggccca | ctggccgtcc | tgcatttctg | gtttccagac | cccaatgcct | cccattcgga | 3060 |
| tggatctctg | cgttttttata | ctgagtgtgc | ctaggttgcc | ccttattttt | tatttttccct | 3120 |
| gttgcgttgc | tatagatgaa | gggtgaggac | aatcgtgtat | atgtactaga | acttttttat | 3180 |
| taaagaaact | tttcccagaa | aaaaa | | | | 3205 |

<210> SEQ ID NO 8
<211> LENGTH: 2603
<212> TYPE: DNA
<213> ORGANISM: Homo sapiens

<400> SEQUENCE: 8

| | | | | | |
|---|---|---|---|---|---|
| atgaagcacc | tgaagcggtg | gtggtcggcc | ggcggcggcc | tcctgcacct | caccctcctg | 60 |
| ctgagcttgg | cggggctccg | cgtagaccta | gatctttacc | tgctgctgcc | gccgcccacc | 120 |
| ctgctgcagg | acgagctgct | gttcctgggc | ggcccggcca | gctccgccta | cgcgctcagc | 180 |
| cccttctcgg | cctcgggagg | gtgggggcgc | gcgggccact | gcaccccaa | gggccgggag | 240 |
| ctggaccctg | ccgcgccgcc | cgagggccag | ctgctccggg | aggtgcgcgc | gctcggggtc | 300 |
| cccttcgtcc | ctcgcaccag | cgtggatgca | tggctggtgc | acagcgtggc | tgccgggagc | 360 |
| gcggacgagg | cccacgggct | gctcggccgcc | gccgccgcct | cgtccaccgg | aggagccggc | 420 |
| gccagcgtgg | acggcggcag | ccaggctgtg | caggggggcg | gcggggaccc | ccgagcggct | 480 |
| cggagtggcc | ccttggacgc | cggggaagag | gagaaggcac | ccgcggaacc | gacggctcag | 540 |
| gtgccggacg | ctggcggatg | tgcgagcgag | gagaatgggg | tactaagaga | aaagcacgaa | 600 |
| gctgtggatc | atagttccca | gcatgaggaa | aatgaagaaa | gggtgtcagc | ccagaaggag | 660 |
| aactcacttc | agcagaatga | tgatgatgaa | acaaaatag | cagagaaacc | tgactgggag | 720 |
| gcagaaaaga | ccactgaatc | tagaaatgag | agacatctga | atgggacaga | tacttctttc | 780 |
| tctctggaag | acttattcca | gttgctttca | tcacagcctg | aaaattcact | ggagggcatc | 840 |
| tcattgggag | atattcctct | tccaggcagt | atcagtgatg | gcatgaattc | ttcagcacat | 900 |
| tatcatgtaa | acttcagcca | ggctataagt | caggatgtga | atcttcatga | ggccatcttg | 960 |
| ctttgtccca | caatacatt | tagaagagat | ccaacagcaa | ggacttcaca | gtcacaagaa | 1020 |
| ccatttctgc | agttaaattc | tcataccacc | aatcctgagc | aaacccttcc | tggaactaat | 1080 |
| ttgacaggat | ttcttcacc | ggttgacaat | catatgagga | atctaacaag | ccaagaccta | 1140 |
| ctgtatgacc | ttgacataaa | tatttgat | gagataaact | taatgtcatt | ggccacagaa | 1200 |
| gacaactttg | atccaatcga | tgtttctcag | cttttgatg | aaccagattc | tgattctggc | 1260 |
| ctttctttag | attcaagtca | caataatacc | tctgtcatca | gtctaattc | ctctcactct | 1320 |
| gtgtgtgatg | aaggtgctat | aggttattgc | actgaccatg | aatctagttc | ccatcatgac | 1380 |
| ttagaaggtg | ctgtaggtgg | ctactaccca | gaacccagta | agctttgtca | cttggatcaa | 1440 |
| agtgattctg | atttccatgg | agatcttaca | tttcaacacg | tatttcataa | ccacacttac | 1500 |
| cacttacagc | caactgcacc | agaatctact | tctgaacctt | ttccgtggcc | tgggaagtca | 1560 |
| cagaagataa | ggagtagata | ccttgaagac | acagatagaa | acttgagccg | tgatgaacag | 1620 |
| cgtgctaaag | ctttgcatat | ccctttttct | gtagatgaaa | ttgtcggcat | gcctgttgat | 1680 |
| tctttcaata | gcatgttaag | tagatattat | ctgacagacc | tacaagtctc | acttatccgt | 1740 |
| gacatcagac | gaagagggaa | aaataaagtt | gctgcgcaga | actgtcgtaa | acgcaaattg | 1800 |
| gacataattt | tgaatttaga | agatgatgta | tgtaacttgc | aagcaaagaa | ggaaactctt | 1860 |

-continued

```
aagagagagc aagcacaatg taacaaagct attaacataa tgaaacagaa actgcatgac    1920
ctttatcatg atattttag tagattaaga gatgaccaag gtaggccagt caatcccaac     1980
cactatgctc tccagtgtac ccatgatgga agtatcttga tagtacccaa agaactggtg   2040
gcctcaggcc acaaaaagga aacccaaaag ggaaagagaa agtgagaaga aactgaagat   2100
ggactctatt atgtgaagta gtaatgttca gaaactgatt atttggatca gaaaccattg   2160
aaactgcttc aagaattgta tctttaagta ctgctacttg aataactcag ttaacgctgt   2220
tttgaagctt acatggacaa atgtttagga cttcaagatc acacttgtgg gcaatctggg   2280
ggagccacaa cttttcatga agtgcattgt atacaaaatt catagttatg tccaaagaat   2340
aggttaacat gaaaacccag taagactttc catcttggca gccatccttt ttaagagtaa   2400
gttggttact tcaaaaagag caaacactgg ggatcaaatt attttaagag gtatttcagt   2460
tttaaatgca aaatagcctt attttcattt agtttgttag cactatagtg agcttttcaa   2520
acactatttt aatctttata tttaacttat aaattttgct ttctatggaa ataaattttg   2580
tatttgtatt aaaaaaaaaa aaa                                          2603
```

<210> SEQ ID NO 9
<211> LENGTH: 1209
<212> TYPE: DNA
<213> ORGANISM: Homo sapiens
<220> FEATURE:
<221> NAME/KEY: misc_feature
<222> LOCATION: 1161
<223> OTHER INFORMATION: n = A,T,C or G

<400> SEQUENCE: 9

```
atgaagttgg aggtgttcgt ccctcgcgcg gcccacgggg acaagcaggg cagtgacctg     60
gagggcgcgg gcggcagcga cgcgccgtcc ccgctgtcgg cggcgggaga cgactccctg    120
ggctcagatg gggactgcgc ggccaagccg tccgcgggcg gcggcgccag agatacgcag    180
ggcgacggcg aacagagtgc gggaggcggg ccggcgcgg aggaggcgat cccggcagca    240
gctgctgcag cggtggtggc ggagggcgcg gaggccgggg cggcggggcc aggcgcgggc    300
ggcgcgggga gcggcgaggg tgcacgcagc aagccatata cgcggcggcc caagcccccc    360
tactcgtaca tcgcgctcat cgccatggcc atccgcgact cggcgggcgg gcgcttgacg    420
ctggcggaga tcaacgagta cctcatgggc aagttccct ttttccgcgg cagctacacg    480
ggctggcgca actccgtgcg ccacaacctt tcgctcaacg actgcttcgt caaggtgctg    540
cgcgacccct cgcggccctg gggcaaggac aactactgga tgctcaaccc caacagcgag    600
tacaccttcg ccgacggggt cttccgccgc cgccgcaagc gcctcagcca ccgcgcgccg    660
gtccccgcgc ccgggctgcg gcccgaggag gccccgggcc tccccgccgc ccgccgccc    720 gcgcccgccg ccccggcctc gcccgcatg cgctcgcccg ccgccagga ggagcgcgcc     780 agccccgcgg gcaagttctc cagctccttc gccatcgaca gcatcctgcg caagcccttc   840
cgcagccgtc gcctcaggga cacggccccc gggacgacgc ttcagtgggg cgccgcgccc   900
tgcccgccgc tgcccgcgtt ccccgcgctc ctccccgcgg cgcccctgcag ggccctgctg   960 ccgctctgcg cgtacggcgc gggcgagccg gcgcggctgg gcgcgcgcga ggccgaggtg   1020
ccaccgaccg cgccgcccct cctgcttgca cctctcccgg cggcggcccc cgccaagcca   1080
ctccgaggcc cggcggccgg cggcgcgcac ctgtactgcc cctgcggct gccgcagcc    1140 ctgcaggcgg ccttagtccg ncgtcctggc ccgcacctgt cgtacccggt ggagacgctc   1200
ctagcttga                                                          1209
```

```
<210> SEQ ID NO 10
<211> LENGTH: 1474
<212> TYPE: DNA
<213> ORGANISM: Homo sapiens

<400> SEQUENCE: 10
ggcagatgaa atataagatt catcaaccac atttgacagc ccatggcagg tttcctgttt       60
tccatcgtcc ctctgcaggt cacagacaca cagagcccag ccgtggcagg ctcagccggg      120
gtccggggct gctaacaacg gctacattcc tcccccaggg ccaagggaaa tcctgagcgc      180
aggccagggt tgtttggttt tgaggtgtgc tgggatgaaa ggcaccctgg aagtggaagg      240
ttcggtcatt cattaattaa ttacatctat aattgagggt tgttcttaa gagcgagtcc       300 tttgaaagta ctttccttca aacagtgact gccacaaagg catcagatat tcaccacctt      360
ctcggctgcc tcagcacagc aagctttatt ctgggacctg agatcctgtt ctgagctggc      420
tttcccttct ccaggctcgc tcaccctccc tttagagata gtggatggta agatgaccaa      480
tgctcagatt attcttctca ttgacaatgc caggatggca gtggatgact caacctcaa       540 gaaatggaga agcatcatgt gccaagtgac ttcaatgtca atgtgaaggt ggatacaggt      600
cccagggaag atctgattaa ggtcctggag gatatgagac aagaatatga gcttataata      660
aagaagaagc atcgagactt ggacacttgg tataaagaac agtctgcagc catgtcccag      720
gaggcagcca gtccagccac tgtgcagagc agacaaggtg acatccacga actgaagcgc      780
acattccagg ccctggagat tgacctgcag gcacagtaca gcacgaaatc tgctttggaa      840
aacatgttat ccgagaccca gtctcggtac tcctgcaagc tccaggacat gcaagagatc      900
atctcccact atgaggagga actgacgcag ctacgccacg aactggagcg gcagaacaat      960
gaataccaag tgctgctggg catcaaaacc cacctggaga aggaaatcac cacgtaccga     1020
cggctcctgg agggagagag tgaagggaca cgggaagaat caagtcgag catgaaagtg      1080 tctgcaactc caaagatcaa ggccataacc caggagacca tcaacggaag attagttctt     1140
tgtcaagtga tgaaatcca aaagcacgca tgagaccaat gaaagtttcc gcctgttgta     1200
aaatctattt tccccccaagg aaagtccttg cacagacacc agtgagtgag ttctaaaaga     1260 taccccttgga attatcagac tcagaaactt ttattttttt tttctgtaac agtctcacca     1320
gacttctcat aatgctctta atatattgca cttttctaat caaagtgcga gtttatgagg     1380
gtaaagctct actttcctac tgcagccttc agattctcat cattttgcat ctattttgta     1440
gccaataaaa ctccgcacta gcaaaaaaaa aaaa                                 1474

<210> SEQ ID NO 11
<211> LENGTH: 411
<212> TYPE: DNA
<213> ORGANISM: Homo sapiens

<400> SEQUENCE: 11
tttttttttt aaaaaaagag gcttggtaag ttttgatgc ttagttgact tttagcatta       60
tccagcattt gtattatgaa ccagtgagta ctgtaatttt tctttccctt tcagaaagac      120
tcaaagggaa catataaatg tttcctatt ttaatgtggc aatagtgtag ctaacactgg       180
tacagacgga ataacacac ctctaatatt ctcctgaaga tttggtgatc cagtttcaaa       240
taaggtatgg gaaaaacaga tgttttcatt atcgccactt aatccttact tccgattata      300
attatacatg tttggctgta ataactatac taaagcatgc ttgtgaaagt agacttctac      360
aaggacagaa aacccacaac aacaaagatc gatcacgaaa gacaaggcat a               411
```

<210> SEQ ID NO 12
<211> LENGTH: 2336
<212> TYPE: DNA
<213> ORGANISM: Homo sapiens

<400> SEQUENCE: 12

```
cttttcttcc gcacggttgg aggaggtcgg ctggttatcg ggagttggag ggctgaggtc      60
gggagggtgg tgtgtacaga gctctaggac tcacgcacca ggccagtcgc ggattttggg     120
ccgaggcctg ggttacaagc agcaagtgcg cggttggggc cactgcgagg ccgttttaga     180
aaactgttta aaacaaagag caattgatgg ataaatcagg aatagattct cttgaccatg     240
tgacatctga tgctgtggaa cttgcaaatc gaagtgataa ctcttctgat agcagcttat     300
ttaaaactca gtgtatccct tactcaccta aggggagaa aagaaacccc attcgaaaat     360
ttgttcgtac acctgaaagt gttcacgcaa gtgattcatc aagtgactca tcttttgaac     420
caataccatt gactataaaa gctattttg aaagattcaa gaacaggaaa aagagatata     480
aaaaaagaa aaagaggagg taccagccaa caggaagacc acggggaaga ccagaaggaa     540
ggagaaatcc tatatactca ctaatagata agaagaaaca atttagaagc agaggatctg     600
gcttcccatt tttagaatca gagaatgaaa aaaacgcacc ttggagaaaa attttaacgt     660
ttgagcaagc tgttgcaaga ggattttta actatattga aaagctgaag tatgaacacc     720
acctgaaaga atcattgaag caaatgaatg ttggtgaaga tttagaaaat gaagattttg     780
acagtcgtag atacaaattt ttggatgatg atggatccat ttctcctatt gaggagtcaa     840
cagcagagga tgaggatgca acacatcttg aagataacga atgtgatatc aaattggcag     900
gggatagttt catagtaagt tctgaattcc ctgtaagact gagtgtatac ttagaagaag     960
aggatattac tgaagaagct gctttgtcta aaaagagagc tacaaaagcc aaaaatactg    1020
gacagagagg cctgaaaatg tgacaggatc atgaatgtca aaggctttta tcttgagaac    1080
atggtgtctg gagttaaagg tattggcata ctccacacat ctgtaccatt cttgagtgat    1140
cgcttaggaa tgaatgtgat ttgaactcat tcatgttgag agggtgtcaa attgagaacc    1200
aggtagatcc ccaccaccta cagtaaaaag gaccctaaag taaattggtt gaagaaatta    1260
gatcccaaag attcttggtg aattttgaag tcttcatcag tatatccata ttaaaacgag    1320
atgacagaag ccaaagtaat tatggcaagt aatggttttt atcttaacta taagttattt    1380
gctcaagggt gtaatggtca ttaccaaggc ttttagaatg cagtttctca tttgctgtgg    1440
acatgaccat aaaaaaaaat ttcccagtag gtttttctatc tgctacgttg ctagcaatca    1500
gcttattggg aacagttgat taactgtaat agaaatgcaa tacaaataaa atgtgaacca    1560
catgtgattt ttctttaaaa tcagtgagat ttgaaaattc tcctagatct cttgaatcat    1620
gcaaatttgc tttgccttta tattgtaacc cttgtgggtt gctaataacc aagcagtttg    1680
tagtagagtt aactcaggct cgttctaggg actcattcat gttcactcac tgtacactca    1740
tctctggaaa tgtaaaattt acttttatac tattgttatg tagggctgac aggacaactg    1800
gatcagtttc attaaaaagg tatgtatgca ttagaaaaga catttgtatg ggtcatttca    1860
aagagggctt atgaggctgt gaaacccaga gctcttaacg ctgtgaccaa agatggaagt    1920
tctctatagg aagccatagc actcctaatg tttggtgcta tgttttcctg aggagatata    1980
aaacgtaata atccatgatt gttgccatgt gagagtttta aaggttaatc aaaatttctc    2040
ttcttcaggg caaacttgaa gataaatctt ttgactccag ctctttagag gatctaaagt    2100
gaccttgatg gacagtggaa gaaatcacaa catggaattc ctcgaataac aatttattga    2160
```

-continued

```
ctttaaataa ttttgtctaa tgctacatat acacaattaa aaaacctta cactatttct    2220 agaaagtcag catgtatttt tggctcgaag tttctctagt gttttctgtg gaaggaataa    2280
aaatttgagt ttcaaaaaaa aaaaaaaaaa aaaaaaaaaa aaaaaaaaaa aaaaaa       2336
```

<210> SEQ ID NO 13
<211> LENGTH: 1361
<212> TYPE: PRT
<213> ORGANISM: Homo sapiens

<400> SEQUENCE: 13

```
Met Gly Ala Ala Gly Arg Gln Asp Phe Leu Phe Lys Ala Met Leu Thr
 1               5                  10                  15

Ile Ser Trp Leu Thr Leu Thr Cys Phe Pro Gly Ala Thr Ser Thr Val
            20                  25                  30

Ala Ala Gly Cys Pro Asp Gln Ser Pro Glu Leu Gln Pro Trp Asn Pro
        35                  40                  45

Gly His Asp Gln Asp His His Val His Ile Gly Gln Gly Lys Thr Leu
    50                  55                  60

Leu Leu Thr Ser Ser Ala Thr Val Tyr Ser Ile His Ile Ser Glu Gly
65                  70                  75                  80

Gly Lys Leu Val Ile Lys Asp His Asp Glu Pro Ile Val Leu Arg Thr
                85                  90                  95

Arg His Ile Leu Ile Asp Asn Gly Gly Glu Leu His Ala Gly Ser Ala
            100                 105                 110

Leu Cys Pro Phe Gln Gly Asn Phe Thr Ile Ile Leu Tyr Gly Arg Ala
        115                 120                 125

Asp Glu Gly Ile Gln Pro Asp Pro Tyr Tyr Gly Leu Lys Tyr Ile Gly
    130                 135                 140

Val Gly Lys Gly Gly Ala Leu Glu Leu His Gly Gln Lys Lys Leu Ser
145                 150                 155                 160

Trp Thr Phe Leu Asn Lys Thr Leu His Pro Gly Gly Met Ala Glu Gly
                165                 170                 175

Gly Tyr Phe Phe Glu Arg Ser Trp Gly His Arg Gly Val Ile Val His
            180                 185                 190

Val Ile Asp Pro Lys Ser Gly Thr Val Ile His Ser Asp Arg Phe Asp
        195                 200                 205

Thr Tyr Arg Ser Lys Lys Glu Ser Glu Arg Leu Val Gln Tyr Leu Asn
    210                 215                 220

Ala Val Pro Asp Gly Arg Ile Leu Ser Val Ala Val Asn Asp Glu Gly
225                 230                 235                 240

Ser Arg Asn Leu Asp Asp Met Ala Arg Lys Ala Met Thr Lys Leu Gly
                245                 250                 255

Ser Lys His Phe Leu His Leu Gly Phe Arg His Pro Trp Ser Phe Leu
            260                 265                 270

Thr Val Lys Gly Asn Pro Ser Ser Val Glu Asp His Ile Glu Tyr
        275                 280                 285

His Gly His Arg Gly Ser Ala Ala Ala Arg Val Phe Lys Leu Phe Gln
    290                 295                 300

Thr Glu His Gly Glu Tyr Phe Asn Val Ser Leu Ser Ser Glu Trp Val
305                 310                 315                 320

Gln Asp Val Glu Trp Thr Glu Trp Phe Asp His Asp Lys Val Ser Gln
                325                 330                 335

Thr Lys Gly Gly Glu Lys Ile Ser Asp Leu Trp Lys Ala His Pro Gly
            340                 345                 350
```

```
Lys Ile Cys Asn Arg Pro Ile Asp Ile Gln Ala Thr Thr Met Asp Gly
        355                 360                 365

Val Asn Leu Ser Thr Glu Val Val Tyr Lys Lys Gly Gln Asp Tyr Arg
        370                 375                 380

Phe Ala Cys Tyr Asp Arg Gly Arg Ala Cys Arg Ser Tyr Arg Val Arg
385                 390                 395                 400

Phe Leu Cys Gly Lys Pro Val Arg Pro Lys Leu Thr Val Thr Ile Asp
                405                 410                 415

Thr Asn Val Asn Ser Thr Ile Leu Asn Leu Glu Asp Asn Val Gln Ser
                420                 425                 430

Trp Lys Pro Gly Asp Thr Leu Val Ile Ala Ser Thr Asp Tyr Ser Met
            435                 440                 445

Tyr Gln Ala Glu Glu Phe Gln Val Leu Pro Cys Arg Ser Cys Ala Pro
        450                 455                 460

Asn Gln Val Lys Val Ala Gly Lys Pro Met Tyr Leu His Ile Gly Glu
465                 470                 475                 480

Glu Ile Asp Gly Val Asp Met Arg Ala Glu Val Gly Leu Leu Ser Arg
                485                 490                 495

Asn Ile Ile Val Met Gly Glu Met Glu Asp Lys Cys Tyr Pro Tyr Arg
                500                 505                 510

Asn His Ile Cys Asn Phe Phe Asp Phe Asp Thr Phe Gly Gly His Ile
            515                 520                 525

Lys Phe Ala Leu Gly Phe Lys Ala Ala His Leu Glu Gly Thr Glu Leu
        530                 535                 540

Lys His Met Gly Gln Gln Leu Val Gly Gln Tyr Pro Ile His Phe His
545                 550                 555                 560

Leu Ala Gly Asp Val Asp Glu Arg Gly Gly Tyr Asp Pro Pro Thr Tyr
                565                 570                 575

Ile Arg Asp Leu Ser Ile His His Thr Phe Ser Arg Cys Val Thr Val
                580                 585                 590

His Gly Ser Asn Gly Leu Leu Ile Lys Asp Val Val Gly Tyr Asn Ser
            595                 600                 605

Leu Gly His Cys Phe Phe Thr Glu Asp Gly Pro Glu Glu Arg Asn Thr
        610                 615                 620

Phe Asp His Cys Leu Gly Leu Leu Val Lys Ser Gly Thr Leu Leu Pro
625                 630                 635                 640

Ser Asp Arg Asp Ser Lys Met Cys Lys Met Ile Thr Glu Asp Ser Tyr
                645                 650                 655

Pro Gly Tyr Ile Pro Lys Pro Arg Gln Asp Cys Asn Ala Val Ser Thr
                660                 665                 670

Phe Trp Met Ala Asn Pro Asn Asn Asn Leu Ile Asn Cys Ala Ala Ala
            675                 680                 685

Gly Ser Glu Glu Thr Gly Phe Trp Phe Ile Phe His His Val Pro Thr
        690                 695                 700

Gly Pro Ser Val Gly Met Tyr Ser Pro Gly Tyr Ser Glu His Ile Pro
705                 710                 715                 720

Leu Gly Lys Phe Tyr Asn Asn Arg Ala His Ser Asn Tyr Arg Ala Gly
                725                 730                 735

Met Ile Ile Asp Asn Gly Val Lys Thr Thr Glu Ala Ser Ala Lys Asp
                740                 745                 750

Lys Arg Pro Phe Leu Ser Ile Ile Ser Ala Arg Tyr Ser Pro His Gln
            755                 760                 765

Asp Ala Asp Pro Leu Lys Pro Arg Glu Pro Ala Ile Ile Arg His Phe
770                 775                 780
```

```
Ile Ala Tyr Lys Asn Gln Asp His Gly Ala Trp Leu Arg Gly Gly Asp
785                 790                 795                 800

Val Trp Leu Asp Ser Cys Arg Phe Ala Asp Asn Gly Ile Gly Leu Thr
                805                 810                 815

Leu Ala Ser Gly Gly Thr Phe Pro Tyr Asp Asp Gly Ser Lys Gln Glu
            820                 825                 830

Ile Lys Asn Ser Leu Phe Val Gly Glu Ser Gly Asn Val Gly Thr Glu
        835                 840                 845

Met Met Asp Asn Arg Ile Trp Gly Pro Gly Leu Asp His Ser Gly
    850                 855                 860

Arg Thr Leu Pro Ile Gly Gln Asn Phe Pro Ile Arg Gly Ile Gln Leu
865                 870                 875                 880

Tyr Asp Gly Pro Ile Asn Ile Gln Asn Cys Thr Phe Arg Lys Phe Val
                885                 890                 895

Ala Leu Glu Gly Arg His Thr Ser Ala Leu Ala Phe Arg Leu Asn Asn
            900                 905                 910

Ala Trp Gln Ser Cys Pro His Asn Asn Val Thr Gly Ile Ala Phe Glu
        915                 920                 925

Asp Val Pro Ile Thr Ser Arg Val Phe Gly Glu Pro Gly Pro Trp
    930                 935                 940

Phe Asn Gln Leu Asp Met Asp Gly Asp Lys Thr Ser Val Phe His Asp
945                 950                 955                 960

Val Asp Gly Ser Val Ser Glu Tyr Pro Gly Ser Tyr Leu Thr Lys Asn
                965                 970                 975

Asp Asn Trp Leu Val Arg His Pro Asp Cys Ile Asn Val Pro Asp Trp
            980                 985                 990

Arg Gly Ala Ile Cys Ser Gly Cys Tyr Ala Gln Met Tyr Ile Gln Ala
        995                 1000                1005

Tyr Lys Thr Ser Asn Leu Arg Met Lys Ile Ile Lys Asn Asp Phe Pro
    1010                1015                1020

Ser His Pro Leu Tyr Leu Glu Gly Ala Leu Thr Arg Ser Thr His Tyr
1025                1030                1035                1040

Gln Gln Tyr Gln Pro Val Val Thr Leu Gln Lys Gly Tyr Thr Ile His
                1045                1050                1055

Trp Asp Gln Thr Ala Pro Ala Glu Leu Ala Ile Trp Leu Ile Asn Phe
            1060                1065                1070

Asn Lys Gly Asp Trp Ile Arg Val Gly Leu Cys Tyr Pro Arg Gly Thr
        1075                1080                1085

Thr Phe Ser Ile Leu Ser Asp Val His Asn Arg Leu Leu Lys Gln Thr
    1090                1095                1100

Ser Lys Thr Gly Val Phe Val Arg Thr Leu Gln Met Asp Lys Val Glu
1105                1110                1115                1120

Gln Ser Tyr Pro Gly Arg Ser His Tyr Tyr Trp Asp Glu Asp Ser Gly
                1125                1130                1135

Leu Leu Phe Leu Lys Leu Lys Ala Gln Asn Glu Arg Glu Lys Phe Ala
            1140                1145                1150

Phe Cys Ser Met Lys Gly Cys Glu Arg Ile Lys Ile Lys Ala Leu Ile
        1155                1160                1165

Pro Lys Asn Ala Gly Val Ser Asp Cys Thr Ala Thr Ala Tyr Pro Lys
    1170                1175                1180

Phe Thr Glu Arg Ala Val Val Asp Val Pro Met Pro Lys Lys Leu Phe
1185                1190                1195                1200

Gly Ser Gln Leu Lys Thr Lys Asp His Phe Leu Glu Val Lys Met Glu
```

```
                      1205                1210                1215
Ser Ser Lys Gln His Phe Phe His Leu Trp Asn Asp Phe Ala Tyr Ile
        1220                1225                1230

Glu Val Asp Gly Lys Lys Tyr Pro Ser Ser Glu Asp Gly Ile Gln Val
        1235                1240                1245

Val Val Ile Asp Gly Asn Gln Gly Arg Val Val Ser His Thr Ser Phe
        1250                1255                1260

Arg Asn Ser Ile Leu Gln Gly Ile Pro Trp Gln Leu Phe Asn Tyr Val
1265                1270                1275                1280

Ala Thr Ile Pro Asp Asn Ser Ile Val Leu Met Ala Ser Lys Gly Arg
                1285                1290                1295

Tyr Val Ser Arg Gly Pro Trp Thr Arg Val Leu Glu Lys Leu Gly Ala
            1300                1305                1310

Asp Arg Gly Leu Lys Leu Lys Glu Gln Met Ala Phe Val Gly Phe Lys
            1315                1320                1325

Gly Ser Phe Arg Pro Ile Trp Val Thr Leu Asp Thr Glu Asp His Lys
            1330                1335                1340

Ala Lys Ile Phe Gln Val Val Pro Ile Pro Val Val Lys Lys Lys Lys
1345                1350                1355                1360

Leu
```

<210> SEQ ID NO 14
<211> LENGTH: 755
<212> TYPE: PRT
<213> ORGANISM: Homo sapiens

<400> SEQUENCE: 14

```
Met Pro Pro Phe Leu Leu Leu Glu Ala Val Cys Val Phe Leu Phe Ser
 1               5                  10                  15

Arg Val Pro Pro Ser Leu Pro Leu Gln Glu Val His Val Ser Lys Glu
                20                  25                  30

Thr Ile Gly Lys Ile Ser Ala Ala Ser Lys Met Met Trp Cys Ser Ala
            35                  40                  45

Ala Val Asp Ile Met Phe Leu Leu Asp Gly Ser Asn Ser Val Gly Lys
        50                  55                  60

Gly Ser Phe Glu Arg Ser Lys His Phe Ala Ile Thr Val Cys Asp Gly
65                  70                  75                  80

Leu Asp Ile Ser Pro Glu Arg Val Arg Val Gly Ala Phe Gln Phe Ser
                85                  90                  95

Ser Thr Pro His Leu Glu Phe Pro Leu Asp Ser Phe Ser Thr Gln Gln
                100                 105                 110

Glu Val Lys Ala Arg Ile Lys Arg Met Val Phe Lys Gly Gly Arg Thr
            115                 120                 125

Glu Thr Glu Leu Ala Leu Lys Tyr Leu Leu Arg Gly Leu Pro Gly
        130                 135                 140

Gly Arg Asn Ala Ser Val Pro Gln Ile Leu Ile Val Thr Asp Gly
145                 150                 155                 160

Lys Ser Gln Gly Asp Val Ala Leu Pro Ser Lys Gln Leu Lys Glu Arg
                165                 170                 175

Gly Val Thr Val Phe Ala Val Gly Val Arg Phe Pro Arg Trp Glu Glu
            180                 185                 190

Leu His Ala Leu Ala Ser Glu Pro Arg Gly Gln His Val Leu Leu Ala
        195                 200                 205

Glu Gln Val Glu Asp Ala Thr Asn Gly Leu Phe Ser Thr Leu Ser Ser
    210                 215                 220
```

-continued

```
Ser Ala Ile Cys Ser Ser Ala Thr Pro Asp Cys Arg Val Glu Ala His
225                 230                 235                 240

Pro Cys Glu His Arg Thr Leu Glu Met Val Arg Gly Phe Ala Gly Asn
            245                 250                 255

Ala Pro Cys Trp Arg Gly Ser Arg Arg Thr Leu Ala Val Leu Ala Ala
                260                 265                 270

His Cys Pro Phe Tyr Ser Trp Lys Arg Val Phe Leu Thr His Pro Ala
            275                 280                 285

Thr Cys Tyr Arg Thr Thr Cys Pro Gly Pro Cys Asp Ser Gln Pro Cys
        290                 295                 300

Gln Asn Gly Gly Thr Cys Val Pro Glu Gly Leu Asp Gly Tyr Gln Cys
305                 310                 315                 320

Leu Cys Pro Leu Ala Phe Gly Gly Glu Ala Asn Cys Ala Leu Lys Leu
                325                 330                 335

Ser Leu Glu Cys Arg Val Asp Leu Leu Phe Leu Leu Asp Ser Ser Ala
            340                 345                 350

Gly Thr Thr Leu Asp Gly Phe Leu Arg Ala Lys Val Phe Val Lys Arg
        355                 360                 365

Phe Val Arg Ala Val Leu Ser Glu Asp Ser Arg Ala Arg Val Gly Val
    370                 375                 380

Ala Thr Tyr Ser Arg Glu Leu Leu Val Ala Val Pro Val Gly Glu Tyr
385                 390                 395                 400

Gln Asp Val Pro Asp Leu Val Trp Ser Leu Asp Gly Ile Pro Phe Arg
                405                 410                 415

Gly Gly Pro Thr Leu Thr Gly Ser Ala Leu Arg Gln Ala Ala Glu Arg
            420                 425                 430

Gly Phe Gly Ser Ala Thr Arg Thr Gly Gln Asp Arg Pro Arg Arg Val
        435                 440                 445

Val Val Leu Leu Thr Glu Ser His Ser Glu Asp Glu Val Ala Gly Pro
450                 455                 460

Ala Arg His Ala Arg Ala Arg Glu Leu Leu Leu Gly Val Gly Ser
465                 470                 475                 480

Glu Ala Val Arg Ala Glu Leu Glu Glu Ile Thr Gly Ser Pro Lys His
                485                 490                 495

Val Met Val Tyr Ser Asp Pro Gln Asp Leu Phe Asn Gln Ile Pro Glu
            500                 505                 510

Leu Gln Gly Lys Leu Cys Ser Arg Gln Arg Pro Gly Cys Arg Thr Gln
        515                 520                 525

Ala Leu Asp Leu Val Phe Met Leu Asp Thr Ser Ala Ser Val Gly Pro
530                 535                 540

Glu Asn Phe Ala Gln Met Gln Ser Phe Val Arg Ser Cys Ala Leu Gln
545                 550                 555                 560

Phe Glu Val Asn Pro Asp Val Thr Gln Val Gly Leu Val Val Tyr Gly
                565                 570                 575

Ser Gln Val Gln Thr Ala Phe Gly Leu Asp Thr Lys Pro Thr Arg Ala
            580                 585                 590

Ala Met Leu Arg Ala Ile Ser Gln Ala Pro Tyr Leu Gly Gly Val Gly
        595                 600                 605

Ser Ala Gly Thr Ala Leu Leu His Ile Tyr Asp Lys Val Met Thr Val
    610                 615                 620

Gln Arg Gly Ala Arg Pro Gly Val Pro Lys Ala Val Val Val Leu Thr
625                 630                 635                 640

Gly Gly Arg Gly Ala Glu Asp Ala Ala Val Pro Ala Gln Lys Leu Arg
```

```
                       645                 650                 655
Asn Asn Gly Ile Ser Val Leu Val Gly Val Gly Pro Val Leu Ser
            660                 665                 670

Glu Gly Leu Arg Arg Leu Ala Gly Pro Arg Asp Ser Leu Ile His Val
            675                 680                 685

Ala Ala Tyr Ala Asp Leu Arg Tyr His Gln Asp Val Leu Ile Glu Trp
690                 695                 700

Leu Cys Gly Glu Ala Lys Gln Pro Val Asn Leu Cys Lys Pro Ser Pro
705                 710                 715                 720

Cys Met Asn Glu Gly Ser Cys Val Leu Gln Asn Gly Ser Tyr Arg Cys
                725                 730                 735

Lys Cys Arg Asp Gly Trp Glu Gly Pro His Cys Glu Asn Arg Phe Leu
            740                 745                 750

Arg Arg Pro
        755

<210> SEQ ID NO 15
<211> LENGTH: 300
<212> TYPE: PRT
<213> ORGANISM: Homo sapiens

<400> SEQUENCE: 15

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Leu
            20                  25                  30

Tyr Asn Lys Tyr Pro Asp Ala Val Ala Thr Trp Leu Asn Pro Asp Pro
        35                  40                  45

Ser Gln Lys Gln Asn Leu Leu Ala Pro Gln Thr Leu Pro Ser Lys Ser
    50                  55                  60

Asn Glu Ser His Asp His Met Asp Asp Met Asp Asp Glu Asp Asp Asp
65                  70                  75                  80

Asp His Val Asp Ser Gln Asp Ser Ile Asp Ser Asn Asp Ser Asp Asp
                85                  90                  95

Val Asp Asp Thr Asp Asp Ser His Gln Ser Asp Glu Ser His His Ser
            100                 105                 110

Asp Glu Ser Asp Glu Leu Val Thr Asp Phe Pro Thr Asp Leu Pro Ala
        115                 120                 125

Thr Glu Val Phe Thr Pro Val Val Pro Thr Val Asp Thr Tyr Asp Gly
    130                 135                 140

Arg Gly Asp Ser Val Val Tyr Gly Leu Arg Ser Lys Ser Lys Lys Phe
145                 150                 155                 160

Arg Arg Pro Asp Ile Gln Tyr Pro Asp Ala Thr Asp Glu Asp Ile Thr
                165                 170                 175

Ser His Met Glu Ser Glu Glu Leu Asn Gly Ala Tyr Lys Ala Ile Pro
            180                 185                 190

Val Ala Gln Asp Leu Asn Ala Pro Ser Asp Trp Asp Ser Arg Gly Lys
        195                 200                 205

Asp Ser Tyr Glu Thr Ser Gln Leu Asp Asp Gln Ser Ala Glu Thr His
    210                 215                 220

Ser His Lys Gln Ser Arg Leu Tyr Lys Arg Lys Ala Asn Asp Glu Ser
225                 230                 235                 240

Asn Glu His Ser Asp Val Ile Asp Ser Gln Glu Leu Ser Lys Val Ser
                245                 250                 255

Arg Glu Phe His Ser His Glu Phe His Ser His Glu Asp Met Leu Val
```

```
            260                 265                 270
Val Asp Pro Lys Ser Lys Glu Glu Asp Lys His Leu Lys Phe Arg Ile
                275                 280                 285
Ser His Glu Leu Asp Ser Ala Ser Ser Glu Val Asn
        290                 295                 300

<210> SEQ ID NO 16
<211> LENGTH: 829
<212> TYPE: PRT
<213> ORGANISM: Homo sapiens

<400> SEQUENCE: 16

Met Gly Leu Pro Arg Gly Pro Leu Ala Ser Leu Leu Leu Leu Gln Val
 1                5                  10                  15

Cys Trp Leu Gln Cys Ala Ala Ser Glu Pro Cys Arg Ala Val Phe Arg
                20                  25                  30

Glu Ala Glu Val Thr Leu Glu Ala Gly Gly Ala Glu Gln Glu Pro Gly
            35                  40                  45

Gln Ala Leu Gly Lys Val Phe Met Gly Cys Pro Gly Gln Glu Pro Ala
        50                  55                  60

Leu Phe Ser Thr Asp Asn Asp Asp Phe Thr Val Arg Asn Gly Glu Thr
65                  70                  75                  80

Val Gln Glu Arg Arg Ser Leu Lys Glu Arg Asn Pro Leu Lys Ile Phe
                85                  90                  95

Pro Ser Lys Arg Ile Leu Arg Arg His Lys Arg Asp Trp Val Val Ala
                100                 105                 110

Pro Ile Ser Val Pro Glu Asn Gly Lys Gly Pro Phe Pro Gln Arg Leu
            115                 120                 125

Asn Gln Leu Lys Ser Asn Lys Asp Arg Asp Thr Lys Ile Phe Tyr Ser
        130                 135                 140

Ile Thr Gly Pro Gly Ala Asp Ser Pro Pro Glu Gly Val Phe Ala Val
145                 150                 155                 160

Glu Lys Glu Thr Gly Trp Leu Leu Leu Asn Lys Pro Leu Asp Arg Glu
                165                 170                 175

Glu Ile Ala Lys Tyr Glu Leu Phe Gly His Ala Val Ser Glu Asn Gly
            180                 185                 190

Ala Ser Val Glu Asp Pro Met Asn Ile Ser Ile Ile Val Thr Asp Gln
        195                 200                 205

Asn Asp His Lys Pro Lys Phe Thr Gln Asp Thr Phe Arg Gly Ser Val
    210                 215                 220

Leu Glu Gly Val Leu Pro Gly Thr Ser Val Met Gln Val Thr Ala Thr
225                 230                 235                 240

Asp Glu Asp Asp Ala Ile Tyr Thr Tyr Asn Gly Val Val Ala Tyr Ser
                245                 250                 255

Ile His Ser Gln Glu Pro Lys Asp Pro His Asp Leu Met Phe Thr Ile
            260                 265                 270

His Arg Ser Thr Gly Thr Ile Ser Val Ile Ser Ser Gly Leu Asp Arg
        275                 280                 285

Glu Lys Val Pro Glu Tyr Thr Leu Thr Ile Gln Ala Thr Asp Met Asp
    290                 295                 300

Gly Asp Gly Ser Thr Thr Thr Ala Val Ala Val Val Glu Ile Leu Asp
305                 310                 315                 320

Ala Asn Asp Asn Ala Pro Met Phe Asp Pro Gln Lys Tyr Glu Ala His
                325                 330                 335

Val Pro Glu Asn Ala Val Gly His Glu Val Gln Arg Leu Thr Val Thr
```

```
              340                 345                 350
Asp Leu Asp Ala Pro Asn Ser Pro Ala Trp Arg Ala Thr Tyr Leu Ile
            355                 360                 365
Met Gly Gly Asp Asp Gly Asp His Phe Thr Ile Thr Thr His Pro Glu
        370                 375                 380
Ser Asn Gln Gly Ile Leu Thr Thr Arg Lys Gly Leu Asp Phe Glu Ala
385                 390                 395                 400
Lys Asn Gln His Thr Leu Tyr Val Glu Val Thr Asn Glu Ala Pro Phe
                405                 410                 415
Val Leu Lys Leu Pro Thr Ser Thr Ala Thr Ile Val Val His Val Glu
            420                 425                 430
Asp Val Asn Glu Ala Pro Val Phe Val Pro Pro Ser Lys Val Val Glu
        435                 440                 445
Val Gln Glu Gly Ile Pro Thr Gly Glu Pro Val Cys Val Tyr Thr Ala
    450                 455                 460
Glu Asp Pro Asp Lys Glu Asn Gln Lys Ile Ser Tyr Arg Ile Leu Arg
465                 470                 475                 480
Asp Pro Ala Gly Trp Leu Ala Met Asp Pro Asp Ser Gly Gln Val Thr
                485                 490                 495
Ala Val Gly Thr Leu Asp Arg Glu Asp Glu Gln Phe Val Arg Asn Asn
            500                 505                 510
Ile Tyr Glu Val Met Val Leu Ala Met Asp Asn Gly Ser Pro Pro Thr
        515                 520                 525
Thr Gly Thr Gly Thr Leu Leu Leu Thr Leu Ile Asp Val Asn Asp His
    530                 535                 540
Gly Pro Val Pro Glu Pro Arg Gln Ile Thr Ile Cys Asn Gln Ser Pro
545                 550                 555                 560
Val Arg Gln Val Leu Asn Ile Thr Asp Lys Asp Leu Ser Pro His Thr
                565                 570                 575
Ser Pro Phe Gln Ala Gln Leu Thr Asp Asp Ser Asp Ile Tyr Trp Thr
            580                 585                 590
Ala Glu Val Asn Glu Glu Gly Asp Thr Val Val Leu Ser Leu Lys Lys
        595                 600                 605
Phe Leu Lys Gln Asp Thr Tyr Asp Val His Leu Ser Leu Ser Asp His
    610                 615                 620
Gly Asn Lys Glu Gln Leu Thr Val Ile Arg Ala Thr Val Cys Asp Cys
625                 630                 635                 640
His Gly His Val Glu Thr Cys Pro Gly Pro Trp Lys Gly Gly Phe Ile
                645                 650                 655
Leu Pro Val Leu Gly Ala Val Leu Ala Leu Leu Phe Leu Leu Leu Val
            660                 665                 670
Leu Leu Leu Leu Val Arg Lys Lys Arg Lys Ile Lys Glu Pro Leu Leu
        675                 680                 685
Leu Pro Glu Asp Asp Thr Arg Asp Asn Val Phe Tyr Tyr Gly Glu Glu
    690                 695                 700
Gly Gly Gly Glu Glu Asp Gln Asp Tyr Asp Ile Thr Gln Leu His Arg
705                 710                 715                 720
Gly Leu Glu Ala Arg Pro Glu Val Val Leu Arg Asn Asp Val Ala Pro
                725                 730                 735
Thr Ile Ile Pro Thr Pro Met Tyr Arg Pro Arg Pro Ala Asn Pro Asp
            740                 745                 750
Glu Ile Gly Asn Phe Ile Glu Asn Leu Lys Ala Ala Asn Thr Asp
        755                 760                 765
```

Pro Thr Ala Pro Pro Tyr Asp Thr Leu Leu Val Phe Asp Tyr Glu Gly
770                 775                 780

Ser Gly Ser Asp Ala Ala Ser Leu Ser Ser Leu Thr Ser Ser Ala Ser
785                 790                 795                 800

Asp Gln Asp Gln Asp Tyr Asp Tyr Leu Asn Glu Trp Gly Ser Arg Phe
                    805                 810                 815

Lys Lys Leu Ala Asp Met Tyr Gly Gly Gly Glu Asp Asp
                820                 825

<210> SEQ ID NO 17
<211> LENGTH: 694
<212> TYPE: PRT
<213> ORGANISM: Homo sapiens

<400> SEQUENCE: 17

Met Lys His Leu Lys Arg Trp Trp Ser Ala Gly Gly Gly Leu Leu His
1               5                   10                  15

Leu Thr Leu Leu Leu Ser Leu Ala Gly Leu Arg Val Asp Leu Asp Leu
                20                  25                  30

Tyr Leu Leu Leu Pro Pro Thr Leu Leu Gln Asp Glu Leu Leu Phe
            35                  40                  45

Leu Gly Gly Pro Ala Ser Ser Ala Tyr Ala Leu Ser Pro Phe Ser Ala
50                  55                  60

Ser Gly Gly Trp Gly Arg Ala Gly His Leu His Pro Lys Gly Arg Glu
65                  70                  75                  80

Leu Asp Pro Ala Ala Pro Pro Glu Gly Gln Leu Leu Arg Glu Val Arg
                85                  90                  95

Ala Leu Gly Val Pro Phe Val Pro Arg Thr Ser Val Asp Ala Trp Leu
            100                 105                 110

Val His Ser Val Ala Ala Gly Ser Ala Asp Glu Ala His Gly Leu Leu
        115                 120                 125

Gly Ala Ala Ala Ser Ser Thr Gly Gly Ala Gly Ala Ser Val Asp
130                 135                 140

Gly Gly Ser Gln Ala Val Gln Gly Gly Gly Asp Pro Arg Ala Ala
145                 150                 155                 160

Arg Ser Gly Pro Leu Asp Ala Gly Glu Glu Glu Lys Ala Pro Ala Glu
                165                 170                 175

Pro Thr Ala Gln Val Pro Asp Ala Gly Gly Cys Ala Ser Glu Glu Asn
            180                 185                 190

Gly Val Leu Arg Glu Lys His Glu Ala Val Asp His Ser Ser Gln His
        195                 200                 205

Glu Glu Asn Glu Glu Arg Val Ser Ala Gln Lys Glu Asn Ser Leu Gln
210                 215                 220

Gln Asn Asp Asp Asp Glu Asn Lys Ile Ala Glu Lys Pro Asp Trp Glu
225                 230                 235                 240

Ala Glu Lys Thr Thr Glu Ser Arg Asn Glu Arg His Leu Asn Gly Thr
                245                 250                 255

Asp Thr Ser Phe Ser Leu Glu Asp Leu Phe Gln Leu Leu Ser Ser Gln
            260                 265                 270

Pro Glu Asn Ser Leu Glu Gly Ile Ser Leu Gly Asp Ile Pro Leu Pro
        275                 280                 285

Gly Ser Ile Ser Asp Gly Met Asn Ser Ser Ala His Tyr His Val Asn
290                 295                 300

Phe Ser Gln Ala Ile Ser Gln Asp Val Asn Leu His Glu Ala Ile Leu
305                 310                 315                 320

Leu Cys Pro Asn Asn Thr Phe Arg Arg Asp Pro Thr Ala Arg Thr Ser
              325                 330                 335

Gln Ser Gln Glu Pro Phe Leu Gln Leu Asn Ser His Thr Thr Asn Pro
              340                 345                 350

Glu Gln Thr Leu Pro Gly Thr Asn Leu Thr Gly Phe Leu Ser Pro Val
              355                 360                 365

Asp Asn His Met Arg Asn Leu Thr Ser Gln Asp Leu Leu Tyr Asp Leu
              370                 375                 380

Asp Ile Asn Ile Phe Asp Glu Ile Asn Leu Met Ser Leu Ala Thr Glu
385                 390                 395                 400

Asp Asn Phe Asp Pro Ile Asp Val Ser Gln Leu Phe Asp Glu Pro Asp
              405                 410                 415

Ser Asp Ser Gly Leu Ser Leu Asp Ser Ser His Asn Asn Thr Ser Val
              420                 425                 430

Ile Lys Ser Asn Ser Ser His Ser Val Cys Asp Glu Gly Ala Ile Gly
              435                 440                 445

Tyr Cys Thr Asp His Glu Ser Ser His His Asp Leu Glu Gly Ala
              450                 455                 460

Val Gly Gly Tyr Tyr Pro Glu Pro Ser Lys Leu Cys His Leu Asp Gln
465                 470                 475                 480

Ser Asp Ser Asp Phe His Gly Asp Leu Thr Phe Gln His Val Phe His
              485                 490                 495

Asn His Thr Tyr His Leu Gln Pro Thr Ala Pro Glu Ser Thr Ser Glu
              500                 505                 510

Pro Phe Pro Trp Pro Gly Lys Ser Gln Lys Ile Arg Ser Arg Tyr Leu
              515                 520                 525

Glu Asp Thr Asp Arg Asn Leu Ser Arg Asp Glu Gln Arg Ala Lys Ala
              530                 535                 540

Leu His Ile Pro Phe Ser Val Asp Glu Ile Val Gly Met Pro Val Asp
545                 550                 555                 560

Ser Phe Asn Ser Met Leu Ser Arg Tyr Tyr Leu Thr Asp Leu Gln Val
              565                 570                 575

Ser Leu Ile Arg Asp Ile Arg Arg Gly Lys Asn Lys Val Ala Ala
              580                 585                 590

Gln Asn Cys Arg Lys Arg Lys Leu Asp Ile Ile Leu Asn Leu Glu Asp
              595                 600                 605

Asp Val Cys Asn Leu Gln Ala Lys Lys Glu Thr Leu Lys Arg Glu Gln
610                 615                 620

Ala Gln Cys Asn Lys Ala Ile Asn Ile Met Lys Gln Lys Leu His Asp
625                 630                 635                 640

Leu Tyr His Asp Ile Phe Ser Arg Leu Arg Asp Asp Gln Gly Arg Pro
              645                 650                 655

Val Asn Pro Asn His Tyr Ala Leu Gln Cys Thr His Asp Gly Ser Ile
              660                 665                 670

Leu Ile Val Pro Lys Glu Leu Val Ala Ser Gly His Lys Lys Glu Thr
              675                 680                 685

Gln Lys Gly Lys Arg Lys
              690

<210> SEQ ID NO 18
<211> LENGTH: 402
<212> TYPE: PRT
<213> ORGANISM: Homo sapiens

<400> SEQUENCE: 18

```
Met Lys Leu Glu Val Phe Val Pro Arg Ala Ala His Gly Asp Lys Gln
 1               5                  10                  15

Gly Ser Asp Leu Glu Gly Ala Gly Gly Ser Asp Ala Pro Ser Pro Leu
             20                  25                  30

Ser Ala Ala Gly Asp Asp Ser Leu Gly Ser Asp Gly Asp Cys Ala Ala
             35                  40                  45

Lys Pro Ser Ala Gly Gly Ala Arg Asp Thr Gln Gly Asp Gly Glu
 50                  55                  60

Gln Ser Ala Gly Gly Pro Gly Ala Glu Glu Ala Ile Pro Ala Ala
 65                  70                  75                  80

Ala Ala Ala Ala Val Val Ala Glu Gly Ala Gly Ala Ala Gly
                 85                  90                  95

Pro Gly Ala Gly Gly Ala Gly Ser Gly Glu Gly Ala Arg Ser Lys Pro
                100                 105                 110

Tyr Thr Arg Arg Pro Lys Pro Tyr Ser Tyr Ile Ala Leu Ile Ala
                115                 120                 125

Met Ala Ile Arg Asp Ser Ala Gly Gly Arg Leu Thr Leu Ala Glu Ile
    130                 135                 140

Asn Glu Tyr Leu Met Gly Lys Phe Pro Phe Phe Arg Gly Ser Tyr Thr
145                 150                 155                 160

Gly Trp Arg Asn Ser Val Arg His Asn Leu Ser Leu Asn Asp Cys Phe
                165                 170                 175

Val Lys Val Leu Arg Asp Pro Ser Arg Pro Trp Gly Lys Asp Asn Tyr
                180                 185                 190

Trp Met Leu Asn Pro Asn Ser Glu Tyr Thr Phe Ala Asp Gly Val Phe
    195                 200                 205

Arg Arg Arg Arg Lys Arg Leu Ser His Arg Ala Pro Val Pro Ala Pro
210                 215                 220

Gly Leu Arg Pro Glu Glu Ala Pro Gly Leu Pro Ala Ala Pro Pro
225                 230                 235                 240

Ala Pro Ala Ala Pro Ala Ser Pro Arg Met Arg Ser Pro Ala Arg Gln
                245                 250                 255

Glu Glu Arg Ala Ser Pro Ala Gly Lys Phe Ser Ser Ser Phe Ala Ile
                260                 265                 270

Asp Ser Ile Leu Arg Lys Pro Phe Arg Ser Arg Arg Leu Arg Asp Thr
            275                 280                 285

Ala Pro Gly Thr Thr Leu Gln Trp Gly Ala Ala Pro Cys Pro Pro Leu
    290                 295                 300

Pro Ala Phe Pro Ala Leu Leu Pro Ala Ala Pro Cys Arg Ala Leu Leu
305                 310                 315                 320

Pro Leu Cys Ala Tyr Gly Ala Gly Glu Pro Ala Arg Leu Gly Ala Arg
                325                 330                 335

Glu Ala Glu Val Pro Pro Thr Ala Pro Pro Leu Leu Leu Ala Pro Leu
            340                 345                 350

Pro Ala Ala Ala Pro Ala Lys Pro Leu Arg Gly Pro Ala Ala Gly Gly
                355                 360                 365

Ala His Leu Tyr Cys Pro Leu Arg Leu Pro Ala Ala Leu Gln Ala Ala
            370                 375                 380

Leu Val Arg Arg Pro Gly Pro His Leu Ser Tyr Pro Val Glu Thr Leu
385                 390                 395                 400

Leu Ala

<210> SEQ ID NO 19
<211> LENGTH: 209
```

<212> TYPE: PRT
<213> ORGANISM: Homo sapiens

<400> SEQUENCE: 19

```
Met Glu Lys His His Val Pro Ser Asp Phe Asn Val Asn Val Lys Val
1               5                   10                  15

Asp Thr Gly Pro Arg Glu Asp Leu Ile Lys Val Leu Glu Asp Met Arg
            20                  25                  30

Gln Glu Tyr Glu Leu Ile Ile Lys Lys His Arg Asp Leu Asp Thr
        35                  40                  45

Trp Tyr Lys Glu Gln Ser Ala Ala Met Ser Gln Glu Ala Ala Ser Pro
    50                  55                  60

Ala Thr Val Gln Ser Arg Gln Gly Asp Ile His Glu Leu Lys Arg Thr
65                  70                  75                  80

Phe Gln Ala Leu Glu Ile Asp Leu Gln Ala Gln Tyr Ser Thr Lys Ser
                85                  90                  95

Ala Leu Glu Asn Met Leu Ser Gly Thr Gln Ser Arg Tyr Ser Cys Lys
            100                 105                 110

Leu Gln Asp Met Gln Glu Ile Ile Ser His Tyr Glu Glu Leu Thr
        115                 120                 125

Gln Leu Arg His Glu Leu Glu Arg Gln Asn Asn Glu Tyr Gln Val Leu
130                 135                 140

Leu Gly Ile Lys Thr His Leu Glu Lys Glu Ile Thr Thr Tyr Arg Arg
145                 150                 155                 160

Leu Leu Glu Gly Glu Ser Glu Gly Thr Arg Glu Glu Ser Lys Ser Ser
                165                 170                 175

Met Lys Val Ser Ala Thr Pro Lys Ile Lys Ala Ile Thr Gln Glu Thr
            180                 185                 190

Ile Asn Gly Arg Leu Val Leu Cys Gln Val Asn Glu Ile Gln Lys His
        195                 200                 205

Ala
```

<210> SEQ ID NO 20
<211> LENGTH: 278
<212> TYPE: PRT
<213> ORGANISM: Homo sapiens

<400> SEQUENCE: 20

```
Met Asp Lys Ser Gly Ile Asp Ser Leu Asp His Val Thr Ser Asp Ala
1               5                   10                  15

Val Glu Leu Ala Asn Arg Ser Asp Asn Ser Ser Asp Ser Ser Leu Phe
            20                  25                  30

Lys Thr Gln Cys Ile Pro Tyr Ser Pro Lys Gly Glu Lys Arg Asn Pro
        35                  40                  45

Ile Arg Lys Phe Val Arg Thr Pro Glu Ser Val His Ala Ser Asp Ser
    50                  55                  60

Ser Ser Asp Ser Ser Phe Glu Pro Ile Pro Leu Thr Ile Lys Ala Ile
65                  70                  75                  80

Phe Glu Arg Phe Lys Asn Arg Lys Lys Arg Tyr Lys Lys Lys Lys
                85                  90                  95

Arg Arg Tyr Gln Pro Thr Gly Arg Pro Arg Gly Arg Pro Glu Gly Arg
            100                 105                 110

Arg Asn Pro Ile Tyr Ser Leu Ile Asp Lys Lys Gln Phe Arg Ser
        115                 120                 125

Arg Gly Ser Gly Phe Pro Phe Leu Glu Ser Glu Asn Glu Lys Asn Ala
130                 135                 140
```

```
Pro Trp Arg Lys Ile Leu Thr Phe Glu Gln Ala Val Ala Arg Gly Phe
145                 150                 155                 160

Phe Asn Tyr Ile Glu Lys Leu Lys Tyr Glu His His Leu Lys Glu Ser
                165                 170                 175

Leu Lys Gln Met Asn Val Gly Glu Asp Leu Glu Asn Glu Asp Phe Asp
            180                 185                 190

Ser Arg Arg Tyr Lys Phe Leu Asp Asp Gly Ser Ile Ser Pro Ile
        195                 200                 205

Glu Glu Ser Thr Ala Glu Asp Glu Asp Ala Thr His Leu Glu Asp Asn
210                 215                 220

Glu Cys Asp Ile Lys Leu Ala Gly Asp Ser Phe Ile Val Ser Ser Glu
225                 230                 235                 240

Phe Pro Val Arg Leu Ser Val Tyr Leu Glu Glu Asp Ile Thr Glu
                245                 250                 255

Glu Ala Ala Leu Ser Lys Lys Arg Ala Thr Lys Ala Lys Asn Thr Gly
            260                 265                 270

Gln Arg Gly Leu Lys Met
            275

<210> SEQ ID NO 21
<211> LENGTH: 488
<212> TYPE: PRT
<213> ORGANISM: Homo sapiens

<400> SEQUENCE: 21

Ala Val Leu Ala Ala His Cys Pro Phe Tyr Ser Trp Lys Arg Val Phe
 1               5                  10                  15

Leu Thr His Pro Ala Thr Cys Tyr Arg Thr Thr Cys Pro Gly Pro Cys
                20                  25                  30

Asp Ser Gln Pro Cys Gln Asn Gly Gly Thr Cys Val Pro Glu Gly Leu
            35                  40                  45

Asp Gly Tyr Gln Cys Leu Cys Pro Leu Ala Phe Gly Gly Glu Ala Asn
        50                  55                  60

Cys Ala Leu Lys Leu Ser Leu Glu Cys Arg Val Asp Leu Leu Phe Leu
65                  70                  75                  80

Leu Asp Ser Ser Ala Gly Thr Thr Leu Asp Gly Phe Leu Arg Ala Lys
                85                  90                  95

Val Phe Val Lys Arg Phe Val Arg Ala Val Leu Ser Glu Asp Ser Arg
                100                 105                 110

Ala Arg Val Gly Val Ala Thr Tyr Ser Arg Glu Leu Leu Val Ala Val
            115                 120                 125

Pro Val Gly Glu Tyr Gln Asp Val Pro Asp Leu Val Trp Ser Leu Asp
        130                 135                 140

Gly Ile Pro Phe Arg Gly Gly Pro Thr Leu Thr Gly Ser Ala Leu Arg
145                 150                 155                 160

Gln Ala Ala Glu Arg Gly Phe Gly Ser Ala Thr Arg Thr Gly Gln Asp
                165                 170                 175

Arg Pro Arg Arg Val Val Val Leu Leu Thr Glu Ser Ser Ser Glu Asp
            180                 185                 190

Glu Val Ala Gly Pro Ala Arg His Ala Arg Ala Arg Glu Leu Leu Leu
        195                 200                 205

Leu Gly Val Gly Ser Glu Ala Val Arg Ala Glu Leu Glu Glu Ile Thr
210                 215                 220

Gly Ser Pro Lys His Val Met Val Tyr Ser Asp Pro Gln Asp Leu Phe
225                 230                 235                 240
```

```
Asn Gln Ile Pro Glu Leu Gln Gly Lys Leu Cys Ser Arg Gln Arg Pro
                245                 250                 255

Gly Cys Arg Thr Gln Ala Leu Asp Leu Val Phe Met Leu Asp Thr Ser
            260                 265                 270

Ala Ser Val Gly Pro Glu Asn Phe Ala Gln Met Gln Ser Phe Val Arg
        275                 280                 285

Ser Cys Ala Leu Gln Phe Glu Val Asn Pro Asp Val Thr Gln Val Gly
    290                 295                 300

Leu Val Val Tyr Gly Ser Gln Val Gln Thr Ala Phe Gly Leu Asp Thr
305                 310                 315                 320

Lys Pro Thr Arg Ala Ala Met Leu Arg Ala Ile Ser Gln Ala Pro Tyr
                325                 330                 335

Leu Gly Gly Val Gly Ser Ala Gly Thr Ala Leu Leu His Ile Tyr Asp
            340                 345                 350

Lys Val Met Thr Val Gln Arg Gly Ala Arg Pro Gly Val Pro Lys Ala
        355                 360                 365

Val Val Val Leu Thr Gly Gly Arg Gly Ala Glu Asp Ala Ala Val Pro
    370                 375                 380

Ala Gln Lys Leu Arg Asn Asn Gly Ile Ser Val Leu Val Val Gly Val
385                 390                 395                 400

Gly Pro Val Leu Ser Glu Gly Leu Arg Arg Leu Ala Gly Pro Arg Asp
                405                 410                 415

Ser Leu Ile His Val Ala Ala Tyr Ala Asp Leu Arg Tyr His Gln Asp
            420                 425                 430

Val Leu Ile Glu Trp Leu Cys Gly Glu Ala Lys Gln Pro Val Asn Leu
        435                 440                 445

Cys Lys Pro Ser Pro Cys Met Asn Glu Gly Ser Cys Val Leu Gln Asn
    450                 455                 460

Gly Ser Tyr Arg Cys Lys Cys Arg Asp Gly Trp Glu Gly Pro His Cys
465                 470                 475                 480

Glu Asn Arg Phe Leu Arg Arg Pro
                485

<210> SEQ ID NO 22
<211> LENGTH: 13
<212> TYPE: PRT
<213> ORGANISM: Homo sapiens

<400> SEQUENCE: 22

Ala Val Leu Ala Ala His Cys Pro Phe Tyr Ser Trp Lys
1               5                   10

<210> SEQ ID NO 23
<211> LENGTH: 403
<212> TYPE: PRT
<213> ORGANISM: Homo sapiens

<400> SEQUENCE: 23

Met Lys Leu Glu Val Phe Val Pro Arg Ala Ala His Gly Asp Lys Gln
1               5                   10                  15

Gly Ser Asp Leu Glu Gly Ala Gly Gly Ser Asp Ala Pro Ser Pro Leu
            20                  25                  30

Ser Ala Ala Gly Asp Asp Ser Leu Gly Ser Asp Gly Asp Cys Ala Ala
        35                  40                  45

Asn Ser Pro Ala Ala Gly Gly Gly Ala Arg Asp Thr Gln Gly Asp Gly
    50                  55                  60
```

```
Glu Gln Ser Ala Gly Gly Pro Gly Ala Glu Ala Ile Pro Ala
65                  70                  75                  80

Ala Ala Ala Ala Ala Val Val Ala Glu Gly Glu Ala Gly Ala Ala
                    85                  90                  95

Gly Pro Gly Ala Gly Gly Ala Gly Ser Gly Glu Gly Ala Arg Ser Lys
                100                 105                 110

Pro Tyr Thr Arg Arg Pro Lys Pro Pro Tyr Ser Tyr Ile Ala Leu Ile
            115                 120                 125

Ala Met Ala Ile Arg Asp Ser Ala Gly Gly Arg Leu Thr Leu Ala Glu
        130                 135                 140

Ile Asn Glu Tyr Leu Met Gly Lys Phe Pro Phe Phe Arg Gly Ser Tyr
145                 150                 155                 160

Thr Gly Trp Arg Asn Ser Val Arg His Asn Leu Ser Leu Asn Asp Cys
                165                 170                 175

Phe Val Lys Val Leu Arg Asp Pro Ser Arg Pro Trp Gly Lys Asp Asn
                180                 185                 190

Tyr Trp Met Leu Asn Pro Asn Ser Glu Tyr Thr Phe Ala Asp Gly Val
            195                 200                 205

Phe Arg Arg Arg Arg Lys Arg Leu Ser His Arg Ala Pro Val Pro Ala
        210                 215                 220

Pro Gly Leu Arg Pro Glu Glu Ala Pro Gly Leu Pro Ala Ala Pro Pro
225                 230                 235                 240

Pro Ala Pro Ala Ala Pro Ala Ser Pro Arg Met Arg Ser Pro Ala Arg
                245                 250                 255

Gln Glu Glu Arg Ala Ser Pro Ala Gly Lys Phe Ser Ser Phe Ala
                260                 265                 270

Ile Asp Ser Ile Leu Arg Lys Pro Phe Arg Ser Arg Leu Arg Asp
            275                 280                 285

Thr Ala Pro Gly Thr Thr Leu Gln Trp Gly Ala Ala Pro Cys Pro Pro
        290                 295                 300

Leu Pro Ala Phe Pro Ala Leu Leu Pro Ala Ala Pro Cys Arg Ala Leu
305                 310                 315                 320

Leu Pro Leu Cys Ala Tyr Gly Ala Gly Glu Pro Ala Arg Leu Gly Ala
                325                 330                 335

Arg Glu Ala Glu Val Pro Pro Thr Ala Pro Pro Leu Leu Leu Ala Pro
                340                 345                 350

Leu Pro Ala Ala Ala Pro Ala Lys Pro Leu Arg Gly Pro Ala Ala Gly
            355                 360                 365

Gly Ala His Leu Tyr Cys Pro Leu Arg Leu Pro Ala Ala Leu Gln Ala
        370                 375                 380

Ala Ser Val Arg Arg Pro Gly Pro His Leu Pro Tyr Pro Val Glu Thr
385                 390                 395                 400

Leu Leu Ala

<210> SEQ ID NO 24
<211> LENGTH: 400
<212> TYPE: PRT
<213> ORGANISM: Mus musculus

<400> SEQUENCE: 24

Met Lys Leu Glu Val Phe Val Pro Arg Ala Ala His Gly Asp Lys Met
1               5                   10                  15

Gly Ser Asp Leu Glu Gly Ala Gly Ser Ser Asp Val Pro Ser Pro Leu
            20                  25                  30

Ser Ala Ala Gly Asp Asp Ser Leu Gly Ser Asp Gly Asp Cys Ala Ala
```

```
              35                  40                  45
Asn Ser Pro Ala Ala Gly Ser Gly Ala Gly Asp Leu Glu Gly Gly
 50                  55                  60

Gly Glu Arg Asn Ser Ser Gly Gly Pro Ser Ala Gln Asp Gly Pro Glu
 65                  70                  75                  80

Ala Thr Asp Asp Ser Arg Thr Gln Ala Ser Ala Ala Gly Pro Cys Ala
                 85                  90                  95

Gly Gly Val Gly Gly Glu Gly Ala Arg Ser Lys Pro Tyr Thr Arg
                100                 105                 110

Arg Pro Lys Pro Pro Tyr Ser Tyr Ile Ala Leu Ile Ala Met Ala Ile
                115                 120                 125

Arg Asp Ser Ala Gly Gly Arg Leu Thr Leu Ala Glu Ile Asn Glu Tyr
 130                 135                 140

Leu Met Gly Lys Phe Pro Phe Phe Arg Gly Ser Tyr Thr Gly Trp Arg
145                 150                 155                 160

Asn Ser Val Arg His Asn Leu Ser Leu Asn Asp Cys Phe Val Lys Val
                165                 170                 175

Leu Arg Asp Pro Ser Arg Pro Trp Gly Lys Asp Asn Tyr Trp Met Leu
                180                 185                 190

Asn Pro Asn Ser Glu Tyr Thr Phe Ala Asp Gly Val Phe Arg Arg Arg
                195                 200                 205

Arg Lys Arg Leu Ser His Arg Thr Thr Val Ser Ala Ser Gly Leu Arg
 210                 215                 220

Pro Glu Glu Ala Pro Pro Gly Pro Ala Gly Thr Pro Gln Pro Ala Pro
225                 230                 235                 240

Ala Ala Arg Ser Ser Pro Ile Ala Arg Ser Pro Ala Arg Gln Glu Glu
                245                 250                 255

Arg Ser Ser Pro Ala Ser Lys Phe Ser Ser Phe Ala Ile Asp Ser
                260                 265                 270

Ile Leu Ser Lys Pro Phe Arg Ser Arg Arg Asp Gly Asp Ser Ala Leu
                275                 280                 285

Gly Val Gln Leu Pro Trp Gly Ala Ala Pro Cys Pro Pro Leu Arg Ala
 290                 295                 300

Tyr Pro Ala Leu Leu Pro Ala Ala Pro Gly Gly Ala Leu Leu Pro Leu
305                 310                 315                 320

Cys Ala Tyr Gly Ala Ser Glu Pro Thr Leu Leu Ala Ser Arg Gly Thr
                325                 330                 335

Glu Val Gln Pro Ala Ala Pro Leu Leu Leu Ala Pro Leu Ser Thr Ala
                340                 345                 350

Ala Pro Ala Lys Pro Phe Arg Gly Pro Glu Thr Ala Gly Ala Ala His
                355                 360                 365

Leu Tyr Cys Pro Leu Arg Leu Pro Thr Ala Leu Gln Ala Ala Ala Ala
 370                 375                 380

Cys Gly Pro Gly Pro His Leu Ser Tyr Pro Val Glu Thr Leu Leu Ala
385                 390                 395                 400

<210> SEQ ID NO 25
<211> LENGTH: 400
<212> TYPE: PRT
<213> ORGANISM: Rattus rattus

<400> SEQUENCE: 25

Met Lys Leu Glu Val Phe Ala Pro Arg Ala Ala His Gly Asp Lys Met
 1               5                  10                  15

Gly Ser Asp Leu Glu Gly Ala Gly Ser Ser Asp Val Pro Ser Pro Leu
```

```
                    20                   25                   30
Ser Ala Ala Gly Asp Asp Ser Leu Gly Ser Asp Gly Asp Cys Ala Ala
        35                   40                   45
Asn Ser Pro Ala Ala Gly Arg Gly Ala Val Asp Leu Glu Gly Gly Gly
    50                   55                   60
Gly Glu Arg Asn Ser Ser Gly Ala Ser Thr Gln Asp Asp Pro Glu
65                   70                   75                   80
Val Thr Asp Gly Ser Arg Thr Gln Ala Ser Pro Val Gly Pro Cys Ala
                85                   90                   95
Gly Ser Val Gly Gly Glu Gly Ala Arg Ser Lys Pro Tyr Thr Arg
            100                  105                  110
Arg Pro Lys Pro Pro Tyr Ser Tyr Ile Ala Leu Ile Ala Met Ala Ile
            115                  120                  125
Arg Asp Ser Ala Gly Gly Arg Leu Thr Leu Ala Glu Ile Asn Glu Tyr
        130                  135                  140
Leu Met Gly Lys Phe Pro Phe Phe Arg Gly Ser Tyr Thr Gly Trp Arg
145                  150                  155                  160
Asn Ser Val Arg His Asn Leu Ser Leu Asn Asp Cys Phe Val Lys Val
                165                  170                  175
Leu Arg Asp Pro Ser Arg Pro Trp Gly Lys Asp Asn Tyr Trp Met Leu
            180                  185                  190
Asn Pro Asn Ser Glu Tyr Thr Phe Ala Asp Gly Val Phe Arg Arg
        195                  200                  205
Arg Lys Arg Leu Ser His Arg Thr Thr Val Ser Ala Ser Gly Leu Arg
    210                  215                  220
Pro Glu Glu Ala Pro Pro Gly Pro Ala Gly Thr Pro Gln Pro Ala Pro
225                  230                  235                  240
Thr Ala Gly Ser Ser Pro Ile Ala Arg Ser Pro Ala Arg Gln Glu Glu
                245                  250                  255
Gly Ser Ser Pro Ala Ser Lys Phe Ser Ser Ser Phe Ala Ile Asp Ser
            260                  265                  270
Ile Leu Ser Lys Pro Phe Arg Ser Arg Arg Asp Gly Asp Pro Ala Leu
        275                  280                  285
Gly Val Gln Leu Pro Trp Ser Ala Ala Pro Cys Pro Pro Leu Arg Ala
    290                  295                  300
Tyr Pro Ala Leu Leu Pro Ala Ser Ser Gly Ala Leu Leu Pro Leu
305                  310                  315                  320
Cys Ala Tyr Gly Ala Gly Glu Pro Thr Leu Leu Ala Ser Arg Gly Ala
                325                  330                  335
Glu Val Gln Pro Ala Ala Pro Leu Leu Leu Ala Pro Leu Ser Thr Ala
            340                  345                  350
Ala Pro Ala Lys Pro Phe Arg Gly Pro Glu Thr Ala Gly Ala Ala His
        355                  360                  365
Leu Tyr Cys Pro Leu Arg Leu Pro Thr Ala Leu Gln Ala Ala Ala Ala
    370                  375                  380
Cys Gly Pro Gly Pro His Leu Ser Tyr Arg Val Glu Thr Leu Leu Ala
385                  390                  395                  400

<210> SEQ ID NO 26
<211> LENGTH: 1212
<212> TYPE: DNA
<213> ORGANISM: Homo sapiens

<400> SEQUENCE: 26
atgaagttgg aggtgttcgt ccctcgcgcg gcccacgggg acaagcaggg cagtgacctg      60
```

```
gagggcgcgg gcggcagcga cgcgccgtcc ccgctgtcgg cggcgggaga cgactccctg      120
ggctcagatg gggactgcgc ggccaacagc ccggccgcgg gcggcggcgc cagagatacg      180
cagggcgacg gcgaacagag tgcgggaggc gggccgggcg cggaggaggc gatcccggca      240
gcagctgctg cagcggtggt ggcggagggc gcggaggccg gggcggcggg gccaggcgcg      300
ggcggcgcgg ggagcggcga gggtgcacgc agcaagccat atacgcggcg gcccaagccc      360
ccctactcgt acatcgcgct catcgccatg gccatccgcg actcggcggg cgggcgcttg      420
acgctggcgg agatcaacga gtacctcatg ggcaagttcc cctttttccg cggcagctac      480
acgggctggc gcaactccgt cgccacaaac ctttcgctca cgactgctt cgtcaaggtg      540 ctgcgcgacc cctcgcggcc ctggggcaag acaactact ggatgctcaa ccccaacagc      600
gagtacacct tcgccgacgg ggtcttccgc cgccgccgca agcgcctcag ccaccgcgcg      660
ccggtccccg cgcccgggct gcggcccgag gaggccccgg gcctcccgc cgccccgccg      720 cccgcgcccg ccgccccggc ctcgccccgc atgcgctcgc ccgcccgcca ggaggagcgc      780
gccagccccg cgggcaagtt ctccagctcc ttcgccatcg acagcatcct gcgcaagccc      840
ttccgcagcc gccgcctcag ggacacggcc cccgggacga cgcttcagtg gggcgccgcg      900
ccctgcccgc cgctgcccgc gttccccgcg ctcctccccg cggcgccctg cagggccctg      960
ctgccgctct gcgcgtacgg cgcgggcgag ccggcgcggc tgggcgcgcg cgaggccgag     1020
gtgccaccga ccgcgccgcc cctcctgctt gcacctctcc cggcggcggc ccccgccaag     1080
ccactccgag gccggcggc cggcggcgcg cacctgtact gccccctgcg gctgccccgca    1140 gccctgcagg cggcctcagt ccgccgccct ggcccgcacc tgccgtaccc ggtggagacg     1200
ctgctagctt ga                                                       1212

<210> SEQ ID NO 27
<211> LENGTH: 1203
<212> TYPE: DNA
<213> ORGANISM: Mus musculus

<400> SEQUENCE: 27
atgaaattgg aggtgttcgt cccacgcgca gcccacgggg acaaaatggg cagcgatctg       60
gagggggccg gcagcagcga cgtgccatct ccactgtccg cggctggtga cgactcctta      120
ggctcagacg gggactgtgc agccaacagc ccggccgcgg gcagcggcgc cggggatctg      180
gaaggtggcg gcggcgagag gaattcgagt ggcgggccga cgcccaagac ggtccggag       240 gcaactgatg acagcagaac gcaggcctcc gcggcagggc cgtgcgcggg cggcgtgggc      300
ggcggcgagg gcgcgcgcag caagccgtac acgcggcggc ccaagccccc atactcctac      360
atcgctctca tcgccatggc catccgcgac tccgcgggcg gacgcctgac actggccgag      420
atcaacgagt acctcatggg caagttcccc ttttccgggg cagctacac gggctggcgc      480 aactccgtgc gccacaacct ctcgctcaac gactgtttcg tcaaggtgct gcgcgacccc      540
tcgcggccct ggggcaagga caactactgg atgctcaacc ccaacagcga atacaccttc      600
gccgacgggg tcttccgccg ccgccgcaag cgcctcagca ccggaccac agtctccgcg      660 tccgggctgc ggccgaggga agccccaccc ggacctgccg ggaccccgca gcccgcgccc      720
gccgcccgct cctccccgat cgcgcgctcg ccggctcgcc aggaggagcg ctccagccct      780
gcgagcaagt ctccagctc cttcgccatc gacagcattc tcagcaagcc ttttcgcagc      840
cgccgcgacg cgcgactcggc tctggggtg cagctaccct ggggcgccgc tcctgcccg       900 ccgctgcgcg cctatcccgc gctccttccc gcggcgcccg gtggcgctct gctaccgctc      960
```

```
tgtgcttacg gcgcaagcga gcctacgctg ctggcgtcgc gcgggaccga ggtgcagccc    1020
gccgcgcccc ttctgctggc gcccctctcc accgcggctc cagccaagcc attccgaggt    1080
ccggagaccg ccggcgcggc gcacctgtac tgcccoctac ggctgcccac ggccctgcag    1140
gcggcagcgg cctgcggtcc cggtccgcac ctgtcctacc cggtggagac tctgctagct    1200
tga                                                                  1203

<210> SEQ ID NO 28
<211> LENGTH: 1203
<212> TYPE: DNA
<213> ORGANISM: Rattus rattus

<400> SEQUENCE: 28
atgaaattgg aggtatttgc cccacgcgca gcccacgggg acaagatggg cagtgacctg     60 gaggggggccg gcagcagcga cgtgccatct ccgctgtccg cggctggcga cgactcctta    120
ggctctgacg gggactgtgc agccaacagc ccggcggcgg gcagaggcgc cgtggatctg    180
gaaggcggcg gcggcgagag gaattcgagt ggcggggcga gcacccaaga cgatcccgag    240
gtgaccgatg gcagcagaac gcaggcctcc ccggtggggc cgtgcgcggg cagcgtgggc    300
ggcggtgagg gcgcgcgcag caagccgtac acgcggcggc ccaagccccc ctactcctac    360
atcgcactca tcgccatggc catccgcgac tccgcgggcg gacgcctgac gctggccgag    420
atcaacgagt acctcatggg caagttcccc tttttccggg gcagctacac gggctggcgc    480
aactccgtgc gccacaacct ctcgctcaac gactgtttcg tcaaggtgct gcgcgacccc    540
tcgcggccct ggggcaagga caattactgg atgctcaacc ccaacagcga atacaccttc    600
gccgacgggg tcttccgccg ccgccgcaag cgcctcagcc accggaccac agtctccgca    660
tcggggctac ggccggagga agccccaccc ggacctgcgg ggaccccgca gcccgcgccc    720
accgccggct cctccccaat cgcgcgctcg cccgctcgcc aggaggaggg ctccagcccg    780
gcgagcaagt tctccagctc cttcgccatc gacagcatcc tcagcaagcc gtttcgcagc    840
cgccgcgacg gcgacccggc tctgggggtg cagctaccct ggagcgctgc tccctgcccg    900
ccgctgcgcg cctatcccgc gctccttccc gcgtcgtccg gcggtgccct gctgccgctc    960
tgtgcttacg gcgcgggcga gcccacgctg ctggcgtcgc gcggggccga ggtgcagccc   1020
gcggcgcccc tgttgctggc gcccctctcc accgcggccc cagccaagcc atttcgaggt   1080
ccggagaccg ccggcgcggc gcacctgtac tgcccoctac ggctgcccac ggccctgcag   1140
gcggccgcgg cctgcggtcc gggtccgcac ctgtcctacc gggtggagac gctgctagct   1200
tga                                                                 1203
```

METHODS AND COMPOSITIONS FOR CATEGORIZING PATIENTS

CROSS-REFERENCE TO RELATED APPLICATIONS

This application is a continuation of U.S. patent application Ser. No. 12/386,176, filed on Apr. 13, 2009, which is a continuation of U.S. patent application Ser. No. 10/649,591 (abandoned), filed Aug. 26, 2003 which is a continuation-in-part of U.S. patent application Ser. No. 10/274,177 (now U.S. Pat. No. 7,118,912), filed Oct. 18, 2002, which is a continuation-in-part of U.S. patent application Ser. No. 10/229,345 (now U.S. Pat. No. 7,081,516), filed Aug. 26, 2002. The disclosures of each of the foregoing applications are hereby incorporated by reference in their entirety.

FUNDING

Work described herein was funded, in part, by grant number 1 U01 CA-88130-01 from the National Cancer Institute. The United States government has certain rights in the invention.

BACKGROUND

Colorectal cancer, also referred to herein as colon cancer, is the second leading cause of cancer mortality in the adult American population. An estimated 135,000 new cases of colon cancer occur each year. Although many people die of colon cancer, early stage colon cancers are often treatable by surgical removal (resection) of the affected tissue. Surgical treatment can be combined with chemotherapeutic agents to achieve an even higher survival rate in certain colon cancers. However, the survival rate drops to 5% or less over five years in patients with metastatic (late stage) colon cancer.

Effective screening and early identification of affected patients coupled with appropriate therapeutic intervention is proven to reduce the number of colon cancer mortalities. It is estimated that 74,000,000 older Americans would benefit from regular screening for colon cancer and precancerous colon adenomas (together, adenomas and colon cancers may be referred to as colon neoplasias). However, present systems for screening for colon neoplasia are inadequate. For example, the Fecal Occult Blood Test involves testing a stool sample from a patient for the presence of blood. This test is relatively simple and inexpensive, but it often fails to detect colon neoplasia (low sensitivity) and often even when blood is detected in the stool, a colon neoplasia is not present (low specificity). Flexible sigmoidoscopy involves the insertion of a short scope into the rectum to visually inspect the lower third of the colon. Because the sigmoidoscope is relatively short, it is also a relatively uncomplicated diagnostic method. However, nearly half of all colon neoplasia occurs in the upper portions of the colon that can not be viewed with the sigmoidoscope. Colonoscopy, in which a scope is threaded through the entire length of the colon, provides a very reliable method of detecting colon neoplasia in a subject, but colonoscopy is costly, time consuming and requires sedation of the patient.

Modern molecular biology has made it possible to identify proteins and nucleic acids that are specifically associated with certain physiological states. These molecular markers have revolutionized diagnostics for a variety of health conditions ranging from pregnancy to viral infections, such as HIV.

Researchers generally identify molecular markers for a health condition by searching for genes and proteins that are expressed at different levels in one health condition versus another (e.g. in pregnant women versus women who are not pregnant). Traditional methods for pursuing this research, such as Northern blots and reverse transcriptase polymerase chain reaction, allow a researcher to study only a handful of potential molecular markers at a time. Microarrays, consisting of an ordered array of hundreds or thousands of probes for detection of hundreds or thousands of gene transcripts, allow researchers to gather data on many potential molecular markers in a single experiment. Researchers now face the challenge of sifting through large quantities of microarray-generated gene expression data to identify genes that may be of genuine use as molecular markers to distinguish different health conditions.

Improved systems for identifying high quality candidate molecular markers in large volumes of gene expression data may help to unlock the power of such tools and increase the likelihood of identifying a molecular marker for important disease states, such as colon neoplasia. Effective molecular markers for colon neoplasia could potentially revolutionize the diagnosis, management and overall health impact of colon cancer.

BRIEF SUMMARY

This application is based at least in part on the selection of useful molecular markers of colon neoplasia. Colon neoplasia is a multi-stage process involving progression from normal healthy tissues to the development of pre-cancerous colon adenomas to more invasive stages of colon cancer such as the Dukes A and Dukes B stages and finally to metastatic stages such as Dukes C and Dukes D stages of colon cancer.

In one aspect, this application provides molecular markers that are useful in the detection or diagnosis of colon neoplasia. In certain embodiments, molecular markers described in the application are helpful in distinguishing normal subjects from those who are likely to develop colon neoplasia or are likely to harbor a colon adenoma. In other aspects the invention provides molecular markers that may be useful in distinguishing subjects who are either normal or precancerous from those who have colon cancer. In another embodiment, the application provides markers that help in staging the colon cancer in patients. In still other embodiments the application contemplates the use of one or more of the molecular markers described herein for the detection, diagnosis, and staging of colon neoplasias.

In one aspect the application provides a method of screening a subject for a condition associated with increased levels of one or more molecular markers that are indicative of colon neoplasia such as for example ColoUp1-ColoUp8 and osteopontin. In a preferred embodiment, the application provides a method for screening a subject for conditions associated with secreted markers such as ColoUp1 or ColoUp2, by detecting in a biological sample an amount of ColoUp1 or ColoUp2 and comparing the amount of ColoUp1 and ColoUp2 found in the subject to one or more of the following: a predetermined standard, the amount of ColoUp1 or ColoUp2 detected in a normal sample from the subject, the subject's historical baseline level of ColoUp1 or ColoUp2, or the ColoUp1 or ColoUp2 level detected in a different, normal subject (a control subject). Detection of a level of ColoUp1 and ColoUp2 in the subject that is greater than that of the predetermined standard or that is increased from a subject's past baseline is indicative of a condition such as colon neoplasia. In certain aspects, an increase in the amount of ColoUp1 or ColoUp2 as compared to the subject's historical baseline would be indicative of a new neoplasm, or progression of an existing neoplasm. Similarly, a decrease in the amount of ColoUp1 or ColoUp2 as compared to the subject's historical baseline would be indicative of regression on an existing neoplasm.

In one aspect the molecular markers described herein are encoded by a nucleic acid sequence that is at least 90%, 95%, 98%, 99%, 99.3%, 99.5% or 99.7% identical to the nucleic acid sequence of SEQ ID Nos: 4-12, and more preferably to the nucleic acid sequences as set forth in SEQ ID Nos: 4-5. In another aspect, the application provides markers that are encoded by a nucleic acid sequence that hybridizes under high stringency conditions to the nucleic acid sequences of SEQ ID Nos: 4-12, more preferably to the nucleic acid sequences as set forth in SEQ ID Nos: 4-5.

In another aspect the application provides molecular markers that are diagnostic of colon neoplasia, said markers having an amino acid sequence that is at least 90%, 95%, 98%, 99%, 99.3%, 99.5% or 99.7% identical to the amino acid sequence as set forth in SEQ ID Nos: 1-3 or 13-20, more preferably the amino acid sequence as set forth in SEQ ID Nos: 3 and 14.

In one aspect, the application provides methods for detecting secreted polypeptide forms of a ColoUp1-ColoUp8 polypeptide or osteopontin in biological samples. In other aspects, the application provides methods for imaging a colon neoplasm by targeting antibodies to any one of the markers ColoUp1 through ColoUp8 described herein, and in preferred embodiments, the antibodies are targeted to ColoUp3. In certain aspects, the application provides methods for administering a imaging agent comprising a targeting moiety and an active moiety. The targeting moiety may be an antibody, Fab, F(Ab)2, a single chain antibody or other binding agent that interacts with an epitope specified by a polypeptide sequence having an amino acid sequence as set forth in SEQ ID Nos: 1-3 and 13-20. The active moiety may be a radioactive agent, such as radioactive technetium, radioactive indium, or radioactive iodine. The imaging agent is administered in an amount effective for diagnostic use in a mammal such as a human and the localization and accumulation of the imaging agent is then detected. The localization and accumulation of the imaging agent may be detected by radioscintigraphy, nuclear magnetic resonance imaging, computed tomography or positron emission tomography.

In a preferred embodiment, the application provides methods for detecting a polypeptide comprising an amino acid sequence as set forth in one of SEQ ID Nos: 1-3. As will be apparent to the skilled artisan, the molecular markers described herein may be detected in a number of ways such as by various assays, including antibody-based assays. Examples of antibody-based assays include immunoprecipitation assays, Western blots, radioimmunoassays or enzyme-linked immunosorbent assays (ELISAs). Molecular markers described herein may be detected by assays that do not employ an antibody, such as by methods employing two-dimensional gel electrophoresis, methods employing mass spectroscopy, methods employing suitable enzymatic activity assays, etc. In a preferred embodiment the application provides methods for the detection of secreted markers such as ColoUp1 or ColoUp2 polypeptides in blood, blood fractions (such as blood serum or blood plasma), urine or stool samples. Increased levels of these markers may be associated with a number of conditions such as for example colon neoplasia, including colon adenomas, colon cancer, and metastatic colon cancer. In certain aspects the application provides methods including the detection of more than one marker that is indicative of colon neoplasia such as methods for detecting both ColoUp1 and ColoUp2. In yet another aspect, combinations of the ColoUp markers may be useful, for instance, a combination of tests including testing biological samples for secreted markers such as ColoUp1 or ColoUp2 in combination with testing for transmembrane markers such as ColoUp3 as targets for imaging agents.

In yet another aspect, the application provides a method of determining whether a subject is likely to develop colon cancer or is more likely to harbor a precancerous colon adenoma by detecting the presence or absence of the molecular markers as set forth in SEQ ID Nos: 1-3. Detection of combinations of these markers is also helpful in staging the colon neoplasias.

In yet another aspect, the application provides markers that are useful in distinguishing normal and precancerous subjects from those subjects having colon cancer. In certain embodiments, the application contemplates determining the levels of markers provided herein such as ColoUp1 through ColoUp8 and osteopontin. In one aspect, markers such as ColoUp6 and osteopontin are helpful in distinguishing between the category of patients that are normal or have precancerous colon adenomas and the category of patients having colon cancer. In another aspect, the application provides detection of one or more of said markers in determining the stages of colon neoplasia.

In certain aspect, the invention provides an immunoassay for determining the presence of any one of the polypeptides having an amino acid sequence as set forth in SEQ ID Nos: 1-3 and 13-20, more preferably any one of the polypeptides having an amino acid sequence as set forth in SEQ ID Nos: 1-3 in a biological sample. The method includes obtaining a biological sample and contacting the sample with an antibody specific for a polypeptide having an amino acid sequence as set forth in SEQ ID Nos: 1-3 and detecting the binding of the antibody.

In some aspects, the application provides methods for the detection of a molecular marker in a biological sample such as blood, including blood fractions such as serum or plasma. For instance, the blood sample obtained from a patient may be further processed such as by fractionation to obtain blood serum, and the serum may then be enriched for certain polypeptides. The serum so enriched is then contacted with an antibody that is reactive with an epitope of the desired marker polypeptide.

In yet another embodiment, the application provides methods for determining the appropriate therapeutic protocol for a subject. For example detection of a colon neoplasia provides the treating physician valuable information in determining whether intensive or invasive protocols such as colonoscopy, surgery or chemotherapy would be needed for effective diagnosis or treatment. Such detection would be helpful not only for patients not previously diagnosed with colon neoplasia but also in those cases where a patient has previously received or is currently receiving therapy for colon cancer, the presence or absence or a change in the level of the molecular markers set forth herein may be indicative that the subject is likely to have a relapse or a progressive, or a persistent colon cancer.

In certain aspects, the application provides molecular markers of colon neoplasia such as ColoUp1 through ColoUp8. In certain instances these markers are secreted proteins such as ColoUp1, ColoUp2 and osteopontin, and are useful for detecting and diagnosing colon neoplasia. In other aspects, these markers may be transmembrane proteins such as ColoUp3 and may be useful as targets for imaging agents, e.g. as targets to label cells of a neoplasm.

In one aspect, the application provides isolated, purified or recombinant polypeptides having an amino acid sequence that is at least 90%, 95% or 98-99% identical to an amino acid sequence as set forth in SEQ ID Nos: 1-3 or an amino acid sequence as set forth in SEQ ID Nos: 13-20. In a more preferred embodiment, the application provides an amino acid sequence that is at least 90%, 95%, 98-99%, 99.3%, 99.5% or 99.7% identical to the amino acid sequence as set forth in SEQ ID No: 3 or SEQ ID No: 14. The application also provides fusion proteins comprising the ColoUp proteins described herein fused to a heterologous protein. In certain embodiments, such polypeptides are useful, for example, for generating antibodies or for use in screening assays to identify candidate therapeutics.

In other aspects the application provides for nucleic acid sequences encoding the polypeptides as set forth in SEQ ID Nos: 1-3 and 13-20. In one aspect the application provides nucleic acids comprising nucleic acid sequences that are at least 90%, 95%, 98-99%, 99.3%, 99.5% or 99.7% identical to the nucleic acid sequence in SEQ ID Nos: 4-12, more preferably 4-5. Also contemplated herein are vectors comprising the nucleic acid sequences set forth in SEQ ID Nos: 4-12, more preferably SEQ ID Nos: 4-5, and host cells expressing the nucleic acid sequences.

In another aspect, the application provides an antibody that interacts with an epitope specified by one of SEQ ID Nos: 1-3 and 13-20 or portions thereof, more preferably SEQ ID Nos: 1-3 or portions thereof. In a preferred embodiment the antibody is useful for detecting colon adenomas and interacts with an epitope specified by one of SEQ ID Nos: 1-3. In certain aspects the application provides for generating such antibodies, including methods for generating monoclonal and polyclonal antibodies, as well as methods for generating other types of antibodies. In other aspects, the application also provides a hybridoma cell line capable of producing an antibody that interacts with an epitope specified by SEQ ID Nos: 1-3 and 13-20, more preferably SEQ ID Nos: 1-3, or portions thereof. In yet other embodiments, the antibody may be a single chain antibody.

In yet other embodiments, the application provides a kit for detecting colon neoplasia in a biological sample, Such kits include one or more antibodies that are capable of interacting with an epitope specified by one of SEQ ID Nos: 1-3 and 13-20, more preferably with an epitope specified by one of SEQ ID Nos: 1-3. In more preferred embodiments, the antibodies may be detectably labeled, such as for example with an enzyme, a fluorescent substance, a chemiluminescent substance, a chromophore, a radioactive isotope or a complexing agent.

In certain embodiments, the application provides the identity of ColoUp1 and ColoUp2 polypeptides that are secreted into the serum in vivo, and that are secreted across the apical and basolateral cell surfaces in cultured intestinal cells. Accordingly, in certain embodiments, the application provides methods for detecting whether a subject to likely to have a colon neoplasia comprising: a) obtaining a biological sample from said subject; and b) detecting one or more polypeptides selected from among: one or more secreted ColoUp1 polypeptides and one or more secreted ColoUp2 polypeptides, wherein the presence of said one or more polypeptides is indicative of colon neoplasia.

In certain embodiments, a secreted ColoUp2 polypeptide is selected from among: a) a secreted polypeptide produced by the expression of a nucleic acid that is at least 95% identical to the amino acid sequence of SEQ ID No: 5; b) a secreted polypeptide produced by the expression of a nucleic acid that is a naturally occurring variant of SEQ ID No: 5; c) a secreted polypeptide produced by the expression of a nucleic acid that hybridizes under stringent conditions to a nucleic acid sequence of SEQ ID No: 5; d) a secreted polypeptide having a sequence that is at least 95% identical to the amino acid sequence of SEQ ID No: 3; and e) a secreted polypeptide having a sequence that is at least 95% identical to the amino acid sequence of SEQ ID No: 21. Optionally, the secreted ColoUp2 polypeptide is produced by the expression of a nucleic acid having the sequence of SEQ ID No: 5, and preferably the secreted ColoUp2 polypeptide is produced by the expression of a nucleic acid sequence that is at least 98%, 99% or 100% identical to the nucleic acid sequence of SEQ ID No: 5. In certain embodiments, the secreted ColoUp2 polypeptide has an amino acid sequence that is at least 98%, 99% or 100% identical to an amino acid sequence selected from among SEQ ID No: 3 and SEQ ID No:21. In certain embodiments, the secreted ColoUp1 polypeptide is selected from among: a) a secreted polypeptide produced by the expression of a nucleic acid that is at least 95% identical to the amino acid sequence of SEQ ID No: 4; b) a secreted polypeptide produced by the expression of a nucleic acid that is a naturally occurring variant of SEQ ID No: 4; c) a secreted polypeptide produced by the expression of a nucleic acid that hybridizes under stringent conditions to a nucleic acid sequence of SEQ ID No: 4; d) a secreted polypeptide having a sequence that is at least 95% identical to the amino acid sequence of SEQ ID No: 1; and e) a secreted polypeptide having a sequence that is at least 95% identical to the amino acid sequence of SEQ ID No: 2. Optionally, the secreted ColoUp1 polypeptide is produced by the expression of a nucleic acid having a sequence that is at least 95%, 98, 99% or 100% identical to the nucleic acid sequence of SEQ ID No: 4. Preferably, the secreted ColoUp1 polypeptide has an amino acid sequence that is at least 95%, 98%, 99% or 100% identical to an amino acid sequence selected from among SEQ ID No: 1 and SEQ ID No:2. Optionally, for detection of basolaterally secreted ColoUp1 or ColoUp2 polypeptides, the biological sample is a blood sample or a fraction derived from blood, such as serum, plasma, cells, or a fraction enriched for apically secreted ColoUp1 or ColoUp2 polypeptide. Optionally, for detection of basolaterally secreted ColoUp1 or ColoUp2 polypeptides, the biological sample is a urine sample or a fraction derived from urine. Optionally, for detection of apically secreted ColoUp1 or ColoUp2 polypeptides, the biological sample is derived from the inner wall and/or lumen of the intestinal tract, such as intestinal mucous or other fluid, excreted stool and stool removed from within the colon. In certain embodiments, the polypeptide is detected by an assay that employs an antibody, such as an immunoprecipitation assay, a Western blot, a radioimmunoassays or an enzyme-linked immunosorbent assay (ELISA). Optionally, an assay comprises contacting the biological sample with an antibody that interacts with a secreted ColoUp1 polypeptide or a secreted ColoUp2 polypeptide. An antibody may, for example, interact with an epitope of an amino acid sequence selected from among: SEQ ID No: 1 and SEQ ID No: 2. An antibody may, for example, interact with an epitope of an amino acid sequence selected from among: SEQ ID No: 3 and SEQ ID No: 21. Optionally, the antibody is detectably labeled, such as with an enzyme, a fluorescent substance, a chemiluminescent substance, a chromophore, a radioactive isotope or a complexing agent. Optionally, the amount of at least one secreted ColoUp1 polypeptide and/or at least one secreted ColoUp2 polypeptide in the biological sample is compared to a predetermined standard (e.g., a known amount of purified ColoUp1 or ColoUp2 polypeptide). Optionally, the amount of at least one secreted ColoUp1 polypeptide and/or at least one secreted ColoUp2 polypeptide in the biological sample is compared to the subject's historical baseline. In certain embodiments, the presence of at least one secreted ColoUp1 polypeptide and/or at least one secreted ColoUp2 polypeptide is indicative that the subject is likely to harbor a colon adenoma or a colon cancer. In certain embodiments, the presence of at least one secreted ColoUp1 polypeptide and/or at least one secreted ColoUp2 polypeptide may be used in determining the therapeutic protocol to be administered to a subject having a colon neoplasia, and the subject may not have been previously diagnosed with colon cancer or the subject may have previously received or is currently receiving a therapy for colon cancer, wherein the presence of at least one secreted ColoUp1 polypeptide and/or at least one secreted ColoUp2 polypeptide indicates that the subject is likely to have a relapse or a persistent or progressive colon cancer. The detection of said secreted polypeptide may indicate the presence of a variety of neoplasias in a subject, such as a colon adenoma, a colon cancer and a metastatic colon cancer. Optionally, a method involves detecting both at least one secreted ColoUp1 polypeptide and at least one secreted ColoUp2 polypeptide in the biological sample.

In certain embodiments, the application provides kits for detecting one or more molecular markers of colon neoplasia in a biological sample. A kit may comprise a) an antibody which interacts with an epitope of a secreted ColoUp1 polypeptide or a secreted ColoUp2 polypeptide; and b) instructions for use. Optionally, the antibody interacts with an epitope of a polypeptide selected from among: the polypeptide of SEQ ID No:1, the polypeptide of SEQ ID No:2, the polypeptide of SEQ ID No:3 and the polypeptide of SEQ ID No:21. Optionally, the antibody is detectably labeled.

In certain embodiments, the application provides a novel purified polypeptide, which is a portion of ColoUp2 that is found in serum. Such a polypeptide may consist essentially of an amino acid sequence that is at least 95%, 98%, 99% or 100% identical to the sequence of SEQ ID No: 21. By "consisting essentially" is meant that there may be, in addition to the indicated amino acid sequence, a variety of modifications, such as phosphorylations, glycosylations, disulfide bonds, unusual or modified amino acids, etc.

In certain embodiments, the application provides novel fusion proteins comprising a first polypeptide domain and a second polypeptide domain, wherein the first polypeptide domain consists essentially of an amino acid sequence that is at least 95%, 98%, 99% or 100% identical to an amino acid sequence of SEQ ID No. 21. The second polypeptide domain may be a domain selected from the group consisting of: a detection domain, a purification domain and an antigenic domain.

In certain embodiments, the application provides antibodies that bind specifically to a ColoUp2 polypeptide consisting essentially of the amino acid sequence of SEQ ID No: 21. The antibody may binds the ColoUp2 polypeptide with a dissociation constant of less than $10^{-6}$M, $10^{-7}$M, $10^{-8}$M or $10^{-9}$M. The antibody may be essentially any type of antibody, including polyclonal, monoclonal, and single chain antibodies, or other fragments. For diagnostic use, there may be little benefit to having a humanized antibody, however, humanized antibodies are highly desirable for therapeutic uses. Preferably, a diagnostic antibody is effective for detecting the ColoUp2 polypeptide in a biological sample, such as a blood, stool or urine sample, or a fraction thereof. Optionally, the antibody is effective for detecting the ColoUp2 polypeptide in a sample comprising cells from a colon neoplasia. The application further provides methods for making such antibodies in a variety of ways. For example, a monoclonal antibody may be produced in a method comprising: (a) administering to a mouse an amount of an immunogenic composition comprising the ColoUp2 polypeptide effective to stimulate a detectable immune response; (b) obtaining antibody-producing cells from the mouse and fusing the antibody-producing cells with myeloma cells to obtain antibody-producing hybridomas; (c) testing the antibody-producing hybridomas to identify a preferred hybridoma, wherein the preferred hybridoma is a hybridoma that produces a monocolonal antibody that binds specifically to the ColoUp2 polypeptide; (d) culturing the preferred hybridoma cell culture that produces the monoclonal antibody that binds specifically to the ColoUp2 polypeptide; and (e) obtaining the monoclonal antibody that binds specifically to the ColoUp2 polypeptide from the cell culture. Optionally, the antibody-producing hybridomas comprises testing whether the antibody-producing hybridomas produce an antibody that binds to the ColoUp2 polypeptide in an assay selected from the group consisting of: an enzyme-linked immunosorbent assay, a Bia-core assay and an immunoprecipitation assay.

The embodiments and practices of the present invention, other embodiments, and their features and characteristics, will be apparent from the description, figures and claims that follow, with all of the claims hereby being incorporated by this reference into this Summary.

BRIEF DESCRIPTION OF THE DRAWINGS

FIG. 1 shows the amino acid sequences (SEQ ID NOs: 1 and 2) of secreted ColoUp1 protein. A. An N-terminal signal peptide is cleaved between amino acids 30-31 of the full-length ColoUp1 protein; B. An N-terminal signal peptide is cleaved between amino acids 33-34 of the full-length ColoUp1 protein.

FIG. 2 shows the amino acid sequence (SEQ ID NO: 3) of secreted ColoUp2 protein.

FIG. 3A-B show the nucleic acid sequence (SEQ ID NO: 4) of ColoUp1.

FIG. 4A-B show the nucleic acid sequence (SEQ ID NO: 5) of ColoUp2.

FIG. 5 shows the nucleic acid sequence (SEQ ID NO: 6) of Osteopontin.

FIG. 6A-B show the nucleic acid sequence (SEQ ID NO: 7) of ColoUp3.

FIG. 7 shows the nucleic acid sequence (SEQ ID NO: 8) of ColoUp4.

FIG. 8 shows the nucleic acid sequence (SEQ ID NO: 9) of ColoUp5.

FIG. 9 shows the nucleic acid sequence (SEQ ID NO: 10) of ColoUp6.

FIG. 10 shows the nucleic acid sequence (SEQ ID NO: 11) of ColoUp7.

FIG. 11 shows the nucleic acid sequence (SEQ ID NO: 12) of ColoUp8.

FIG. 12 shows the amino acid sequence (SEQ ED NO: 13) of full-length ColoUp1 protein.

FIG. 13 shows the amino acid sequence (SEQ ID NO: 14) of full-length ColoUp2 protein.

FIG. 14 shows the amino acid sequence (SEQ ID NO: 15) of full-length Osteopontin protein.

FIG. 15 shows the amino acid sequence (SEQ ID NO: 16) of full-length ColoUp3 protein.

FIG. 16 shows the amino acid sequence (SEQ ID NO: 17) of full-length ColoUp4 protein.

FIG. 17 shows the amino acid sequence (SEQ ID NO: 18) of full-length ColoUp5 protein.

FIG. 18 shows the amino acid sequence (SEQ ID NO: 19) of full-length ColoUp6 protein.

FIG. 19 shows the amino acid sequence (SEQ ID NO: 20) of full-length ColoUp8 protein.

FIG. 35A-H illustrate an alignment of the human (SEQ ID NO: 26), mouse (SEQ ID NO: 27), and rat (SEQ ID NO: 28) ColoUp5 (FoxQ1) nucleic acid sequences.

FIG. 41 shows the amino acid sequence of the approximately 55 kDa C-terminal fragment of ColoUp2 that is a prominent secreted and serum form of ColoUp2.

DETAILED DESCRIPTION

Figure 20:
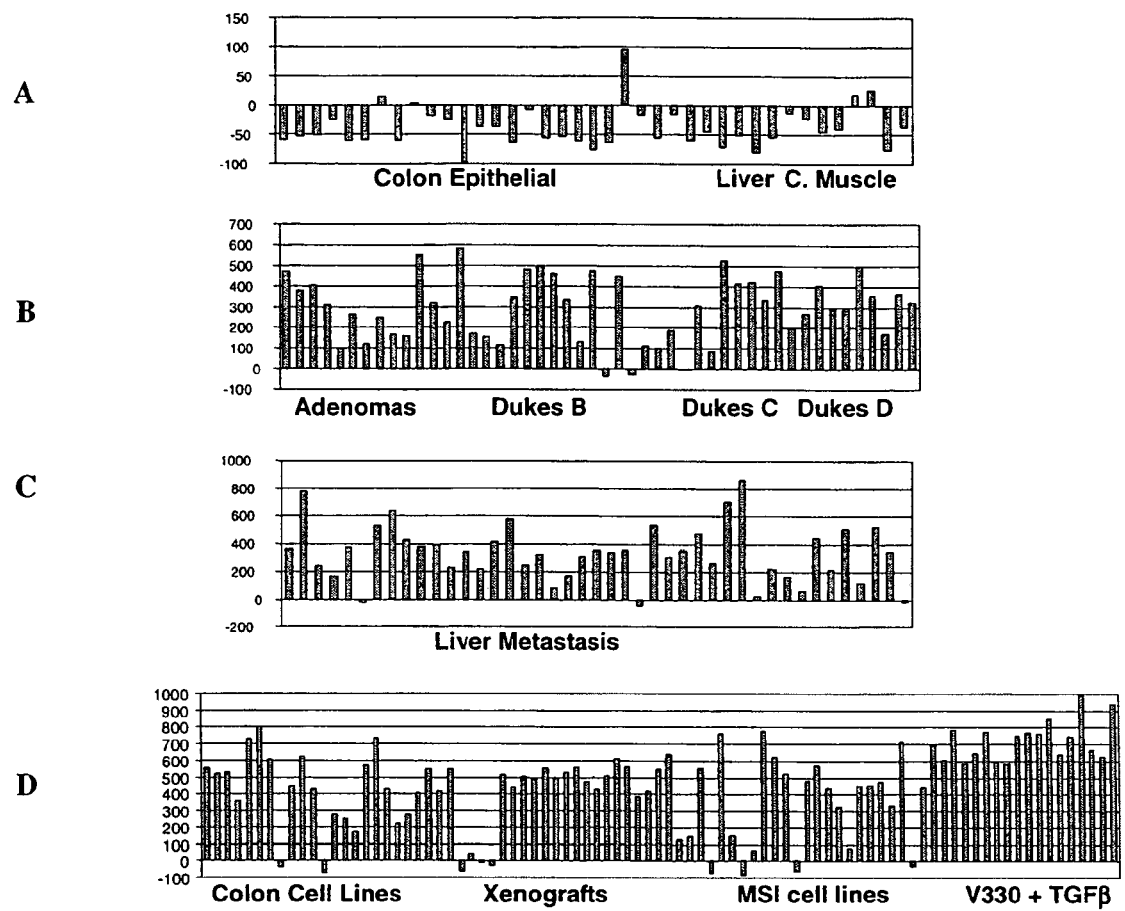
FIG. 20 is a graphical display of ColoUp1 expression levels measured by micro-array profiling in different samples. A. In normal colon epithelial strips, normal liver, and colonic muscle; B. In premalignant colon adenomas as well as in colon cancers of Dukes stages B, Dukes stage C, and Duke stages D; C. In colon cancer liver metastasis; D. In colon cancer cell lines, colon cancer xenografts grown in athymic mice, MSI cell lines, and V330 cell lines treated with TGFβ.

1. Definitions:

For convenience, certain terms employed in the specification, examples, and appended claims are collected here. Unless defined otherwise, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article. By way of example, "an element" means one element or more than one element.

The terms "adenoma", "colon adenoma" and "polyp" are used herein to describe any precancerous neoplasia of the colon.

The term "antibody" as used herein is intended to include whole antibodies, e.g., of any isotype (IgG, IgA, IgM, IgE, etc), and includes fragments thereof which are also specifically reactive with a vertebrate, e.g., mammalian, protein. Antibodies can be fragmented using conventional techniques and the fragments screened for utility and/or interaction with a specific epitope of interest. Thus, the term includes segments of proteolytically-cleaved or recombinantly-prepared portions of an antibody molecule that are capable of selectively reacting with a certain protein. Non-limiting examples of such proteolytic and/or recombinant fragments include Fab, F(ab')$_2$, Fab', Fv, and single chain antibodies (scFv) containing a V[L] and/or V[H] domain joined by a peptide linker. The scFv's may be covalently or non-covalently linked to form antibodies having two or more binding sites. The term antibody also includes polyclonal, monoclonal, or other purified preparations of antibodies and recombinant antibodies.

The term "colon" as used herein is intended to encompass the right colon (including the cecum), the transverse colon, the left colon and the rectum.

The terms "colorectal cancer" and "colon cancer" are used interchangeably herein to refer to any cancerous neoplasia of the colon (including the rectum, as defined above).

The term "ColoUpX" (e.g. ColoUp1, ColoUp2 . . . ColoUp8) is used to refer to a nucleic acid encoding a ColoUp protein or a ColoUp protein itself, as well as distinguishable fragments of such nucleic acids and proteins, longer nucleic acids and polypeptides that comprise distinguishable fragments or full length nucleic acids or polypeptides, and variants thereof. Variants include polypeptides that are at least 90% identical to the relevant human ColoUp SEQ ID Nos. referred to in the application, and nucleic acids encoding such variant polypeptides. In addition, variants include different post-translational modifications, such as glycosylations, methylations, etc. Particularly preferred variants include any naturally occurring variants, such as allelic differences, mutations that occur in a neoplasia and secreted or processed forms. The terms "variants" and "fragments" are overlapping.

As used herein, the phrase "gene expression" or "protein expression" includes any information pertaining to the amount of gene transcript or protein present in a sample, as well as information about the rate at which genes or proteins are produced or are accumulating or being degraded (eg. reporter gene data, data from nuclear runoff experiments, pulse-chase data etc.). Certain kinds of data might be viewed as relating to both gene and protein expression. For example, protein levels in a cell are reflective of the level of protein as well as the level of transcription, and such data is intended to be included by the phrase "gene or protein expression information". Such information may be given in the form of amounts per cell, amounts relative to a control gene or protein, in unitless measures, etc.; the term "information" is not to be limited to any particular means of representation and is intended to mean any representation that provides relevant information. The term "expression levels" refers to a quantity reflected in or derivable from the gene or protein expression data, whether the data is directed to gene transcript accumulation or protein accumulation or protein synthesis rates, etc.

The term "detection" is used herein to refer to any process of observing a marker, in a biological sample, whether or not the marker is actually detected. In other words, the act of probing a sample for a marker is a "detection" even if the marker is determined to be not present or below the level of sensitivity. Detection may be a quantitative, semi-quantitative or non-quantitative observation.

The terms "healthy", "normal" and "non-neoplastic" are used interchangeably herein to refer to a subject or particular cell or tissue that is devoid (at least to the limit of detection) of a disease condition, such as a neoplasia, that is associated with increased expression of a ColoUp gene. These terms, are often used herein in reference to tissues and cells of the colon. Thus, for the purposes of this application, a patient with severe heart disease but lacking a ColoUp-associated disease would be termed "healthy".

The term "including" is used herein to mean, and is used interchangeably with, the phrase "including but not limited to".

As used herein, the term "nucleic acid" refers to polynucleotides such as deoxyribonucleic acid (DNA), and, where appropriate, ribonucleic acid (RNA). The term should also be understood to include analogs of either RNA or DNA made from nucleotide analogs, and, as applicable to the embodiment being described, single-stranded (such as sense or antisense) and double-stranded polynucleotides.

The term "or" is used herein to mean, and is used interchangeably with, the term "and/or", unless context clearly indicates otherwise.

The term "percent identical" refers to sequence identity between two amino acid sequences or between two nucleotide sequences. Identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology/similarity or identity refers to a function of the number of identical or similar amino acids at positions shared by the compared sequences. Various alignment algorithms and/or programs may be used, including FASTA, BLAST or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

The terms "polypeptide" and "protein" are used interchangeably herein.

The term "purified protein" refers to a preparation of a protein or proteins which are preferably isolated from, or otherwise substantially free of, other proteins normally associated with the protein(s) in a cell or cell lysate. The term "substantially free of other cellular proteins" (also referred to herein as "substantially free of other contaminating proteins") is defined as encompassing individual preparations of each of the component proteins comprising less than 20% (by dry weight) contaminating protein, and preferably comprises less than 5% contaminating protein. Functional forms of each of the component proteins can be prepared as purified preparations by using a cloned gene as described in the attached examples. By "purified", it is meant, when referring to component protein preparations used to generate a reconstituted protein mixture, that the indicated molecule is present in the substantial absence of other biological macromolecules, such as other proteins (particularly other proteins which may substantially mask, diminish, confuse or alter the characteristics of the component proteins either as purified preparations or in their function in the subject reconstituted mixture). The term "purified" as used herein preferably means at least 80% by dry weight, more preferably in the range of 85% by weight, more preferably 95-99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above.

A "recombinant nucleic acid" is any nucleic acid that has been placed adjacent to another nucleic acid by recombinant DNA techniques. A "recombinant nucleic acid" also includes any nucleic acid that has been placed next to a second nucleic acid by a laboratory genetic technique such as, for example, transformation and integration, transposon hopping or viral insertion. In general, a recombined nucleic acid is not naturally located adjacent to the second nucleic acid.

The term "recombinant protein" refers to a protein that is produced by expression from a recombinant nucleic acid.

A "sample" includes any material that is obtained or prepared for detection of a molecular marker, or any material that is contacted with a detection reagent or detection device for the purpose of detecting a molecular marker.

A "subject" is any organism of interest, generally a mammalian subject, such as a mouse, and preferably a human subject.

2. Overview

In certain aspects, the invention relates to methods for determining whether a subject is likely or unlikely to have a colon neoplasia. In other aspects, the invention relates to methods for determining whether a patient is likely or unlikely to have a colon cancer. In further aspects, the invention relates to methods for monitoring colon neoplasia in a subject. In further aspects, the invention relates to methods for staging a subject's colon neoplasia. A colon neoplasia is any cancerous or precancerous growth located in, or derived from, the colon. The colon is a portion of the intestinal tract that is roughly three feet in length, stretching from the end of the small intestine to the rectum. Viewed in cross section, the colon consists of four distinguishable layers arranged in concentric rings surrounding an interior space, termed the lumen, through which digested materials pass. In order, moving outward from the lumen, the layers are termed the mucosa, the submucosa, the muscularis propria and the subserosa. The mucosa includes the epithelial layer (bells adjacent to the lumen), the basement membrane, the lamina propria and the muscularis mucosae. In general, the "wall" of the colon is intended to refer to the submucosa and the layers outside of the submucosa. The "lining" is the mucosa.

Precancerous colon neoplasias are referred to as adenomas or adenomatous polyps. Adenomas are typically small mushroom-like or wart-like growths on the lining of the colon and do not invade into the wall of the colon. Adenomas may be visualized through a device such as a colonoscope or flexible sigmoidoscope. Several studies have shown that patients who undergo screening for and removal of adenomas have a decreased rate of mortality from colon cancer. For this and other reasons, it is generally accepted that adenomas are an obligate precursor for the vast majority of colon cancers.

When a colon neoplasia invades into the basement membrane of the colon, it is considered a colon cancer, as the term "colon cancer" is used herein. In describing colon cancers, this specification will generally follow the so-called "Dukes" colon cancer staging system. Other staging systems have been devised, and the particular system selected is, for the purposes of this disclosure, unimportant. The characteristics that the describe a cancer are of greater significance than the particular term used to describe a recognizable stage. The most widely used staging systems generally use at least one of the following characteristics for staging: the extent of tumor penetration into the colon wall, with greater penetration generally correlating with a more dangerous tumor; the extent of invasion of the tumor through the colon wall and into other neighboring tissues, with greater invasion generally correlating with a more dangerous tumor; the extent of invasion of the tumor into the regional lymph nodes, with greater invasion generally correlating with a more dangerous tumor; and the extent of metastatic invasion into more distant tissues, such as the liver, with greater metastatic invasion generally correlating with a more dangerous disease state.

"Dukes A" and "Dukes B" colon cancers are neoplasias that have invaded into the wall of the colon but have not spread into other tissues. Dukes A colon cancers are cancers that have not invaded beyond the submucosa. Dukes B colon cancers are subdivided into two groups: "Dukes B1" and "Dukes B2". "Dukes B1" colon cancers are neoplasias that have invaded up to but not through the muscularis propria. Dukes B2 colon cancers are cancers that have breached completely through the muscularis propria. Over a five year period, patients with Dukes A cancer who receive surgical treatment (i.e. removal of the affected tissue) have a greater than 90% survival rate. Over the same period, patients with Dukes B1 and Dukes B2 cancer receiving surgical treatment have a survival rate of about 85% and 75%, respectively. Dukes A, B1 and B2 cancers are also referred to as T1, T2 and T3-T4 cancers, respectively.

"Dukes C" colon cancers are cancers that have spread to the regional lymph nodes, such as the lymph nodes of the gut. Patients with Dukes C cancer who receive surgical treatment alone have a 35% survival rate over a five year period, but this survival rate is increased to 60% in patients that receive chemotherapy.

"Dukes D" colon cancers are cancers that have metastasized to other organs. The liver is the most common organ in which metastatic colon cancer is found. Patients with Dukes D colon cancer have a survival rate of less than 5% over a five year period, regardless of the treatment regimen.

As noted above, early detection of colon neoplasia, coupled with appropriate intervention, is important for increasing patient survival rates. Present systems for screening for colon neoplasia are deficient for a variety of reasons, including a lack of specificity or sensitivity (e.g. Fecal Occult Blood Test, flexible sigmoidoscopy) or a high cost and intensive use of medical resources (e.g. colonoscopy). Alternative systems for detection of colon neoplasia would be useful in a wide range of other clinical circumstances as well. For example, patients who receive surgical or pharmaceutical therapy for colon cancer may experience a relapse. It would be advantageous to have an alternative system for determining whether such patients have a recurrent or relapsed colon neoplasia. As a further example, an alternative diagnostic system would facilitate monitoring an increase, decrease or persistence of colon neoplasia in a patient known to have a colon neoplasia. A patient undergoing chemotherapy may be monitored to assess the effectiveness of the therapy.

Accordingly, in certain embodiments, the invention provides molecular markers that distinguish between cells that are not part of a colon neoplasia, referred to herein as "healthy cells", and cells that are part of a colon neoplasia (e.g. an adenoma or a colon cancer), referred to herein as "colon neoplasia cells". Certain molecular markers of the invention, including ColoUp1 and ColoUp2, are expressed at significantly higher levels in adenomas, Dukes A, Dukes B1, Dukes B2 and metastatic colon cancer of the liver (liver metastases) than in healthy colon tissue, healthy liver or healthy colon muscle. Certain molecular markers, including ColoUp1 and ColoUp2 are expressed at significantly higher levels in cell lines derived from colon cancer or cell lines engineered to imitate an aspect of a colon cancer cell. Particularly preferred molecular markers of the invention are markers that distinguish between healthy cells and cells of an adenoma. While not wishing to be bound to theory, it is contemplated that because adenomas are thought to be an obligate precursor for greater than 90% of colon cancers, markers that distinguish between healthy cells and cells of an adenoma are particularly valuable for screening apparently healthy patients to determine whether the patient is at increased risk for (predisposed to) developing a colon cancer. Furthermore, particularly preferred molecular markers are those that are actually present in the serum of an animal having a colon neoplasia, and in general, a secreted protein will generally occur in the serum only if it is secreted from a cell contacting a blood vessel, or a compartment in diffusional contact with a blood vessel. For example, protein secreted from a large or advanced colon cancer will generally be found in the blood stream, but a protein secreted from a colon adenoma may not be present in the blood unless it is secreted from the basolateral face of the cell. Molecular markers that occur in the urine are generally derived from a polypeptide that is present in the blood. Optionally, a molecular marker is one that is present in the lumen of the colon (e.g., may be found in the intestinal mucous or in stool samples), and such a marker will generally be one that is secreted from the apical face of a cell.

In certain embodiments, the invention provides methods for using ColoUp molecular markers for determining whether a patient has or does not have a condition characterized by increased expression of one or more ColoUp nucleic acids or proteins described herein. In certain embodiments, the invention provides methods for determining whether a patient is or is not likely to have a colon neoplasia. In further embodiments, the invention provides methods for determining whether the patient is having a relapse or determining whether a patient's colon neoplasia is responding to treatment.

3. Methods for Identifying Candidate Molecular Markers for Colon Neoplasia

In certain aspects, the invention relates to the observation that when gene expression data is analyzed using carefully selected criteria, the likelihood of identifying strong candidate molecular markers of a colon neoplasia is quite high. Accordingly, in certain embodiments, the invention provides methods and criteria for analyzing gene expression data to identify candidate molecular markers for colon neoplasia. Although methods and criteria of the invention may be applied to essentially any relevant gene expression data, the benefits of using the inventive methods and criteria are readily apparent when applied to the copious data produced by highly parallel gene expression measurement systems, such as microarray systems. The human genome is estimated to be capable of producing roughly 20,000 to 100,000 different gene transcripts, thousands of which may show a change in expression level in healthy cells versus colon neoplasia cells. It is relatively cost-effective to obtain large quantities of gene expression data and to use this data to identify thousands of candidate molecular markers. However, a significant amount of labor intensive experimentation is generally needed to move from the identification of a candidate molecular marker to an effective diagnostic test for a health condition of interest. In fact, as of the time of filing of this application, the resources required to generate a diagnostic test from a single candidate molecular marker identified by gene expression data are large enough that it is essentially impossible to extract commercially valuable and clinically useful diagnostics from a list of hundreds or thousands of genes whose expression levels change in a particular situation. Accordingly, there is a substantial practical value in being able to select a small number (e.g. ten or fewer) of high-quality molecular markers for further study.

In certain embodiments, candidate molecular markers for colon neoplasia may be selected by comparing gene expression in liver metastatic colon cancer samples ("liver mets"), normal (non-neoplastic) colon samples and normal liver samples. In this embodiment, candidate molecular markers are those genes (and their gene products) that have a level of expression in liver mets (assessed as a median expression level across the sample set) that is at least four times greater than the level of expression in normal colon samples (also assessed as a median expression level across the sample set). Furthermore, in this embodiment, the median level of expression in liver mets should be greater than the median level of expression in normal liver samples. The criteria employed in this embodiment provide a high threshold to eliminate most lower quality markers and further eliminate contaminants from liver tissue.

In certain embodiments, candidate molecular markers for colon neoplasia may be selected by comparing gene expression in normal colon to gene expression in a plurality of different cell lines cultured from metastatic colon cancer samples. For example median metastatic colon cancer cell line gene expression may be calculated as the median of 8 colon cancer cell lines of the Vaco colon cancer cell line series (Markowitz, S. et al. Science. 268: 1336-1338, 1995), such as the following liver metastatses-derived cell lines: V394, V576, V241, V9M, V400, V10M, V503, V786. In embodiments employing this criterion, candidate molecular markers are those genes (and their gene products) that have at least a three-fold higher median level of expression across the cell lines tested than in the normal colon tissue.

In certain embodiments, candidate molecular markers for colon neoplasia may be selected by comparing gene expression in normal colon to gene expression in a plurality of colon cancer xenografts grown in athymic mice ("xenografts"). In embodiments employing this criterion, candidate molecular markers are those genes (and their gene products) that have at least a four-fold higher median level of expression across the xenografts tested than in the normal colon tissue.

In certain embodiments, candidate molecular markers for colon neoplasia may be selected by comparing maximum gene expression in normal colon to minimum gene expression in liver mets. In these embodiments, candidate molecular markers are those genes (and their gene products) that have a minimum gene expression in liver mets that is at least equal to the maximum gene expression in normal colon. Furthermore, in this embodiment, the median level of expression in liver mets should be greater than the median level of expression in normal liver samples.

In a preferred embodiment, a list of candidate molecular markers for colon neoplasia is selected by first identifying a subset of genes having a four-fold greater median expression in liver mets that in normal colon and in normal liver. This subset is then further narrowed to a final list by identifying those genes that have a three-fold greater median expression across colon cancer cell lines than in normal colon. Optionally, a particularly preferred list may be generated by further selecting those genes having a minimum gene expression in liver mets that is greater than or equal to the maximum gene expression in normal colon. The gene products (e.g. proteins and nucleic acids) of the short list of genes generated in these preferred embodiments constitute a list of high-quality candidate molecular markers for colon cancer.

In another preferred embodiment, a list of candidate molecular markers for colon neoplasia is selected by first identifying a subset of genes having a four-fold greater median expression in liver mets that in normal colon and in normal liver. This subset is then further narrowed by identifying those genes that have a nine-fold greater median expression in liver mets than in normal colon. This subset is then further narrowed to a final list by identifying those genes that have a four-fold greater median expression across colon cancer cell lines than in normal colon. The gene products (e.g. proteins and nucleic acids) of the short list of genes generated in these preferred embodiments constitute a list of high-quality candidate molecular markers for colon cancer.

Depending on the nature of the intended use for the molecular marker it may be desirable to add further criteria to any of the preceding embodiments. In certain embodiments, the invention relates to candidate molecular markers for categorizing a patient as likely to have or not likely to have a colon neoplasia (including adenomas and colon cancers), and in these embodiments, a high-quality candidate molecular marker will be expressed from a gene having an increased expression in both adenomas and liver mets relative to normal colon, and preferably in other colon cancer stages, including Dukes A, Dukes B1, Dukes B2 and Dukes C. In certain embodiments the invention relates to candidate molecular markers for categorizing a patient as likely to have or not likely to have a colon cancer (including metastatic and non-metastatic forms), and in these embodiments, a high-quality candidate molecular marker will be expressed from a gene having an increased expression in liver mets relative to adenomas and normal colon, and preferably there will be elevated expression in other colon cancer stages, including Dukes A, Dukes B1, Dukes B2 and Dukes C. In certain embodiments, the invention relates to candidate molecular markers for categorizing a patient as likely or not likely to have a metastatic colon cancer, and in such embodiments, a comparison to gene expression in other colon neoplasias (e.g. adenomas, Dukes A, Dukes B1, Dukes B2, Dukes C), while potentially useful, is not necessary, although it is noted that expression in non-metastatic states may indicate that a candidate molecular marker is not of high quality for distinguishing metastatic colon cancer from non-metastatic states.

Furthermore, in those embodiments pertaining to molecular markers to be used for detection in a body fluid, such as blood, a high quality molecular marker will preferably be a secreted protein. In those embodiments pertaining to neoplasia identification or targeting, a high quality molecular marker will preferably be a protein with a portion adherent to and exposed on the extracellular surface of a neoplasia, such as a transmembrane protein with a significant extracellular portion.

Gene expression data may be gathered using one or more of the many known and appropriate techniques that, in view of this specification, may be selected to one of skill in the art. In certain preferred embodiments, gene expression data is gathered by a highly parallel system, meaning a system that allows simultaneous or near-simultaneous collection of expression data for one hundred or more gene transcripts. Exemplary highly parallel systems include probe arrays ("arrays") that are often divided into microarrays and macroarrays, where microarrays have a much higher density of individual probe species per area. Arrays generally consist of a surface to which probes that correspond in sequence to gene products (e.g., cDNAs, mRNAs, oligonucleotides) are bound at known positions. The probes can be, e.g., a synthetic oligomer, a full-length cDNA, a less-than full length cDNA, or a gene fragment. Usually a microarray will have probes corresponding to at least 100 gene products and more preferably, 500, 1000, 4000 or more. Probes may be small oligomers or larger polymers, and there may be a plurality of overlapping or non-overlapping probes for each transcript.

The nucleic acids to be contacted with the microarray may be prepared in a variety of ways. Methods for preparing total and poly(A)+ RNA are well known and are described generally in Sambrook et al., supra. Labeled cDNA may be prepared from mRNA by oligo dT-primed or random-primed reverse transcription, both of which are well known in the art (see e.g., Klug and Berger, 1987, Methods Enzymol. 152:

316-325). cDNAs may be labeled by incorporation of labeled nucleotides or by labeling after synthesis. Preferred labels are fluorescent labels.

Nucleic acid hybridization and wash conditions are chosen so that the population of labeled nucleic acids will specifically hybridize to appropriate, complementary probes affixed to the matrix. Optimal hybridization conditions will depend on the length (e.g., oligomer versus polynucleotide greater than 200 bases) and type (e.g., RNA, DNA, PNA) of labeled nucleic acids and immobilized polynucleotide or oligonucleotide. General parameters for specific (i.e., stringent) hybridization conditions for nucleic acids are described in Sambrook et al., supra, and in Ausubel et al., 1987, Current Protocols in Molecular Biology, Greene Publishing and Wiley-Interscience, New York, which is incorporated in its entirety for all purposes. Non-specific binding of the labeled nucleic acids to the array can be decreased by treating the array with a large quantity of non-specific DNA—a so-called "blocking" step.

Signals, such as fluorescent emissions for each location on an array are generally recorded, quantitated and analyzed using a variety of computer software. Signal for any one gene product may be normalized by a variety of different methods. Arrays preferably include control and reference probes. Control probes are nucleic acids which serve to indicate that the hybridization was effective. Reference probes allow the normalization of results from one experiment to another, and to compare multiple experiments on a quantitative level. Reference probes are typically chosen to correspond to genes that are expressed at a relatively constant level across different cell types and/or across different culture conditions. Exemplary reference nucleic acids include housekeeping genes of known expression levels, e.g., GAPDH, hexokinase and actin.

Following the data gathering operation, the data will typically be reported to a data analysis system. To facilitate data analysis, the data obtained by the reader from the device will typically be analyzed using a digital computer. Typically, the computer will be appropriately programmed for receipt and storage of the data from the device, as well as for analysis and reporting of the data gathered, e.g., subtraction of the background, deconvolution multi-color images, flagging or removing artifacts, verifying that controls have performed properly, normalizing the signals, interpreting fluorescence data to determine the amount of hybridized target, normalization of background and single base mismatch hybridizations, and the like. Various analysis methods that may be employed in such a data analysis system, or by a separate computer are described herein.

A number of methods for constructing or using arrays are described in the following references. Schena et al., 1995, Science 270:467-470; DeRisi et al., 1996, Nature Genetics 14:457-460; Shalon et al., 1996, Genome Res. 6:639-645; Schena et al., 1995, Proc. Natl. Acad. Sci. USA 93:10539-11286; Fodor et al., 1991, Science 251:767-773; Pease et al., 1994, Proc. Natl. Acad. Sci. USA 91:5022-5026; Lockhart et al., 1996, Nature Biotech 14:1675; U.S. Pat. Nos. 6,051,380; 6,083,697; 5,578,832; 5,599,695; 5,593,839; 5,631,734; 5,556,752; 5,510,270; EP No. 0 799 897; PCT No. WO 97/29212; PCT No. WO 97/27317; EP No. 0 785 280; PCT No. WO 97/02357; EP No. 0 728 520; EP No. 0 721 016; PCT No. WO 95/22058.

A variety of companies provide microarrays and software for extracting certain information from microarray data. Such companies include Affymetrix (Santa Clara, Calif.), GeneLogic (Gaithersburg, Md.) and Eos Biotechnology Inc. (South San Francisco, Calif.).

While the above discussion focuses on the use of arrays for the collection of gene expression data, such data may also be obtained through a variety of other methods, that, in view of this specification, are known to one of skill in the art. Such methods include the serial analysis of gene expression (SAGE) technique, first described in Velculescu et al. (1995) Science 270, 484-487. Reverse transcriptase-polymerase chain reaction (RT-PCR) may be used, and particularly in combination with fluorescent probe systems such as the Taqman™ fluorescent probe system. Numerous RT-PCR samples can be analyzed simultaneously by conducting parallel PCR amplification, e.g., by multiplex PCR. Further techniques include dotblot analysis and related methods (see, e.g., G. A. Beltz et al., in Methods in Enzymology, Vol. 100, Part B, R. Wu, L. Grossmam, K. Moldave, Eds., Academic Press, New York, Chapter 19, pp. 266-308, 1985), Northern blots and in situ hybridization (probing a tissue sample directly).

The quality and biological relevance of gene expression data will be significantly affected by the quality of the biological material used to obtain gene expression. In preferred embodiments, the methods described herein for identifying candidate molecular markers for colon neoplasia employ tissue samples obtained with appropriate consent from human patients and rapidly frozen. At a point prior to gene expression analysis, the tissue sample is preferably prepared by carefully dissecting away as much heterogeneous tissue as is possible with the available tools. In other words, for a colon cancer sample, adherent non-cancerous tissue should be dissected away, to the extent that it is possible. In preferred embodiments, healthy tissue is obtained from a subject that has a colon neoplasia but is tissue that is not directly entangled in a neoplasia.

Example 1, below, illustrates the operation of a method of selecting high-quality molecular markers, and the following markers were selected, using criteria disclosed herein, from microarray expression data: ColoUp1, ColoUp2, ColoUp3, ColoUp4, ColoUp5, ColoUp6, ColoUp7 and ColoUp8. In addition, osteopontin was identified as having expression characteristics very similar to those identified using the selection criteria. Further experimentation (see Examples) demonstrated that these molecular markers fall into four categories: "secreted" (ColoUp1, ColoUp2 and osteopontin), "transmembrane" (ColoUp3), "transcription factors" (ColoUp4, ColoUp5) and "other" (ColoUp6, ColoUp7, ColoUp8). Further experimentation also demonstrated that ColoUp1, ColoUp2, ColoUp3, ColoUp5 and ColoUp7 are, generally speaking, expressed at higher levels in a variety of colon neoplasias (adenomas, Dukes B tumors, Dukes C tumors and liver mets) than in healthy cells. In addition, further experimentation demonstrated that osteopontin is overexpressed in colon cancers (Dukes B, Dukes C and liver mets) relative to adenomas and normal colon.

In certain embodiments, a preferred molecular marker for use in a diagnostic test that employs a body fluid sample, such as a blood or urine sample, or an excreted sample material, such as stool, is a secreted protein, such as the secreted portion of a ColoUp1 protein, ColoUp2 protein or osteopontin protein.

In certain embodiments, a preferred molecular marker for a method that involves targeting or marking a colon neoplasia is a transmembrane protein, such as ColoUp3, and particularly the extracellular portion of ColoUp3. Transmembrane proteins are desirable for such methods because they are both anchored to the neoplastic cell and exposed to the extracellular surface.

In certain embodiments, a preferred molecular marker for use in a diagnostic test to distinguish subjects likely to have a colon neoplasia from those not likely to have a colon neoplasia is a gene product of the ColoUp1, ColoUp2, ColoUp3, ColoUp4 or ColoUp5 genes. Examples of suitable gene products include proteins, both secreted and not secreted and transcripts. In embodiments employing proteins that are not secreted, such as ColoUp3, ColoUp4 and ColoUp5, a preferred embodiment of the diagnostic test is a test for the presence of the protein or transcript in cells shed from the colon or colon neoplasia (which, in the case of metastases is not necessarily located in the colon) into a sample material, such as stool. In embodiments employing proteins that are secreted, such as ColoUp1 and ColoUp2, a preferred embodiment of the diagnostic test is a test for the presence of the protein in a body fluid, such as urine or blood or an excreted material, such as stool. It should be noted, however, that intracellular protein may be present in a body fluid if there is significant cell lysis or through some other process. Likewise, secreted proteins are likely to be adherent, even if at a relatively low level, to the cells in which they were produced.

In certain embodiments, a preferred molecular marker for distinguishing subjects having a colon cancer from those having an adenoma or a normal colon is gene product of the ColoUp6 and osteopontin genes. In embodiments preferably employing marker proteins that are secreted, such as a test using a body fluid sample, a preferred marker is a secreted osteopontin protein.

ColoUp1:

A human ColoUp1 nucleic acid sequence encodes a full-length protein of 1361 amino acids. SignalP V1.1 predicts that human ColoUp1 protein has an N-terminal signal peptide that is cleaved between either amino acids 30-31 (ATS-TV) or amino acids 33-34 (TVA-AG). Four potential glycosylation sites are identified in ColoUp1 protein. Further, ColoUp1 protein is predicted to have multiple serine, threonine, and tyrosine phosphorylation sites for kinases such as protein kinase C, cAMP- and cGMP-dependent protein kinases, casein kinase II, and tyrosine kinases. The ColoUp1 protein shares limited sequence homology to a human transmembrane protein 2 (See Scott et al. 2000 Gene 246:265-74). A mouse ColoUp1 homolog is identified in existing GenBank databases and is linked with mesoderm development (see Wines et al. 2001 Genomics. 88-98; GenBank entry AAG41062, AY007815 for the 1179 bp nucleic acid sequence entry, with 363/390 (93%) identities with human ColoUp1).

As demonstrated herein, ColoUp1 is secreted from both the basolateral and apical surfaces of intestinal cells.

ColoUp2:

The ColoUp2 nucleic acid sequence encodes a full-length protein of 755 amino acids. The application also discloses certain polymorphisms that have been observed, for example at nucleotide 113 GCC→SACC (Ala-Thr); nt 480 GAA→GGA (Glu-Gly); and at nt 2220 CAG-→CGG (Gln-Arg). The sequence of ColoUp2 protein is similar to that of alpha 3 type VI collagen, isoform 2 precursor. In addition, a few domains are identified in the ColoUp2 protein such as a von Willebrand factor type A domain (vWF) and an EGF-like domain. The vWF domain is found in various plasma proteins such as some complement factors, the integrins, certain collagen, and other extracellular proteins. Proteins with vWF domains participate in numerous biological events which involve interaction with a large array of ligands, for example, cell adhesion, migration, homing, pattern formation, and signal transduction. The EGF-like domain consisting of about 30-40 amino acid residues has been found many proteins. The functional significance of EGF domains is not yet clear. However, a common feature is that these EGF-like repeats are found in the extracellular domain of membrane-bound proteins or in proteins known to be secreted.

As demonstrated herein, ColoUp2 is secreted from both the apical and basolateral surfaces of intestinal cells, and can be found in the blood in two different forms, a full-length secreted form and a C-terminal fragment (approximately 55 kDa).

Osteopontin:

The Osteopontin nucleic acid sequence encodes a full-length protein of 300 amino acids. Osteopontin is an acidic glycoprotein and is produced primarily by osteoclasts, macrophages, T-cells, kidneys, and vascular smooth muscle cells. As a cytokine, Osteopontin is known to contribute substantially to metastasis formation by various cancers. In addition, it contributes to macrophage homing and cellular immunity, mediates neovascularization, inhibits apoptosis, and maintains the homeostasis of free calcium (see a review, Weber G F. 2001 Biochim Biophys Acta. 1552:61-85).

ColoUp3:

The ColoUp3 nucleic acid sequence encodes a full-length protein of 829 amino acids. ColoUp3 is referred to in the literature as P-cadherin (or cadherin 3, type 1). P-cadherin belongs to a cadherin family that includes E-cadherin and N-cadherin. P-cadherin is expressed in placenta and stratified squamous epithelia (see Shimoyama et al. 1989 J. Cell Biol. 109:1787-94), but not in normal colon. P-cadherin null mice develop mammary gland hyperplasia, dysplasia, and abnormal lymphoid infiltration (see Radice et al. 1997 J. Cell Biol. 139:1025-32), demonstrating that loss of normal P-cadherin expression leads to cellular and glandular abnormalities. It has been shown that P-cadherin is aberrantly expressed in inflamed and dysplastic colitic mucosa, with concomitant E-cadherin downregulation. Recently, aberrant P-cadherin expression is found as an early event in hyperplastic and dysplastic transformation in the colon (see Hardy et al. 2002 Gut. 50:513-514).

ColoUp4:

The ColoUp4 nucleic acid sequence encodes a full-length protein of 694 amino acids. ColoUp4 is referred to in the literature as NF-E2 related factor 3 (NRF3). NRF3 was identified and characterized as a novel Cap'n' collar (CNC) factor, with a basic region-leucine zipper domain highly homologous to those of other CNC proteins such as NRF1 and NRF2. These CNC factors bind to Maf recognition elements (MARE) through heterodimer formation with small Maf proteins In vitro and in vivo analyses showed that NRF3 can heterodimerize with MafK and that this complex binds to the MARE in the chicken β-globin enhancer and can activate transcription. NRF3 mRNA is highly expressed in human placenta and B cell and monocyte lineage. (see Kobayashi et al. 1999 J Biol. Chem. 274:6443-52).

ColoUp5:

The ColoUp5 nucleic acid sequence encodes a full-length protein of 402 amino acids. ColoUp5 is referred to in the literature as FoxQ1 (Forkhead box, subclass q, member 1, formerly known as HFH-1). FoxQ1 is a member of the evolutionarily conserved winged helix/forkhead transcription factor gene family. The hallmark of this family is a conserved DNA binding region of approximately 110 amino acids (FOX domain). Members of the FOX gene family are found in a broad range of organisms from yeast to human. Human FoxQ1 gene is expressed in different tissues such as stomach, trachea, bladder, and salivary gland. FoxQ1 gene plays important roles in tissue-specific gene regulation and development, for example, embryonic development, cell cycle regulation, cell signaling, and tumorigenesis. The FoxQ1 gene is located on chromosome 6p23-25. Sequence analysis indicates that human FoxQ1 shows 82% homology with the mouse Foxq1 gene (formerly Hfh-1L) and with a revised sequence of the rat FoxQ1 gene (formerly Hfh-1). Mouse FoxQ1 was shown to regulate differentiation of hair in Satin mice. The DNA-binding motif (i.e., the FOX domain) is well conserved, showing 100% identity in human, mouse, and rat. The human FoxQ1 protein sequence contains two putative transcriptional activation domains, which share a high amino acid identity with the corresponding mouse and rat domains (see Bieller et al. 2001 DNA Cell Biol. 20:555-61).

ColoUp6:

The ColoUp6 nucleic acid sequence encodes a full-length protein of 209 amino acids. The ColoUp6 protein is 99% identical to the C-terminal portion of keratin 23 (or cytokeratin 23, or the type I intermediate filament cytokeratin), and accordingly the term ColoUp6 includes both the 209 amino acid protein (and related nucleic acids, fragments, variants, etc.) and the cytokeratin 23 amino acid sequence of GenBank entry BAA92054.1 (and related nucleic acids, fragments, variants, etc.). Keratin 23 mRNA was found highly induced in different pancreatic cancer cell lines in response to sodium butyrate. The keratin 23 protein has 422 amino acids, and has an intermediate filament signature sequence and extensive homology to type I keratins. It is suggested that keratin 23 is a novel member of the acidic keratin family that is induced in pancreatic cancer cells undergoing differentiation by a mechanism involving histone hyperacetylation (See Zhang et al. 2001 Genes Chromosomes Cancer. 30:123-35).

ColoUp7:

The ColoUp7 nucleic acid sequence is an EST sequence. No information relating to the function of the ColoUp7 gene is identified.

ColoUp8:

The ColoUp8 nucleic acid sequence encodes a full-length protein of 278 amino acids. No function has been suggested relating to the ColoUp8 gene.

Accordingly, in certain embodiments, the application provides isolated, purified or recombinant ColoUp1, ColoUp2, ColoUp3, ColoUp4, ColoUp5, ColoUp6, ColoUp7, ColoUp8 and osteopontin nucleic acids. In certain embodiments, such nucleic acids may encode a complete or partial ColoUp polypeptide or such nucleic acids may also be probes or primers useful for methods involving detection or amplification of ColoUp nucleic acids. In certain embodiments, a ColoUp nucleic acid is single-stranded or double-stranded and composed of natural nucleic acids, nucleotide analogs, or mixtures thereof. In certain embodiments, the application provides isolated, purified or recombinant nucleic acids comprising a nucleic acid sequence that is at least 90% identical to a nucleic acid sequence of any of SEQ ID Nos: 3-12, or a complement thereof, and optionally at least 95%, 97%, 98%, 99%, 99.3%, 99.5%, 99.7% or 100% identical to a nucleic acid of any of SEQ ID Nos: 3-12, or a complement thereof. In certain preferred embodiments, the application provides a isolated, purified or recombinant nucleic acids comprising a nucleic acid sequence that is at least 90%, 95%, 97%, 98%, 99%, 99.3%, 99.5%, 99.7% or 100% identical to a nucleic acid of any of SEQ ID Nos: 3-12, or a complement thereof. In certain embodiments, the application provides isolated, purified or recombinant nucleic acids comprising a nucleic acid sequence that encodes a polypeptide that is at least 90% identical to an amino acid sequence of any of SEQ ID Nos: 1-3 or 13-21, or a complement thereof, and optionally at least 95%, 97%, 98%, 99%, 99.3%, 99.5%, 99.7% or 100% identical to an amino acid sequence of any of SEQ ID Nos: 1-3 or 13-21, or a complement thereof. In certain preferred embodiments, the application provides isolated, purified or recombinant nucleic acids comprising a nucleic acid sequence that encodes a polypeptide that is at least 90% identical to an amino acid sequence of any of SEQ ID Nos: 3, 14 or 21, or a complement thereof, and optionally at least 95%, 97%, 98%, 99%, 99.3%, 99.5%, 99.7% or 100% identical to an amino acid sequence of any of SEQ ID Nos: 3, 14 or 21, or a complement thereof.

In further embodiments, the application provides expression constructs, vectors and cells comprising a ColoUp nucleic acid. Expression constructs are nucleic acid constructs that are designed to permit expression of an expressible nucleic acid (e.g. a ColoUp nucleic acid) in a suitable cell type or in vitro expression system. A variety of expression construct systems are, in view of this specification, well known in the art, and such systems generally include a promoter that is operably linked to the expressible nucleic acid. The promoter may be a constitutive promoter, as in the case of many viral promoters, or the promoter may be a conditional promoter, as in the case of the prokaryotic lad-repressible, IPTG-inducible promoter and as in the case of the eukaryotic tetracycline-inducible promoter. Vectors refer to any nucleic acid that is capable of transporting another nucleic acid to which it has been linked between different cells or viruses. One type of vector is an episome, i.e., a nucleic acid capable of extra-chromosomal replication, such as a plasmid. Episome-type vectors typically carry an origin of replication that directs replication of the vector in a host cell. Another type of vector is an integrative vector that is designed to recombine with the genetic material of a host cell. Vectors may be both autonomously replicating and integrative, and the properties of a vector may differ depending on the cellular context (i.e. a vector may be autonomously replicating in one host cell type and purely integrative in another host cell type). Vectors capable of directing the expression of genes to which they are operatively linked are referred to herein as "expression vectors". Vectors that carry an expression construct are generally expression vectors. Vectors have been designed for a variety of cell types. For example, in the bacterium E. coli, commonly used vectors include pUC plasmids, pBR322 plasmids, pBlueScript and M13 plasmids. In insect cells (e.g. SF-9, SF-21 and High-Five cells), commonly used vectors include BacPak6 (Clontech) and BaculoGold (Pharmingen) (both Clontech and Pharmingen are divisions of Becton, Dickinson and Co., Franklin Lakes, N.J.). In mammalian cells (e.g. Chinese hamster ovary (CHO) cells, Vaco cells and human embryonic kidney (HEK) cells), commonly used vectors include pCMV vectors (Stratagene, Inc., La Jolla, Calif.), and pRK vectors. In certain embodiments, the application provides cells that comprise a ColoUp nucleic acid, particularly a recombinant ColoUp nucleic acid, such as an expression construct or vector that comprises a ColoUp nucleic acid. Cells may be eukaryotic or prolaryotic, depending on the anticipated use. Prokaryotic cells, especially E. coli, are particularly useful for storing and replicating nucleic acids, particularly nucleic acids carried on plasmid or viral vectors. Bacterial cells are also particularly useful for expressing nucleic acids to produce large quantities of recombinant protein, but bacterial cells do not usually mimic eukaryotic post-translational modifications, such as glycosylations or lipid-modifications, and so will tend to be less suitable for production of proteins in which the post-translational modification state is significant. Eukaryotic cells, and especially cell types such as insect cells that work with baculovirus-based protein expression systems, and Chinese hamster ovary cells, are good systems for expressing eukaryotic proteins that have significant post-translational modifications. Eukaryotic cells are also useful for studying various aspects of the function of eukaryotic proteins. For example, colon cancer cell lines are good model systems for studying the role of ColoUp genes and proteins in colon cancers.

In certain aspects the application further provides methods for preparing ColoUp polypeptides. In general, such methods comprise obtaining a cell that comprises a nucleic acid encoding a ColoUp polypeptide, and culturing the cell under conditions that cause production of the ColoUp polypeptide. Polypeptides produced in this manner may be obtained from the appropriate cell or culture fraction. For example, secreted proteins are most readily obtained from the culture supernatant, soluble intracellular proteins are most readily obtained from the soluble fraction of a cell lysate, and membrane proteins are most readily obtained from a membrane fraction. However, proteins of each type can generally be found in all three types of cell or culture fraction. Crude cellular or culture fractions may be subjected to further purification procedures to obtain substantially purified ColoUp polypeptides. Common purification procedures include affinity purification (e.g. with hexahistidine-tagged polypeptides), ion exchange chromatography, reverse phase chromatography, gel filtration chromatography, etc.

In certain aspects the application provides recombinant, isolated, substantially purified or purified ColoUp1, ColoUp2, ColoUp3, ColoUp4, ColoUp5, ColoUp6, ColoUp7, ColoUp8 and osteopontin polypeptides. In certain embodiments, such polypeptides may encode a complete or partial ColoUp polypeptide. In certain embodiments, a ColoUp polypeptide is composed of natural amino acids, amino acid analogs, or mixtures thereof. ColoUp polypeptides may also include one or more post-translational modifications, such as glycosylation, phosphorylation, lipid modification, acetylation, etc. In certain embodiments, the application provides isolated, substantially purified, purified or recombinant polypeptides comprising an amino acid sequence that is at least 90% identical to an amino acid sequence of any of SEQ ID Nos: 1-3 or 13-21 and optionally at least 95%, 97%, 98%, 99%, 99.3%, 99.5% or 99.7% identical to a nucleic acid of any of SEQ ID Nos: 1-3 or 13-21. In certain preferred embodiments, the application provides a isolated, substantially purified, purified or recombinant polypeptide comprising an amino acid sequence that is at least 90%, 95%, 97%, 98%, 99%, 99.3%, 99.5% or 99.7% identical to a nucleic acid of any of SEQ ID Nos: 3, 14 or 21. In certain preferred embodiments, the application provides an isolated, substantially purified, purified or recombinant polypeptide comprising an amino acid sequence that differs from SEQ ID Nos. 3, 14 or 21 by no more than 4 amino acid substitutions, additions or deletions. Optionally, a polypeptide of the invention comprises an additional moiety, such as an additional polypeptide sequence or other added compound, with a particular function, such as an epitope tag that facilitates detection of the recombinant polypeptide with an antibody, a purification moiety that facilitates purification (e.g. by affinity purification), a detection moiety, that facilitates detection of the polypeptide in vivo or in vitro, or an antigenic moiety that increases the antigenicity of the polypeptide so as to facilitate antibody production. Often, a single moiety will provide multiple functionalities. For example, an epitope tag will generally also assist in purification, because an antibody that recognizes the epitope can be used in an affinity purification procedure as well. Examples of commonly used epitope tags are: an HA tag, a hexahistidine tag, a V5 tag, a Glu-Glu tag, a c-myc tag, a VSV-G tag, a FLAG tag, an enterokinase cleavage site tag and a T7 tag. Commonly used purification moieties include: a hexahistidine tag, a glutathione-S-transferase domain, a cellulose binding domain and a biotin tag. Commonly used detection moieties include fluorescent proteins (e.g. green fluorescent proteins), a biotin tag, and chromogenic/fluorogenic enzymes (e.g. beta-galactosidase and luciferase). Commonly used antigenic moieties include the keyhole limpet hemocyanin and serum albumins. Note that these moieties need not be polypeptides and need not be connected to the polypeptide by a traditional peptide bond.

4. Antibodies and Uses Therefor

Another aspect of the invention pertains to an antibody specifically reactive with a ColoUp polypeptide, preferably antibodies that are specifically reactive with ColoUp polypeptides such as ColoUp1 and ColoUp2 polypeptides. For example, by using immunogens derived from a ColoUp polypeptide, e.g., based on the cDNA sequences, anti-protein/anti-peptide antisera or monoclonal antibodies can be made by standard protocols (See, for example, Antibodies: A Laboratory Manual ed. by Harlow and Lane (Cold Spring Harbor Press: 1988)). A mammal, such as a mouse, a hamster or rabbit can be immunized with an immunogenic form of the peptide (e.g., a ColoUp polypeptide or an antigenic fragment which is capable of eliciting an antibody response, or a fusion protein). Techniques for conferring immunogenicity on a protein or peptide include conjugation to carriers or other techniques well known in the art. An immunogenic portion of a ColoUp polypeptide can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of a ColoUp polypeptide of a mammal, e.g., antigenic determinants of a protein set forth in SEQ ID Nos: 1-3 and 13-21, more preferably SEQ ID Nos: 1-3 or 21.

In one embodiment, antibodies are specific for the secreted proteins as encoded by nucleic acid sequences as set forth in SEQ ID Nos: 4-5. In another embodiment, the antibodies are immunoreactive with one or more proteins having an amino acid sequence that is at least 80% identical to an amino acid sequence as set forth in SEQ ID Nos: 1-3 and 13-21, preferably SEQ ID Nos: 1-3 or 21. In other embodiments, an antibody is immunoreactive with one or more proteins having an amino acid sequence that is at least 85%, 90%, 95%, 98%, 99%, 99.3%, 99.5%, 99.7% identical or 100% identical to an amino acid sequence as set forth in SEQ ID Nos: 1-3 and 13-21. More preferably, the antibody is immunoreactive with one or more proteins having an amino acid sequence that is at least 85%, 90%, 95%, 98%, 99%, 99.3%, 99.5%, 99.7% or identical to an amino acid sequence as set forth in SEQ ID NOs: 1-3 or 21. In certain preferred embodiments, the invention provides an antibody that binds to an epitope including the C-terminal portion of the polypeptide of SEQ ID Nos: 3, 14 or 21. In certain preferred embodiments, the invention provides an antibody that binds to an epitope of a ColoUp2 polypeptide that is prevalent in the blood of an animal having a colon neoplasia, such SEQ ID No: 3 or 21.

Following immunization of an animal with an antigenic preparation of a ColoUp polypeptide, anti-ColoUp antisera can be obtained and, if desired, polyclonal anti-ColoUp antibodies can be isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495-497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with a mammalian ColoUp polypeptide of the present invention and monoclonal antibodies isolated from a culture comprising such hybridoma cells. In one embodiment anti-human ColoUp antibodies specifically react with the protein encoded by a nucleic acid having SEQ ID Nos: 4-12; more preferably the antibodies specifically react with the protein encoded by a nucleic acid having SEQ ID Nos: 4 or 5, and preferably a secreted protein that is produced by the expression of a nucleic acid having a sequence of SEQ ID Nos: 4 or 5.

The term antibody as used herein is intended to include fragments thereof which are also specifically reactive with one of the subject ColoUp polypeptides. Antibodies can be fragmented using conventional techniques and the fragments screened for utility in the same manner as described above for whole antibodies. For example, $F(ab)_2$ fragments can be generated by treating antibody with pepsin. The resulting $F(ab)_2$ fragment can be treated to reduce disulfide bridges to produce Fab fragments. The antibody of the present invention is further intended to include bispecific, single-chain, and chimeric and humanized molecules having affinity for a ColoUp polypeptide conferred by at least one CDR region of the antibody. In preferred embodiments, the antibodies, the antibody further comprises a label attached thereto and able to be detected, (e.g., the label can be a radioisotope, fluorescent compound, enzyme or enzyme co-factor).

In certain preferred embodiments, an antibody of the invention is a monoclonal antibody, and in certain embodiments the invention makes available methods for generating novel antibodies. For example, a method for generating a monoclonal antibody that binds specifically to a ColoUp polypeptide, such as a ColoUp2 polypeptide may comprise administering to a mouse an amount of an immunogenic composition comprising the ColoUp2 polypeptide effective to stimulate a detectable immune response, obtaining antibody-producing cells (e.g. cells from the spleen) from the mouse and fusing the antibody-producing cells with myeloma cells to obtain antibody-producing hybridomas, and testing the antibody-producing hybridomas to identify a hybridoma that produces a monocolonal antibody that binds specifically to the ColoUp2 polypeptide. Once obtained, a hybridoma can be propagated in a cell culture, optionally in culture conditions where the hybridoma-derived cells produce the monoclonal antibody that binds specifically to the ColoUp2 polypeptide. The monoclonal antibody may be purified from the cell culture.

Anti-ColoUp antibodies can be used, e.g., to detect ColoUp polypeptides in biological samples and/or to monitor ColoUp polypeptide levels in an individual, for determining whether or not said patient is likely to develop colon cancer or is more likely to harbor colon adenomas, or allowing determination of the efficacy of a given treatment regimen for an individual afflicted with colon neoplasia, colon cancer, metastatic colon cancer and colon adenomas. The level of ColoUp polypeptide may be measured in a variety of sample types such as, for example, in cells, stools, and/or in bodily fluid, such as in whole blood samples, blood serum, blood plasma and urine. The adjective "specifically reactive with" as used in reference to an antibody is intended to mean, as is generally understood in the art, that the antibody is sufficiently selective between the antigen of interest (e.g. a ColoUp polypeptide) and other antigens that are not of interest that the antibody is useful for, at minimum, detecting the presence of the antigen of interest in a particular type of biological sample. In certain methods employing the antibody, a higher degree of specificity in binding may be desirable. For example, an antibody for use in detecting a low abundance protein of interest in the presence of one or more very high abundance protein that are not of interest may perform better if it has a higher degree of selectivity between the antigen of interest and other cross-reactants. Monoclonal antibodies generally have a greater tendency (as compared to polyclonal antibodies) to discriminate effectively between the desired antigens and cross-reacting polypeptides. In addition, an antibody that is effective at selectively identifying an antigen of interest in one type of biological sample (e.g. a stool sample) may not be as effective for selectively identifying the same antigen in a different type of biological sample (e.g. a blood sample). Likewise, an antibody that is effective at identifying an antigen of interest in a purified protein preparation that is devoid of other biological contaminants may not be as effective at identifying an antigen of interest in a crude biological sample, such as a blood or urine sample. Accordingly, in preferred embodiments, the application provides antibodies that have demonstrated specificity for an antigen of interest (particularly, although not limited to, a ColoUp1 or ColoUp2 polypeptide) in a sample type that is likely to be the sample type of choice for use of the antibody. In a particularly preferred embodiment, the application provides antibodies that bind specifically to a ColoUp1 or ColoUp2 polypeptide in a protein preparation from blood (optionally serum or plasma) from a patient that has a colon neoplasia or that bind specifically in a crude blood sample (optionally a crude serum or plasma sample).

One characteristic that influences the specificity of an antibody:antigen interaction is the affinity of the antibody for the antigen. Although the desired specificity may be reached with a range of different affinities, generally preferred antibodies will have an affinity (a dissociation constant) of about $10^{-6}$, $10^{-7}$, $10^{-8}$, $10^{-9}$ or less.

In addition, the techniques used to screen antibodies in order to identify a desirable antibody may influence the properties of the antibody obtained. For example, an antibody to be used for certain therapeutic purposes will preferably be able to target a particular cell type. Accordingly, to obtain antibodies of this type, it may be desirable to screen for antibodies that bind to cells that express the antigen of interest (e.g. by fluorescence activated cell sorting). Likewise, if an antibody is to be used for binding an antigen in solution, it may be desirable to test solution binding. A variety of different techniques are available for testing antibody:antigen interactions to identify particularly desirable antibodies. Such techniques include ELISAs, surface plasmon resonance binding assays (e.g. the Biacore binding assay, Bia-core AB, Uppsala, Sweden), sandwich assays (e.g. the paramagnetic bead system of IGEN International, Inc., Gaithersburg, Md.), western blots, immunoprecipitation assays and immunohistochemistry.

Another application of anti-ColoUp antibodies of the present invention is in the immunological screening of cDNA libraries constructed in expression vectors such as gt11, gt18-23, ZAP, and ORFS. Messenger libraries of this type, having coding sequences inserted in the correct reading frame and orientation, can produce fusion proteins. For instance, gt11 will produce fusion proteins whose amino termini consist of β-galactosidase amino acid sequences and whose carboxy termini consist of a foreign polypeptide. Antigenic epitopes of a ColoUp polypeptide, e.g., other orthologs of a particular protein or other paralogs from the same species, can then be detected with antibodies, as, for example, reacting nitrocellulose filters lifted from infected plates with the appropriate anti-ColoUp antibodies. Positive phage detected by this assay can then be isolated from the infected plate. Thus, the presence of ColoUp homologs can be detected and cloned from other animals, as can alternate isoforms (including splice variants) from humans.

5. Methods for Detecting Molecular Markers in a Patient

In certain embodiments, the invention provides methods for detecting molecular markers, such as proteins or nucleic acid transcripts of the ColoUp markers described herein. In certain embodiments, a method of the invention comprises providing a biological sample and probing the biological sample for the presence of a ColoUp marker. Information regarding the presence or absence of the ColoUp marker, and optionally the quantitative level of the ColoUp marker, may then be used to draw inferences about the nature of the biological sample and, if the biological sample was obtained from a subject, the health state of the subject.

Samples for use with the methods described herein may be essentially any biological material of interest. For example, a sample may be a tissue sample from a subject, a fluid sample from a subject, a solid or semi-solid sample from a subject, a primary cell culture or tissue culture of materials derived from a subject, cells from a cell line, or medium or other extracellular material from a cell or tissue culture, or a xenograft (meaning a sample of a colon cancer from a first subject, e.g. a human, that has been cultured in a second subject, e.g. an immunocompromised mouse). The term "sample" as used herein is intended to encompass both a biological material obtained directly from a subject (which may be described as the primary sample) as well as any manipulated forms or portions of a primary sample. For example, in certain embodiments, a preferred fluid sample is a blood sample. In this case, the term sample is intended to encompass not only the blood as obtained directly from the patient but also fractions of the blood, such as plasma, serum, cell fractions (e.g. platelets, erythrocytes, lymphocytes), protein preparations, nucleic acid preparations, etc. A sample may also be obtained by contacting a biological material with an exogenous liquid, resulting in the production of a lavage liquid containing some portion of the contacted biological material. Furthermore, the term "sample" is intended to encompass the primary sample after it has been mixed with one or more additive, such as preservatives, chelators, anti-clotting factors, etc. In certain embodiments, a fluid sample is a urine sample. In certain embodiments, a preferred solid or semi-solid sample is a stool sample. In certain embodiments, a preferred tissue sample is a biopsy from a tissue known to harbor or suspected of harboring a colon neoplasia. In certain embodiments, a preferred cell culture sample is a sample comprising cultured cells of a colon cancer cell line, such as a cell line cultured from a metastatic colon cancer tumor or a colon-derived cell line lacking a functional TGF-β, TGF-β receptor or TGF-β signaling pathway. A subject is preferably a human subject, but it is expected that the molecular markers disclosed herein, and particularly their homologs from other animals, are of similar utility in other animals. In certain embodiments, it may be possible to detect a marker directly in an organism without obtaining a separate portion of biological material. In such instances, the term sample is intended to encompass that portion of biological material that is contacted with a reagent or device involved in the detection process.

In certain embodiments, a method of the invention comprises detecting the presence of a ColoUp protein in a sample. Optionally, the method involves obtaining a quantitative measure of the ColoUp protein in the sample. In view of this specification, one of skill in the art will recognize a wide range of techniques that may be employed to detect and optionally quantitate the presence of a protein. In preferred embodiments, a ColoUp protein is detected with an antibody. Suitable antibodies are described in a separate section below. In many embodiments, an antibody-based detection assay involves bringing the sample and the antibody into contact so that the antibody has an opportunity to bind to proteins having the corresponding epitope. In many embodiments, an antibody-based detection assay also typically involves a system for detecting the presence of antibody-epitope complexes, thereby achieving a detection of the presence of the proteins having the corresponding epitope. Antibodies may be used in a variety of detection techniques, including enzyme-linked immunosorbent assays (ELISAs), immunoprecipitations, Western blots. Antibody-independent techniques for identifying a protein may also be employed. For example, mass spectroscopy, particularly coupled with liquid chromatography, permits detection and quantification of large numbers of proteins in a sample. Two-dimensional gel electrophoresis may also be used to identify proteins, and may be coupled with mass spectroscopy or other detection techniques, such as N-terminal protein sequencing. RNA aptamers with specific binding for the protein of interest may also be generated and used as a detection reagent.

In certain preferred embodiments, methods of the invention involve detection of a secreted form of a ColoUp protein or osteopontin, particularly ColoUp1 protein or ColoUp2 protein.

Samples should generally be prepared in a manner that is consistent with the detection system to be employed. For example, a sample to be used in a protein detection system should generally be prepared in the absence of proteases. Likewise, a sample to be used in a nucleic acid detection system should generally be prepared in the absence of nucleases. In many instances, a sample for use in an antibody-based detection system will not be subjected to substantial preparatory steps. For example, urine may be used directly, as may saliva and blood, although blood will, in certain preferred embodiments, be separated into fractions such as plasma and serum.

In certain embodiments, a method of the invention comprises detecting the presence of a ColoUp expressed nucleic acid, such as an mRNA, in a sample. Optionally, the method involves obtaining a quantitative measure of the ColoUp expressed nucleic acid in the sample. In view of this specification, one of skill in the art will recognize a wide range of techniques that may be employed to detect and optionally quantitate the presence of a nucleic acid. Nucleic acid detection systems generally involve preparing a purified nucleic acid fraction of a sample, and subjecting the sample to a direct detection assay or an amplification process followed by a detection assay. Amplification may be achieved, for example, by polymerase chain reaction (PCR), reverse transcriptase (RT) and coupled RT-PCR. Detection of a nucleic acid is generally accomplished by probing the purified nucleic acid fraction with a probe that hybridizes to the nucleic acid of interest, and in many instances detection involves an amplification as well. Northern blots, dot blots, microarrays, quantitative PCR and quantitative RT-PCR are all well known methods for detecting a nucleic acid in a sample.

In certain embodiments, the invention provides nucleic acid probes that bind specifically to a ColoUp nucleic acid. Such probes may be labeled with, for example, a fluorescent moiety, a radionuclide, an enzyme or an affinity tag such as a biotin moiety. For example, the TaqMan® system employs nucleic acid probes that are labeled in such a way that the fluorescent signal is quenched when the probe is free in solution and bright when the probe is incorporated into a larger nucleic acid.

In certain embodiments, the application provides methods for imaging a colon neoplasm by targeting antibodies to any one of the markers ColoUp1 through ColoUp8 or osetopontin described herein, more preferably the antibodies are targeted to ColoUp3. The markers described herein may be targeted using monoclonal antibodies which may be labeled with radioisotopes for clinical imaging of tumors or with toxic agents to destroy them.

In other embodiments, the application provides methods for administering a imaging agent comprising a targeting moiety and an active moiety. The targeting moiety may be an antibody, Fab, F(Ab)2, a single chain antibody or other binding agent that interacts with an epitope specified by a polypeptide sequence having an amino acid sequence as set forth in SEQ ID Nos: 1-3 and 13-21, preferably an epitope specified by SEQ ID No: 16. The active moiety may be a radioactive agent, such as: radioactive heavy metals such as iron chelates, radioactive chelates of gadolinium or manganese, positron emitters of oxygen, nitrogen, iron, carbon, or gallium, $^{43}$K, $^{52}$Fe, $^{57}$Co, $^{67}$Cu, $^{67}$Ga, $^{68}$Ga, $^{123}$I, $^{125}$I, $^{131}$I, $^{132}$I, or $^{99}$Tc. The imaging agent is administered in an amount effective for diagnostic use in a mammal such as a human and the localization and accumulation of the imaging agent is then detected. The localization and accumulation of the imaging agent may be detected by radioscintigraphy, nuclear magnetic resonance imaging, computed tomography or positron emission tomography.

Immunoscintigraphy using monoclonal antibodies directed at the ColoUp markers may be used to detect and/or diagnose colon neoplasia. For example, monoclonal antibodies against the ColoUp marker such as ColoUp3 labeled with .$^{99}$Technetium, $^{111}$Indium, $^{125}$Iodine—may be effectively used for such imaging. As will be evident to the skilled artisan, the amount of radioisotope to be administered is dependent upon the radioisotope. Those having ordinary skill in the art can readily formulate the amount of the imaging agent to be administered based upon the specific activity and energy of a given radionuclide used as the active moiety. Typically 0.1-100 millicuries per dose of imaging agent, preferably 1-10 millicuries, most often 2-5 millicuries are administered. Thus, compositions according to the present invention useful as imaging agents comprising a targeting moiety conjugated to a radioactive moiety comprise 0.1-100 millicuries, in some embodiments preferably 1-10 millicuries, in some embodiments preferably 2-5 millicuries, in some embodiments more preferably 1-5 millicuries.

EXEMPLIFICATION

The invention now being generally described, it will be more readily understood by reference to the following examples, which are included merely for purposes of illustration of certain aspects and embodiments of the present invention, and are not intended to limit the invention.

Example 1

Selection of Eight Molecular Markers for Colon Neoplasia

Expression micro-array profiling was used to find genes whose expression was different between normal colon and metastatic colon cancer. Normal colon and metastatic colon cancer samples were analyzed for gene expression using DNA expression microarray techniques that profiled expression patterns of nearly 50,000 genes, ESTs and predicted exons. Analysis of the data identified eight molecular markers for colon neoplasia, as shown in Table 2.

TABLE 2

Eight Selected Molecular Markers for Colon Neoplasia

| Marker Name | Example Sequences (SEQ ID Nos.) | (Median Liver Mets)/ (Median Normal Colon) | (Median Liver Mets)/ (Median Normal Liver) | (Minimum Liver Mets)/ (Maximum Normal Colon) | (Median Met Cell Lines)/ (Median Normal Colon) | (Median Met Xenografts)/ Median Normal Colon) |
|---|---|---|---|---|---|---|
| ColoUp1 | 1, 2, 4, 13 | 13.94 | 13.94 | 0.26 | 14.08 | 15.48 |
| ColoUp2 | 3, 5, 14 | 5.70 | 5.70 | 1.00 | 5.32 | 1.24 |
| ColoUp3 | 7, 16 | 16.36 | 16.36 | 0.80 | 21.50 | 15.68 |
| ColoUp4 | 8, 17 | 4.68 | 4.68 | 1.00 | 4.88 | 1.56 |
| ColoUp5 | 9, 18 | 4.58 | 4.74 | 1.15 | 4.82 | 4.63 |
| ColoUp6 | 10, 19 | 9.52 | 9.52 | 0.52 | 11.58 | 1.92 |
| ColoUp7 | 11 | 9.20 | 9.20 | 0.18 | 4.30 | 9.00 |
| ColoUp8 | 12, 20 | 4.78 | 4.78 | 1.27 | 3.76 | 2.72 |

Osteopontin was also identified as a molecular marker having similar characteristics (Example sequences SEQ ID Nos: 6, 15). Each of these molecular markers was subjected to additional analysis in various types of colon neoplasia. In the case of ColoUp1 and ColoUp2, the microarray expression was confirmed by Northern blot and secretion of the protein was established.

Example 2

Expression Pattern of ColoUp1 in Various Cell Types

Shown in FIG. 20 is a graphical display of ColoUp1 expression levels measured for different tissue samples. ColoUp1 transcript was essentially undetectable (AI expression levels less than 0) in normal colon epithelial strips (labeled colon epithelial), in normal liver and in colonic muscle (labeled c. muscle). In contrast ColoUp1 expression was clearly detected in premalignant colon adenomas as well as in 90% of Dukes stage B (early node negative colon cancers), Dukes stage C (node positive colon cancer), Dukes stage D (primary colon cancers with associated metastatic spread) and in colon cancer liver metastasis (labeled liver metastasis).

ColoUp1 expression was also demonstrated in colon cancer cell lines (labeled colon cell lines) and in colon cancer xenografts grown in athymic mice (labeled xenografts). The expression in cell lines and xenografts confirms that colon neoplasia cells are the source of ColoUp1 expression in the tumors.

The probe for ColoUp1 was designed to recognize transcripts corresponding to gene KIAA1199, Genbank entry AB033025, Unigene entry Hs.50081. A transcript corresponding to this gene was amplified by RT-PCR from colon cancer cell line Vaco-394. The sequence of this transcript is presented in FIG. 3.

Example 3

Confirmed Gene Expression Pattern of ColoUp1

Figure 29A:
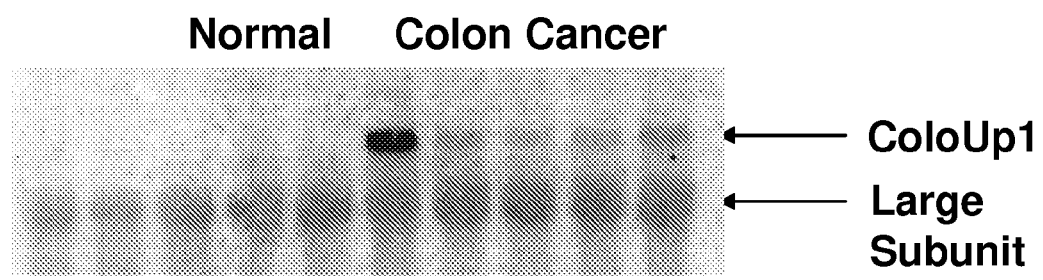
FIG. 29 shows northern blot analysis of ColoUp1 mRNA levels in normal colon tissues and colon cancer cell lines or tissues. A. In normal colon tissue samples and a group of colon cancer cell lines; B. and C. In normal colon tissues and colon neoplasms from 15 individuals with colon cancers and one individual with a colon adenoma.

FIG. 29 shows a northern analysis using the cloned ColoUp1 cDNA that identifies a transcript running above the large ribosomal subunit (to which the probe cross hybridizes) that is not expressed in normal colon tissue samples and is ubiquitously expressed in a group of colon cancer cell lines.

Figure 29B:
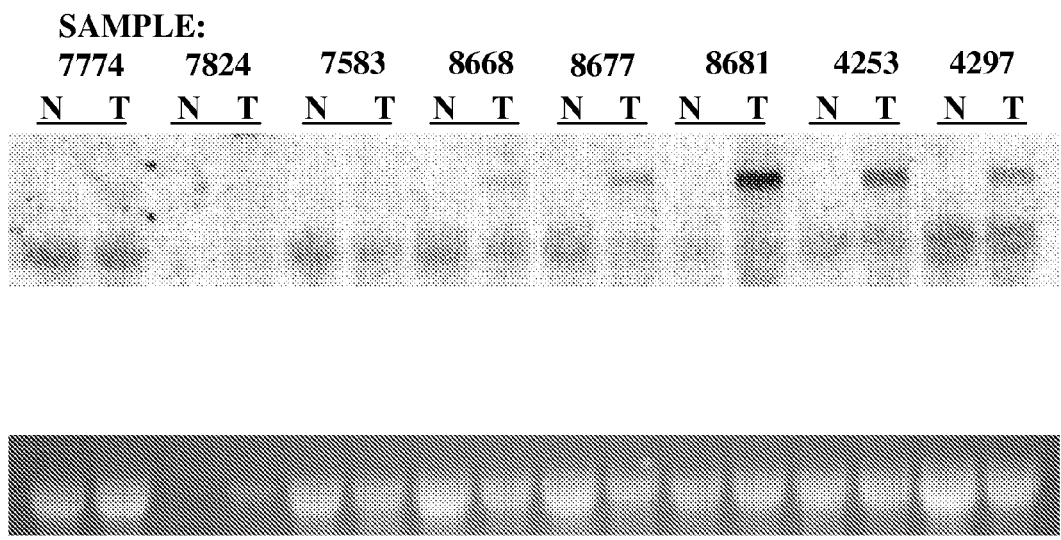
Figure 29C:
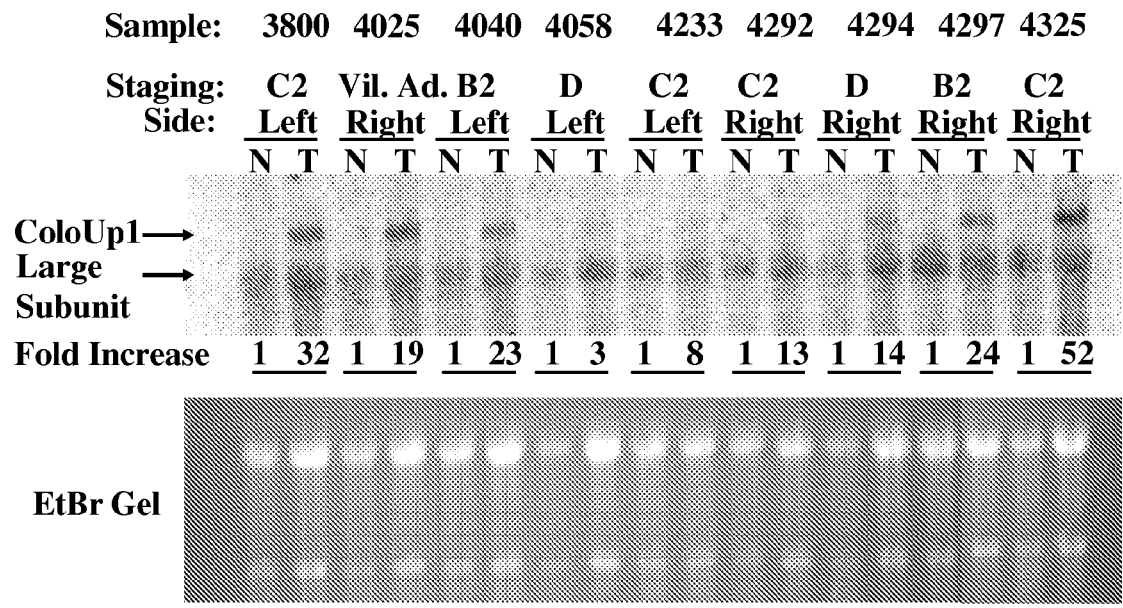

FIGS. 29B and 29C show the results of northern analysis of ColoUp1 in normal colon tissue and colon neoplasms from 15 individuals with colon cancers and one individual with a colon adenoma. No normal colon sample expresses ColoUp1. However, expression is see in 13 of 15 colon cancers, and in the one colon adenoma. Expression is seen in cancers arising in both the right and left colon, and in cancers of Dukes Stage B2, C and D.

Example 4

ColoUp1 is a Secreted Protein

Figure 30A:
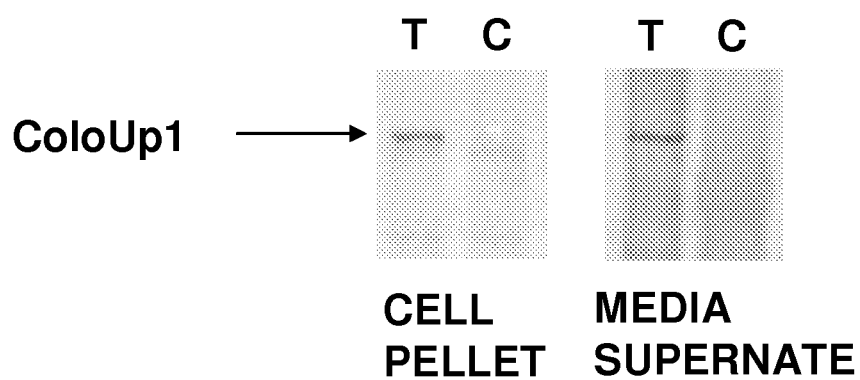
FIG. 30 shows detection of T7 epitope-tagged ColoUp1 protein levels in transfected FET cells and Vaco400 cells. A. Secretion of epitope-tagged ColoUp1 protein in V400 cell growth media by Western blot ("T" are transfectants with an epitope tagged ColoUp1 expression vector; "C" are transfectants with an empty control vector); B. Expression of T7 epitope-tagged ColoUp1 protein in transfected NET cells and V400 cells by Western blot (left panel), and secretion of epitope-tagged ColoUp1 protein in growth media by serial immunoprecipitation and Western blot (right panel)(Cell extract amounts loaded: PET=75 mg/well; V400=31.1 mg/well; Volume of media used for immuno-precipitation=1 ml of 20 ml).

The cloned ColoUp1 colonic transcript was inserted into a cDNA expression vector with a C-terminal T7 epitope tag. FIG. 30A shows a summary of the behavior of the tagged protein expressed by transfection of the vector into Vaco400 cells. An anti T7 western blot shows expression of the transfected tagged protein detected in the lysate of a pellet of transfected cells (lane T of cell pellet) which is absent in cells transfected with a control empty expression vector (lane C of cell pellet). Moreover, serial immunoprecipitation and western blotting of T7 tagged protein from media in which V400 cells were growing (which had been clarified by centrifugation prior to immunoprecipatation) also clearly demonstrates secretion of ColoUp1 protein into the growth medium.

Figure 30B:
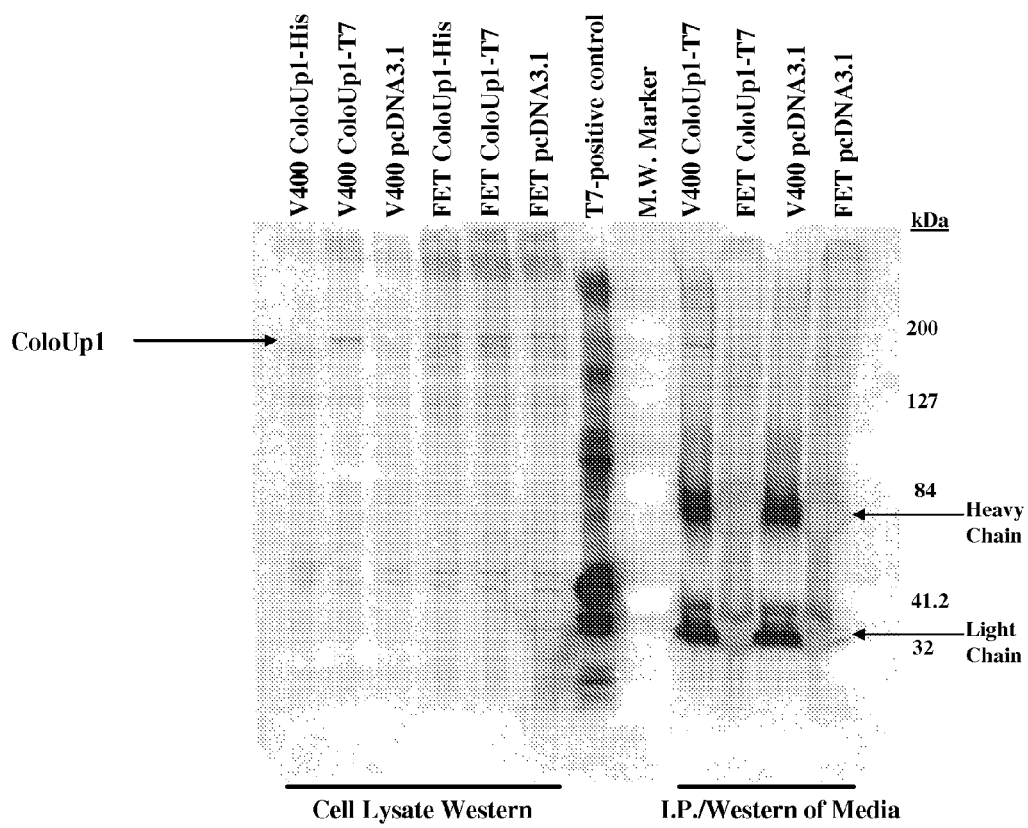

FIG. 30B shows the full gels demonstrating expression of tagged 409041 protein in V400 cells demonstrated by western analysis at left and shows detection of secreted 409041 protein in growth media as detected at right by serial immunoprecipitation and western analysis. (Antibody from the high level of serum in which FET cells are grown blocked the ability of staphA conjugated beads to precipitate anti-T7 bound to 409041 in growth media from FET cells).

Example 5

Expression Pattern of in Various Cell Types

Figure 21:
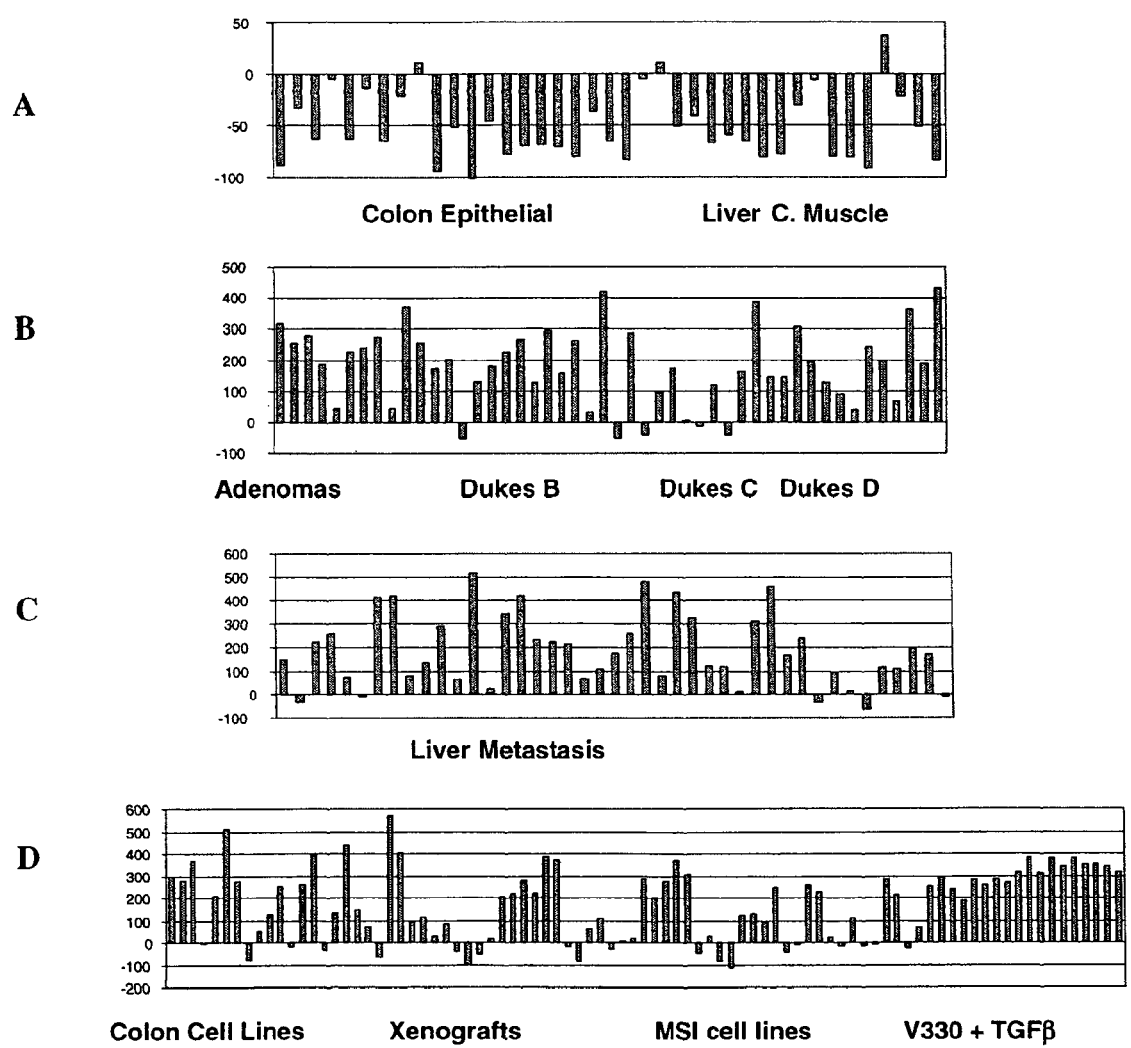
FIG. 21 is a graphical display of ColoUp2 expression levels measured by micro-array profiling in different samples. A. In normal colon epithelial strips, normal liver, and colonic muscle; B. In premalignant colon adenomas as well as in colon cancers of Dukes stages B, Dukes stage C, and Duke stages D; C. In colon cancer liver metastasis; D. In colon cancer cell lines, colon cancer xenografts grown in athymic mice, MSI cell lines, and V330 cell lines treated with TGFβ.
Figure 22A:
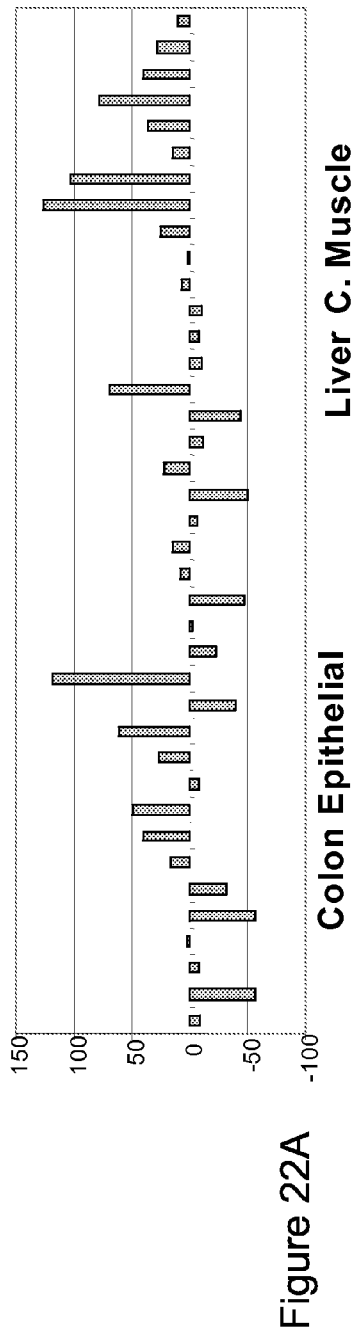
FIG. 22 is a graphical display of Osteopontin expression levels measured by micro-array profiling in different samples. A. In normal colon epithelial strips, normal liver, and colonic muscle; B. In premalignant colon adenomas as well as in colon cancers of Dukes stages B, Dukes stage C, and Duke stages D; C. In colon cancer liver metastasis; D. In colon cancer cell lines, colon cancer xenografts grown in athymic mice, MSI cell lines, and V330 cell lines treated with TGFβ.
Figure 22B:
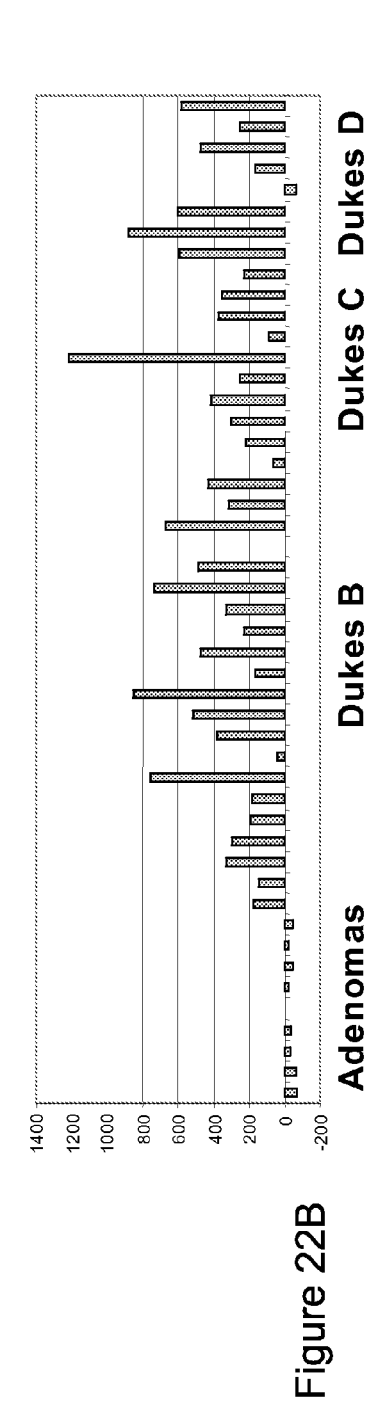
Figure 22C:
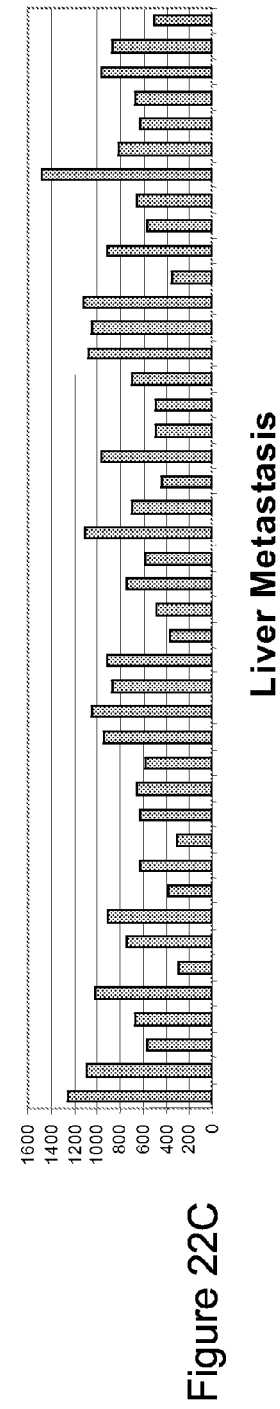
Figure 22D:
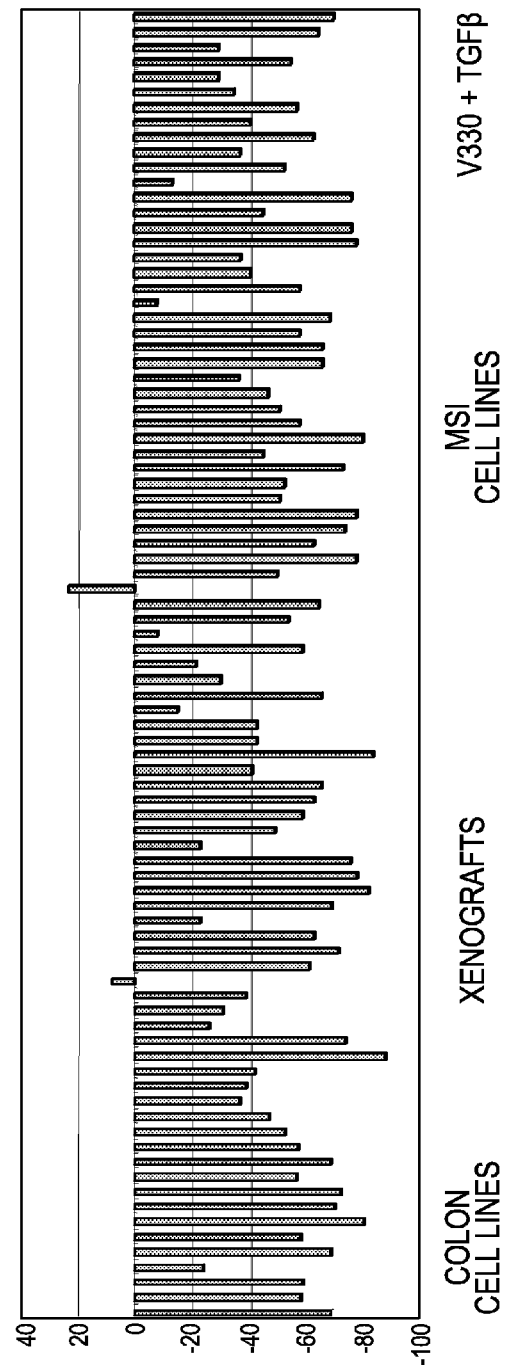
Figure 23A:
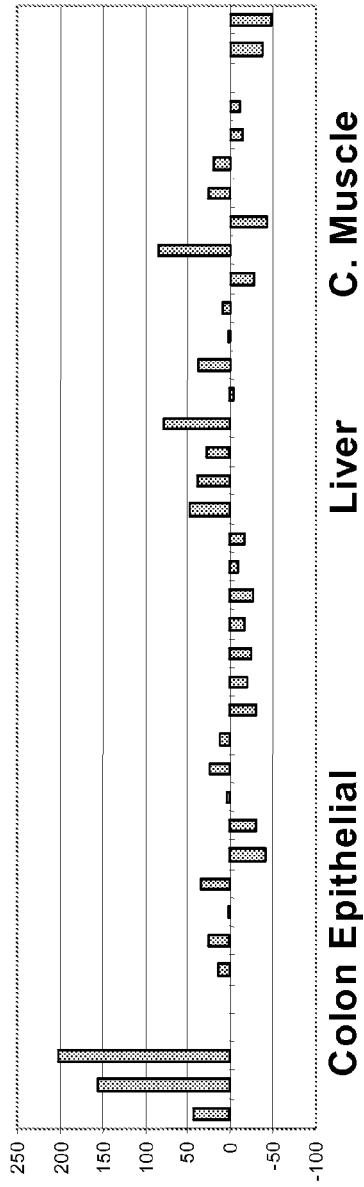
FIG. 23 is a graphical display of ColoUp3 expression levels measured by micro-array profiling in different samples. A. In normal colon epithelial strips, normal liver, and colonic muscle; B. In premalignant colon adenomas as well as in colon cancers of Dukes stages B, Dukes stage C, and Duke stages D; C. In colon cancer liver metastasis; D. In colon cancer cell lines, colon cancer xenografts grown in athymic mice, MSI cell lines, and V330 cell lines treated with TGFβ.
Figure 23B:
Figure 23C:
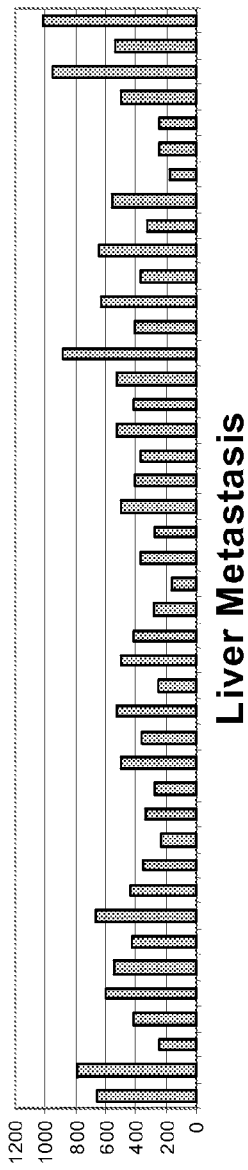
Figure 23D:
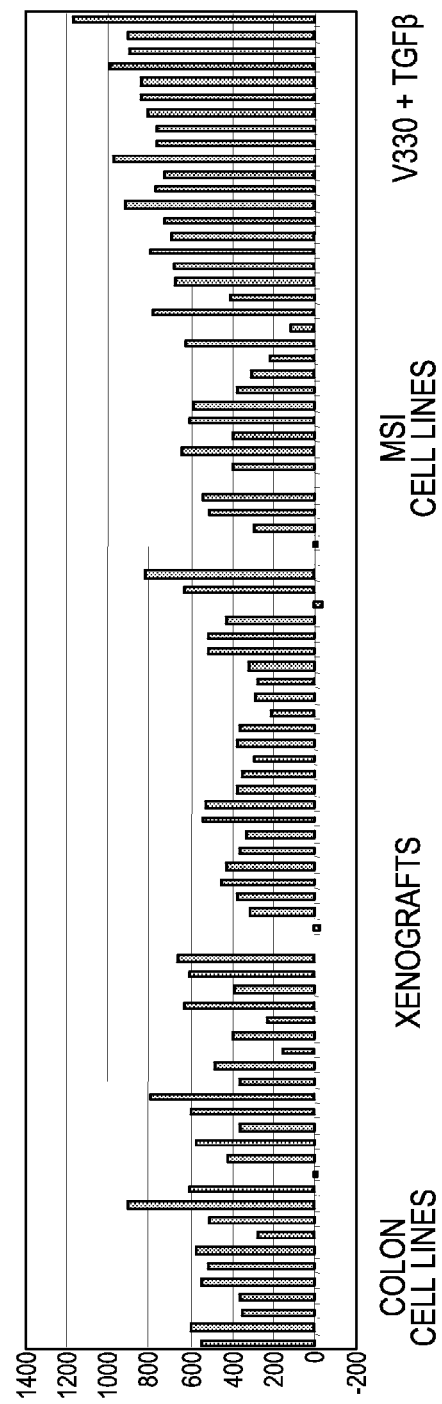
Figure 24A:
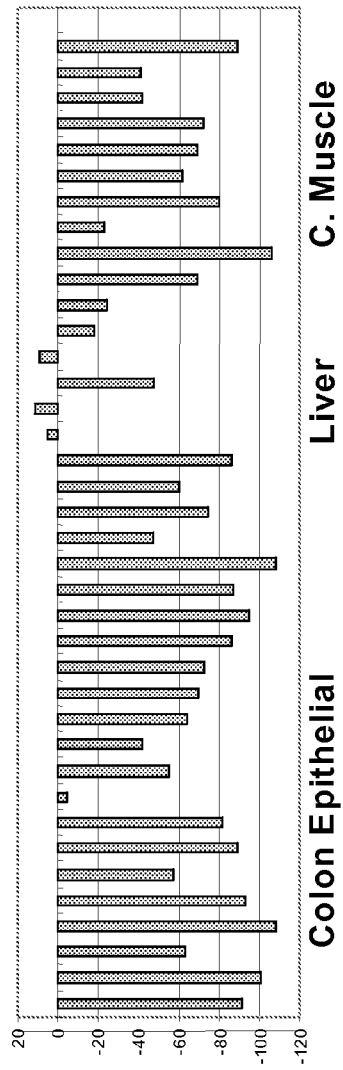
FIG. 24 is a graphical display of ColoUp4 expression levels measured by micro-array profiling in different samples. A. In normal colon epithelial strips, normal liver, and colonic muscle; B. In premalignant colon adenomas as well as in colon cancers of Dukes stages B, Dukes stage C, and Duke stages D; C. In colon cancer liver metastasis; D. In colon cancer cell lines, colon cancer xenografts grown in athymic mice, MSI cell lines, and V330 cell lines treated with TGFβ.
Figure 24B:
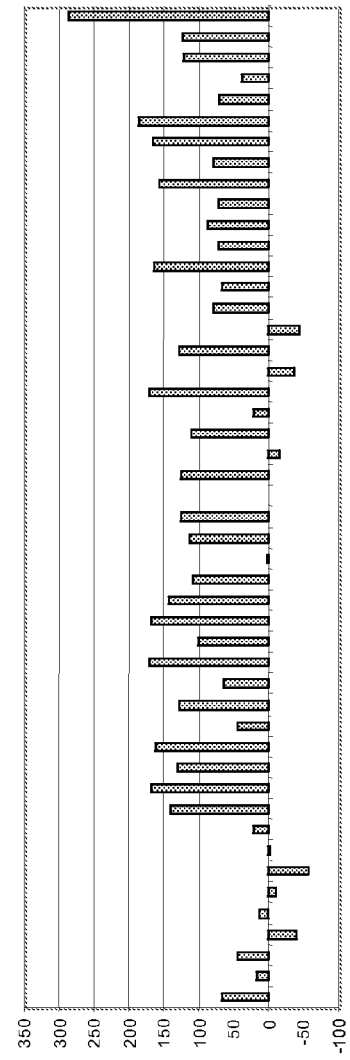
Figure 24C:
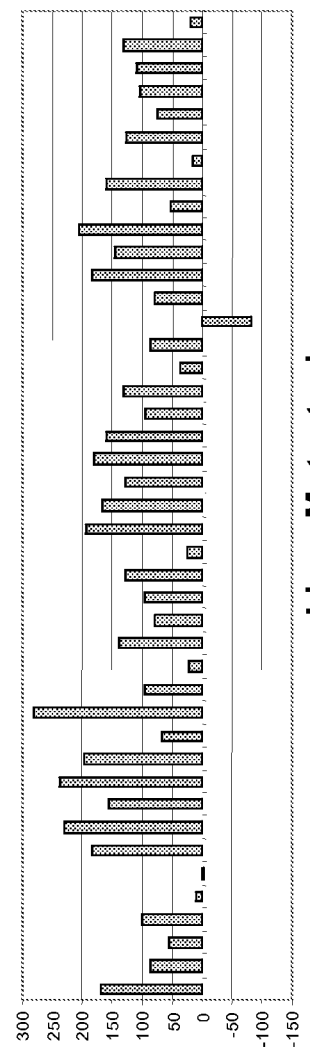
Figure 24D:
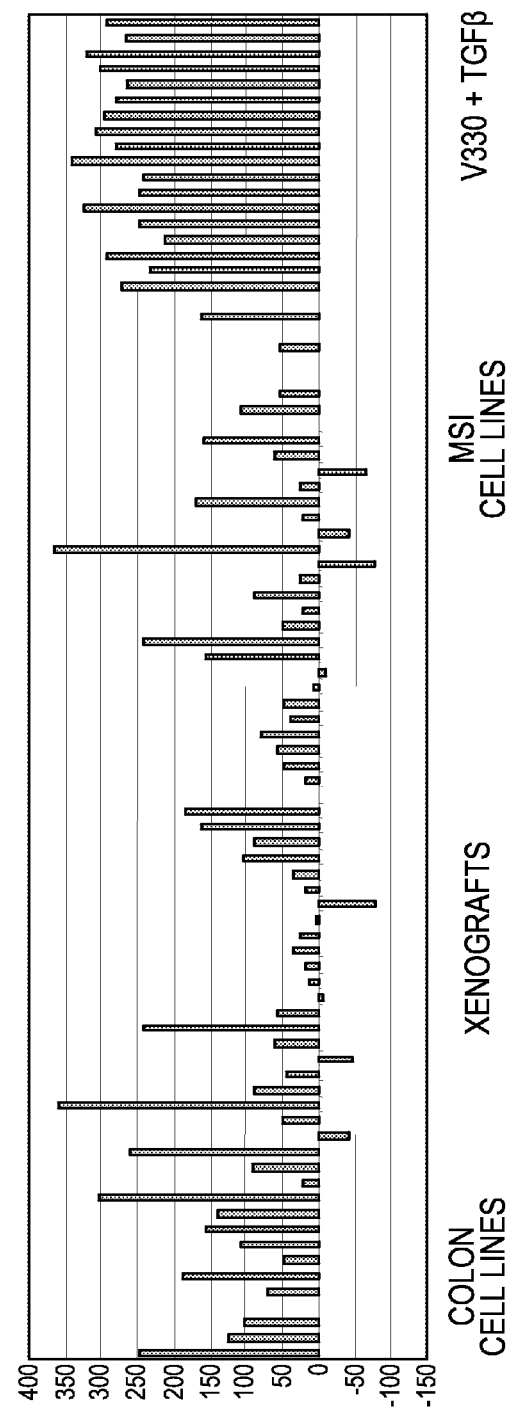
Figure 25A:
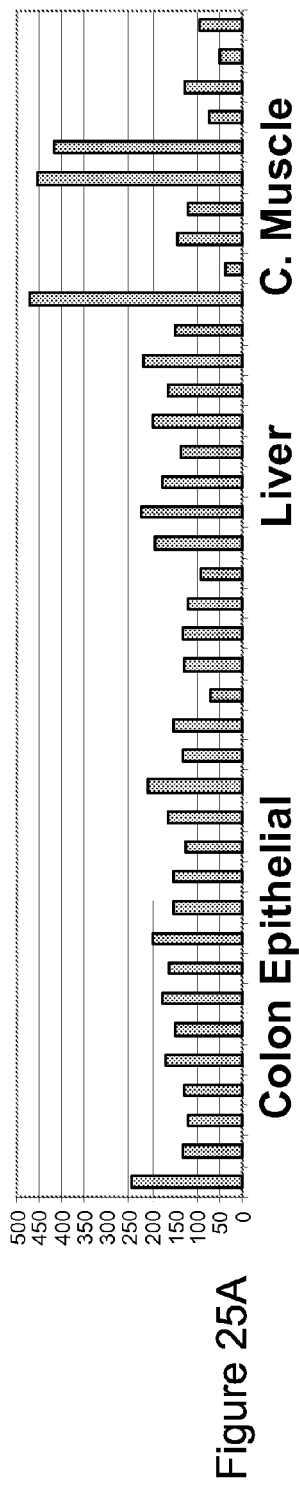
FIG. 25 is a graphical display of ColoUp5 expression levels measured by micro-array profiling in different samples. A. In normal colon epithelial strips, normal liver, and colonic muscle; B. In premalignant colon adenomas as well as in colon cancers of Dukes stages B, Dukes stage C, and Duke stages D; C. In colon cancer liver metastasis; D. In colon cancer cell lines, colon cancer xenografts grown in athymic mice, MSI cell lines, and V330 cell lines treated with TGFβ.
Figure 25B:
Figure 25C:
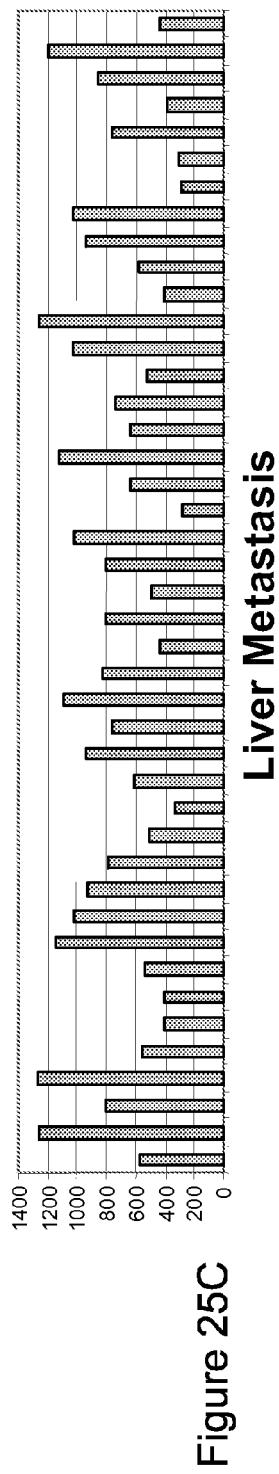
Figure 25D:
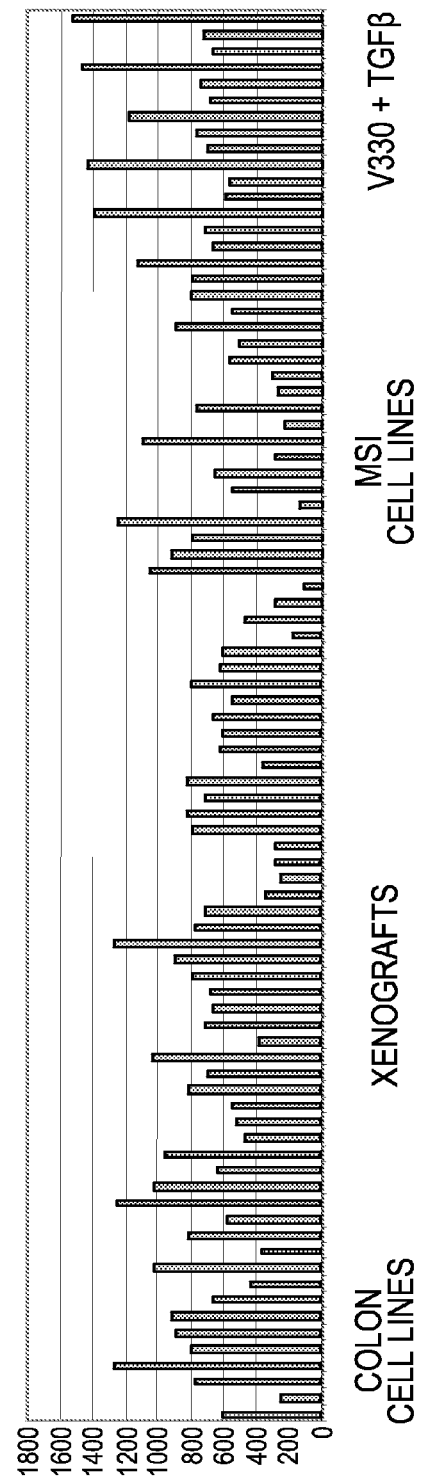
Figure 26A:
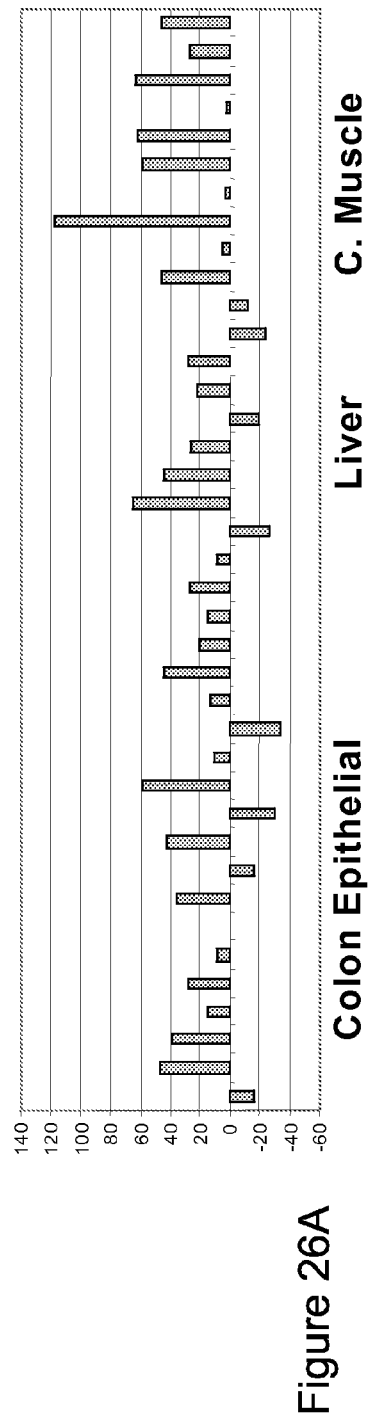
FIG. 26 is a graphical display of ColoUp6 expression levels measured by micro-array profiling in different samples. A. In normal colon epithelial strips, normal liver, and colonic muscle; B. In premalignant colon adenomas as well as in colon cancers of Dukes stages B, Dukes stage C, and Duke stages D; C. In colon cancer liver metastasis; D. In colon cancer cell lines, colon cancer xenografts grown in athymic mice, MSI cell lines, and V330 cell lines treated with TGFβ.
Figure 26B:
Figure 26C:
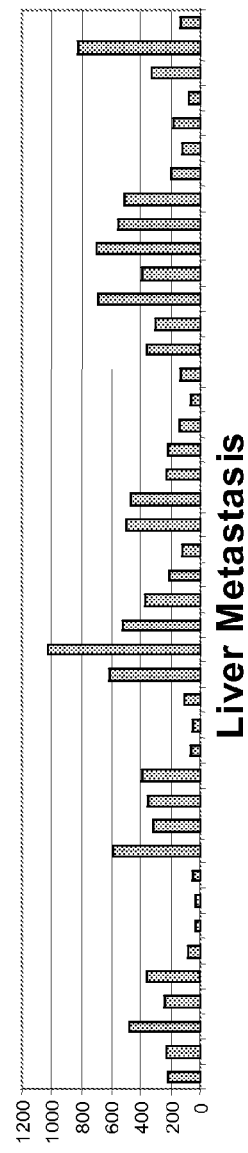
Figure 26D:
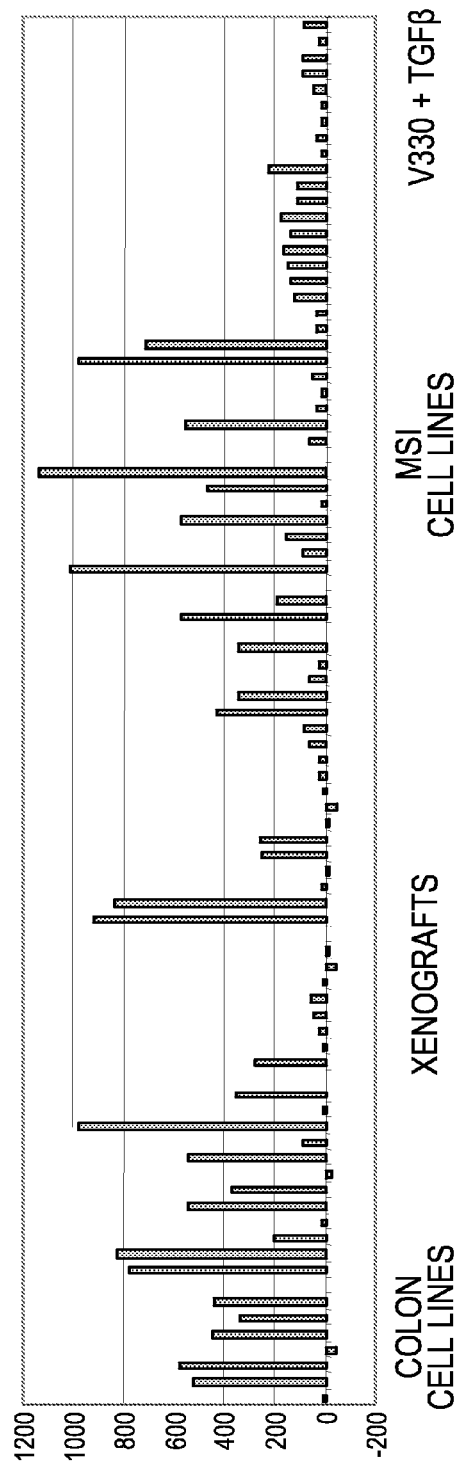
Figure 27D:
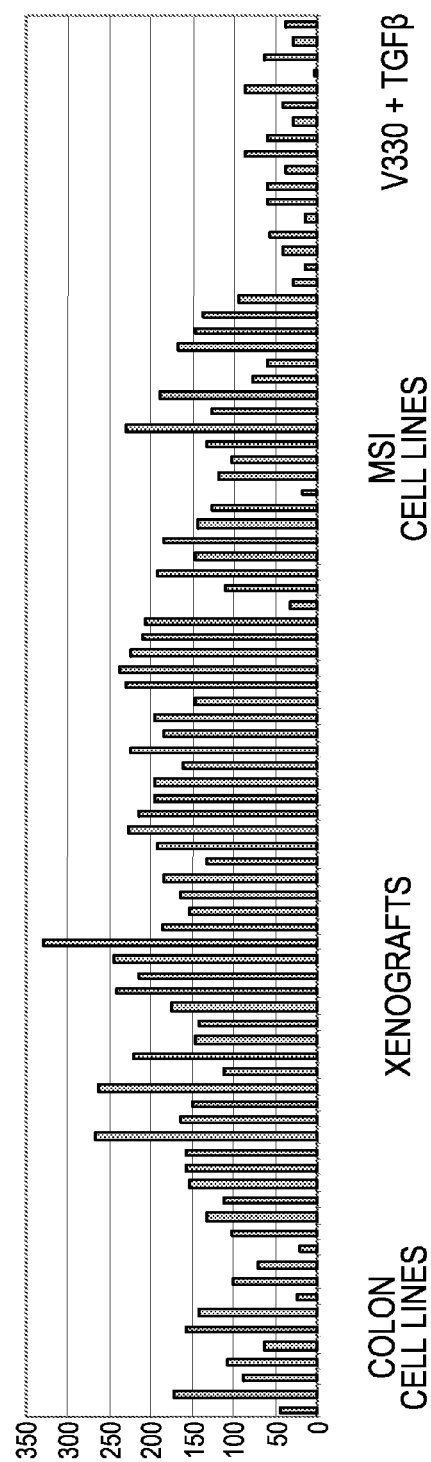
FIG. 27 is a graphical display of ColoUp7 expression levels measured by micro-array profiling in different samples. A. In normal colon epithelial strips, normal liver, and colonic muscle; B. In premalignant colon adenomas as well as in colon cancers of Dukes stages B, Dukes stage C, and Duke stages D; C. In colon cancer liver metastasis; D. In colon cancer cell lines, colon cancer xenografts grown in athymic mice, MSI cell lines, and V330 cell lines treated with TGFβ.
Figure 28A:
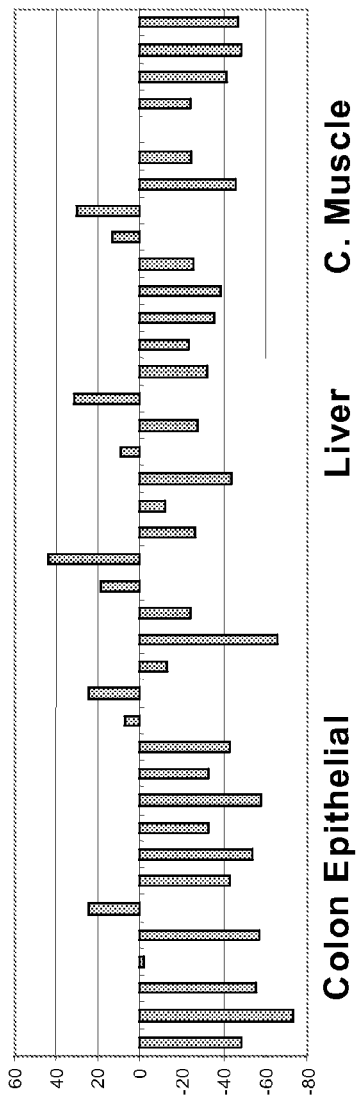
FIG. 28 is a graphical display of ColoUp8 expression levels measured by micro-array profiling in different samples. A. In normal colon epithelial strips, normal liver, and colonic muscle; B. In premalignant colon adenomas as well as in colon cancers of Dukes stages B, Dukes stage C, and Duke stages D; C. In colon cancer liver metastasis; D. In colon cancer cell lines, colon cancer xenografts grown in athymic mice, MSI cell lines, and V330 cell lines treated with TGFβ.
Figure 28B:
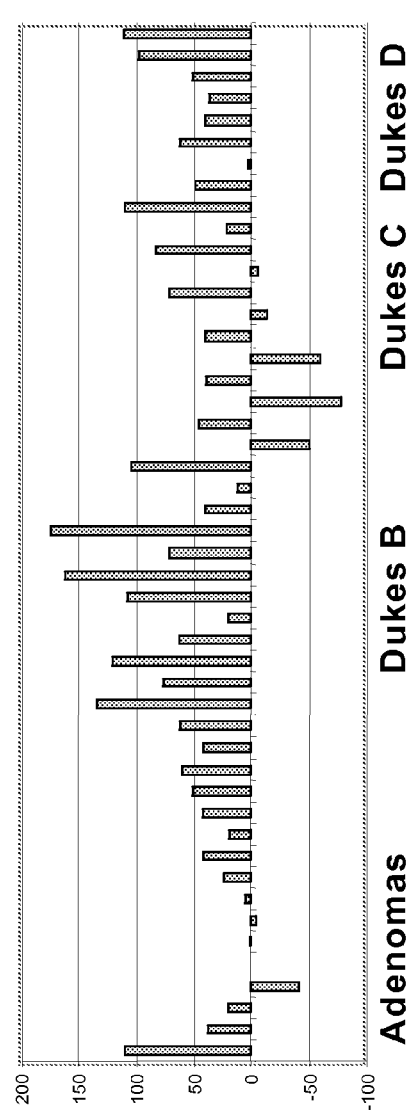
Figure 28C:
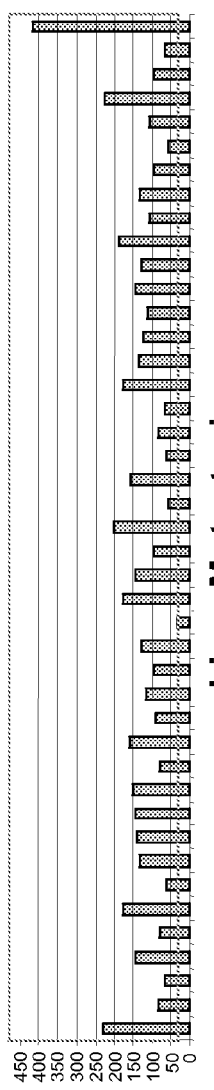
Figure 28D:
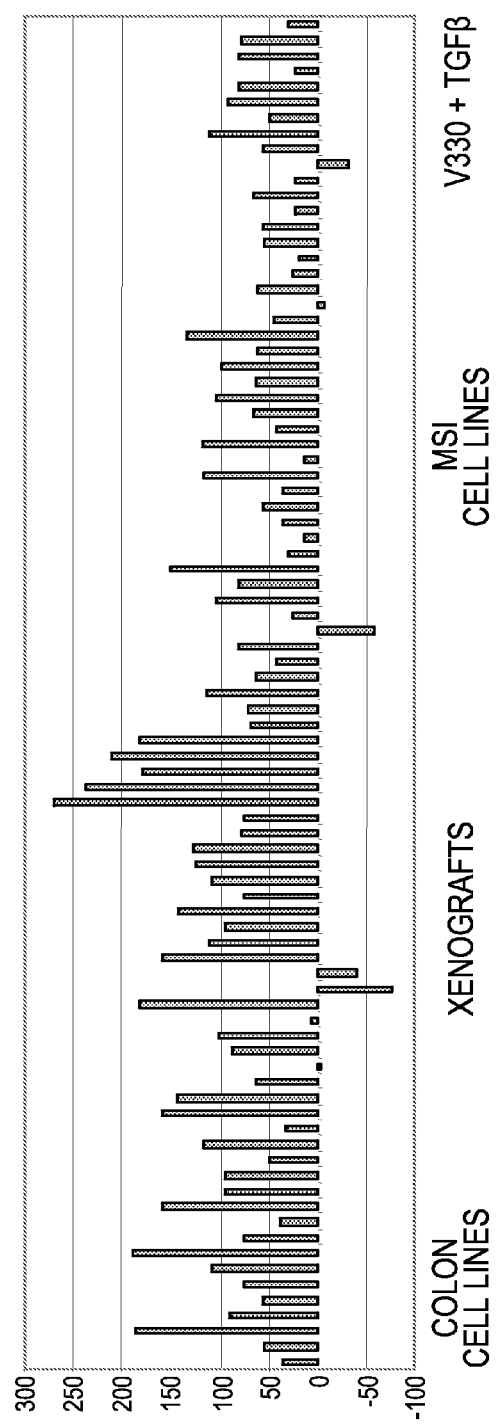

Shown in FIG. 21 is the graphical display of ColoUp2 expression levels measured for different samples analyzed. ColoUp2 transcript was essentially undetectable (AI expression levels less than 0) in normal colon epithelial strips (labeled colon epithelial), in normal liver and in colonic muscle (labeled c. muscle). In contrast ColoUp2 expression was clearly detected in premalignant colon adenomas as well as in 90% of Dukes stage B (early node negative colon cancers), Dukes stage C (node positive colon cancer), Dukes stage D (primary colon cancers with associated metastatic spread) and in colon cancer liver metastasis (labeled liver metastasis). ColoUp2 expression was also demonstrated in colon cancer cell lines (labeled colon cell lines) and in colon cancer xenografts grown in athymic mice (labeled xenografts). The expression in cell lines and xenografts confirms that colon neoplasia cells are the source of ColoUp2 expression in the tumors.

Probe ColoUp2 was designed to recognize transcripts corresponding to a noncoding EST, Genbank entry A1357412, Unigene entry Hs.157601. By 5' RACE, database assembly, and ultimately RT-PCR, we cloned from a colon cancer cell line a novel protein encoding RNA transcript whose noncoding 3' UTR was shown to correspond to the ColoUp2 specified EST. This full length coding sequence was determined by RT-PCR amplification from colon cancer cell line Vaco503 and sequences are provided in FIG. 4.

ColoUp2 is a "class identifier" (that is, it is higher in all colon cancer samples than in all normal colon samples), it is not-expressed in normal body tissues and it contains a signal sequence predicting that the protein product will be secreted (as well as several other recognizable protein motifs including domains from the epidermal growth factor protein and from the Von Willebrands protein).

Example 6

Confirmed Gene Expression Pattern of ColoUp2

Figure 31:
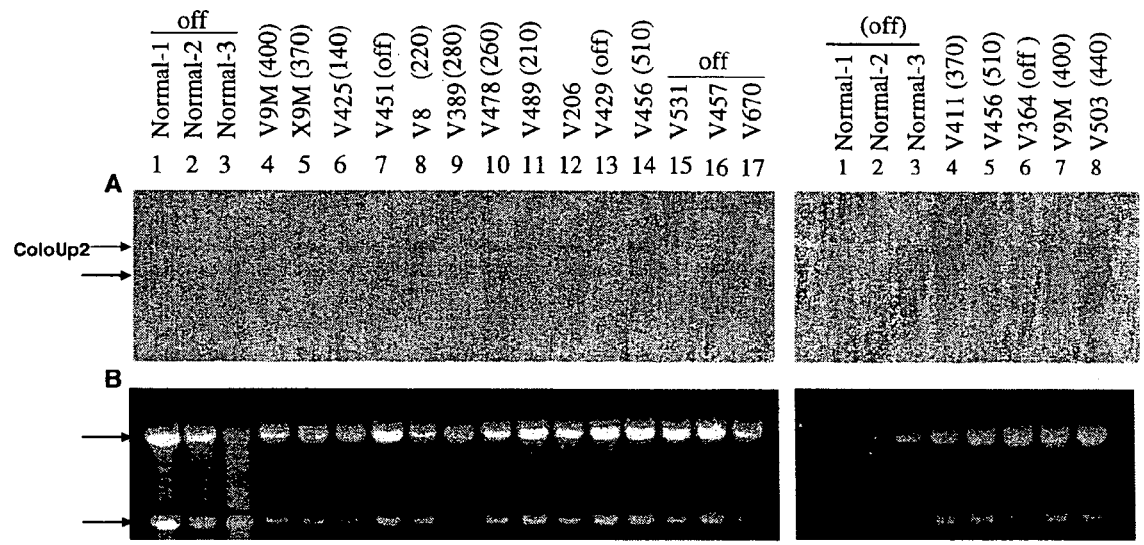
FIG. 31 shows northern blot analysis of ColoUp2 mRNA levels in normal colon tissue samples and a group of colon cancer cell lines (top panel). The bottom panel shows the ethidium bromide stained gel corresponding to the blot.

FIG. 31 shows a northern analysis using the cloned ColoUp2 cDNA that identifies a transcript running above the large ribosomal subunit (to which the probe cross hybridizes) that is not expressed in normal colon tissue samples and is expressed in the majority of group of colon cancer cell lines. Panel A of the figure shows the northern hybridization. The red arrow designates the ColoUp2 transcript. Above each lane is the name of the sample and the level (in parenthesis) of ColoUp2 expression recorded. The black arrow designates the cross hybridizing ribosomal large subunit. Panel B shows the eithidum bromide stained gel corresponding to the blot, and the black arrows designate the large and small ribosomal subunits.

Example 7

ColoUp2 is a Secreted Protein

Figure 32:
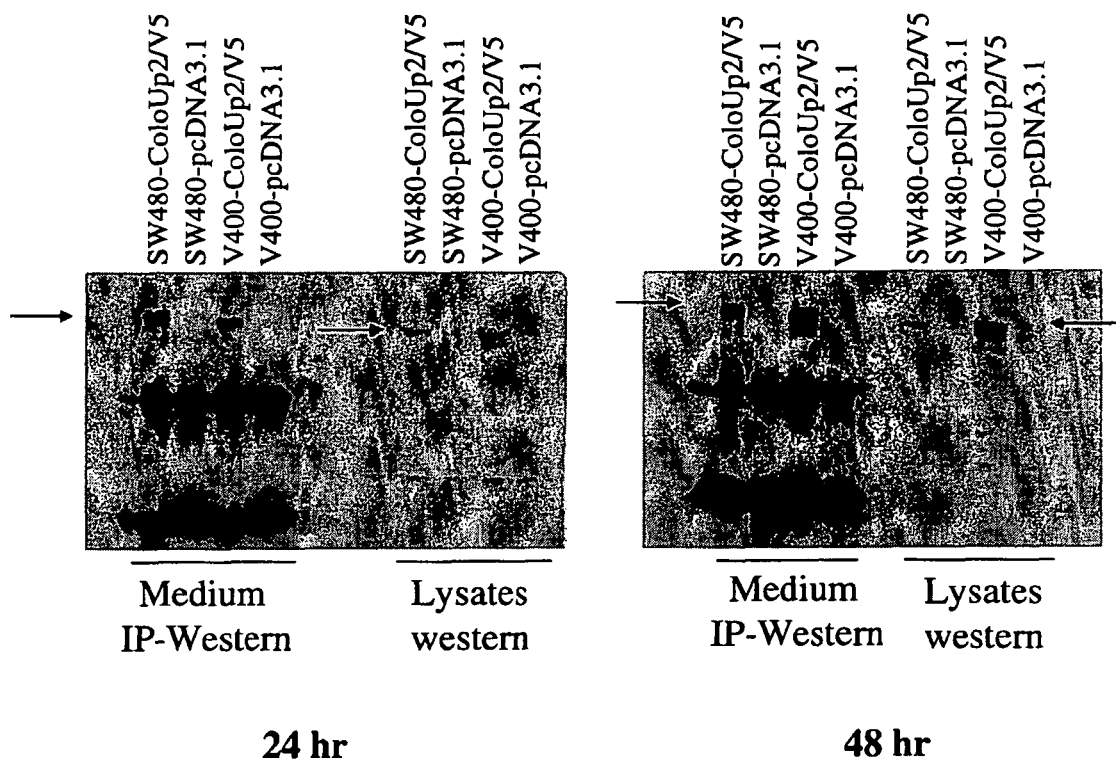
FIG. 32 shows detection of V5 epitope-tagged ColoUp2 protein levels in transfected SW480 cells and Vaco400 cells (24 hours and 48 hours after transfection). Expression of epitope-tagged ColoUp2 protein in transfected cells by Western blot (right panel), and secretion of epitope-tagged ColoUp2 protein in growth media by serial immunoprecipitation and Western blot (left panel).

The cloned ColoUp2 colonic transcript was inserted into a cDNA expression vector with a C-terminal V5 epitope tag. FIG. 32 shows a summary of the behavior of the tagged protein expressed by transfection of the vector into SW480 and Vaco400 cells. An anti V5 western blot shows (red arrows) expression of the transfected tagged protein detected in the lysate of a pellet of transfected cells (lysates western panel, lanes labeled ColoUp2/V5) which is absent in cells transfected with a control empty expression vector (lanes labeled pcDNA3.1). Moreover, serial immunoprecipitation and western blotting of V5 tagged protein from media in which V400 and SW480 cells were growing (which had been clarified by centrifugation prior to immunoprecipatation) also clearly demonstrates secretion of the ColoUp2 protein into the growth medium (panel labeled medium IP-western). Antibody bands from the immunoprecipitation are also present on the IP-western blot. Detection of secreted ColoUp2 protein was shown in cells assayed both 24 hours and 48 hours after transfection.

Example 8

Expression Pattern of ColoUp3-ColoUp8 and Osteopontin in Various Cell Types

Shown in FIGS. 22-28 are the graphical displays of ColoUp3-ColoUp8 and osteopontin expression levels measured for different samples analyzed.

Example 9

Confirmed Gene Expression Pattern of ColoUp5

Figure 33:
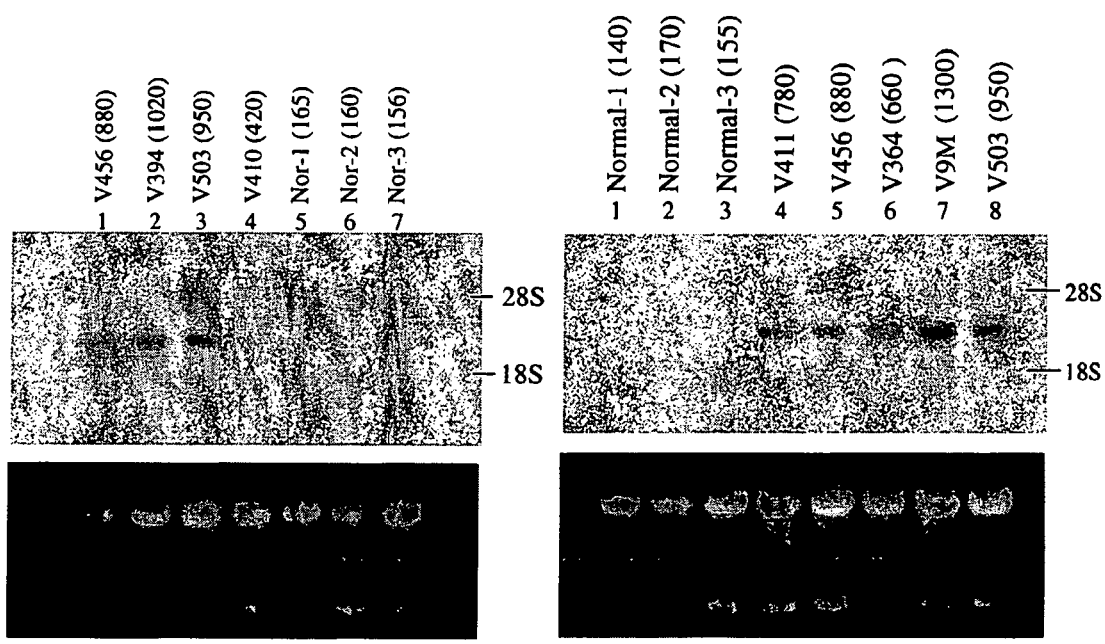
FIG. 33 shows two northern blot analysis of ColoUp5 mRNA levels in normal colon tissues and a group of colon cancer cell lines (top panels). The bottom panels show the ethidium bromide stained gel corresponding to the blot.
Figure 34:
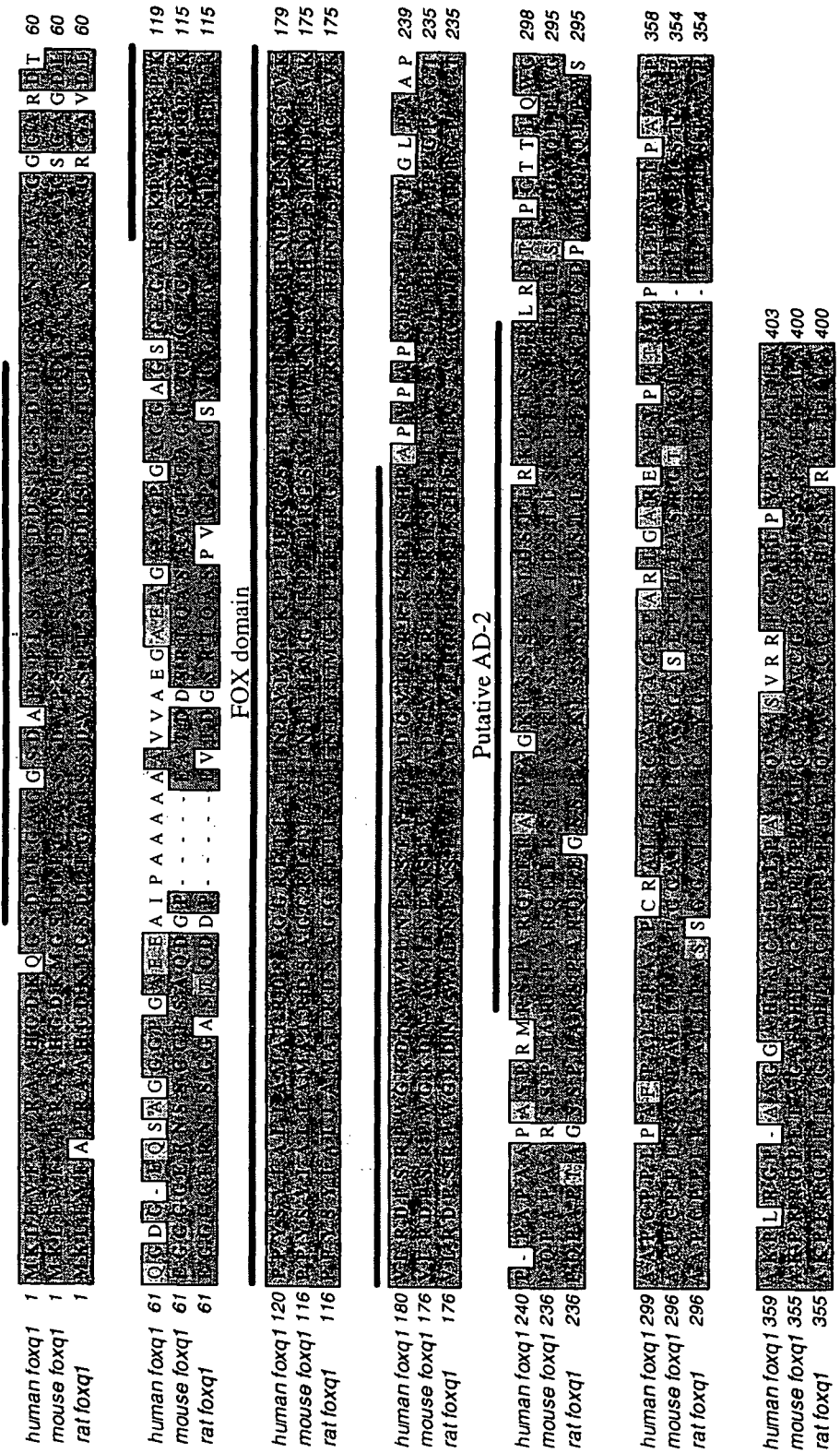
FIG. 34 illustrates an alignment of the human (SEQ ID NO: 23), mouse (SEQ ID NO: 24), and rat (SEQ ID NO: 25) ColoUp5 (FoxQ1) amino acid sequences.
Figure 35F:
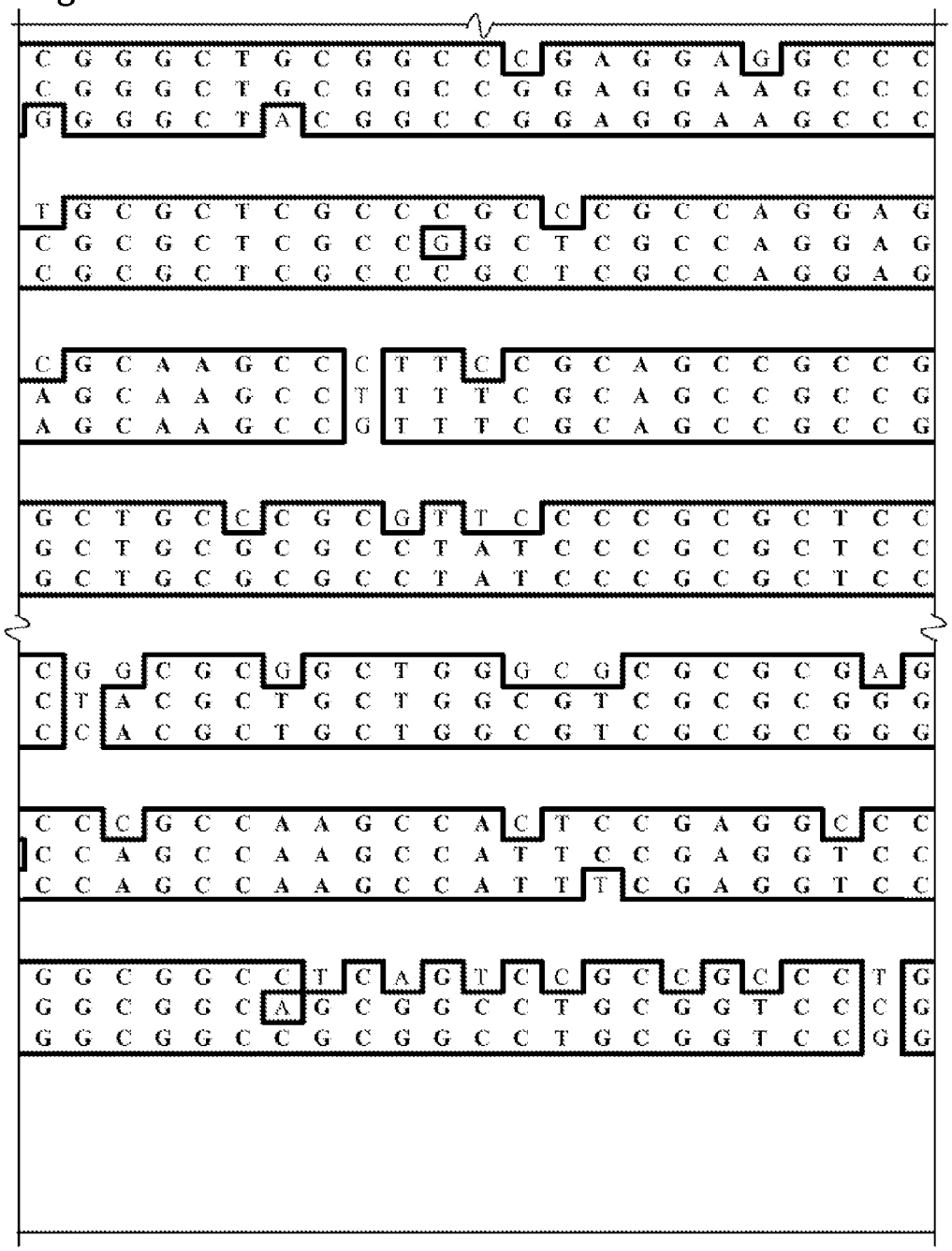

Shown in FIG. 33 is a northern blot showing that ColoUp5 is expressed in colon cancer cell lines and not expressed in non-neoplastic material. FIG. 33 shows two northern blot analysis of ColoUp5 mRNA levels in normal colon tissues and a group of colon cancer cell lines (top panels). The bottom panels show the ethidium bromide stained gel corresponding to the blot. Homologs for ColoUp5 are found in other mammals, including mouse and rat, and sequence alignments are shown in FIGS. 34 and 35.

Example 10

Figure 36:
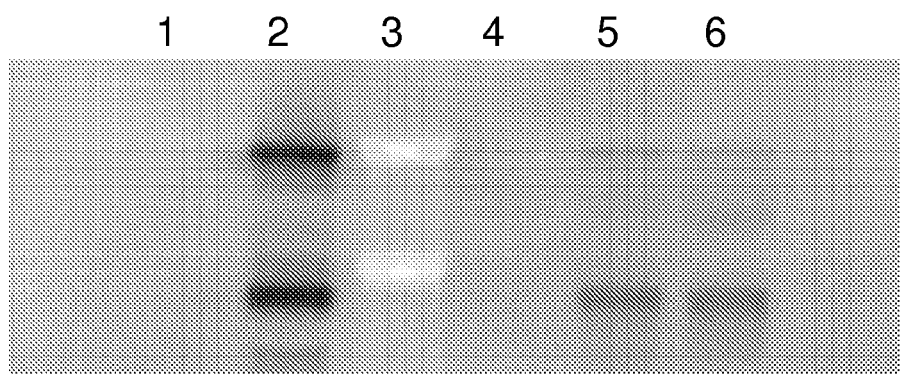
FIG. 36 shows a western blot of V5 tagged ColoUp2 protein detected by anti-V5 antibody. Lane 1: media supernate from SW480 colon cancer cells transfected with an empty expression vector. Lane 2: media supernate from ColoUp2-V5 expressing cells. Lane 3: size markers. Lane 4 shows assay of serum from a mouse xenografted with control SW480 cells corresponding to lane 1. Lanes 5 and 6 show detection of circulating ColoUp2 proteins in blood from two-mice bearing human colon cancer xenografts from ColoUp2-V5 expressing SW480 colon cells shown in lane 2. ColoUp2 is secreted as an 85 KD and a companion 55 KD size protein.

Detection of Xenograft Derived ColoUp1 and ColoUp2 Proteins Circulating in the Blood of Mice To determine that ColoUp1 and ColoUp2 proteins are effective serologic markers of colon neoplasia, we derived transfected cell lines that stably expressed and secreted V5-epitope tagged ColoUp1 and ColoUp2 proteins. These cells lines were then injected into athymic mice and grown as tumor xenografts. Mice were sacrificed and serum was obtained. V5 tagged proteins were then precipitated from the serum using beads conjugated to anti-V5 antibodies. Precipitated serum proteins were run out on SDS-PAGE, and visualized by western blotting using HRP-conjugated anti-V5 antibodies (thereby eliminating visualization of any contaminating mouse immunoglobulin). FIG. 36 shows detection of circulating ColoUp2 protein in mouse serum. The ColoUp2 protein is secreted as 2 bands of 85 KD and 55 KD in size, of which the 55 KD band predominates in the serum. The 55 KD band is presumably a processed form of the 85 KD band. This observation demonstrates that, in this mouse model, ColoUp2 is indeed a secreted marker of colon cancers and adenomas, and that ColoUp2 can gain access to and circulate stably in patient serum. This observation provides the surprising result that a processed fragment of ColoUp2 is the predominant serum form of the protein and therefore detection reagents targeted to this portion would be particularly suitable for diagnostic testing.

A time course experiment showed that ColoUp2 protein was detectable in mouse blood at the earliest time assayed, 1 week after injection of ColoUp2 secreting colon cancer cells, at which time xenograft tumor volume as only 100 mm$^3$.

Figure 37:
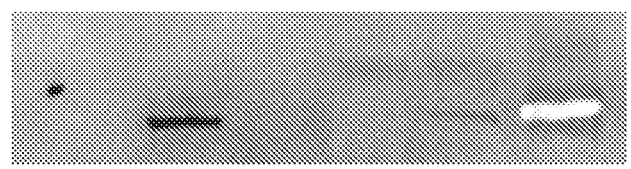
FIG. 37 shows a western blot with anti-V5 antibody of V5 tagged ColoUp1 protein. Lane 1: media supernate from SW480 colon cancer cells transfected with an empty expression vector. Lane 2: media supernate from ColoUp1-V5 expressing SW480 cells. Lane 3 shows assay of serum from a mouse xenografted with control SW480 cells corresponding to lane 1. Lanes 4 shows detection of circulating ColoUp1 proteins in blood from a mouse bearing tumor xenografts from ColoUp1-V5 expressing SW480 cells shown in lane 2. Lane 5: size markers.

Similar observations were also made for ColoUp1, as shown in FIG. 37.

Example 11

Purification of ColoUp1 and ColoUp2 Proteins

Figure 38:
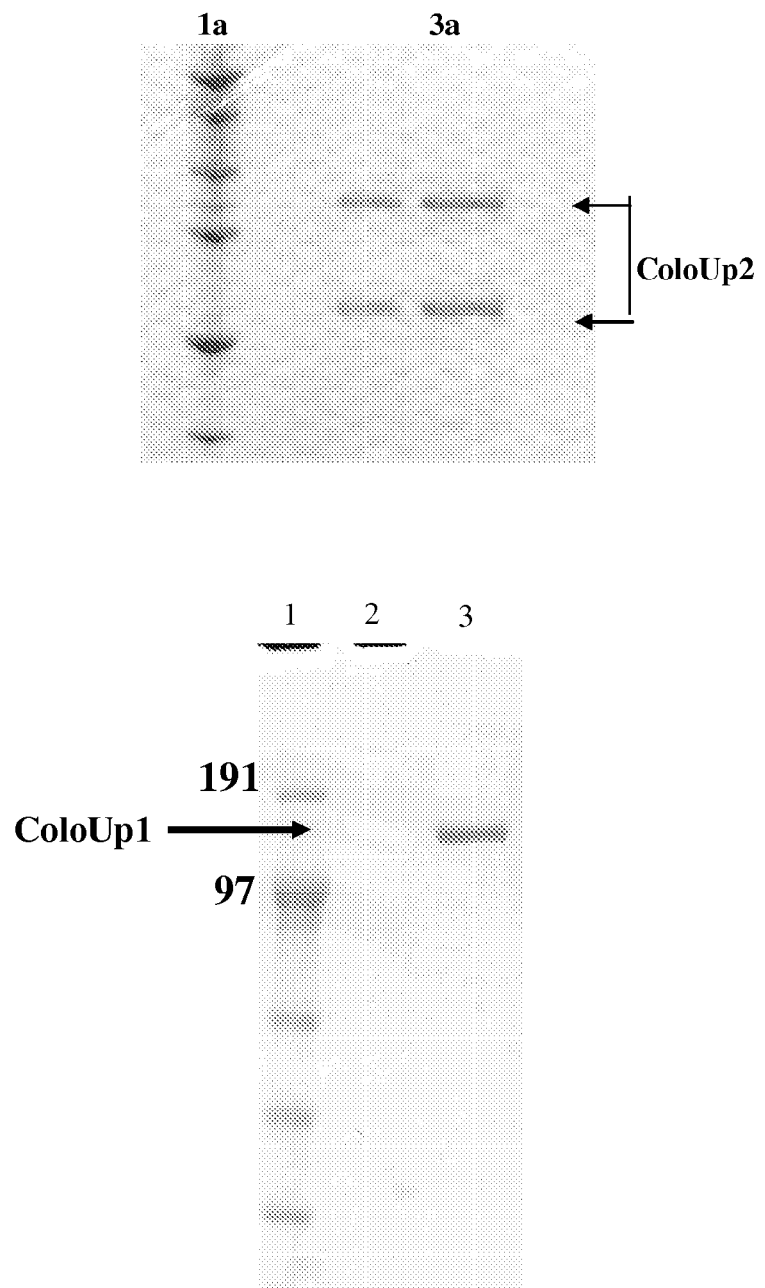
FIG. 38 shows, in the upper panel, the purification of ColoUp2 protein. Shown is a Coomassie blue staining of 250 ng (lane 2a) and 500 ng (lane 3a) of a purified ColoUp2 protein preparation. Size markers are in lane 1a. In the lower panel is shown a Coomassie blue stained gel showing purification of His-tagged ColoUp1 protein on Ni-NTA beads. Lane 1: markers, Lane 2 media from mock transfected cells, Lane 3 purification of media from ColoUp1 transfected cells. Clearly shown is purification to homogeneity of the 180 kd ColoUp protein.

In order to develop monoclonal antibodies against native ColoUp1 and ColoUp2 proteins, we devised a protocol for purification on Ni-NTA agarose (QIAGEN) nickel beads of recombinant His tagged ColoUp1 and ColoUp2 proteins from the media supernate of SW480 cells engineered to express these proteins. Currently we have purified both ColoUp1 and ColoUp2 proteins to sufficient purity to generate antibodies. As shown in FIG. 38, a Coomassie blue stained gel of purified ColoUp2 shows only the 85 KD and 55 KD size bands that correspond to the tagged ColoUp2 proteins visualized on western blot Similarly, a Coomassie blue stained gel of purified ColoUp1 shows the preparation is highly purified and composed of a single 180 KD band that corresponds perfectly to the size band seen on western blotting of the epitope tagged ColoUp1 protein. Thus we have purified ColoUp2 and ColoUp1 to sufficient homogeneity and yield. Scaled up purification of these proteins from a 50 liter media preparation should yield 2.5 mg of protein, more than adequate for immunizing mice and screening fusion supernates for development of monoclonal antibodies specific for native ColoUp1 and ColoUp2.

Example 12

Measuring Apical and Basolateral Secretion of ColoUp1 and ColoUp2

Figure 39:
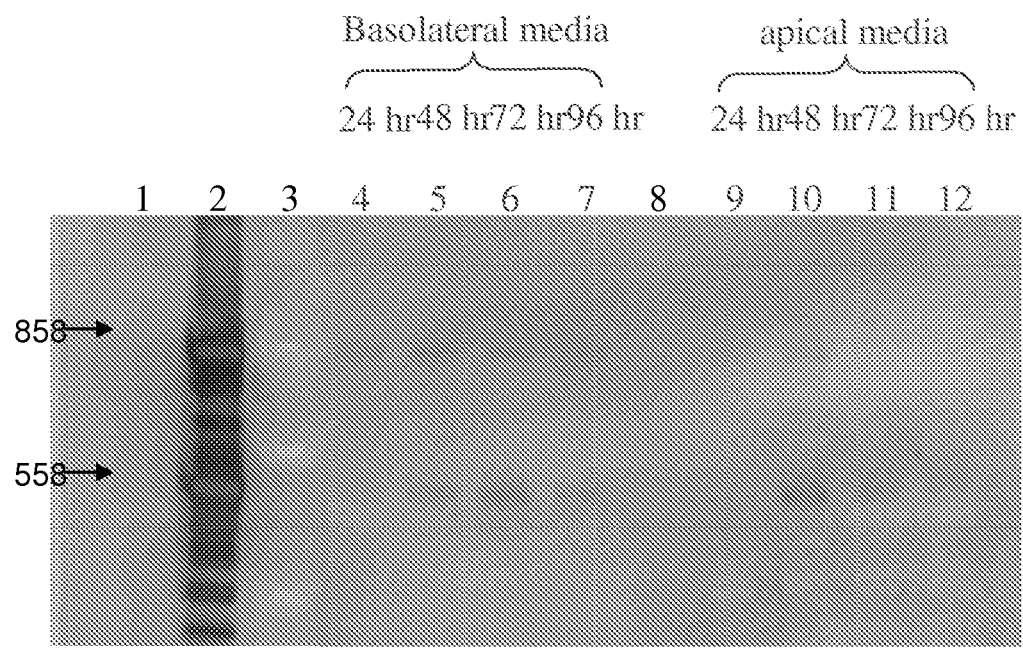
FIG. 39 shows, in the top panel, detection on an anti-V5 western of V5-tagged ColoUp2 protein. Lane 1: media from mock transfected Caco2 cells. Lane 2: detection of secreted ColoUp2 protein from transiently transfected Caco2 cells grown in standard culture dishes. Seen are the typical 85 KD and 55 KD secreted bands (the lane is heavily overloaded and minor degradation products are also visualized). Lane 3: molecular weight markers. Lanes 4-7: detection of ColoUp2 secreted into the basolateral compartment (lower chamber) of transiently transfected Caco2 grown as a monolayer on a transwell filter. Lanes 9-12 show the general absence of ColoUp2 in the corresponding apical apical compartment, with the exception of the 48 hour time point. The table shows the electrical resistance and transfection efficiency (gfp expression) measured at each time point. A dip in the electrical resistance at 48 hours suggests some leakiness of the monolayer at that time point.
Figure 40:
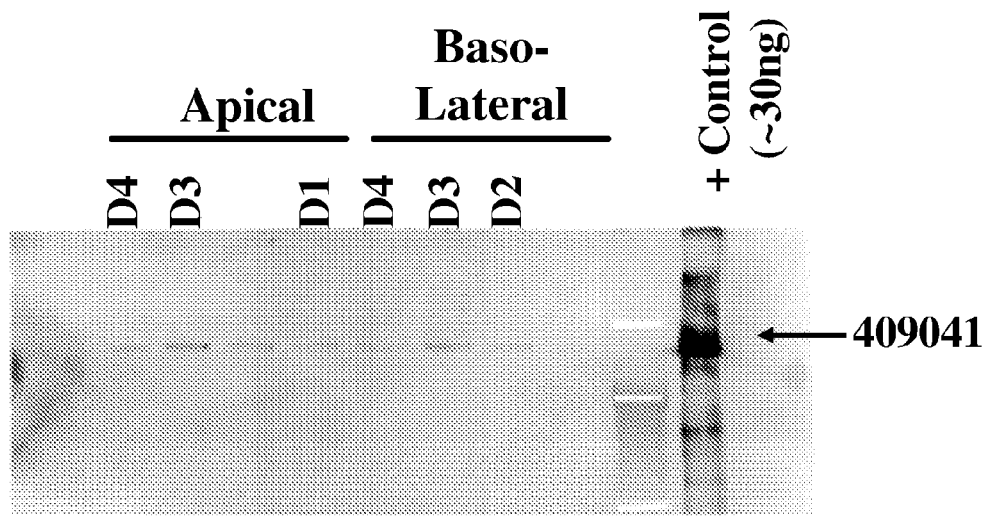
FIG. 40: Top panel shows detection on anti-V5 western of V5-tagged ColoUp1 protein. Control lane shows detection of purified recombinant ColoUp1. Identical bands are seen in media harvested on days 1-4 (lanes D1-D4) from both apical and basolateral compartments. The table shows the electrical resistance and transfection efficiency (gfp expression) measured at each time point.

We expected that ColoUp2 will serve as a serologic marker detection not only of colon cancers but also of large colon adenomas that also express ColoUp2. Adenomas, unlike colon cancers, are non-invasive. Thus, for adenomas to move ColoUp2 proteins into the circulation they would need to secrete this protein from the basolateral cell surface facing capillaries and lymphatics, rather than from the apical cell surface facing the colon lumen. To determine the polarity of ColoUp2 secretion we transiently transfected a monolayer of polarized Caco2 colon cancer cells with an expression vector for V5-epitope tagged ColoUp2 protein. This cell monolayer was grown in transwell dishes on filters that separate an upper transwell chamber (representing media exposed to the apical surface of the monlayer) from a lower transwell chamber (representing media exposed to the basolateral surface of the monolayer). Integrity of the sealing of the monolayer was assayed by measuring electrical resistance across the filters, and efficiency of transient transfection was monitored by expression of a gfp marker. Media from upper and lower chambers was harvested at 24, 48, 72, and 96 hours post transfection, and secreted tagged ColoUp2 protein was detected by western analysis directed against the V5 epitope tag. As FIG. 39 shows, characteristic 85 KD and 55 KD secreted forms of ColoUp2 were detected in media sampling the basolateral monolayer compartment at all time points assayed. At a single time point, 48 hours, ColoUp2 was additionally detected in media representing the apical secretion face; however, a dip in the transfilter electrical resistance at 48 hours suggests the likelihood of some leaking across the monolayer at this time point. Certainly, the data clearly shows secretion of ColoUp2 into the basolateral monolayer compartment, and hence establishes ColoUp2 as demonstrating the requisite biology for a candidate serologic marker of colon adenomas. As was done for ColoUp2, ColoUp1 expression vectors were used to transiently transfect Caco2 cell monolayers grown on transwell filters. Secretion of ColoUp1 was then assayed in media collected respectively from the upper and lower transwell chambers. Western blot assays demonstrated equal secretion of ColoU1 from both apical and basolateral monolayer surfaces. Studies of ColoUp1 were done in parallel with those of ColoUp2, and electrical resistance of the ColoUp1 monolayers exceeded that of the ColoUp2 monolayers, supporting that the ColoUp1 transfected monolayers were well sealed. Additionally, levels of secreted ColoUp1 protein were similar to those of secreted ColoUp2, suggesting that ColoUp1 secretion by both apical and basolateral compartments was not simply due to overexpression. Accordingly, we predict that native ColoUp1 protein is likely secreted at least in part from the basolateral epithelial face, and hence should be detectable as a serologic marker of large colon adenomas.

Example 13

Determining the Sequence of the 55 kDa ColoUp2 Fragment

The protein sequence of C-terminal fragment of ColoUp2 that is secreted by human cell lines and detected as predominant fragment in blood. (488 aa) was determined. As described above, we have found on western blots and on purified preparations of C-terminal epitope tagged (V5-His epitope) ColoUp2 protein secreted by transfected human colon cancer cells, both a full sized band of approximately 90 kDa and a smaller approximately 55 kDa C-terminal fragment (as demonstrated by the retention of the C-terminal epitope tag). Moreover, when these cells were injected into athymic mice, the 55 kDa C-terminal tagged protein was the predominant species detected as circulating in the mouse blood, when mouse serum is analyzed by serial immunoprecipitation and western blot analysis directed against the V5 tag. The precise location of the cleavage site accounting for the C-terminal fragment was established by excising the acrylamide gel band containing the purified C-terminal fragment and performing mass spectroscopy analysis of tryptic fragments from the protein. A peptide of sequence AVLAAHCPFYSWK was present only in the digest of the 55 KD fragment, but was absent from the digest of the full length protein, demonstrating that this peptide corresponded to the unique amino terminus of the 55 KD fragment. The complete sequence of the 55 KD C-terminal fragment is shown in FIG. 41.

Incorporation by Reference

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. A method of determining whether a subject is likely to have a colon neoplasm comprising:
(a) obtaining a biological sample from said subject
(b) detecting any ColoUp1 polypeptide present in the sample, wherein said ColoUp1 polypeptide is encoded by a nucleic acid sequence comprising SEQ ID NO: 4,
(c) determining that the subject may be likely to have a colon neoplasm if any ColoUp1 polypeptide is detected in the sample.

2. The method of claim 1, wherein said ColoUp1 polypeptide is a secreted polypeptide comprising SEQ ID NO: 1 or SEQ ID NO: 2, and wherein said biological sample is selected from the group consisting of whole blood or a fraction thereof.

3. The method of claim 1, wherein said ColoUp1 polypeptide is a secreted polypeptide comprising SEQ ID NO: 1 or SEQ ID NO: 2, and wherein said biological sample is selected from the group consisting of urine or stool samples.

4. The method of claim 1, wherein said ColoUp1 polypeptide is a secreted polypeptide comprising SEQ ID NO: 1 or SEQ ID NO: 2, and wherein said biological sample is a blood sample.

5. The method of claim 4, wherein said blood sample is fractionated to obtain blood serum and/or blood plasma.

6. The method of claim 5, wherein said biological sample is enriched for said ColoUp1 polypeptide.

7. The method of claim 1, wherein the polypeptide is detected by an assay.

8. The method of claim 7, wherein said assay employs an antibody.

9. The method of claim 8, where said assay is selected from the group consisting of an immunoprecipitation assay, a Western blot, a radioimmunoassay, and an enzyme-linked immunosorbent assay (ELISA).

10. The method of claim 8, wherein said assay comprises contacting the biological sample with an antibody that interacts with the ColoUp1 polypeptide.

11. The method of claim 10, wherein the antibody is detectably labeled.

12. The method of claim 11, wherein the label is selected from the group consisting of an enzyme, a fluorescent substance, a chemiluminescent substance, a chromophore, a radioactive isotope and a complexing agent.

13. The method of claim 1, wherein the ColoUp1 polypeptide comprises SEQ ID NO: 13 and wherein said biological sample is a tissue sample.

\* \* \* \* \*